US011179571B2

(12) United States Patent
Manicka

(10) Patent No.: US 11,179,571 B2
(45) Date of Patent: Nov. 23, 2021

(54) SUBCUTANEOUS DEVICE FOR MONITORING AND/OR PROVIDING THERAPIES

(71) Applicant: Manicka Institute LLC, Woodbury, MN (US)

(72) Inventor: Yatheendhar D. Manicka, Woodbury, MN (US)

(73) Assignee: Manicka Institute LLC, Woodbury, MN (US)

( * ) Notice: Subject to any disclaimer, the term of this patent is extended or adjusted under 35 U.S.C. 154(b) by 158 days.

(21) Appl. No.: 16/680,375

(22) Filed: Nov. 11, 2019

(65) Prior Publication Data

US 2020/0147403 A1 May 14, 2020

Related U.S. Application Data

(63) Continuation-in-part of application No. 16/051,451, filed on Jul. 31, 2018, now Pat. No. 10,471,251.

(51) Int. Cl.
*A61N 1/39* (2006.01)
*A61N 1/365* (2006.01)
*A61N 1/05* (2006.01)

(52) U.S. Cl.
CPC ......... *A61N 1/39622* (2017.08); *A61N 1/059* (2013.01); *A61N 1/365* (2013.01); *A61N 1/3956* (2013.01)

(58) Field of Classification Search
CPC .. A61N 1/39622; A61N 1/365; A61N 1/3956; A61N 1/059; A61N 1/37; A61N 1/3925
See application file for complete search history.

(56) References Cited

U.S. PATENT DOCUMENTS

| 3,923,060 | A | 12/1975 | Ellinwood, Jr. |
| 4,030,509 | A | 6/1977 | Heilman et al. |
| 4,256,115 | A | 3/1981 | Bilitch |
| 4,291,707 | A | 9/1981 | Heilman et al. |

(Continued)

FOREIGN PATENT DOCUMENTS

| EP | 458265 A2 | 11/1991 |
| EP | 280564 B1 | 6/1993 |

(Continued)

OTHER PUBLICATIONS

Invitation to Pay Additional Fees and, Where Applicable, Protest Fee for PCT Application No. PCT/US2019/028373, dated Jun. 6, 2019, 2 pages.

(Continued)

*Primary Examiner* — Paula J Stice
(74) *Attorney, Agent, or Firm* — Kinney & Lange, P.A.

(57) ABSTRACT

A subcutaneously implantable device includes a clip that is configured to anchor the subcutaneously implantable device to a muscle, a bone, and/or a first tissue, and a first prong with a proximal end attached to the clip and a distal end extending away from the clip that is configured to contact an organ, a nerve, and/or a second tissue. A first electrode on the first prong is configured to contact the organ, the nerve, and/or the second tissue. A wire conductively connected to the first electrode is configured to be connected to an external device that is positioned outside of a patient's body to electrically connect the subcutaneously implantable device to the external device.

22 Claims, 72 Drawing Sheets

(56) References Cited

U.S. PATENT DOCUMENTS

| | | |
|---|---|---|
| 4,683,895 A | 8/1987 | Pohndorf |
| 4,817,634 A | 4/1989 | Holleman et al. |
| 4,827,932 A | 5/1989 | Ideker et al. |
| 4,971,070 A | 11/1990 | Holleman et al. |
| 4,991,578 A | 2/1991 | Cohen |
| 5,042,463 A | 8/1991 | Lekholm |
| 5,243,977 A | 9/1993 | Trabucco et al. |
| 5,247,945 A | 9/1993 | Heinze et al. |
| 5,327,909 A | 7/1994 | Kiser et al. |
| 5,496,362 A | 3/1996 | Kenknight et al. |
| 5,509,924 A | 4/1996 | Paspa et al. |
| 5,545,202 A | 8/1996 | Dahl et al. |
| 5,674,259 A | 10/1997 | Gray |
| 5,792,208 A | 8/1998 | Gray |
| 5,897,586 A | 4/1999 | Molina |
| 5,916,243 A | 6/1999 | Kenknight et al. |
| 5,954,757 A | 9/1999 | Gray |
| 6,044,300 A | 3/2000 | Gray |
| 6,152,955 A | 11/2000 | Kenknight et al. |
| 6,169,922 B1 | 1/2001 | Alferness et al. |
| 6,411,845 B1 | 6/2002 | Mower |
| 6,564,094 B2 | 5/2003 | Alferness et al. |
| 6,567,699 B2 | 5/2003 | Alferness et al. |
| 6,647,292 B1 | 11/2003 | Bardy et al. |
| 6,662,035 B2 | 12/2003 | Sochor |
| 7,085,606 B2 | 8/2006 | Flach et al. |
| 7,146,226 B2 | 12/2006 | Lau et al. |
| 7,155,295 B2 | 12/2006 | Lau et al. |
| 7,158,839 B2 | 1/2007 | Lau |
| 7,164,952 B2 | 1/2007 | Lau et al. |
| 7,197,362 B2 | 3/2007 | Westlund |
| 7,225,036 B2 | 5/2007 | Lau et al. |
| 7,239,918 B2 | 7/2007 | Strother et al. |
| 7,272,448 B1 | 9/2007 | Morgan et al. |
| 7,288,096 B2 | 10/2007 | Chin |
| 7,460,911 B2 | 12/2008 | Cosendai et al. |
| 7,526,342 B2 | 4/2009 | Chin et al. |
| 7,558,631 B2 | 7/2009 | Cowan et al. |
| 7,587,238 B2 | 9/2009 | Moffitt et al. |
| 7,610,092 B2 | 10/2009 | Cowan et al. |
| 7,765,012 B2 | 7/2010 | Gerber |
| 7,899,537 B1 | 3/2011 | Kroll et al. |
| 8,036,757 B2 | 10/2011 | Worley |
| 8,060,219 B2 | 11/2011 | Ross et al. |
| 8,131,362 B2 | 3/2012 | Moffitt et al. |
| 8,315,701 B2 | 11/2012 | Cowan et al. |
| 8,359,094 B2 | 1/2013 | Bonner et al. |
| 8,469,874 B2 | 6/2013 | Forsell |
| 8,475,355 B2 | 7/2013 | Forsell |
| 8,483,841 B2 | 7/2013 | Sanghera et al. |
| 8,506,474 B2 | 8/2013 | Chin et al. |
| 8,509,894 B2 | 8/2013 | Forsell |
| 8,630,710 B2 | 1/2014 | Kumar et al. |
| 8,688,211 B2 | 4/2014 | Libbus et al. |
| 8,696,745 B2 | 4/2014 | Forsell |
| 8,886,311 B2 | 11/2014 | Anderson et al. |
| 9,005,104 B2 | 4/2015 | Forsell |
| 9,008,776 B2 | 4/2015 | Cowan et al. |
| 9,079,035 B2 | 7/2015 | Sanghera et al. |
| 9,180,235 B2 | 11/2015 | Forsell |
| 9,364,595 B2 | 6/2016 | Forsell |
| 9,393,407 B2 | 7/2016 | Bar-Cohen et al. |
| 9,398,901 B2 | 7/2016 | Tischendorf et al. |
| 9,457,137 B2 | 10/2016 | Forsell |
| 9,492,669 B2 | 11/2016 | Demmer et al. |
| 9,511,233 B2 | 12/2016 | Sambelashvili |
| 9,597,514 B2 | 3/2017 | Khairkhahan et al. |
| 9,656,009 B2 | 5/2017 | Kheradvar et al. |
| 9,717,898 B2 | 8/2017 | Thompson-Nauman et al. |
| 9,717,923 B2 | 8/2017 | Thompson-Nauman et al. |
| 9,731,055 B2 | 8/2017 | Forsell |
| 9,789,319 B2 | 10/2017 | Sambelashvili |
| 9,925,318 B2 | 3/2018 | Forsell |
| 10,086,206 B2 | 10/2018 | Sambelashvili |
| 10,092,745 B2 | 10/2018 | Tockman et al. |
| 10,226,618 B2 | 3/2019 | Reddy et al. |
| 10,279,170 B2 | 5/2019 | Syed et al. |
| 10,471,251 B1 | 11/2019 | Manicka |
| 10,556,047 B2 | 2/2020 | Forsell |
| 10,596,383 B2 | 3/2020 | Ghosh |
| 10,603,487 B2 | 3/2020 | Tockman et al. |
| 10,661,080 B2 | 5/2020 | Tholakanahalli et al. |
| 10,765,858 B2 | 9/2020 | Marshall et al. |
| 2004/0054391 A1 | 3/2004 | Wildon |
| 2004/0230273 A1 | 11/2004 | Cates et al. |
| 2005/0137673 A1 | 6/2005 | Lau et al. |
| 2005/0171589 A1 | 8/2005 | Lau et al. |
| 2005/0288715 A1 | 12/2005 | Lau et al. |
| 2006/0009675 A1 | 1/2006 | Meyer |
| 2006/0009831 A1 | 1/2006 | Lau et al. |
| 2006/0116746 A1 | 6/2006 | Chin |
| 2006/0155180 A1 | 7/2006 | Brister et al. |
| 2006/0287682 A1 | 12/2006 | Cohen et al. |
| 2006/0293740 A1 | 12/2006 | Heil et al. |
| 2007/0004979 A1 | 1/2007 | Wojciechowicz et al. |
| 2007/0043394 A1 | 2/2007 | Zhang et al. |
| 2007/0043416 A1 | 2/2007 | Callas et al. |
| 2007/0055091 A1 | 3/2007 | Lau et al. |
| 2007/0055310 A1 | 3/2007 | Lau |
| 2007/0106359 A1 | 5/2007 | Schaer et al. |
| 2007/0112390 A1 | 5/2007 | Lau et al. |
| 2007/0173915 A1 | 7/2007 | Westlund |
| 2007/0197859 A1 | 8/2007 | Schaer et al. |
| 2008/0243217 A1 | 10/2008 | Wildon |
| 2008/0319503 A1 | 12/2008 | Honeck et al. |
| 2009/0030469 A1 | 1/2009 | Meiry |
| 2009/0209986 A1 | 8/2009 | Stewart et al. |
| 2009/0275998 A1 | 11/2009 | Burnes et al. |
| 2009/0275999 A1 | 11/2009 | Burnes et al. |
| 2009/0287266 A1 | 11/2009 | Zdeblick |
| 2009/0299447 A1 | 12/2009 | Jensen et al. |
| 2010/0042108 A1 | 2/2010 | Hibino |
| 2010/0114287 A1 | 5/2010 | Privitera et al. |
| 2010/0152798 A1 | 6/2010 | Sanghera et al. |
| 2010/0241181 A1 | 9/2010 | Savage et al. |
| 2011/0196193 A1 | 8/2011 | Forsell |
| 2012/0029335 A1 | 2/2012 | Sudam et al. |
| 2012/0172892 A1 | 7/2012 | Grubac et al. |
| 2012/0330123 A1 | 12/2012 | Doerr |
| 2013/0073003 A1 | 3/2013 | Pless et al. |
| 2014/0074093 A9 | 3/2014 | Nelson et al. |
| 2014/0088611 A1 | 3/2014 | Richardson |
| 2014/0114371 A1 | 4/2014 | Westlund et al. |
| 2014/0128935 A1 | 5/2014 | Kumar et al. |
| 2014/0163579 A1 | 6/2014 | Tischendorf et al. |
| 2014/0309699 A1 | 10/2014 | Houff |
| 2014/0330248 A1 | 11/2014 | Thompson-Nauman et al. |
| 2014/0330287 A1 | 11/2014 | Thompson-Nauman et al. |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |
| 2015/0057563 A1 | 2/2015 | Kowalski et al. |
| 2015/0126833 A1 | 5/2015 | Anderson et al. |
| 2015/0306377 A1 | 10/2015 | Brantigan |
| 2015/0321016 A1 | 11/2015 | O'Brien et al. |
| 2015/0342627 A1 | 12/2015 | Thompson-Nauman et al. |
| 2015/0343176 A1 | 12/2015 | Asleson et al. |
| 2015/0343197 A1 | 12/2015 | Gardeski et al. |
| 2015/0359513 A1 | 12/2015 | Caluser |
| 2016/0067478 A1 | 3/2016 | McGeehan et al. |
| 2016/0067479 A1 | 3/2016 | Marcovecchio et al. |
| 2016/0067480 A1 | 3/2016 | Sanghera et al. |
| 2016/0067488 A1 | 3/2016 | Sanghera et al. |
| 2016/0121106 A1 | 5/2016 | Marshall et al. |
| 2016/0129169 A1 | 5/2016 | Forsell |
| 2016/0144192 A1 | 5/2016 | Sanghera et al. |
| 2016/0158567 A1 | 6/2016 | Marshall et al. |
| 2016/0175580 A1 | 6/2016 | Marshall et al. |
| 2016/0228713 A1 | 8/2016 | Bar-Cohen et al. |
| 2017/0021159 A1 | 1/2017 | Reddy et al. |
| 2017/0043173 A1 | 2/2017 | Sharma et al. |
| 2017/0224995 A1 | 8/2017 | Sanghera et al. |

(56) References Cited

U.S. PATENT DOCUMENTS

| | | | |
|---|---|---|---|
| 2017/0304019 A1 | 10/2017 | Sanghera et al. |
| 2017/0304634 A1 | 10/2017 | Sanghera et al. |
| 2017/0319863 A1 | 11/2017 | Thompson-Nauman et al. |
| 2018/0021572 A1 | 1/2018 | McGeehan et al. |
| 2018/0036547 A1 | 2/2018 | Reddy |
| 2018/0050199 A1 | 2/2018 | Sanghera et al. |
| 2018/0085593 A1 | 3/2018 | Fayram et al. |
| 2018/0117307 A1 | 5/2018 | Whitman et al. |
| 2018/0133494 A1 | 5/2018 | Reddy |
| 2018/0272122 A1 | 9/2018 | Rys |
| 2018/0361145 A1 | 12/2018 | Mahapatra et al. |
| 2019/0105489 A1 | 4/2019 | Thompson-Nauman et al. |
| 2019/0117959 A1 | 4/2019 | Reddy |
| 2019/0224477 A1 | 7/2019 | Syed et al. |
| 2019/0321624 A1 | 10/2019 | De Kock et al. |
| 2019/0374695 A1 | 12/2019 | Kheradvar |
| 2020/0023177 A1 | 1/2020 | Sanghera et al. |
| 2020/0129755 A1 | 4/2020 | Thompson-Nauman et al. |
| 2020/0139108 A1 | 5/2020 | Strommer et al. |
| 2020/0147365 A1 | 5/2020 | Marshall et al. |
| 2020/0215320 A1 | 7/2020 | Tockman et al. |

FOREIGN PATENT DOCUMENTS

| | | | |
|---|---|---|---|
| EP | 602356 A2 | 6/1994 |
| EP | 627237 A1 | 12/1994 |
| EP | 460324 B1 | 3/1996 |
| EP | 2119471 B1 | 8/2011 |
| EP | 2069012 B1 | 5/2017 |
| EP | 2349381 B1 | 12/2019 |
| EP | 2349382 B1 | 12/2019 |
| EP | 2349385 B1 | 12/2019 |
| WO | 8202664 A1 | 8/1982 |
| WO | 9220402 A1 | 11/1992 |
| WO | 9408657 A1 | 4/1994 |
| WO | 0028918 A1 | 5/2000 |
| WO | 0191850 A1 | 12/2001 |
| WO | 2004073506 A2 | 9/2004 |
| WO | 2005046789 A1 | 5/2005 |
| WO | 2005092431 A1 | 10/2005 |
| WO | 2006083617 A2 | 8/2006 |
| WO | 2006107590 A2 | 10/2006 |
| WO | 2007005641 A2 | 1/2007 |
| WO | 2007103262 A2 | 9/2007 |
| WO | 2007133947 A2 | 11/2007 |
| WO | 2008051926 A1 | 5/2008 |
| WO | 2010014472 A1 | 2/2010 |
| WO | 2010042014 A1 | 4/2010 |
| WO | 2010042016 A1 | 4/2010 |
| WO | 2010042017 A1 | 4/2010 |
| WO | 2010042018 A1 | 4/2010 |
| WO | 2013152259 A1 | 10/2013 |
| WO | 2020102331 A1 | 5/2020 |

OTHER PUBLICATIONS

International Search Report and Written Opinion for PCT/US2019/028373, dated Aug. 19, 2019, 15 pages.
International Search Report and Written Opinion for PCT Application No. PCT/US2020/059732 dated Feb. 4, 2021, 10 pages.
International Search Report and Written Opinion for PCT Application No. PCT/US2020/059733, dated Feb. 5, 2021, 7 pages.
International Search Report and Written Opinion for PCT Application No. PCT/US2021/029151, dated Aug. 17, 2021, 8 pages.

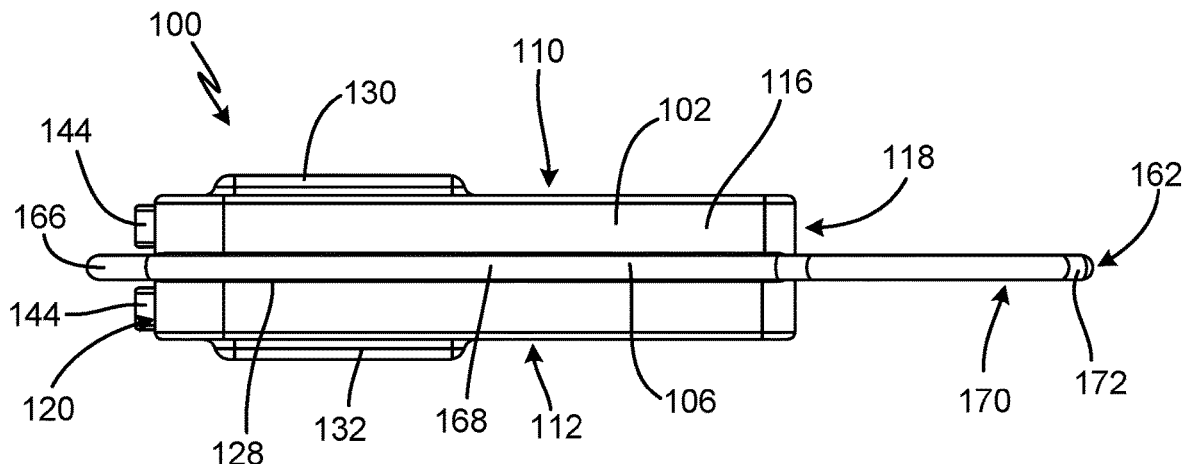
Fig. 6C
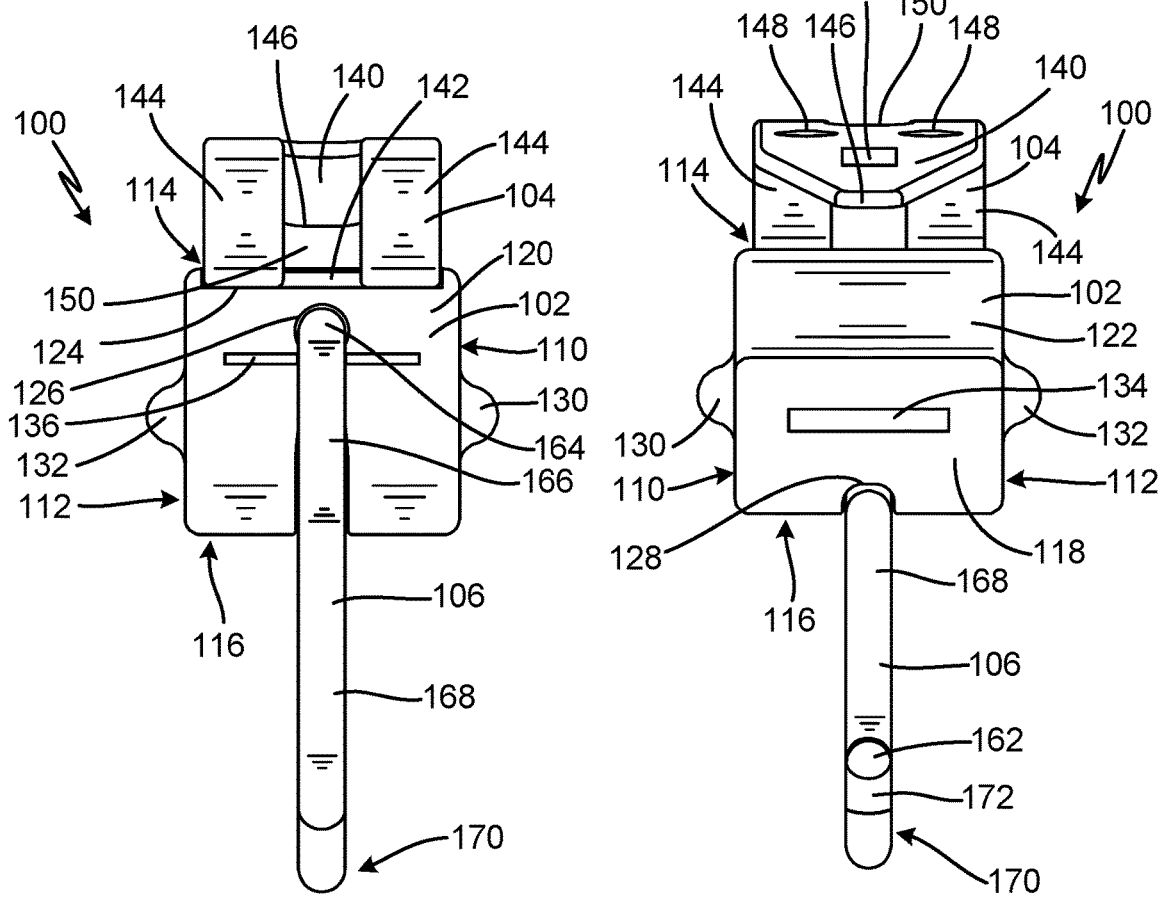
Fig. 6D
Fig. 6E

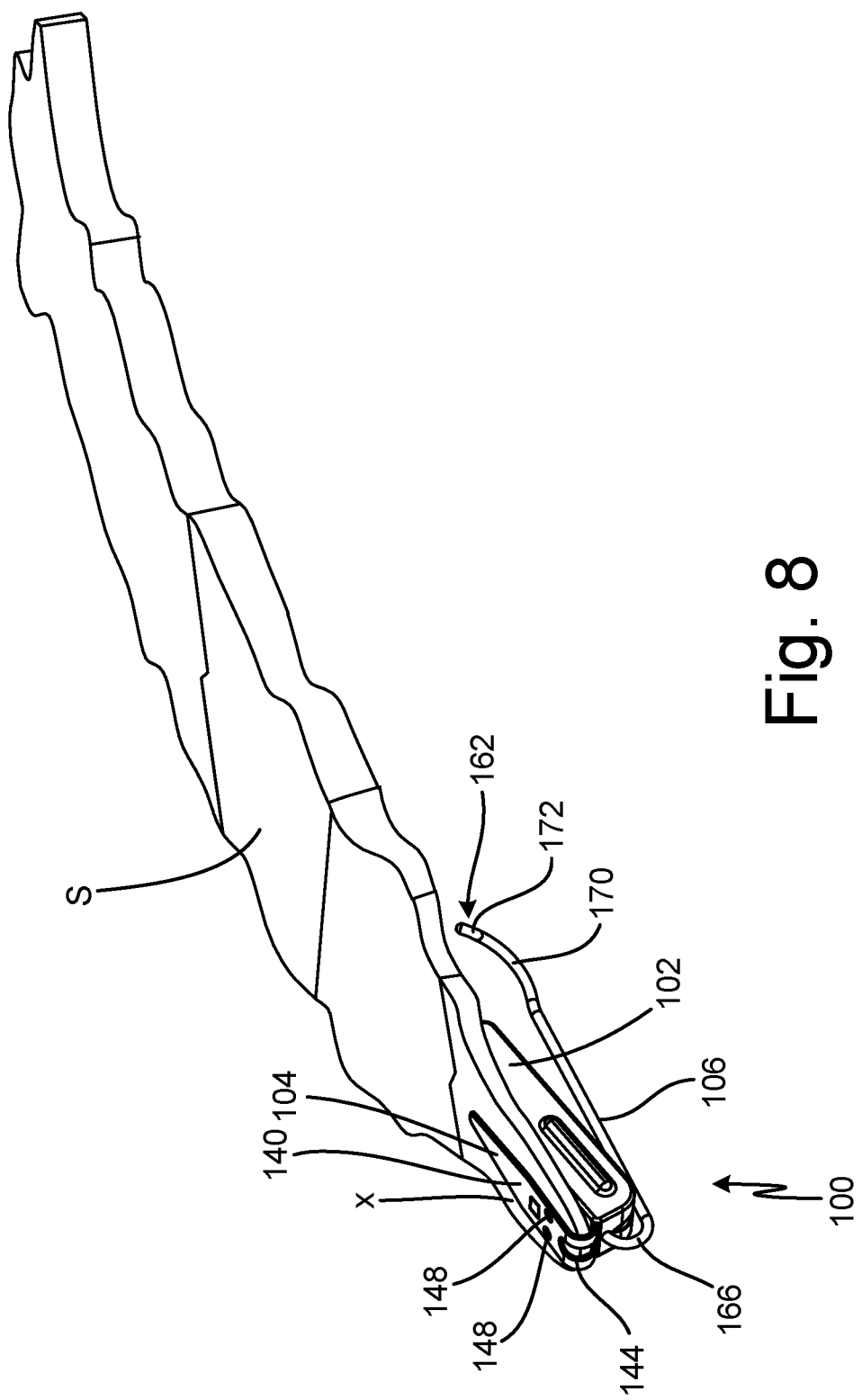

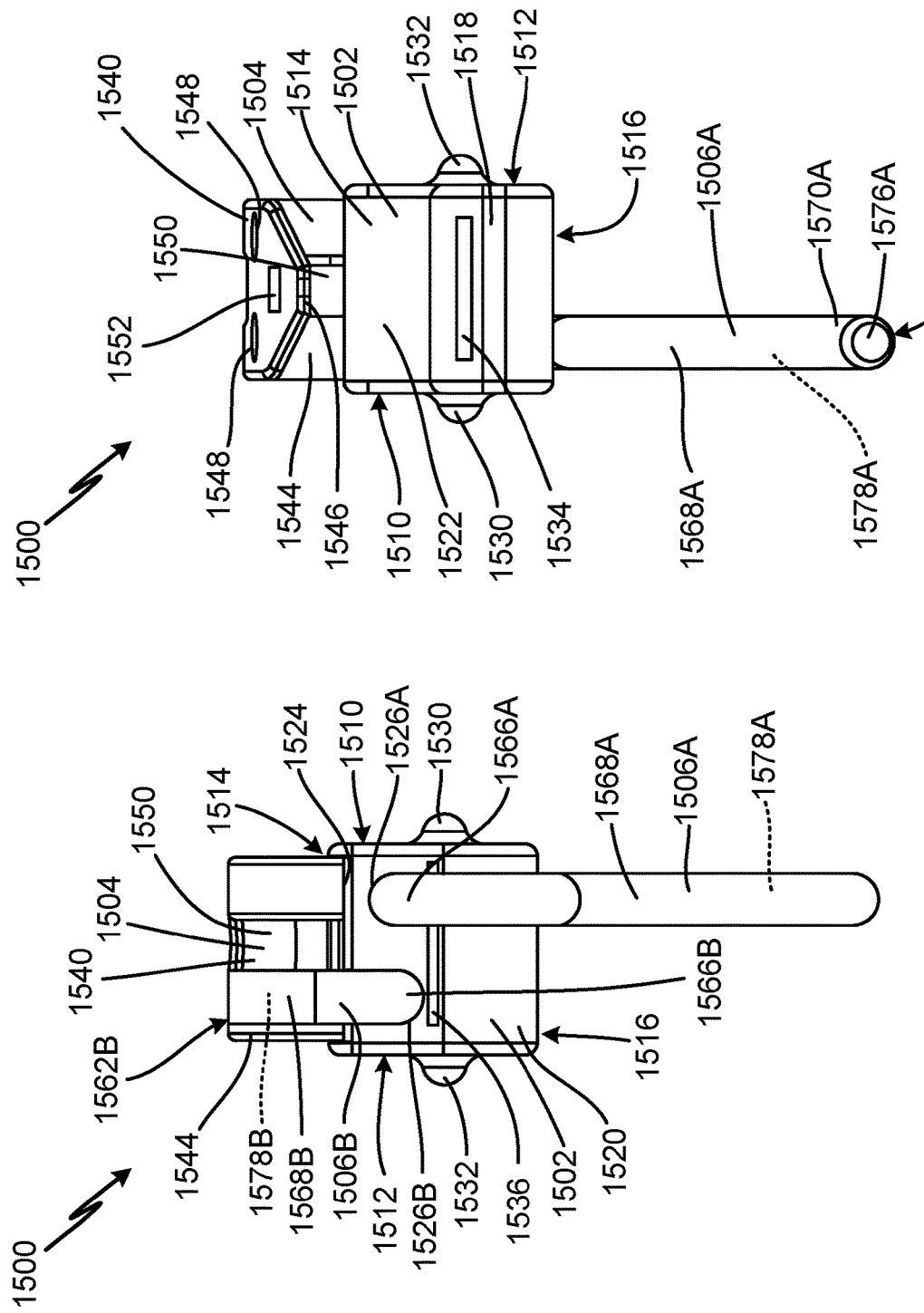

SUBCUTANEOUS DEVICE FOR MONITORING AND/OR PROVIDING THERAPIES

CROSS-REFERENCE TO RELATED APPLICATION(S)

This application is a continuation-in-part of U.S. Pat. No. 10,576,291, filed on Jul. 31, 2018, entitled "Subcutaneous Device for Monitoring and/or Providing Therapies," the disclosure of which is incorporated by reference in its entirety.

This application is related to U.S. Pat. No. 10,576,291, filed on Jul. 31, 2018, entitled "Subcutaneous Device," the disclosure of which is incorporated by reference in its entirety.

This application is related to U.S. Pat. No. 10,646,721, filed on Jul. 31, 2018, entitled "Injectable Subcutaneous Device," the disclosure of which is incorporated by reference in its entirety.

BACKGROUND

The present invention relates to implantable medical devices, and in particular, to a subcutaneous device.

Implantable medical devices include medical devices that are implanted in the body. Examples of implantable medical devices can include cardiac monitors, pacemakers, and implantable cardioverter-defibrillators, amongst many others. These implantable medical devices can receive signals from the body and use those signals for diagnostic purposes. These implantable medical devices can also transmit electrical stimulation or deliver drugs to the body for therapeutic purposes. For instance, a pacemaker can sense a heart rate of a patient, determine whether the heart is beating too fast or too slow, and transmit electrical stimulation to the heart to speed up or slow down different chambers of the heart. An implantable cardioverter-defibrillator can sense a heart rate of a patient, detect a dysrhythmia, and transmit an electrical shock to the patient.

Traditionally, cardiac monitors, pacemakers, and implantable cardioverter-defibrillators include a housing containing electrical circuitry. A proximal end of a lead is connected to the housing and a distal end of the lead is positioned in or on the heart. The distal end of the lead contains electrodes that can receive and transmit signals. Implantable medical devices such as cardiac monitors, pacemakers, and implantable cardioverter-defibrillators typically require invasive surgeries to implant the medical device in the body.

SUMMARY

A subcutaneously implantable device includes a clip that is configured to anchor the subcutaneously implantable device to a muscle, a bone, and/or a first tissue, and a first prong with a proximal end attached to the clip and a distal end extending away from the clip that is configured to contact an organ, a nerve, and/or a second tissue. A first electrode on the first prong is configured to contact the organ, the nerve, and/or the second tissue. A wire conductively connected to the first electrode is configured to be connected to an external device that is positioned outside of a patient's body to electrically connect the subcutaneously implantable device to the external device.

A system includes a subcutaneously implantable device and an external device positioned outside of a patient's body. The subcutaneously implantable device includes a clip that is configured to anchor the subcutaneously implantable device to a muscle, a bone, and/or a first tissue, and a first prong with a proximal end attached to the clip and a distal end extending away from the clip that is configured to contact a heart. A first electrode on the first prong is configured to contact the heart, and a wire is conductively connected to the first electrode. The wire is electrically connected to the external device to electrically connect the subcutaneously implantable device to the external device.

BRIEF DESCRIPTION OF THE DRAWINGS

Subcutaneous Device 100

FIG. 6C is a bottom view of the first embodiment of the subcutaneous device.

FIG. 6D is a back view of the first embodiment of the subcutaneous device.

FIG. 6E is a front view of the first embodiment of the subcutaneous device.

FIG. 8 is a perspective view of the first embodiment of the subcutaneous device positioned on a xiphoid process and a sternum.

Subcutaneous Device 500

Subcutaneous Device 1300

Figure 33:
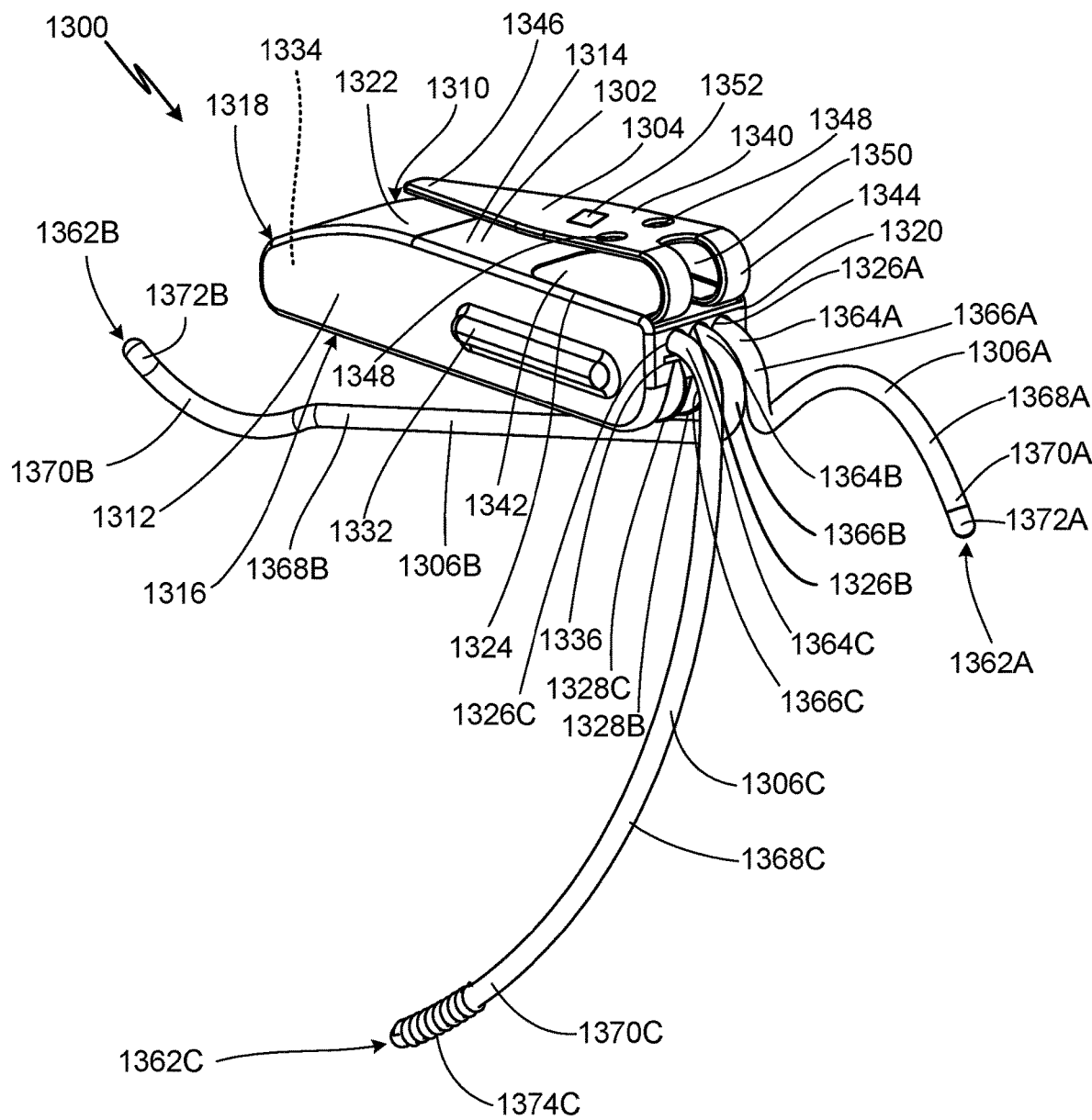

FIG. 33 is a perspective view of an eleventh embodiment of a subcutaneous device.

Subcutaneous Device 1400

Figure 34A:
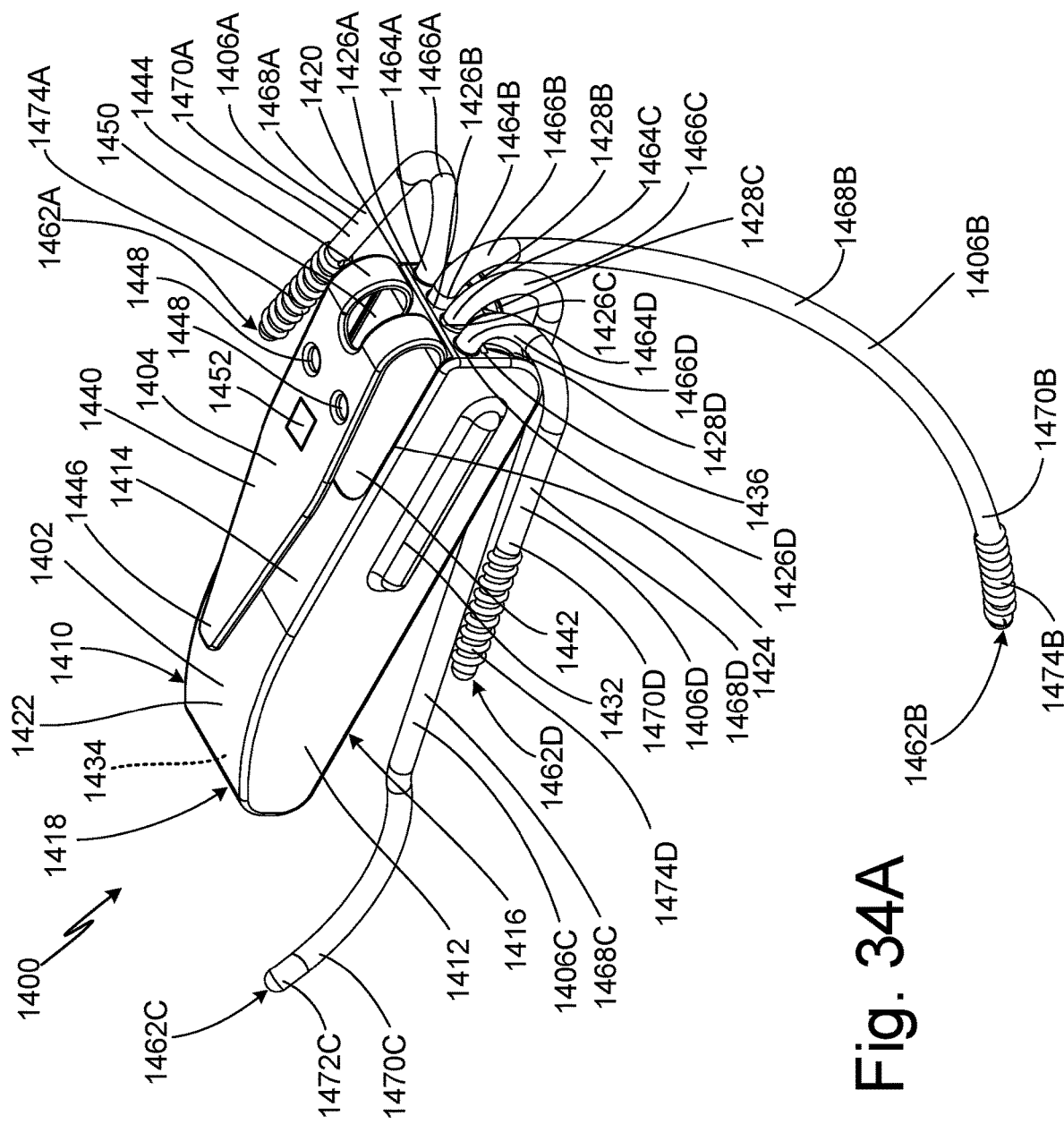

FIG. 34A is a perspective view of a twelfth embodiment of a subcutaneous device.

Figure 34B:
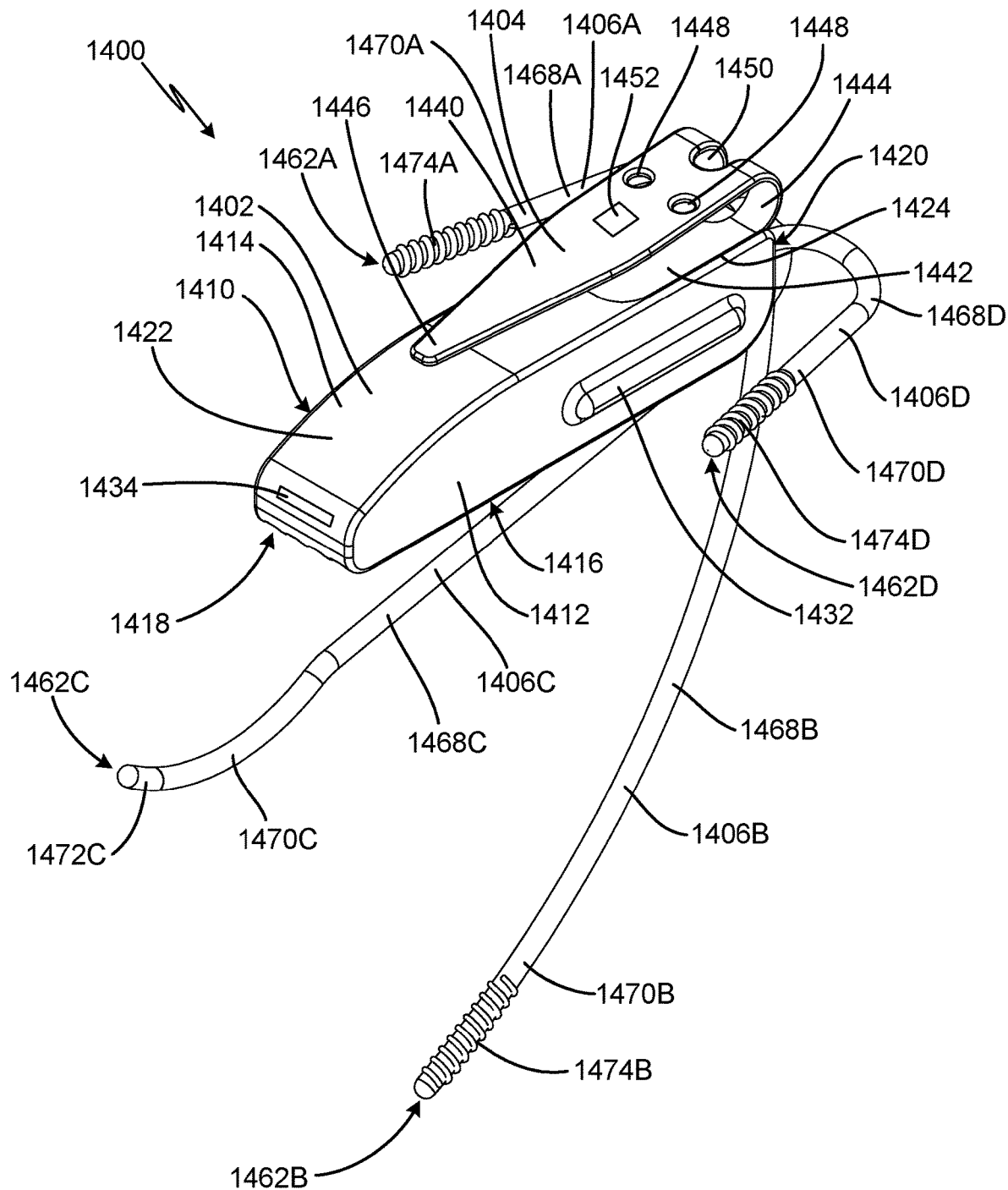

FIG. 34B is a perspective view of the twelfth embodiment of the subcutaneous device.

Figure 34C:
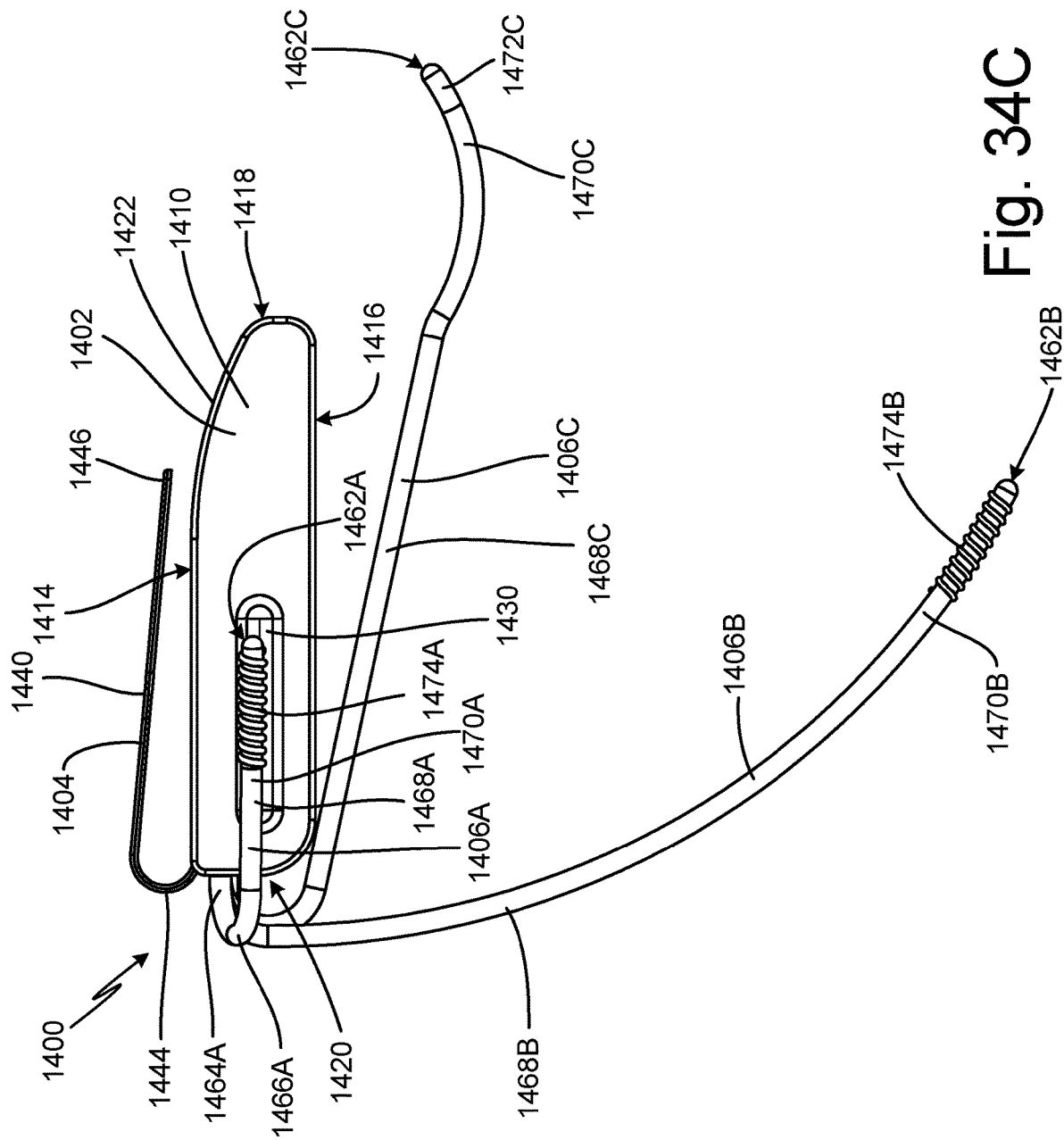

FIG. 34C is a side view of the twelfth embodiment of the subcutaneous device.

Subcutaneous Device 1500

Figure 35A:
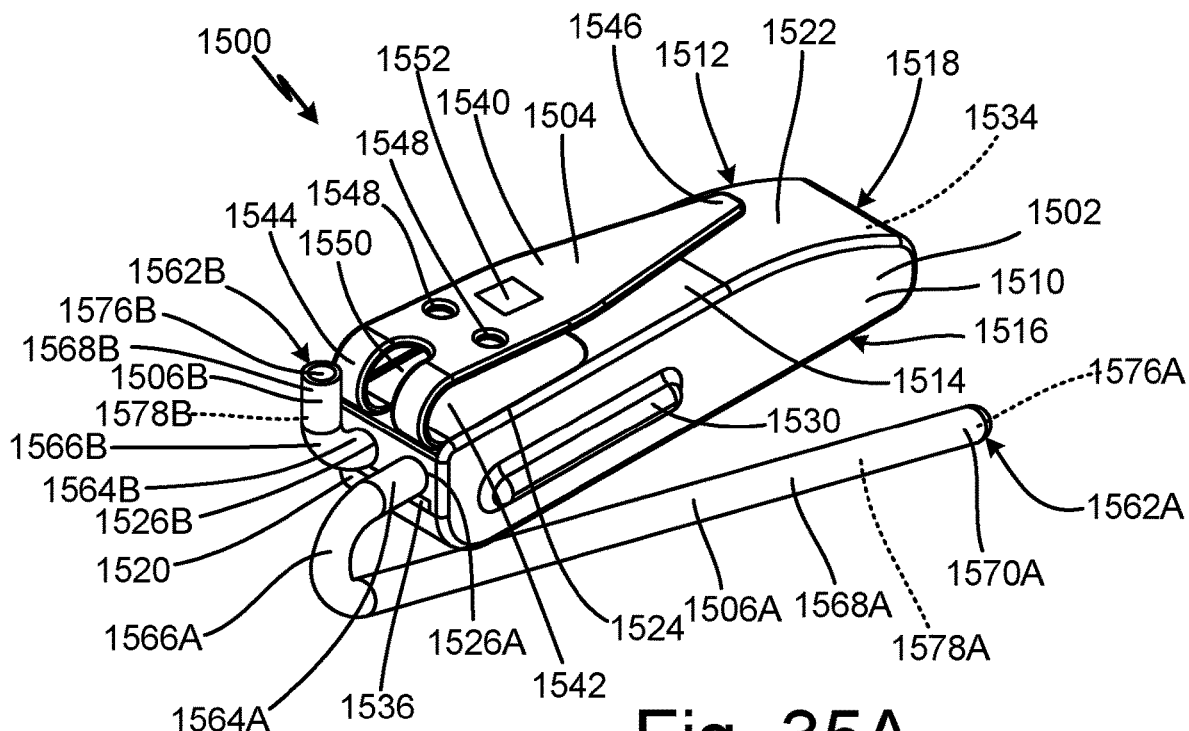

FIG. 35A is a perspective view of a thirteenth embodiment of a subcutaneous device.

Figure 35B:
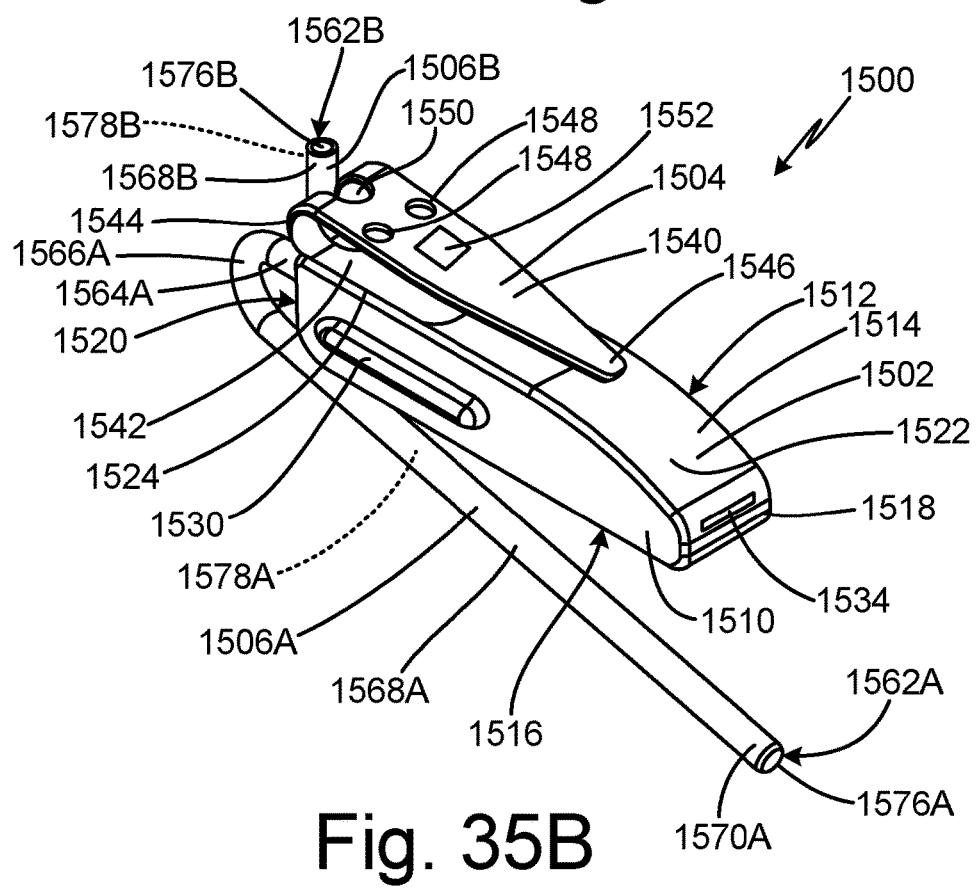

FIG. 35B is a perspective view of the thirteenth embodiment of the subcutaneous device.

Figure 35C:
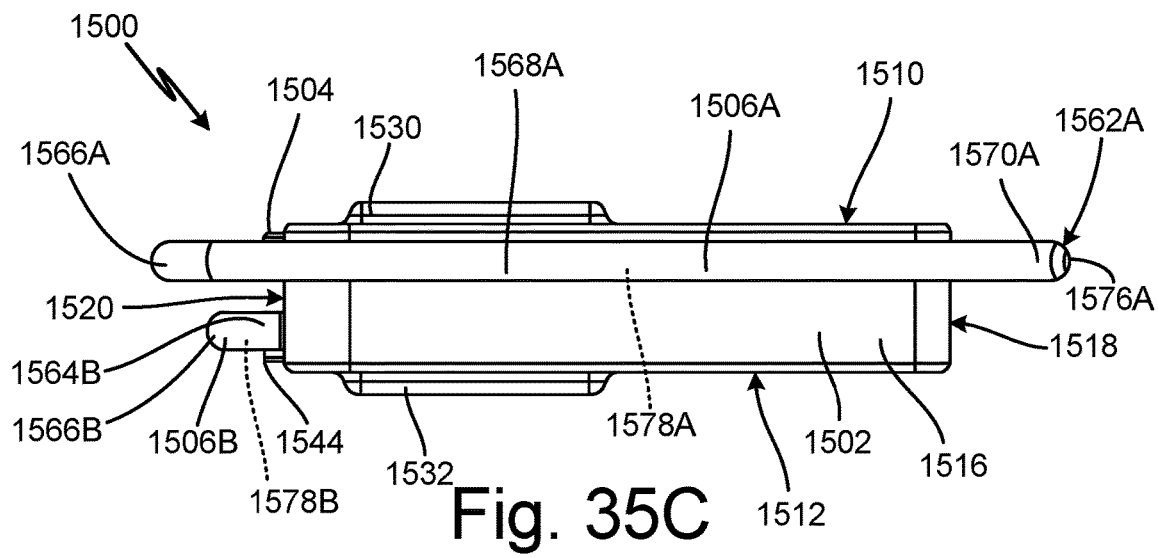

FIG. 35C is a bottom view of the thirteenth embodiment of the subcutaneous device.

Figure 35D:
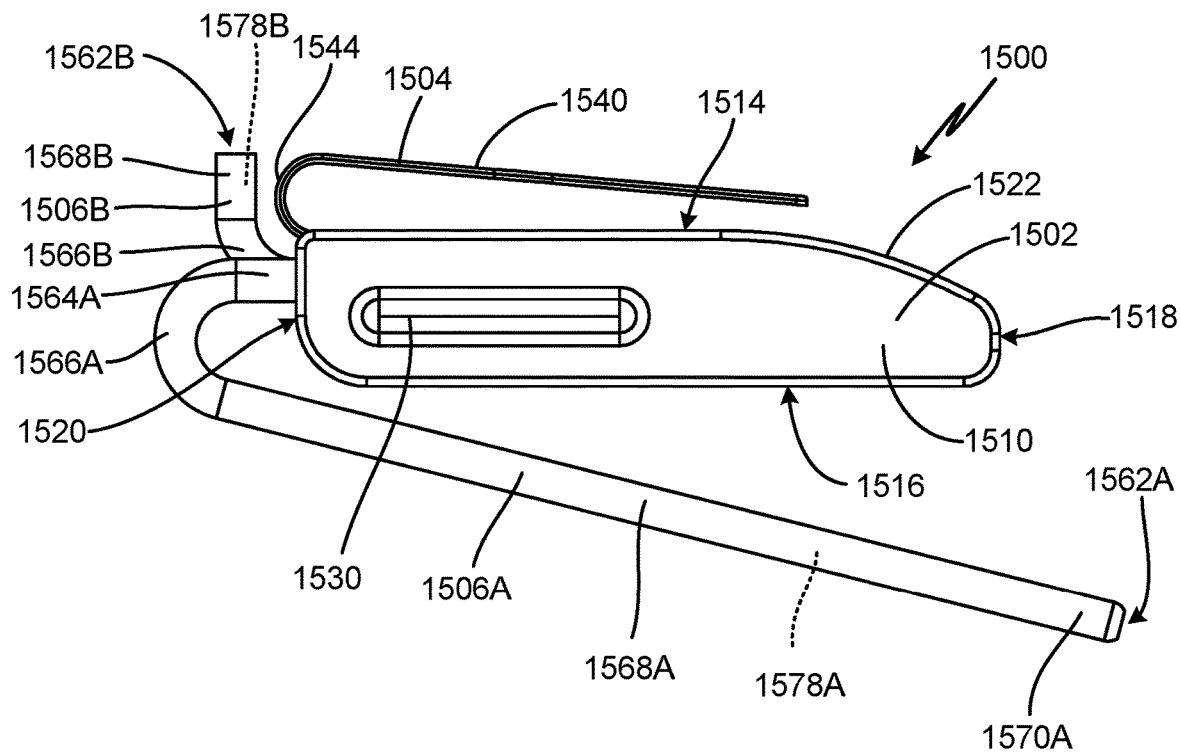

FIG. 35D is a side view of the thirteenth embodiment of the subcutaneous device.

FIG. 35E is a back view of the thirteenth embodiment of the subcutaneous device.

FIG. 35F is a front view of the thirteenth embodiment of the subcutaneous device.

Figure 36A:
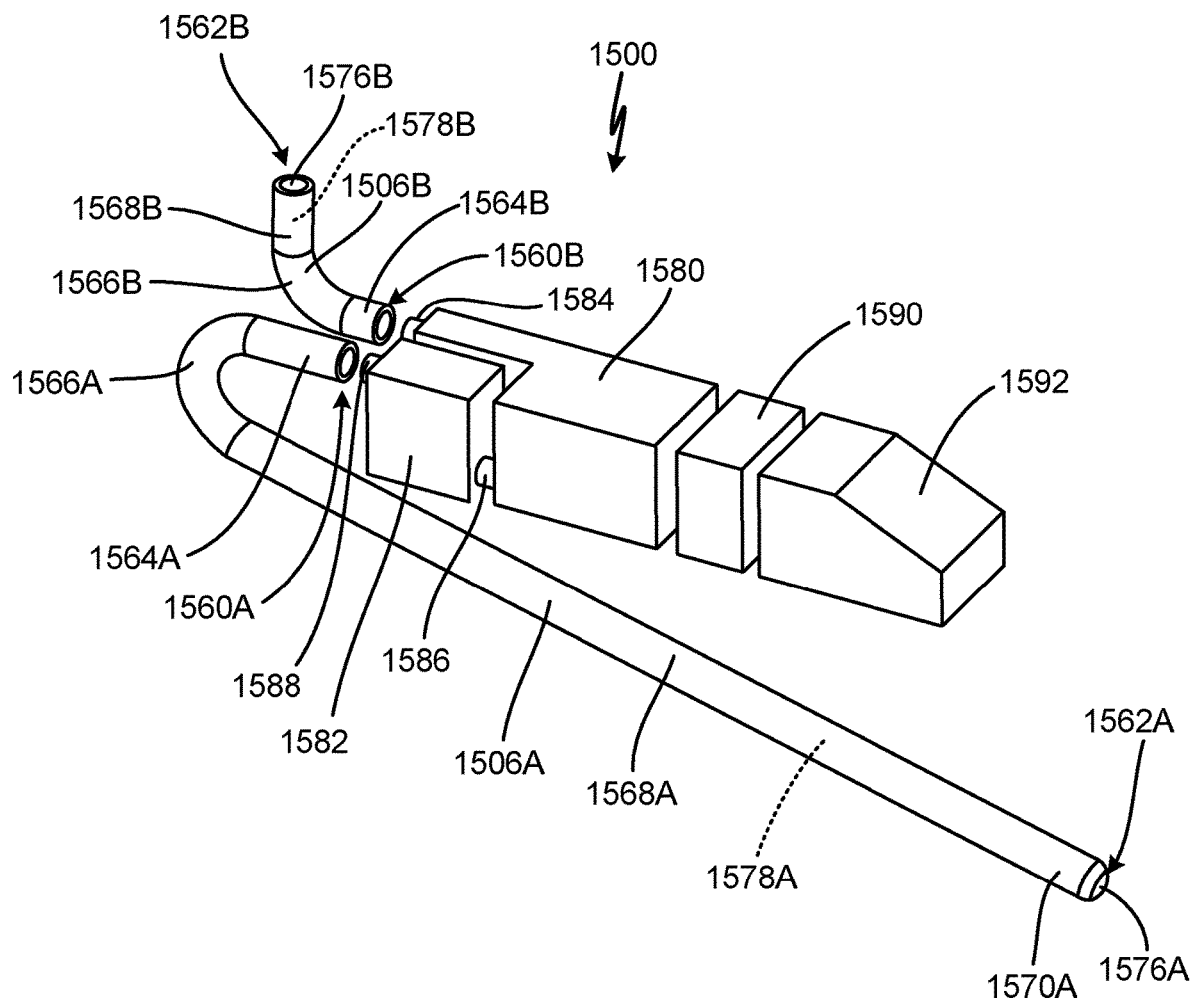

FIG. 36A is a schematic diagram of the thirteenth embodiment of the subcutaneous device.

Figure 36B:
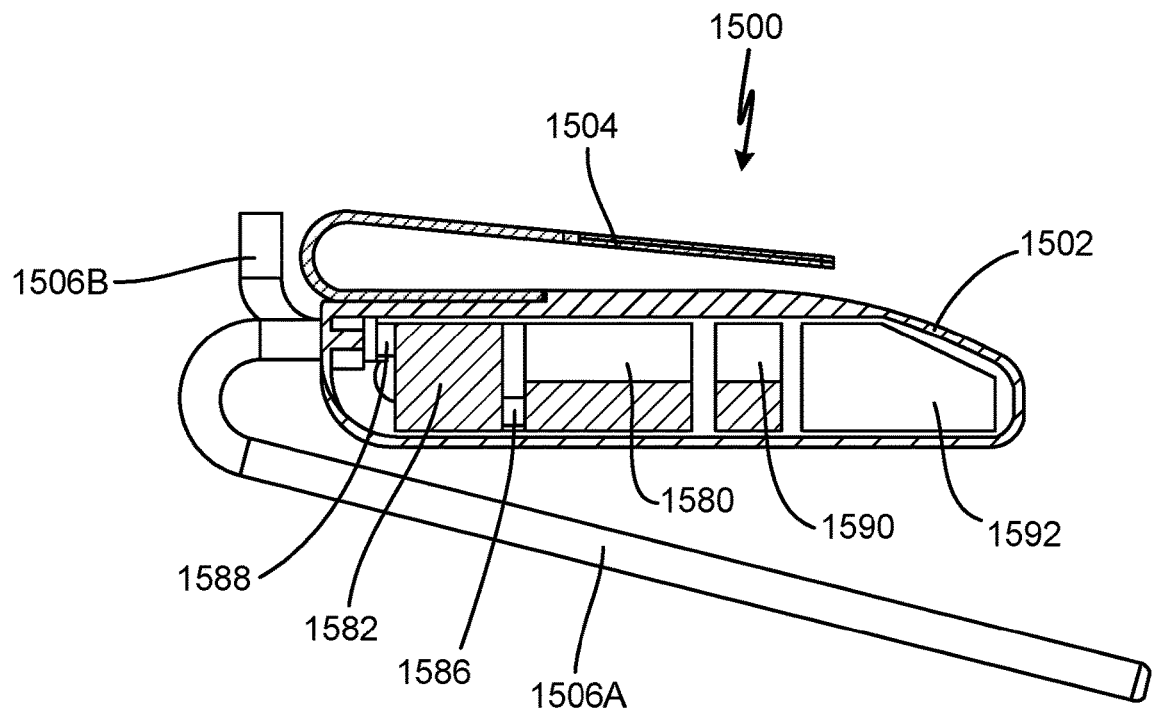

FIG. 36B is a sectional diagram illustrating portions of the thirteenth embodiment of the subcutaneous device from the side.

Figure 36C:
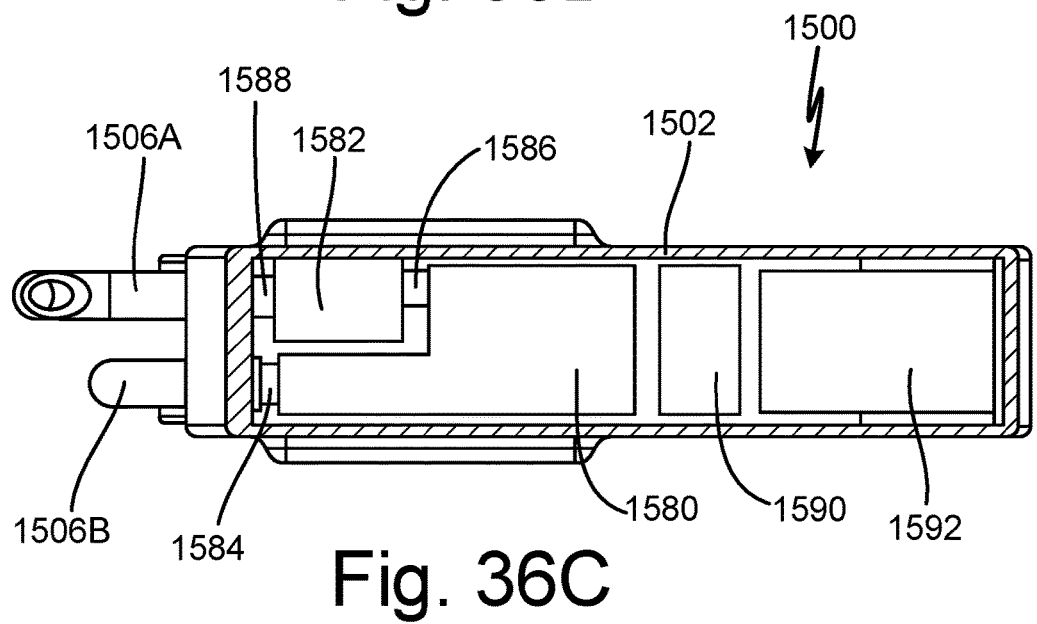

FIG. 36C is a sectional diagram illustrating portions of the thirteenth embodiment of the subcutaneous device from the bottom.

Figure 37:
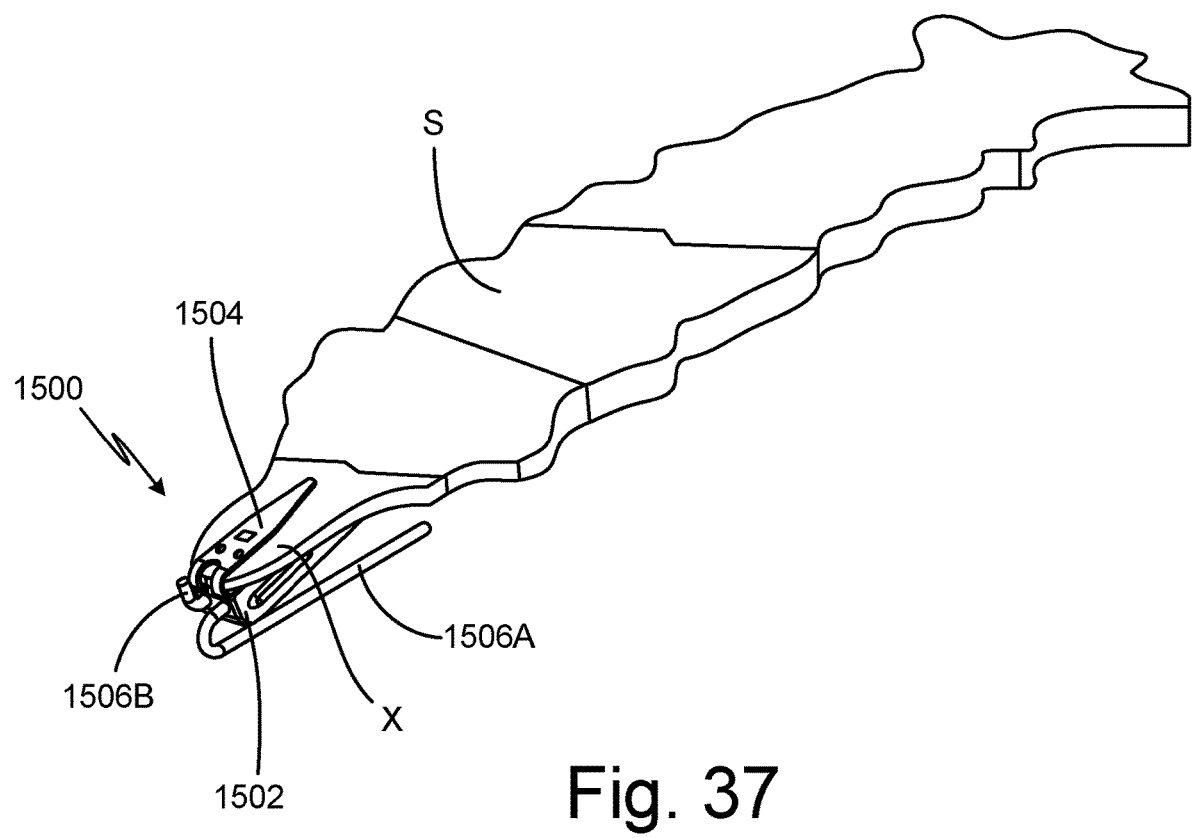

FIG. 37 is a perspective view of the thirteenth embodiment of the subcutaneous device positioned on a xiphoid process and a sternum.

Subcutaneous Device 1600

Figure 38:
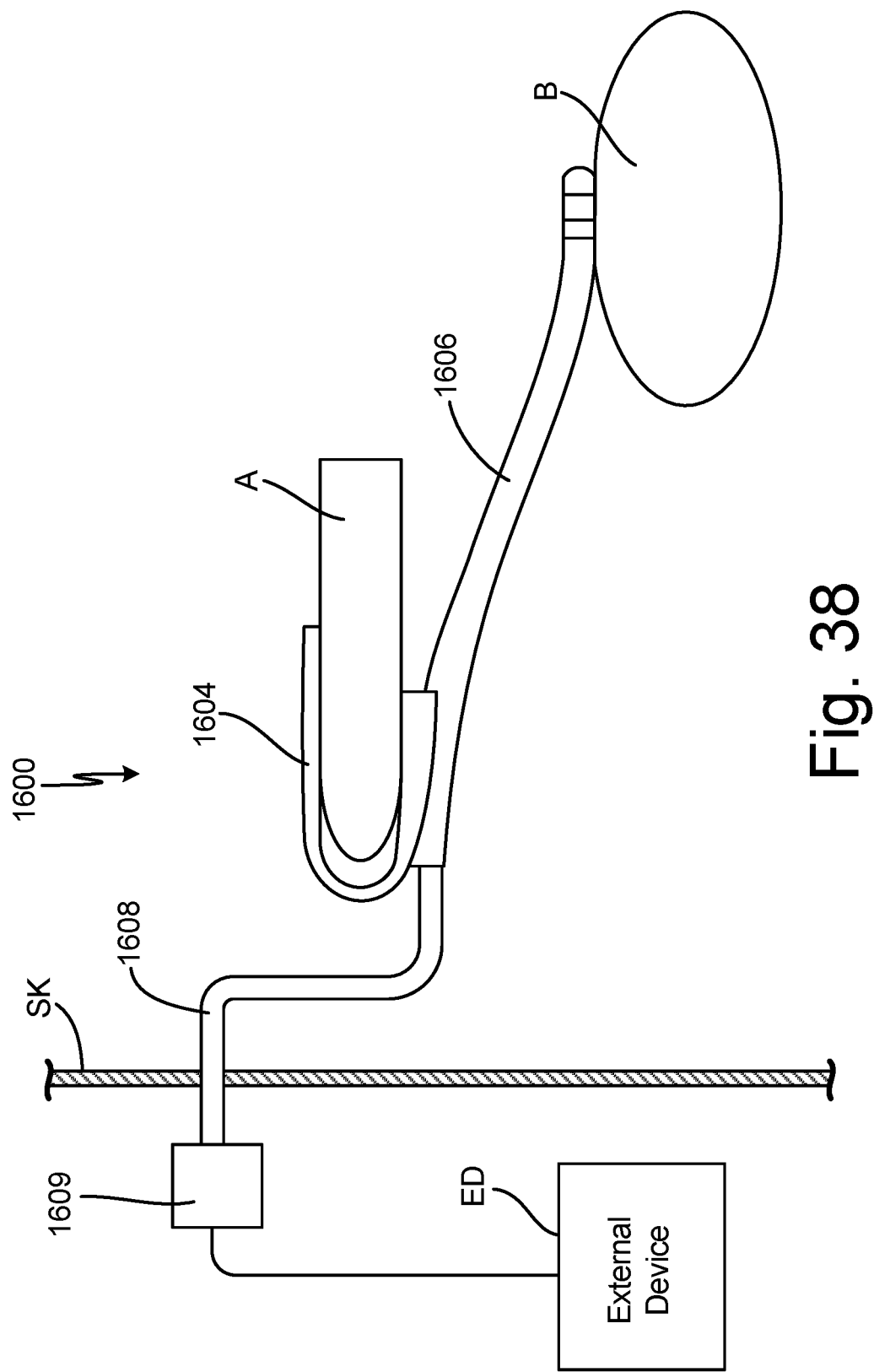

FIG. 38 is a side view of a fourteenth embodiment of a subcutaneous device anchored to a structural body component.

Figure 39A:
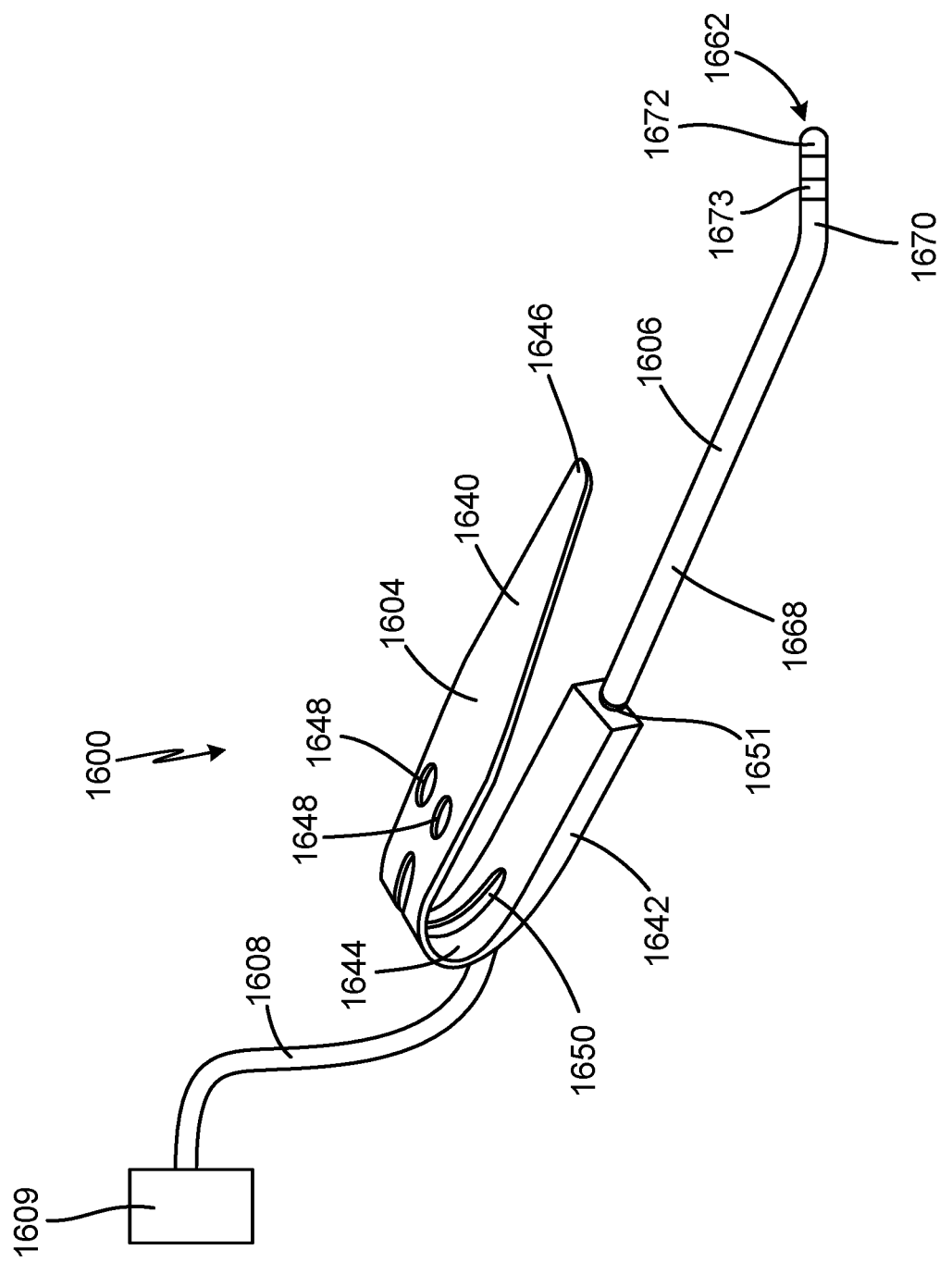

FIG. 39A is a perspective view of the fourteenth embodiment of the subcutaneous device.

Figure 39B:
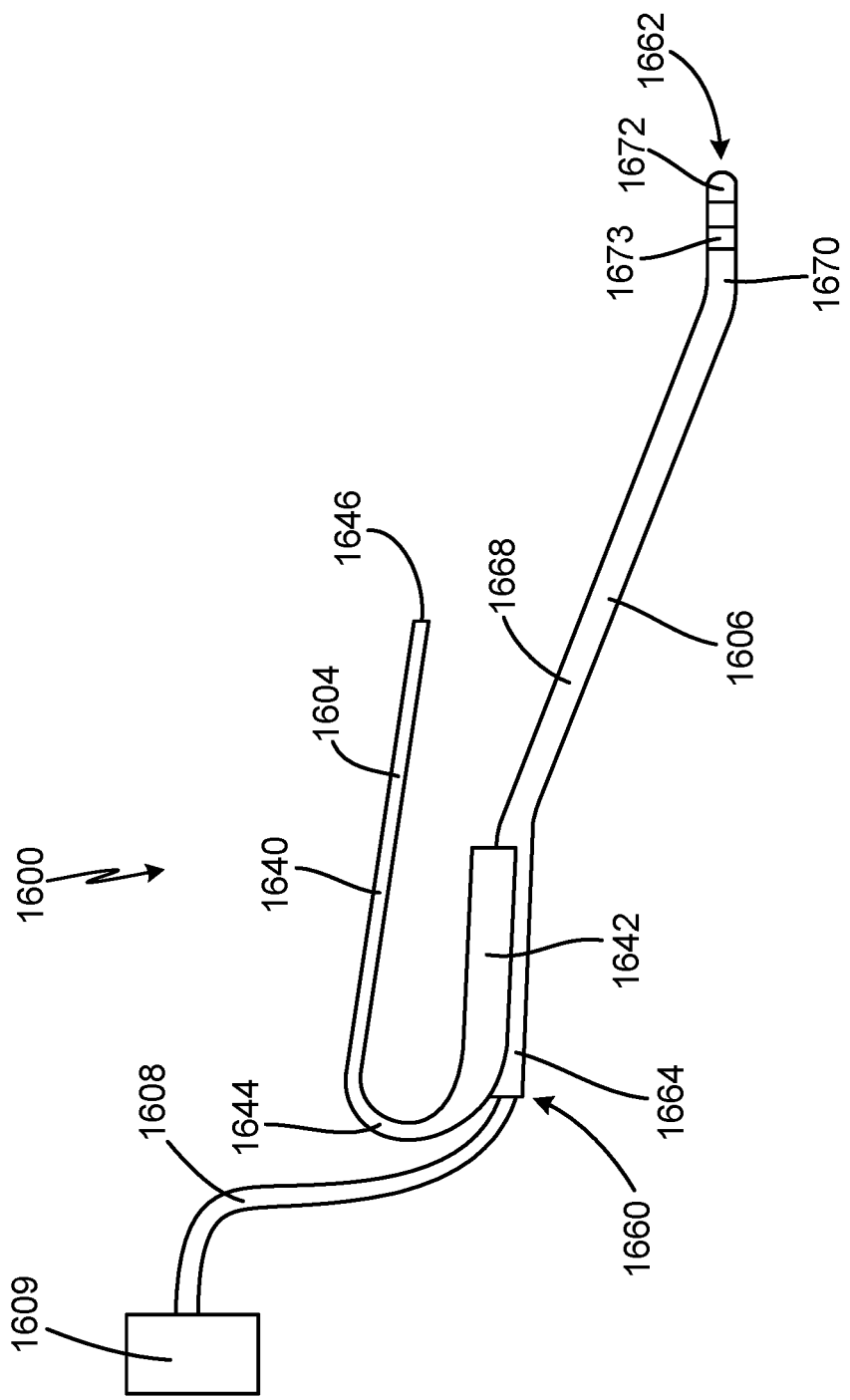

FIG. 39B is a side view of the fourteenth embodiment of the subcutaneous device.

Figure 39C:
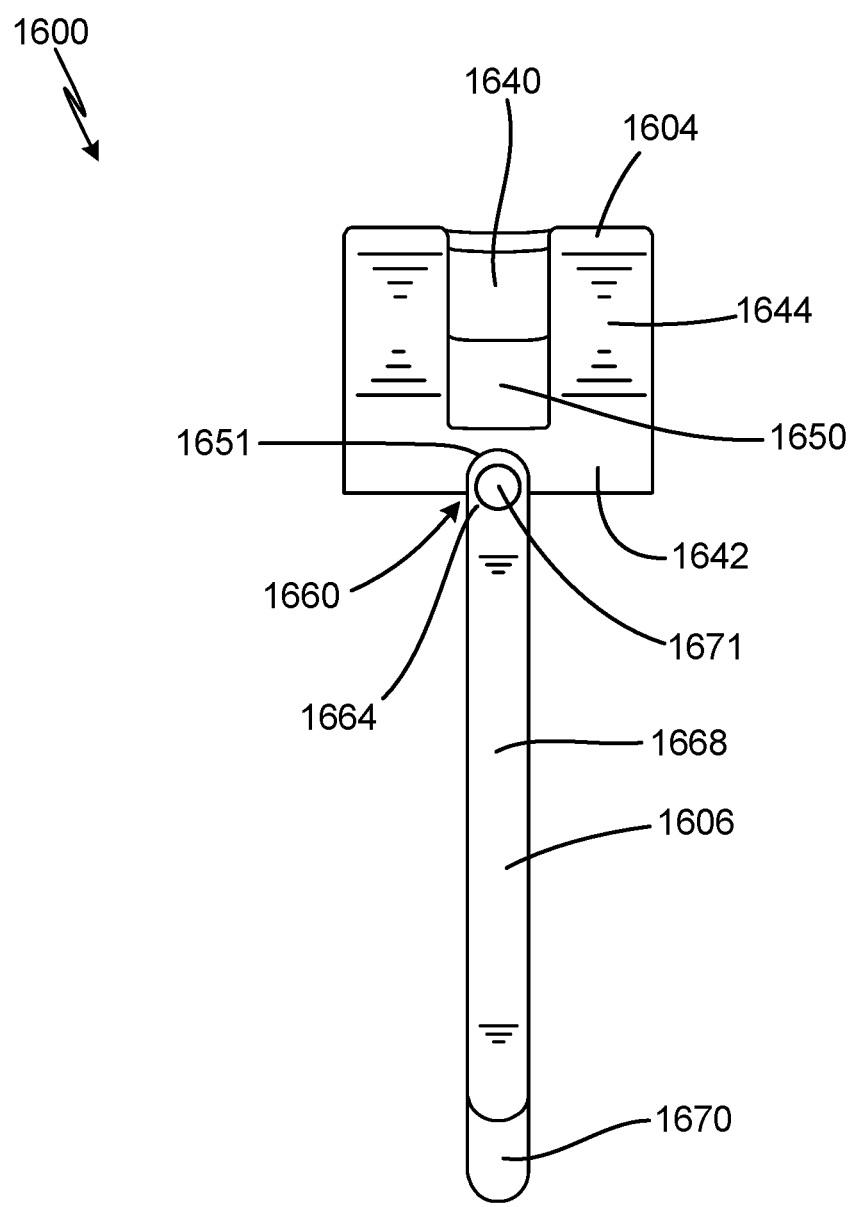

FIG. 39C is a back view of a clip and a prong of the fourteenth embodiment of the subcutaneous device.

Figure 40:
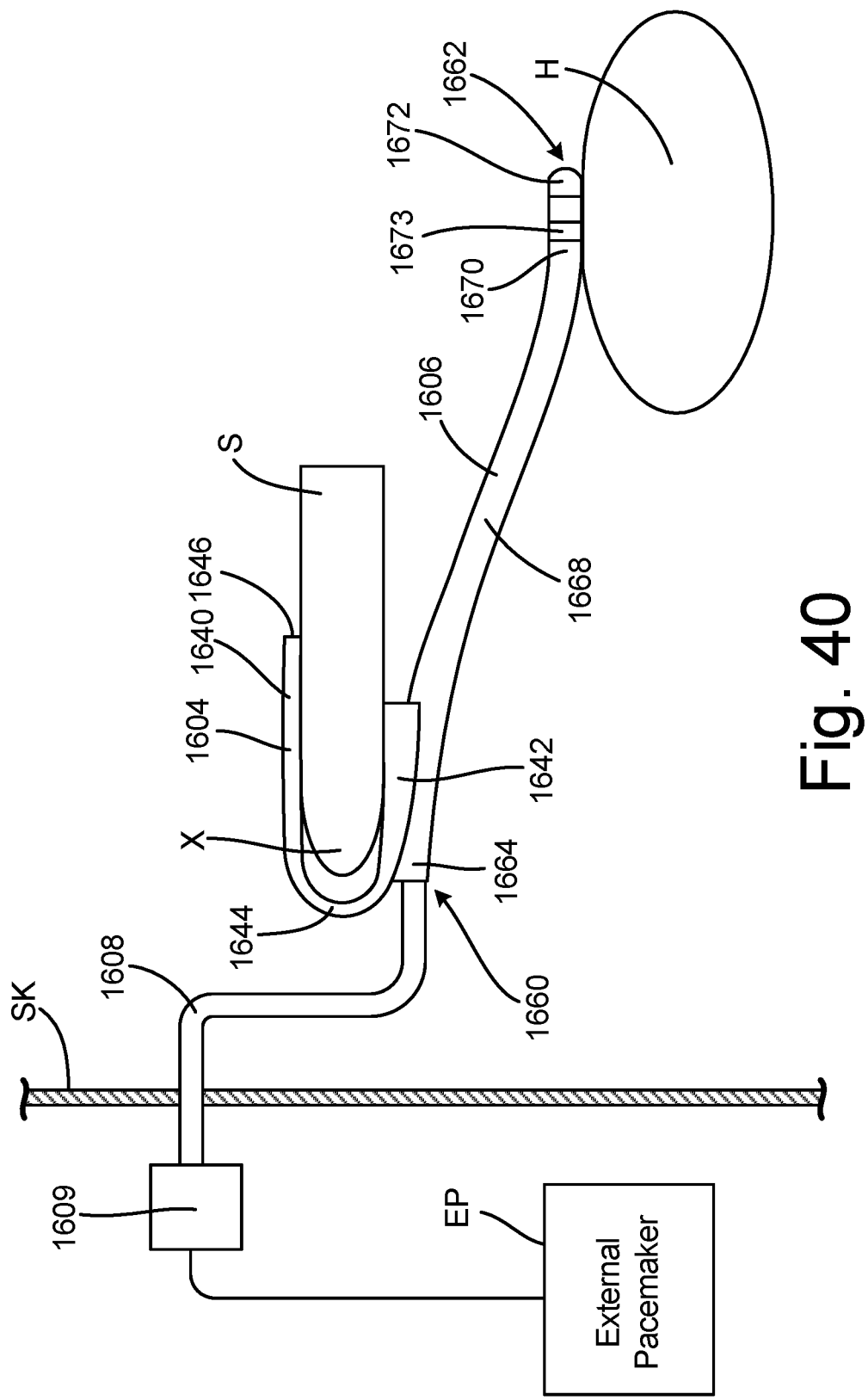

FIG. 40 is a side view of the fourteenth embodiment of the subcutaneous device anchored to a xiphoid process and/or a sternum.

Subcutaneous Device 1700

Figure 41:
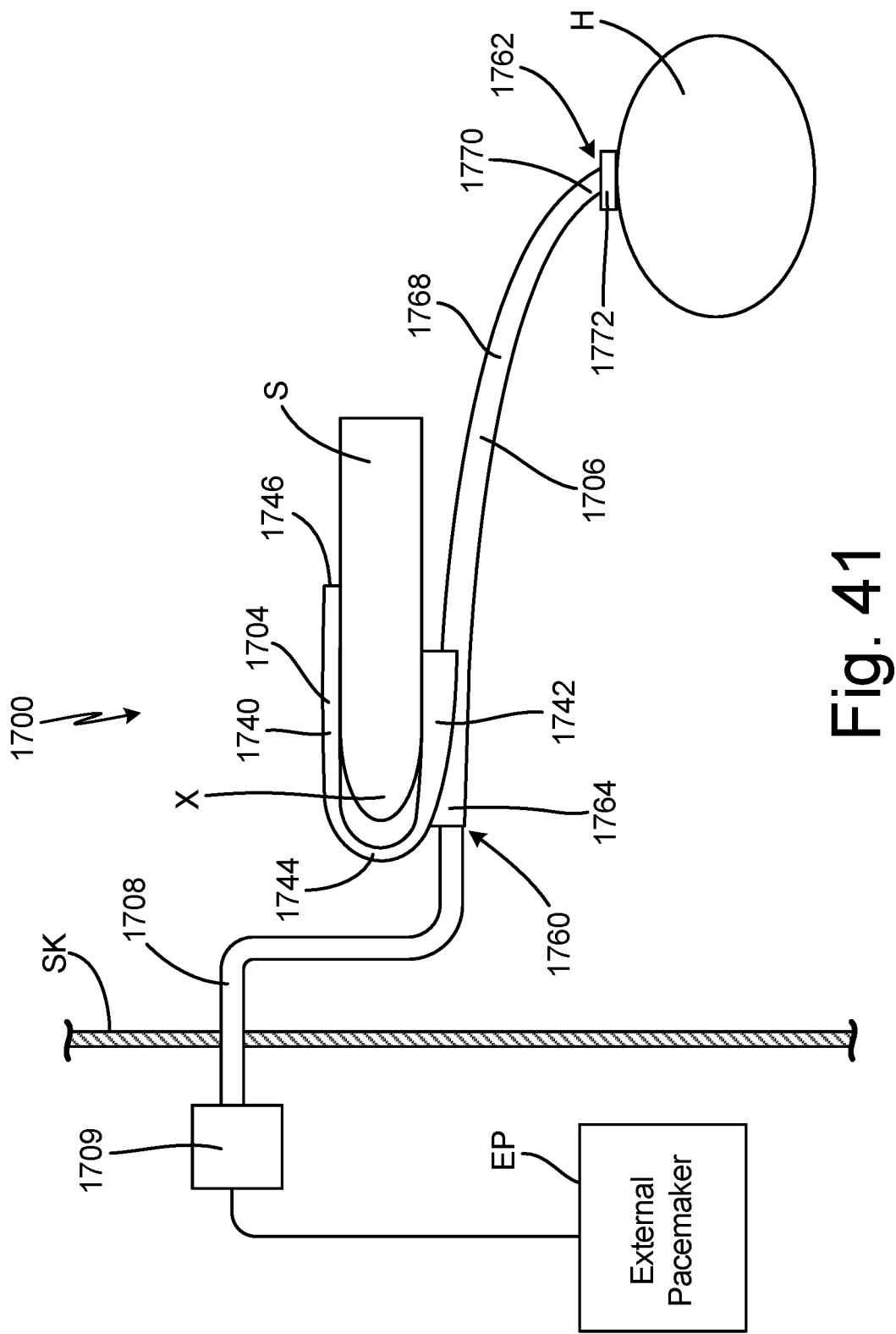

FIG. 41 is a side view of a fifteenth embodiment of a subcutaneous device anchored to a structural body component.

Subcutaneous Device 1800

Figure 42A:
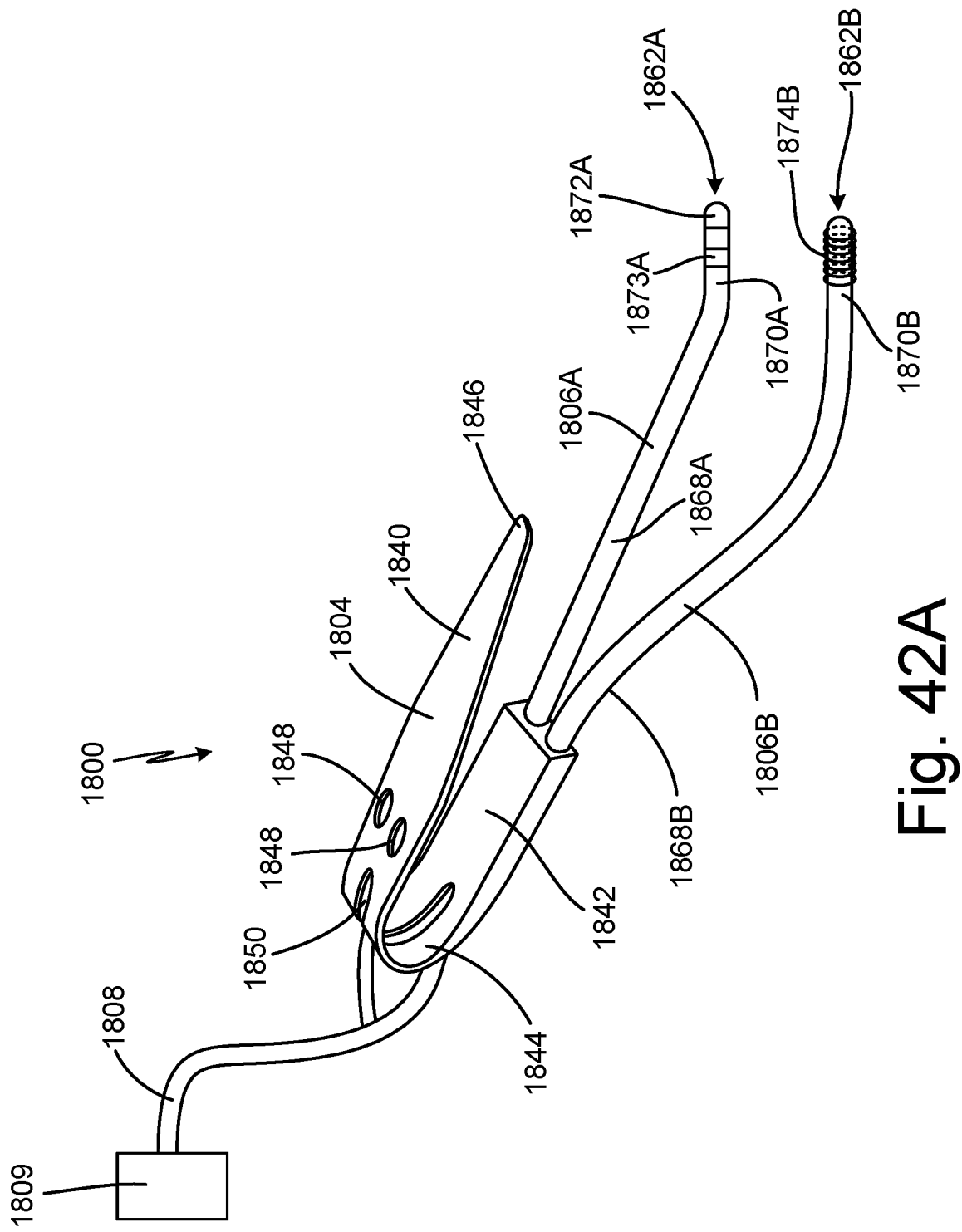

FIG. 42A is a perspective view of a sixteenth embodiment of a subcutaneous device.

Figure 42B:
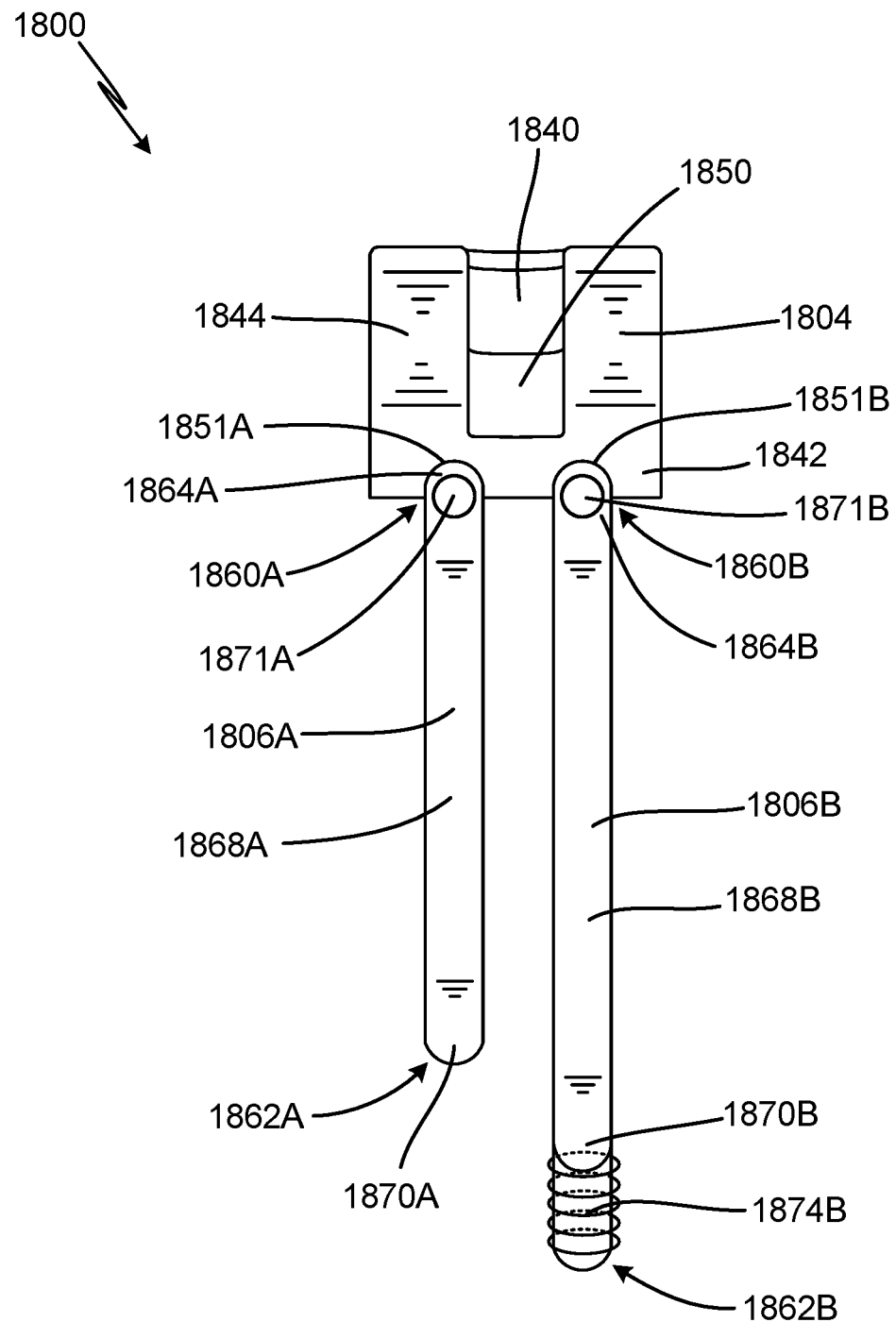

FIG. 42B is a back view of clip, a first prong, and a second prong of the sixteenth embodiment of the subcutaneous device.

Figure 43:
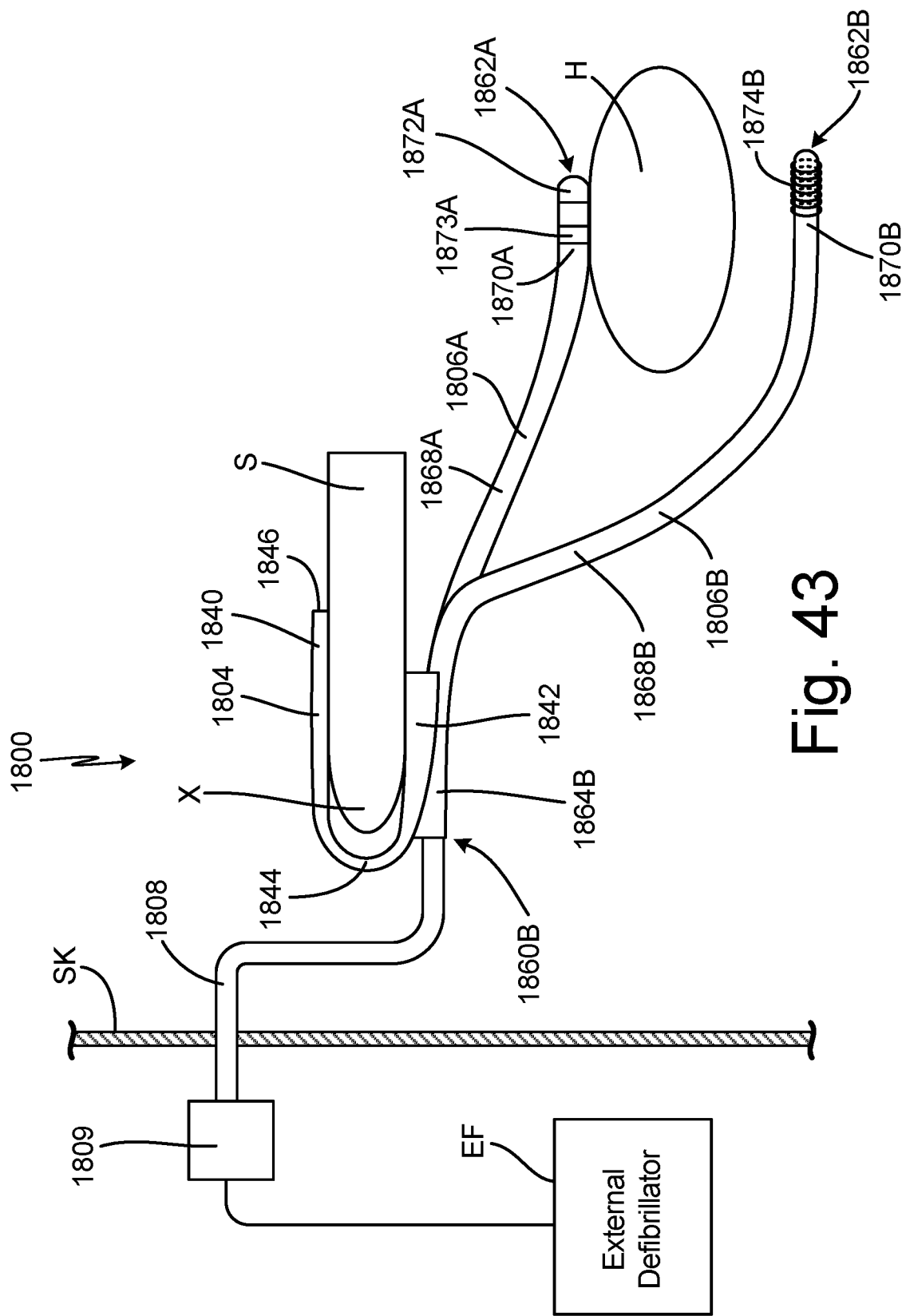

FIG. 43 is a side view of the sixteenth embodiment of the subcutaneous device anchored to a xiphoid process and/or a sternum.

DETAILED DESCRIPTION

In general, the present disclosure relates to a subcutaneous device that can be injected into a patient for monitoring, diagnostic, and therapeutic purposes. The subcutaneous device includes a housing that contains the electrical circuitry of the subcutaneous device, a clip on a top side of the housing, and one or more prongs extending away from the housing. The clip is configured to attach and anchor the subcutaneous device onto a muscle, a bone, or tissue. The prong extends away from the housing and a distal end of the prong comes into contact with an organ, a nerve, or tissue remote from the subcutaneous device.

The subcutaneous device can be a monitoring device, a diagnostic device, a pacemaker, an implantable cardioverter-defibrillator, a general organ/nerve/tissue stimulator, and/or a drug delivery device. A monitoring device can monitor physiological parameters of a patient. A diagnostic device can measure physiological parameters of a patient for diagnostic purposes. A pacemaker and an implantable cardioverter-defibrillator can sense a patient's heart rate and provide a therapeutic electrical stimulation to the patient's heart if an abnormality is detected. A pacemaker will provide an electrical stimulation to the heart in response to an arrhythmia, such as bradycardia, tachycardia, atrial flutter, and atrial fibrillation. The electrical stimulation provided by a pacemaker will contract the heart muscles to regulate the heart rate of the patient. An implantable cardioverter-defibrillator will provide an electrical stimulation to the heart in response to ventricular fibrillation and ventricular tachycardia, both of which can lead to sudden cardiac death. An implantable cardioverter-defibrillator will provide cardioversion or defibrillation to the patient's heart. Cardioversion includes providing an electrical stimulation to the heart at a specific moment that is in synchrony with the cardiac cycle to restore the patient's heart rate. Cardioversion can be used to restore the patient's heart rate when ventricular tachycardia is detected. If ventricular fibrillation is detected, defibrillation is needed. Defibrillation includes providing a large electrical stimulation to the heart at an appropriate moment in the cardiac cycle to restore the patient's heart rate. An implantable cardioverter-defibrillator can also provide pacing to multiple chambers of a patient's heart. A general organ/nerve/tissue stimulator can provide electrical stimulation to an organ, nerve, or tissue of a patient for therapeutic purposes. A drug delivery device can provide targeted or systemic therapeutic drugs to an organ, nerve, or tissue of a patient.

The subcutaneous device described in this disclosure can, in some embodiments, be anchored to a patient's xiphoid process and/or a distal end of a patient's sternum. The xiphoid process is a process on the lower part of the sternum. At birth, the xiphoid process is a cartilaginous process. The xiphoid process ossifies over time, causing it to fuse to the sternum with a fibrous joint. The subcutaneous device can be anchored to the xiphoid process so that the housing of the subcutaneous device is positioned below the xiphoid process and sternum. In some patients, the xiphoid process is absent, small, narrow, or elongated. In such cases, the subcutaneous device can be attached directly to the distal end of the patient's sternum. When the subcutaneous device is anchored to the xiphoid process and/or sternum, the one or more prongs of the subcutaneous device extend into the anterior mediastinum.

Different embodiments of the subcutaneous device are described in detail below. The different embodiments of the subcutaneous device can include: a single prong cardiac monitoring device, a multi-prong cardiac monitoring device, a pulmonary monitoring device, a single chamber pacemaker, a dual chamber pacemaker, a triple chamber pacemaker, an atrial defibrillator, a single-vector ventricular defibrillator, a multi-vector ventricular defibrillator, and an implantable drug pump and/or drug delivery device. These embodiments are included as examples and are not intended to be limiting. The subcutaneous device can have any suitable design and can be used for any suitable purpose in other embodiments. The features of each embodiment may be combined and/or substituted with features of any other embodiment, unless explicitly disclosed otherwise. Further, many of the embodiments can be used for multiple purposes. For example, a defibrillator device can also be used for monitoring and pacing. A surgical instrument and a method for implanting the subcutaneous device into a body of a patient is also described.

Subcutaneous Device 100

Figure 1:
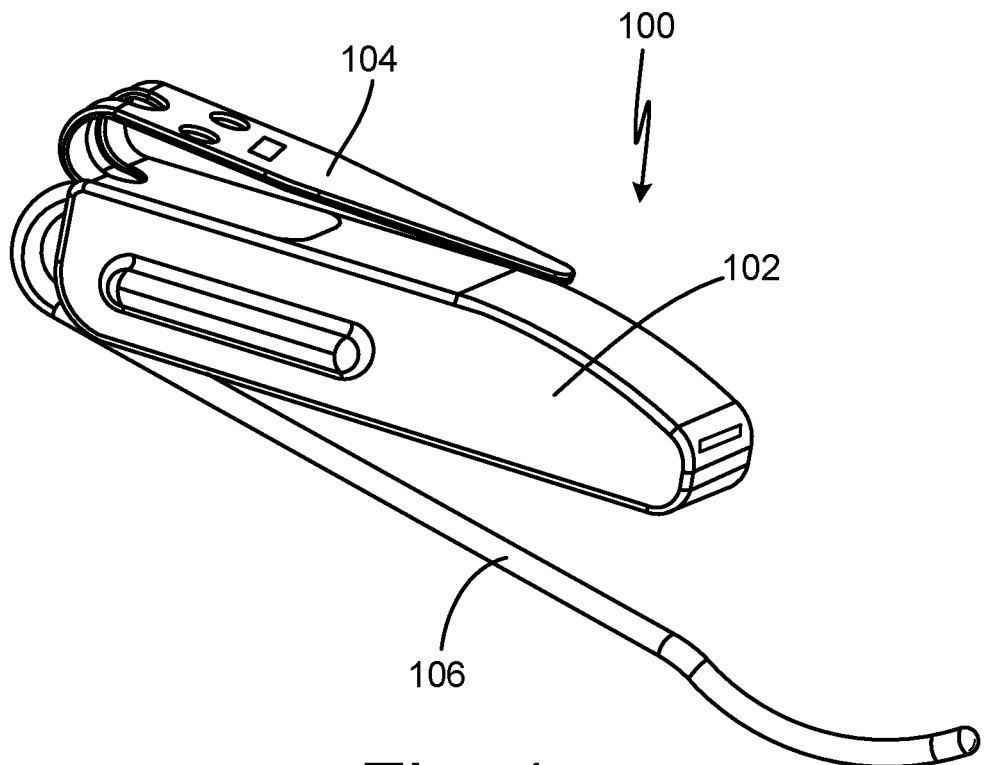
FIG. 1 is a perspective view of a first embodiment of a subcutaneous device.
Figure 2:
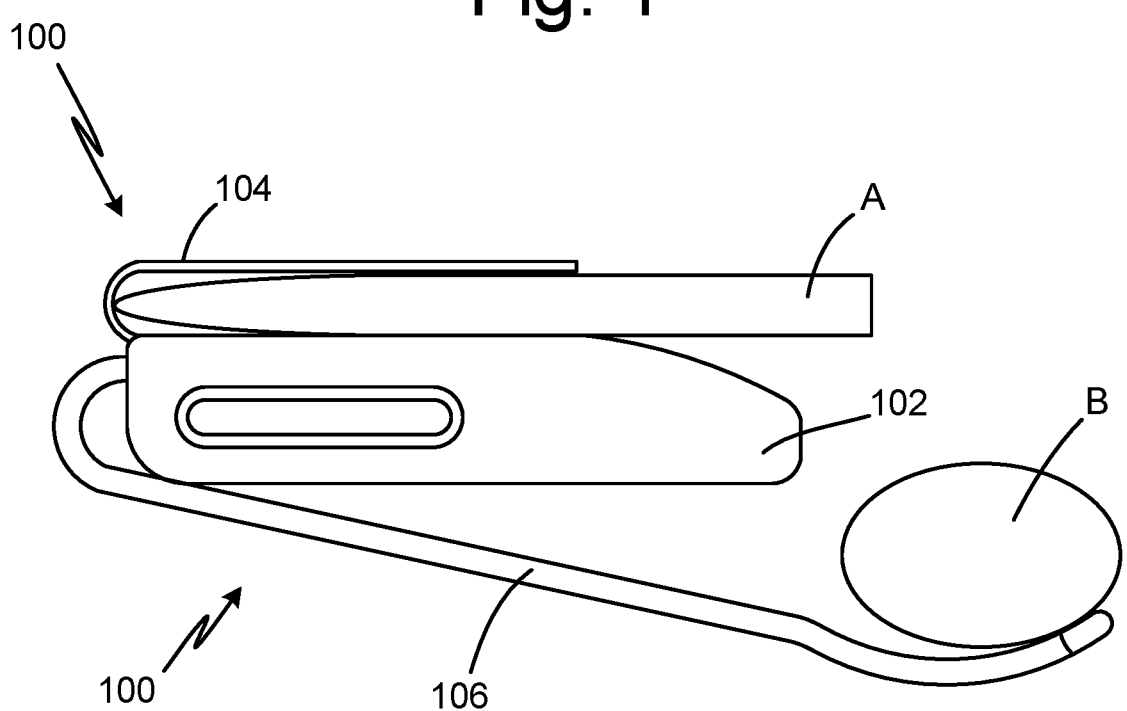
FIG. 2 is a side view of the first embodiment of the subcutaneous device anchored to a structural body component.

FIG. 1 is a perspective view of subcutaneous device 100. FIG. 2 is a side view of subcutaneous device 100 anchored to structural body component A. Subcutaneous device 100 includes housing 102, clip 104, and prong 106. FIG. 2 shows structural body component A and remote body component B.

Subcutaneous device 100 is a medical device that is anchored to structural body component A. Structural body component A may be a muscle, a bone, or a tissue of a patient. Subcutaneous device 100 can be a monitoring device, a diagnostic device, a therapeutic device, or any combination thereof. For example, subcutaneous device 100 can be a pacemaker device that is capable of monitoring a patient's heart rate, diagnosing an arrhythmia of the patient's heart, and providing therapeutic electrical stimulation to the patient's heart. Subcutaneous device 100 includes housing 102. Housing 102 can contain a power source, a controller, a memory, a transceiver, sensors, sensing circuitry, therapeutic circuitry, and/or any other component of the medical device. Housing 102 can also include one or more electrodes that are capable of sensing an electrical activity or physiological parameter of tissue surrounding housing 102 and/or provide therapeutic electrical stimulation to the tissue surrounding housing 102.

Clip 104 is attached to housing 102. Clip 104 is configured to anchor subcutaneous device 100 to structural body component A. Clip 104 will expand as it is advanced around structural body component A. Clip 104 can be a passive clip or an active clip. A passive clip only uses the stiffness of clamping components to attach to the bone, the muscle, or the tissue. This stiffness can be the result of design or active crimping during the implant procedure. An active clip may additionally use an active fixation method such as sutures, tines, pins, or screws to secure the clip to the bone, the muscle, or the tissue. In the embodiment shown in FIGS. 1-2, clip 104 has a spring bias that will put tension on structural body component A when it is expanded and fit onto structural body component A. The spring bias of clip 104 will anchor subcutaneous device 100 to structural body component A. Clip 104 can include one or more electrodes that are capable of sensing an electrical activity or physiological parameter of tissue surrounding clip 104 and/or provide therapeutic electrical stimulation to the tissue surrounding clip 104.

Prong 106 is connected to and extends away from housing 102 of subcutaneous device 100. Prong 106 is configured to contact remote body component B that is positioned away from structural body component A. Remote body component B may be an organ, a nerve, or tissue of the patient. For example, remote body component B can include a heart, a lung, or any other suitable organ in the body. Prong 106 includes one or more electrodes that are capable of sensing an electrical activity or physiological parameter of remote body component B and/or providing therapeutic electrical stimulation to remote body component B.

In one example, subcutaneous device 100 can be a pacemaker and the one or more electrodes on prong 106 of subcutaneous device 100 can sense the electrical activity of a heart. The sensed electrical activity can be transmitted to sensing circuitry and a controller in housing 102 of subcutaneous device 100. The controller can determine the heart rate of the patient and can detect whether an arrhythmia is present. If an arrhythmia is detected, the controller can send instructions to therapeutic circuitry to provide a therapeutic electrical stimulation to the heart. In this manner, subcutaneous device 100 functions as a monitoring device, a diagnostic device, and a therapeutic device.

Subcutaneous device 100 will be discussed in greater detail in relation to FIGS. 3A-9 below. Subcutaneous device 100 will be discussed as a pacemaker that can be used for monitoring, diagnostics, and therapeutics in the discussion of FIGS. 3A-9 below. Subcutaneous device 100 can also be used only for monitoring, diagnostics, or a combination of the two in alternate embodiments. Further, subcutaneous device 100 can be a unipolar pacemaker or a bipolar pacemaker.

Figure 3A:
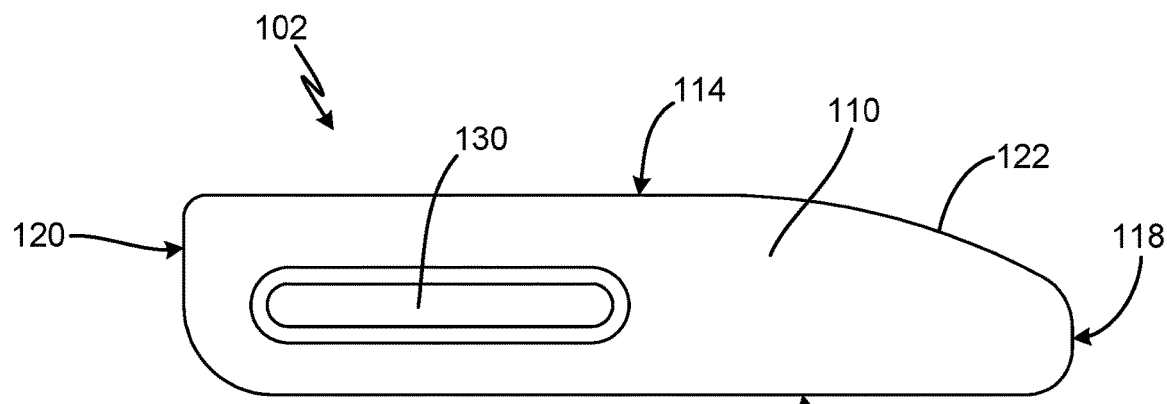
FIG. 3A is a side view of a housing of the first embodiment of the subcutaneous device.
Figure 3B:
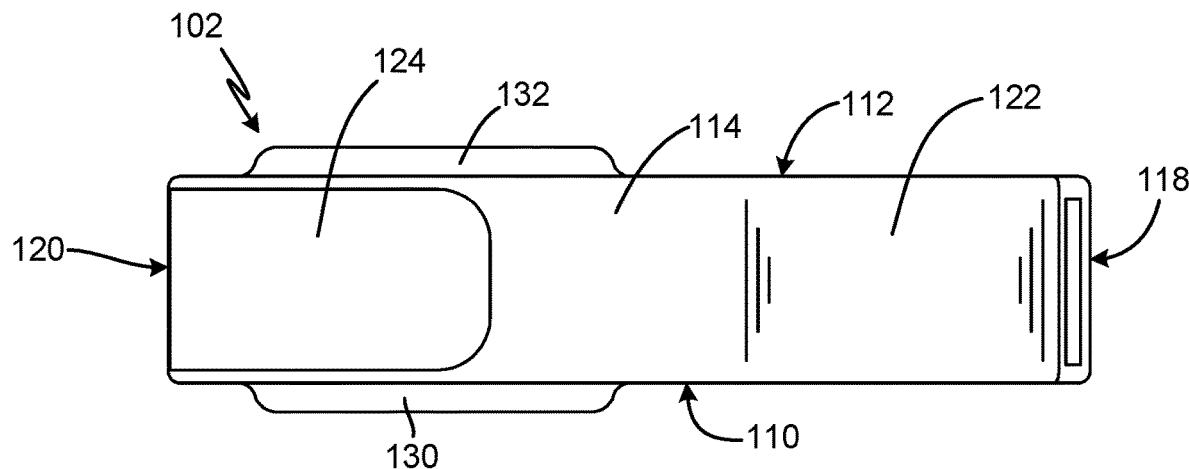
FIG. 3B is a top view of the housing of the first embodiment of the subcutaneous device.
Figure 3C:
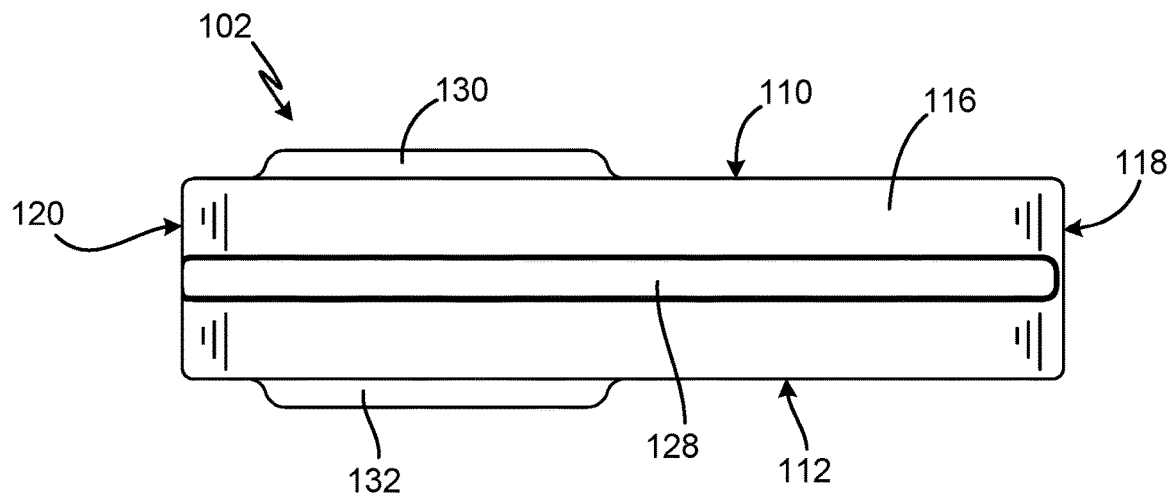
FIG. 3C is a bottom view of the housing of the first embodiment of the subcutaneous device.
Figure 3D:
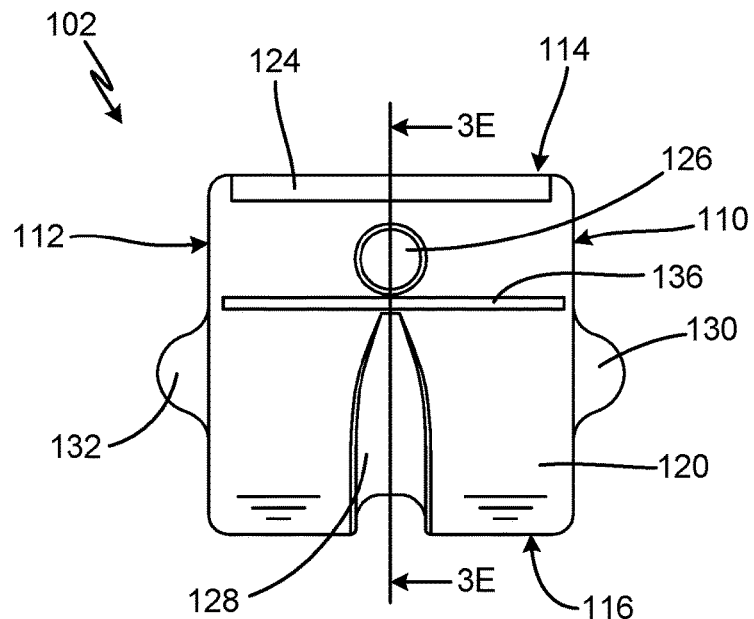
FIG. 3D is a back end view of the housing of the first embodiment of the subcutaneous device.
Figure 3E:
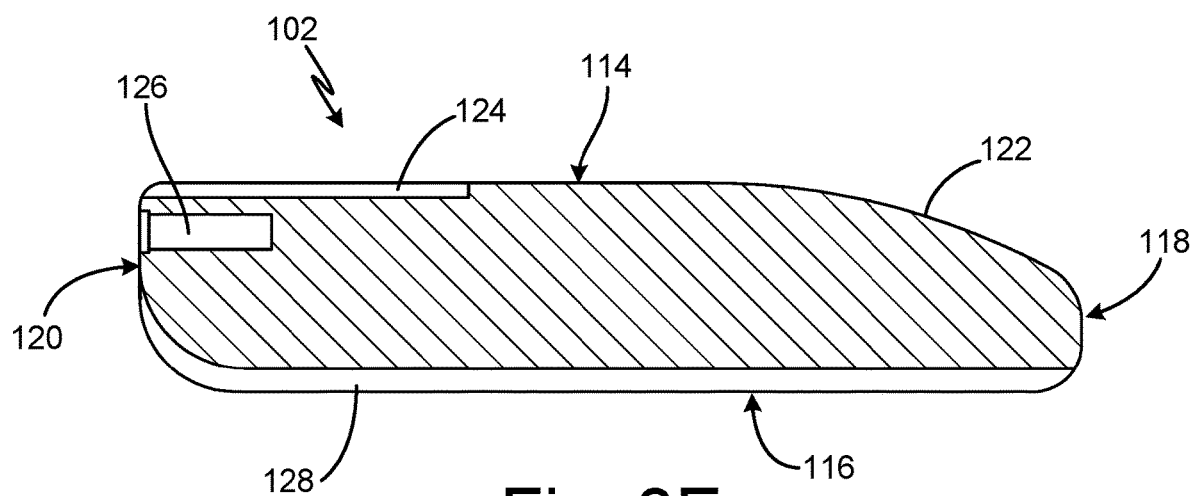
FIG. 3E is a cross-sectional view of the housing of the first embodiment of the subcutaneous device, taken along line 3E-3E of FIG. 3D.

FIG. 3A is a side view of housing 102 of subcutaneous device 100. FIG. 3B is a top view of housing 102 of subcutaneous device 100. FIG. 3C is a bottom view of housing 102 of subcutaneous device 100. FIG. 3D is a back end view of housing 102 of subcutaneous device 100. FIG. 3E is a cross-sectional view of housing 102 of subcutaneous device 100. Housing 102 includes first side 110, second side 112, top side 114, bottom side 116, front end 118, back end 120, curved surface 122, recess 124, port 126, channel 128, first guide 130, second guide 132, electrode 134, and electrode 136.

Housing 102 includes first side 110, second side 112, top side 114, bottom side 116, front end 118, and back end 120. First side 110 is opposite of second side 112; top side 114 is opposite of bottom side 116; and front end 118 is opposite of back end 120. Housing 102 is substantially rectangular-shaped in the embodiment shown. In alternate embodiments, housing 102 can be shaped as a cone, frustum, or cylinder. Housing 102 can be made out of stainless steel, titanium, nitinol, epoxy, silicone, polyurethane with metallic reinforcements, or any other material that is suitable for non-porous implants. Housing 102 can also include an exterior coating. Curved surface 122 is positioned on top side 114 of housing 102 adjacent front end 118 of housing 102. Curved surface 122 creates a tapered front end 118 of housing 102 of subcutaneous device 100. In an alternate embodiment, front end 118 of housing 102 can be wedge shaped. The tapered front end 118 of housing 102 helps front end 118 of housing 102 to push through tissue in a body of a patient to permit easier advancement of subcutaneous device 100 during the implantation or injection process.

Housing 102 includes recess 124 on top side 114. Recess 124 is a groove that extends into housing 102 on top side 114 of housing 102 adjacent back end 120 of housing 102. A portion of clip 104 of subcutaneous device 100 (shown in FIGS. 1-2) is positioned in recess 124 to attach clip 104 to housing 102. In an alternate embodiment, recess 124 may not be included on housing 102 and clip 104 can be welded to top side 114 of housing 102 or connected to a header. Housing 102 further includes port 126 on back end 120. Port 126 is a bore that extends into housing 102 on back end 120 of housing 102. A proximal end of prong 106 of subcutaneous device 100 (shown in FIGS. 1-2) is positioned in port 126 to attach prong 106 to housing 102. In an alternate embodiment, port 126 can be positioned in a header. Housing 102 also includes channel 128 on back end 120 and bottom side 116. Channel 128 is a groove that extends into housing 102 on back end 120 and bottom side 116 of housing 102. Channel 128 is configured to receive a portion of prong 106 of subcutaneous device 100 (shown in FIGS. 1-2) when subcutaneous device 100 is in a stowed position.

Housing 102 also includes first guide 130 on first side 110 and second guide 132 on second side 112. First guide 130 is a ridge that extends out from first side 110 of housing 102. Second guide 132 is a ridge that extends out from second side 112 of housing 102. First guide 130 and second guide 132 are configured to guide housing 102 of subcutaneous device 100 through a surgical instrument used to implant subcutaneous device 100 in a patient.

Housing 102 further includes electrode 134 on front end 118 of housing 102 and electrode 136 on back end 120 of housing 102. In the embodiment shown in FIGS. 3A-3E, there are two electrodes 134 and 136 positioned on housing 102. In alternate embodiments, any number of electrodes can be positioned on housing 102 or housing 102 can include no electrodes. Electrode 134 and electrode 136 are positioned to sense an electrical activity or physiological parameter of the tissue surrounding housing 102. Electrode 134 and electrode 136 can also provide therapeutic electrical stimulation to the tissue surrounding housing 102.

Figure 4A:
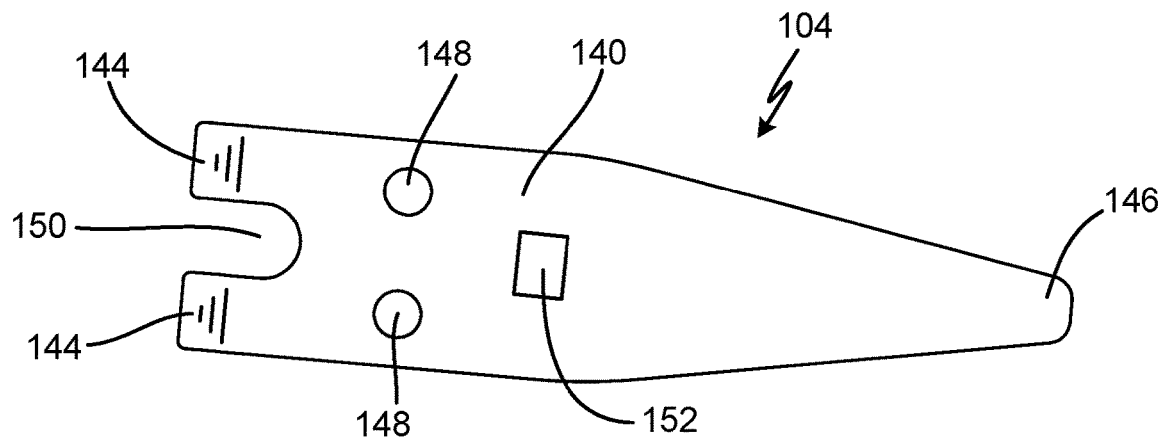
FIG. 4A is a top view of a clip of the first embodiment of the subcutaneous device.
Figure 4B:
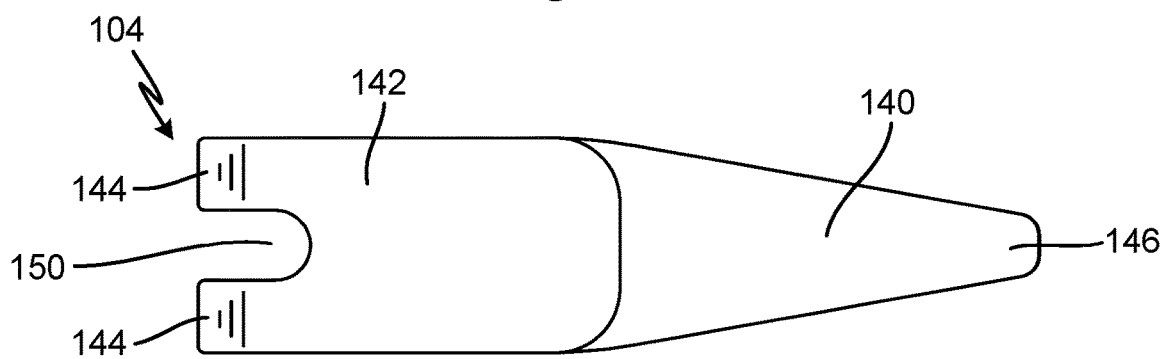
FIG. 4B is a bottom view of the clip of the first embodiment of the subcutaneous device.
Figure 4C:
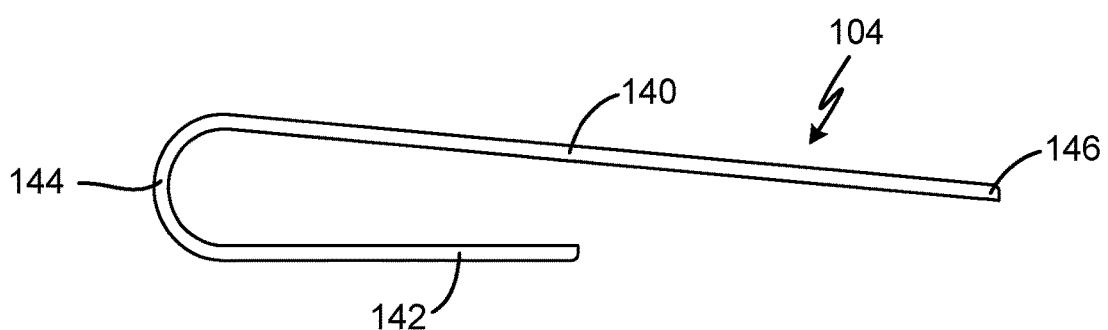
FIG. 4C is a side view of the clip of the first embodiment of the subcutaneous device.
Figure 4D:
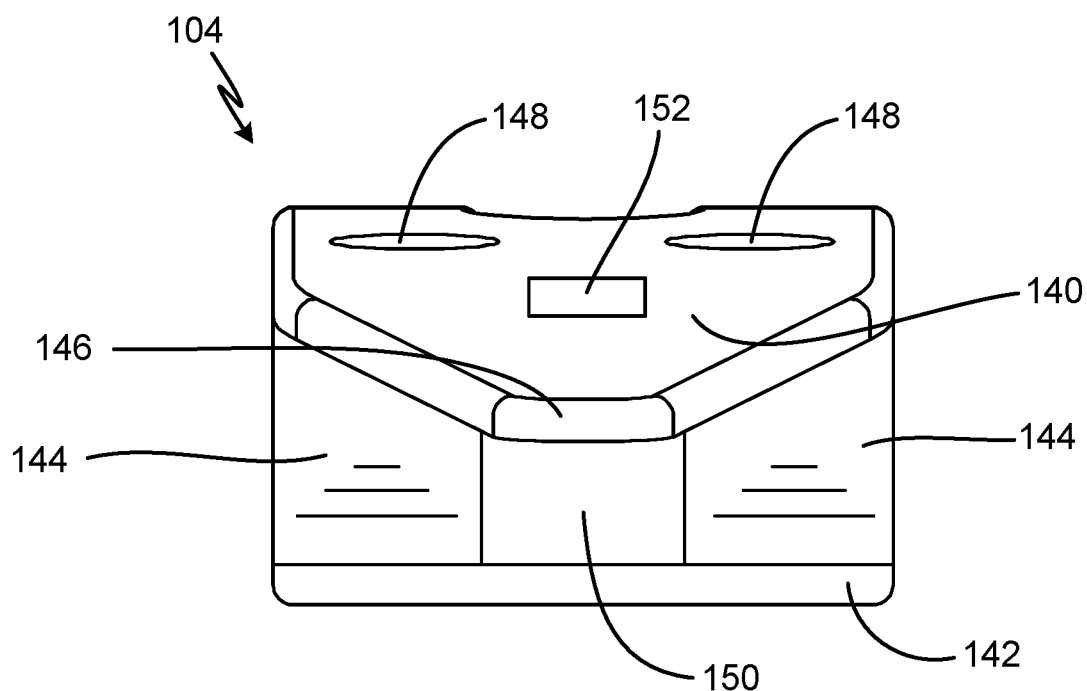
FIG. 4D is a front view of the clip of the first embodiment of the subcutaneous device.
Figure 4E:
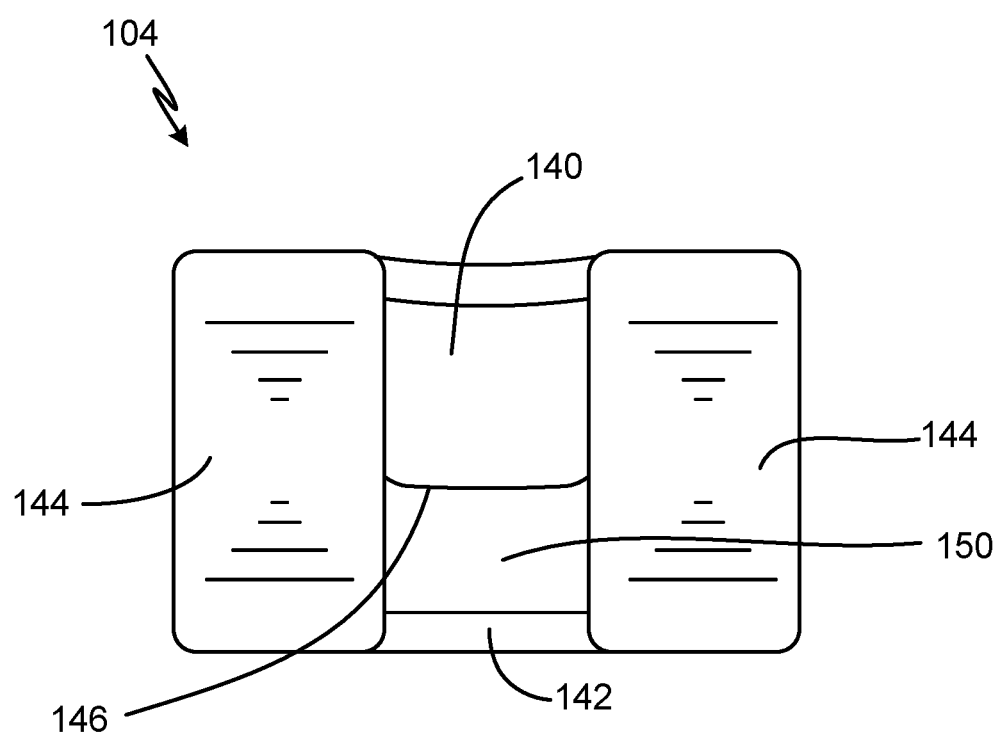
FIG. 4E is a back view of the clip of the first embodiment of the subcutaneous device.

FIG. 4A is a top view of clip 104 of subcutaneous device 100. FIG. 4B is a bottom view of clip 104 of subcutaneous device 100. FIG. 4C is a side view of clip 104 of subcutaneous device 100. FIG. 4D is a front view of clip 104 of subcutaneous device 100. FIG. 4E is a back view of clip 104 of subcutaneous device 100. Clip 104 includes top portion 140, bottom portion 142, spring portion 144, tip 146, openings 148, slot 150, and electrode 152.

Clip 104 includes top portion 140, bottom portion 142, and spring portion 144. Top portion 140 is a flat portion that forms a top of clip 104, and bottom portion 142 is a flat portion that forms a bottom of clip 104. Bottom portion 142 is configured to be attached to housing 102 of subcutaneous device 100 (shown in FIGS. 1-3E). Spring portion 144 is a curved portion positioned on a back end of clip 104 that extends between and connects top portion 140 to bottom portion 142. Clip 104 can be made out of stainless steel, titanium, nitinol, epoxy, silicone, polyurethane with metallic reinforcements, or any other material that is suitable for non-porous implants.

Top portion 140 of clip 104 includes tip 146 adjacent to a front end of clip 104. Top portion 140 tapers from a middle of top portion 140 to tip 146. The taper of tip 146 of top portion 140 of clip 104 helps clip 104 push through tissue when clip 104 is being anchored to a muscle, a bone, or a tissue of a patient. A surgeon does not have to cut a path through the tissue of the patient, as the taper of tip 146 of top portion 140 of clip 104 will create a path through the tissue.

Top portion 140 further includes openings 148. Openings 148 extend through top portion 140. There are two openings 148 in top portion 140 in the embodiment shown in FIGS. 3A-3E, but there could be any number of openings 148 in alternate embodiments. Openings 148 are configured to allow clip 104 to be sutured to a muscle, a bone, or a tissue in a patient to secure subcutaneous device 100 to the muscle, the bone, or the tissue. Further, openings 148 can receive additional fixation mechanisms, such as tines, pins, or screws, to secure subcutaneous device 100 to the muscle, the bone, or the tissue. These additional fixation mechanisms can be made from bioabsorbable materials. Clip 104 also includes slot 150. Slot 150 is an opening that extends through spring portion 144 of clip 104. Slot 150 is configured to receive a blade of a surgical instrument that is used to implant subcutaneous device 100 in a patient.

Spring portion 144 acts as a spring for clip 104 and is under tension. Top portion 140 acts as a tension arm and the forces from spring portion 144 translate to and push down on top portion 140. In its natural state, a spring bias of spring portion 144 forces tip 146 of top portion 140 towards bottom portion 142 of clip 104. Tip 146 of top portion 140 can be lifted up and clip 104 can be positioned on a muscle, a bone, or tissue of a patient. When clip 104 is positioned on a muscle, a bone, or tissue of a patient, the tension in spring portion 144 will force top portion 140 down onto the muscle, the bone, or the tissue. This tension will anchor clip 104 to the muscle, the bone, or the tissue. Additional fixation mechanisms, such as tines, pins, or screws can also be used to anchor clip 104 to the bone, the muscle, or the tissue.

Clip 104 also includes electrode 152 on top surface 140 of clip 104. In the embodiment shown in FIGS. 4A-4E, there is a single electrode 152 positioned on clip 104. In alternate embodiments, any number of electrodes can be positioned on clip 104 or clip 104 can include no electrodes. Electrode 152 is positioned on top surface 140 of clip 104 to sense an electrical activity or physiological parameter of the tissue surrounding clip 104. Electrode 152 can also provide therapeutic electrical stimulation to the tissue surrounding clip 104.

Figure 5A:
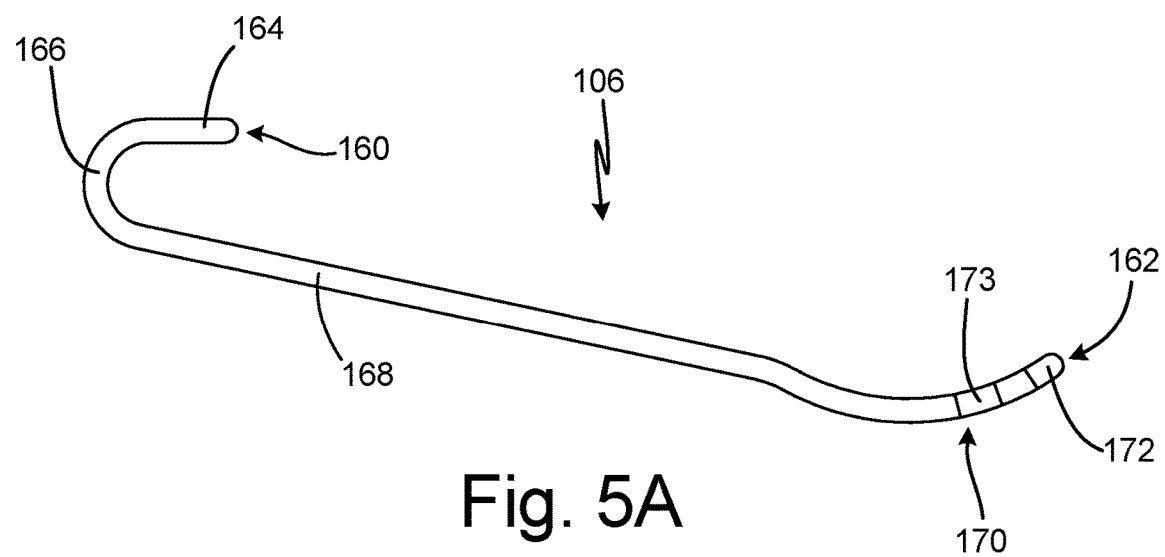
FIG. 5A is a side view of a prong of the first embodiment of the subcutaneous device.
Figure 5B:
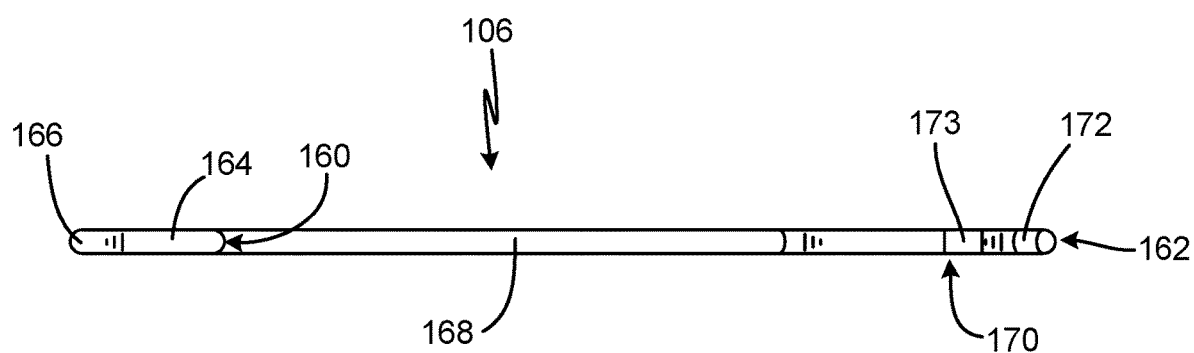
FIG. 5B is a top view of the prong of the first embodiment of the subcutaneous device.

FIG. 5A is a side view of prong 106 of subcutaneous device 100. FIG. 5B is a top view of prong 106 of subcutaneous device 100. Prong 106 includes proximal end 160, distal end 162, base portion 164, spring portion 166, arm portion 168, contact portion 170, and electrode 172.

Prong 106 includes proximal end 160 and distal end 162 that is opposite of proximal end 160. Proximal end 160 of prong 106 may have strain relief or additional material to support movement. Prong 106 includes base portion 164, spring portion 166, arm portion 168, and contact portion 170. A first end of base portion 164 is aligned with proximal end 160 of prong 106, and a second end of base portion 164 is connected to a first end of spring portion 166. Base portion 164 is a straight portion that positioned in port 126 of housing 102 (shown in FIGS. 3D-3E). The first end of spring portion 166 is connected to the second end of base portion 164, and a second end of spring portion 166 is connected to a first end of arm portion 168. The first end of arm portion 168 is connected to the second end of spring portion 166, and a second end of arm portion 168 is connected to a first end of contact portion 170. Arm portion 168 is a straight portion. The first end of contact portion 170 is connected to the second end of arm portion 168, and a second end of contact portion 170 is aligned with distal end 162 of prong 106. Contact portion 170 can be positioned to contact remote body component B (shown in FIG. 2). Spring portion 166 acts as a spring for prong 106 and is under tension. Arm portion 168 acts as a tension arm and the forces from spring portion 166 translate to and push down on arm portion 168. In its natural state, a spring bias of spring portion 166 forces distal end 162 of prong 106 away from bottom side 116 of housing 102.

Prong 106 further includes electrode 172. Electrode 172 is shown as being on distal end 162 in the embodiment shown in FIGS. 5A-5B. In alternate embodiments, electrode 172 can be positioned at any point on contact portion 170 and can have any shape and configuration. Further, prong 106 is shown as having a single electrode 172 in the embodiment shown in FIGS. 5A-5B. Prong 106 can have any number of electrodes in alternate embodiments. Electrode 172 is positioned on distal end 162 of prong 106 to sense an electrical activity or physiological status of remote body component B. Electrode 172 can also provide therapeutic electrical stimulation to remote body component B. In the embodiment shown in FIGS. 5A-5B, prong 106 additionally includes electrode 173 that is capable of sensing an electrical activity or physiological status of remote body component B and/or providing therapeutic electrical stimulation to remote body component B.

Prong 106 is made of a stiff material so that it is capable of pushing through tissue in the body when subcutaneous device 100 in implanted into a patient. Prong 106 can be made out of nickel titanium, also known as Nitinol. Nitinol is a shape memory alloy with superelasticity, allowing prong 106 to go back to its original shape and position if prong 106 is deformed as subcutaneous device 100 is implanted into a patient. Prong 106 can also be made out of silicone, polyurethane, stainless steel, titanium, epoxy, polyurethane with metallic reinforcements, or any other material that is suitable for non-porous implants. As an example, prong 106 can be made out of a composite made of polyurethane and silicone and reinforced with metal to provide spring stiffness.

Spring portion 166 of prong 106 allows prong 106 to be flexible once it is positioned in the body. For example, if remote body component B is a heart of a patient and contact portion 170 of prong 106 is positioned against the heart, spring portion 166 of prong 106 allows prong 106 to move with up and down as the heart beats. This ensures that prong 106 does not puncture or damage the heart when contact portion 170 of prong 106 is in contact with the heart. Distal end 162 of prong 106 has a rounded shape to prevent prong 106 from puncturing or damaging the heart when contact portion 170 of prong 106 is in contact with the heart. The overall axial stiffness of prong 106 can be adjusted so that prong 106 gently presses against the heart and moves up and down in contact with the heart as the heart beats, but is not stiff or sharp enough to pierce or tear the pericardial or epicardial tissue.

Figure 6A:
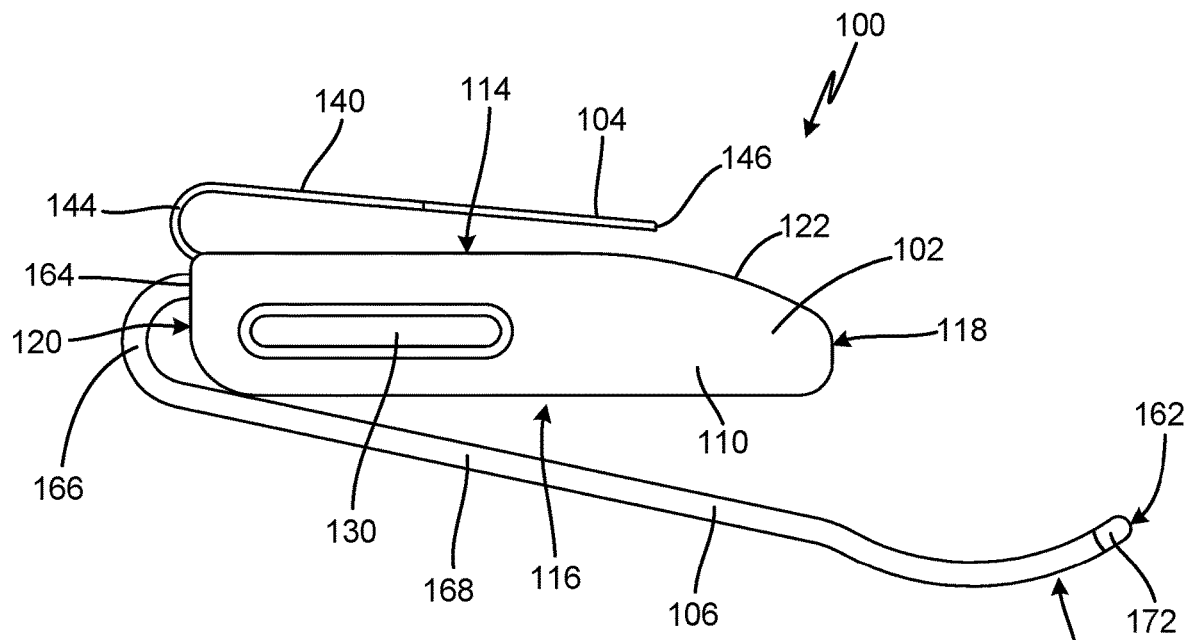
FIG. 6A is a side view of the first embodiment of the subcutaneous device.
Figure 6B:
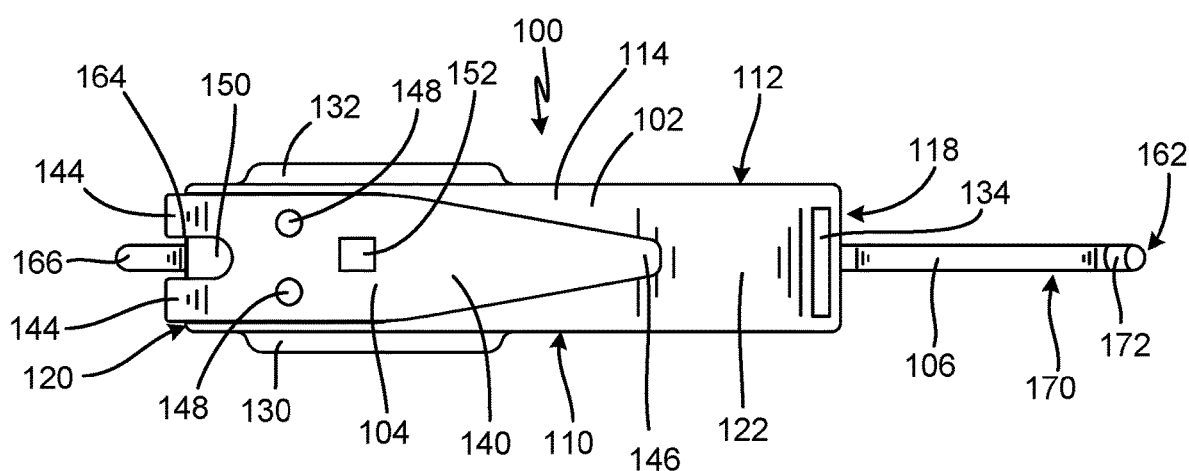
FIG. 6B is a top view of the first embodiment of the subcutaneous device.

FIG. 6A is a side view of subcutaneous device 100. FIG. 6B is a top view of subcutaneous device 100. FIG. 6C is a bottom view of subcutaneous device 100. FIG. 6D is a back view of subcutaneous device 100. FIG. 6E is a front view of subcutaneous device 100. Subcutaneous device 100 includes housing 102, clip 104, and prong 106. Housing 102 includes first side 110, second side 112, top side 114, bottom side 116, front end 118, back end 120, curved surface 122, recess 124, port 126, channel 128, first guide 130, second guide 132, electrode 134, and electrode 136. Clip 104 includes top portion 140, bottom portion 142, spring portion 144, tip 146, openings 148, slot 150, and electrode 152. Prong 106 includes proximal end 160, distal end 162, base portion 164, spring portion 166, arm portion 168, contact portion 170, and electrode 172.

Subcutaneous device 100 includes housing 102, clip 104, and prong 106. Housing 102 is described in detail in reference to FIGS. 3A-3E above. Clip 104 is described in detail in reference to FIGS. 4A-4E above. Prong 106 is described in detail in reference to FIGS. 6A-6B above.

Clip 104 is connected to top side 114 of housing 102 of subcutaneous device 100. Recess 124 of housing 102 is shaped to fit bottom portion 142 of clip 104. Bottom portion 142 is positioned in and connected to recess 124 of housing 102, for example by welding. Spring portion 144 of clip 104 is aligned with back side 120 of housing 102. Top portion 140 of clip 104 extends along top side 114 of housing 102. The spring bias in clip 104 will force tip 146 of clip 104 towards housing 102. Clip 104 can be expanded by lifting up tip 146 of clip 104 to position clip 104 on a bone, a muscle, or a tissue of a patient. When clip 104 is positioned on a muscle, a bone, or a tissue of a patient, the tension in spring portion 144 will force top portion 140 of clip 104 down onto the muscle, the bone, or the tissue. This tension will anchor clip 104, and thus subcutaneous device 100, to the muscle, the bone, or the tissue.

Prong 106 is connected to back side 120 of housing 102 of subcutaneous device 100. Port 126 of housing 102 is shaped to fit base portion 164 of prong 106. Base portion 164 of prong 106 is positioned in port 126 of housing 102. Base portion 164 of prong 106 is electrically connected to the internal components of housing 102, for example with a feedthrough. Base portion 164 of prong 106 is also hermetically sealed in port 126 of housing 102. Spring portion 166 of prong 106 curves around back side 120 of housing 102 and arm portion 168 extends underneath bottom side 116 of housing 102. Arm portion 168 extends past front end 118 of housing 102 so that contact portion 170 is positioned outwards from front end 118 of housing 102. In alternate embodiments, prong 106 can have different shapes and lengths. Further, prong 106 can extend from housing 102 in any direction.

Subcutaneous device 100 is shown in a deployed position in FIGS. 6A-6E. Subcutaneous device 100 will be in the deployed position when subcutaneous device 100 is implanted in a patient. In the deployed position, prong 106 only contacts housing 102 at base portion 164. Subcutaneous device also has a stowed position. Subcutaneous device 100 is in the stowed position when subcutaneous device 100 is loaded in a surgical instrument prior to delivery to the patient. In the stowed position, arm portion 168 of prong 106 is positioned in channel 128 of housing 102. Channel 128 of housing 102 holds arm portion 168 of prong 106 in a centered position with respect to housing 102 when subcutaneous device 100 is in a stowed position. When subcutaneous device is implanted in a patient, subcutaneous device 100 will deploy. The tension of spring portion 166 of prong 106 will force arm portion 168 outwards away from channel 128 of housing 102.

Subcutaneous device 100 can function as a pacemaker. Prong 106 can be shaped so that contact portion 170 of prong 106 contacts the right ventricle, left ventricle, right atrium, or left atrium of the heart. Subcutaneous device 100 can function as a unipolar pacemaker, utilizing electrode 172 on prong 106 and one of electrode 134 or electrode 136 on housing 102 or electrode 152 on clip 104. Further, subcutaneous device 100 can function as a bipolar pacemaker, utilizing electrode 172 on prong 106 and a second electrode also positioned on prong 106.

Figure 7:
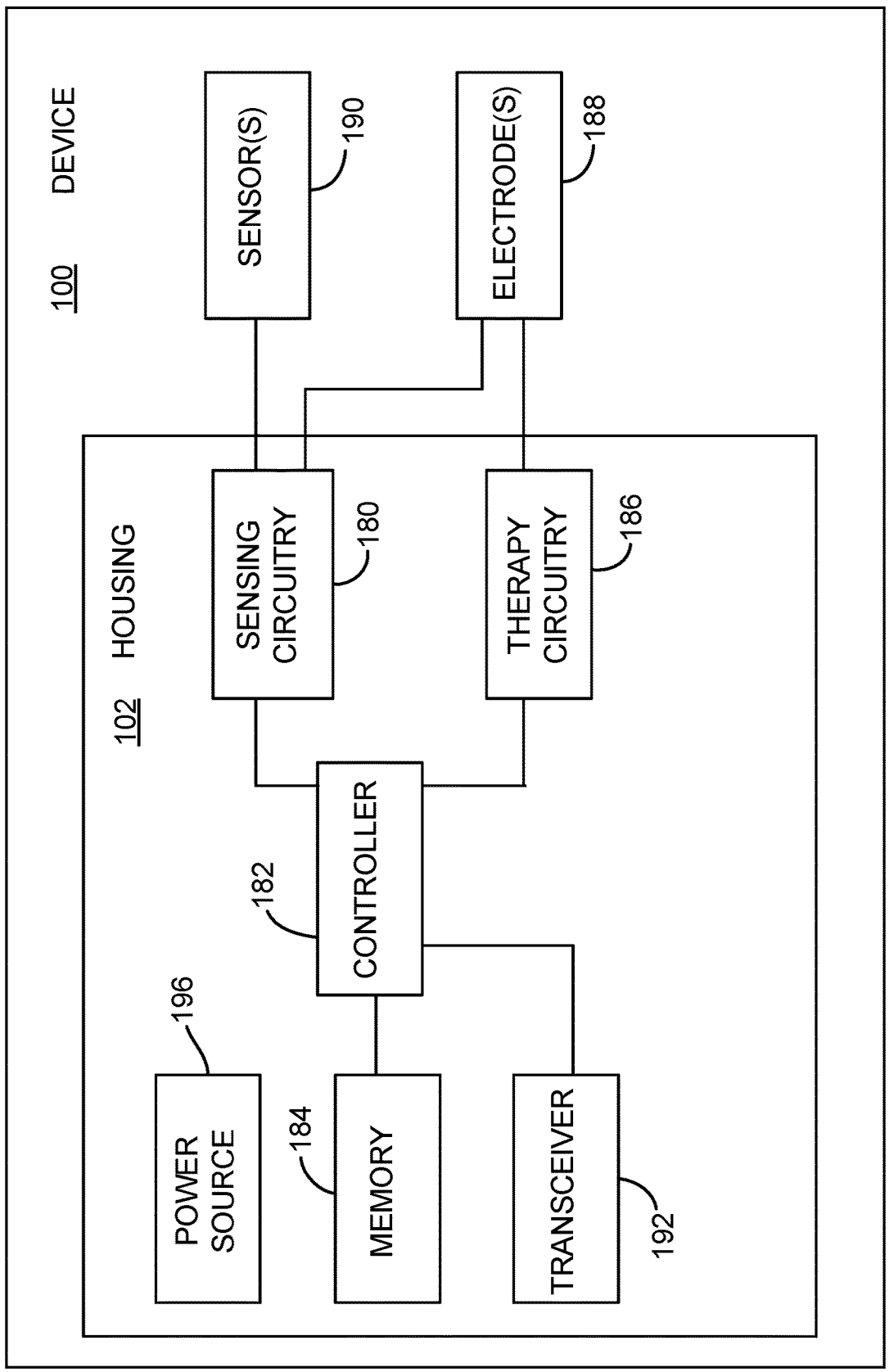
FIG. 7 is a functional block diagram of the first embodiment of the subcutaneous device.

FIG. 7 is a functional block diagram of subcutaneous device 100. Subcutaneous device 100 includes housing 102, sensing circuitry 180, controller 182, memory 184, therapy circuitry 186, electrode(s) 188, sensor(s) 190, transceiver 192, and power source 194. The functional block diagram of subcutaneous device 100 shown in FIG. 7 applies to all embodiments of a subcutaneous device disclosed herewith.

Housing 102 contains sensing circuitry 180, controller 182, memory 184, and therapy circuitry 186. Sensing circuitry 180 receives electrical signals from the heart and communicates the electrical signals to controller 182. Controller 182 analyzes the electrical signals and executes instructions stored in memory 184 to determine if there is an arrhythmia in the patient's heart rate. If controller 182 determines that there is an arrhythmia, controller 182 will send instructions to therapy circuitry 186 to send electrical stimulation to the heart to regulate the heart rate of the patient. Sensing circuitry 180 and therapy circuitry 186 are both in communication with electrode(s) 188. Electrode(s) 188 can be positioned in housing 102, clip 104, and/or prong 106 and are in contact with an organ, a nerve, or a tissue when subcutaneous device 100 is implanted in a patient. Electrode(s) 188 sense electrical signals from the organ, the nerve, or the tissue and provide electrical stimulation to the heart.

Controller 182 is also in communication with sensor(s) 190 through sensing circuitry 180. Sensor(s) 190 can be positioned in housing 102 and/or prong 106. Sensor(s) 190 can be used with controller 182 to determine physiological parameters of the patient. Controller 182 is further in communication with transceiver 192 that is positioned in housing 102. Transceiver 192 can receive information and instructions from outside of subcutaneous device 100 and send information gathered in subcutaneous device 100 outside of subcutaneous device 100. Power source 194 is also positioned in housing 102 and provides power to the components in housing 102, clip 104, and prong 106, as needed. Power source 194 can be a battery that provides power to the components in housing 102.

Sensing circuitry 180 is electrically coupled to electrode(s) 188 via conductors extending through prong 106 and into housing 102. Sensing circuitry 180 is configured to receive a sensing vector formed by electrode(s) 188 and translate the sensing vector into an electrical signal that can be communicated to controller 182. Sensing circuitry 180 can be any suitable circuitry, including electrodes (including positive and negative ends), analog circuitry, analog to digital converters, amps, microcontrollers, and power sources.

Controller 182 is configured to implement functionality and/or process instructions for execution within subcutaneous device 100. Controller 182 can process instructions stored in memory 184. Examples of controller 182 can include any one or more of a microcontroller, a microprocessor, a digital signal processor (DSP), an application specific integrated circuit (ASIC), a field-programmable gate array (FPGA), or other equivalent discrete or integrated logic circuitry.

Memory 184 can be configured to store information within subcutaneous device 100 during operation. Memory 184, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 184 is a temporary memory, meaning that a primary purpose of memory 184 is not long-term storage. Memory 184, in some examples, is described as volatile memory, meaning that memory 184 does not maintain stored contents when power to subcutaneous device 100 is turned off. Examples of volatile memories can include random access memories (RAM), dynamic random access memories (DRAM), static random access memories (SRAM), and other forms of volatile memories. In some examples, memory 184 is used to store program instructions for execution by controller 182. Memory 184, in one example, is used by software or applications running on subcutaneous device 100 to temporarily store information during program execution.

Memory 184, in some examples, also includes one or more computer-readable storage media. Memory 184 can be configured to store larger amounts of information than volatile memory. Memory 184 can further be configured for long-term storage of information. In some examples, memory 184 can include non-volatile storage elements. Examples of such non-volatile storage elements can include magnetic hard discs, optical discs, floppy discs, flash memories, or forms of electrically programmable memories (EPROM) or electrically erasable and programmable (EEPROM) memories.

Controller 182 can receive electrical signals from sensing circuitry 180, analyze the electrical signals, and execute instructions stored in memory 184 to determine whether an arrhythmia is present in the heart rate of a patient. If an arrhythmia is detected, controller 182 can send instructions to therapy circuitry 186 to deliver an electrical stimulation to the heart via electrode(s) 188.

Therapy circuitry 186 is electrically coupled to electrode(s) 188 via conductors extending through prong 106 and into housing 102. Therapy circuitry 186 is configured to deliver an electrical stimulation to the heart via electrode(s) 188. Therapy circuitry 186 will include a capacitor to generate the electrical stimulation. Therapy circuitry 180 can be any suitable circuitry, including microcontroller, power sources, capacitors, and digital to analog converters.

Controller 182 can also receive information from sensor(s) 190. Sensor(s) 190 can include any suitable sensor, including, but not limited to, temperature sensors, accelerometers, pressure sensors, proximity sensors, infrared sensors, optical sensors, and ultrasonic sensors. The information from sensor(s) 190 allows subcutaneous device 100 to sense physiological parameters of a patient. For example, the data from the sensors can be used to calculate heart rate, heart rhythm, respiration rate, respiration waveform, activity, movement, posture, oxygen saturation, photoplethysmogram (PPG), blood pressure, core body temperature, pulmonary edema, and pulmonary wetness. The accelerometer can also be used for rate responsive pacing.

Subcutaneous device 100 also includes transceiver 192. Subcutaneous device 100, in one example, utilizes transceiver 192 to communicate with external devices via wireless communication. Subcutaneous device 100, in a second example, utilizes transceiver 192 to communication with other devices implanted in the patient via wireless communication. Transceiver 192 can be a network interface card, such as an Ethernet card, an optical transceiver, a radio frequency transceiver, or any other type of device that can send and receive information. Other examples of such network interfaces can include Bluetooth, 3G, 4G, WiFi radio computing devices, Universal Serial Bus (USB), standard inductive coupling, low frequency medical frequency radio (MICS), ultra-wide band radio, standard audio, and ultrasonic radio. Examples of external devices that transceiver 192 can communicate with include laptop computers, mobile phones (including smartphones), tablet computers, personal digital assistants (PDAs), desktop computers, servers, mainframes, cloud servers, or other devices. Other devices implanted in the body can include other implantable medical devices, such as other pacemakers, implantable cardioversion-defibrillators, nerve stimulators, and the like. Transceiver 192 can also be connected to an antenna.

Subcutaneous device 100 includes power source 194 positioned in housing 102. Subcutaneous device 100 can also include a battery or device outside of housing 102 that transmits power and data to subcutaneous device 100 through wireless coupling or RF. Further, power source 194 can be a rechargeable battery.

The internal components of subcutaneous device 100 described above in reference to FIG. 7 is intended to be exemplary. Subcutaneous device 100 can include more, less, or other suitable components. For example, when subcutaneous device 100 is only used for diagnostics, subcutaneous device 100 will not include therapy circuitry 186. As a further example, subcutaneous device 100 can function as a pacemaker without sensor(s) 190.

Figure 9A:
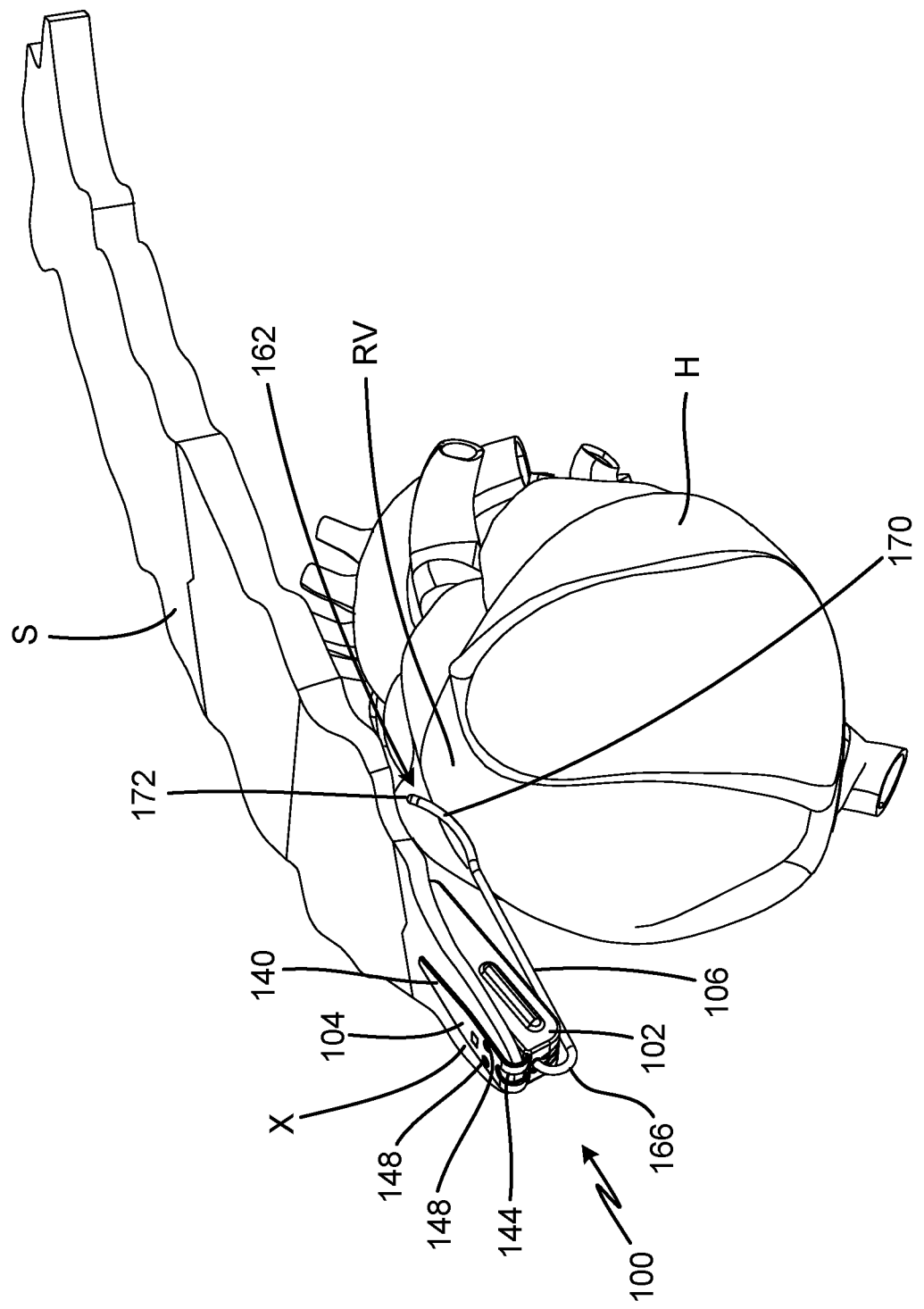
FIG. 9A is a perspective view of the first embodiment of the subcutaneous device positioned on the xiphoid process and the sternum and showing a positioning of a prong on a heart.
Figure 9B:
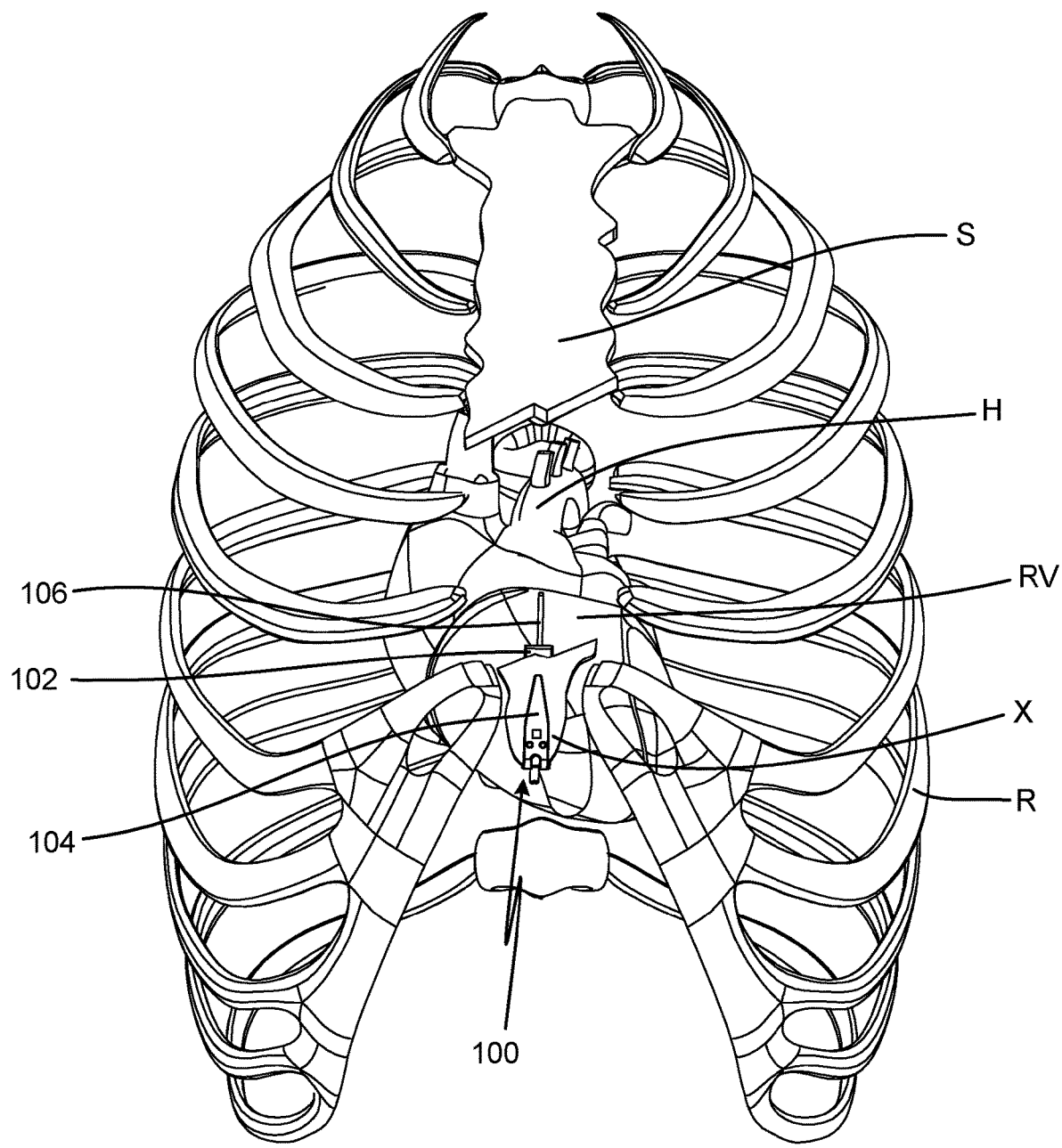
FIG. 9B is a front cut away view of the first embodiment of the subcutaneous device positioned on the xiphoid process and the sternum and showing a positioning of the prong on the heart.
Figure 9C:
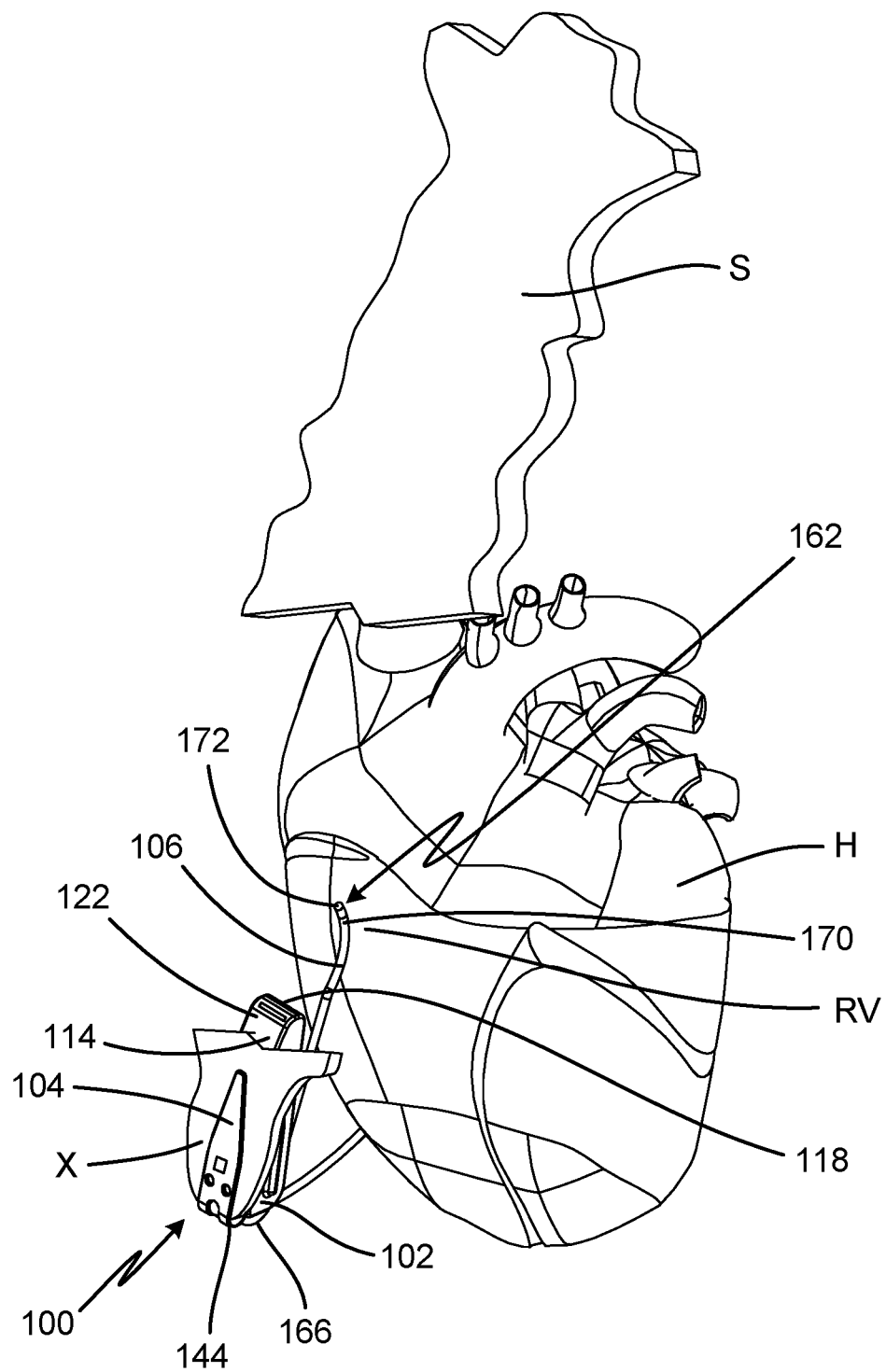
FIG. 9C is a perspective cut away view of the first embodiment of the subcutaneous device positioned on the xiphoid process and the sternum and showing a positioning of the prong on the heart.
Surgical Instrument 200

FIG. 8 is a perspective view of subcutaneous device 100 positioned on xiphoid process X and sternum S. FIG. 9A is a perspective view of subcutaneous device 100 positioned on xiphoid process X and sternum S and showing a positioning of prong 104 on heart H. FIG. 9B is a front cut away view of subcutaneous device 100 positioned on xiphoid process X and sternum S and showing a positioning of prong 104 on heart H. FIG. 9C is a perspective cut away view of subcutaneous device 100 positioned on xiphoid process X and sternum S and showing a positioning of prong 104 on heart H. Subcutaneous device 100 includes housing 102, clip 104, and prong 106. Housing 102 includes top side 114, front end 118, and curved surface 122. Clip 104 includes top portion 140, spring portion 144, and openings 148. Prong 106 includes distal end 162, spring portion 166, contact portion 170, and electrode 172. FIGS. 8-9C show xiphoid process X and sternum S. FIGS. 9A-9C further show heart H and right ventricle RV. FIG. 9B also shows ribs R.

FIGS. 8-9C show xiphoid process X and sternum S. FIG. 9B further shows xiphoid process X and sternum S in relation to ribs R. Subcutaneous device 100 can be anchored to xiphoid process X and sternum S of a patient. Xiphoid process X is a process extending from a lower end of sternum S. When subcutaneous device 100 is anchored to xiphoid process X, housing 102 of subcutaneous device 100 will be partially positioned underneath sternum S of the patient. In some patients, xiphoid process X is absent, small, narrow, or elongated, and subcutaneous device 100 can be attached directly to a distal end of sternum S. Subcutaneous device will be positioned in the anterior mediastinum of the patient when it is anchored to the xiphoid process X and sternum S. The anterior mediastinum is an area that is anterior to the pericardium, posterior to sternum S, and inferior to the thoracic plane. The anterior mediastinum includes loose connective tissues, lymph nodes, and substernal musculature.

When subcutaneous device 100 is deployed onto xiphoid process X and sternum S, housing 102 and prong 106 of subcutaneous device 100 will move through the anterior mediastinum. Curved surface 122 on top side 114 of housing 102 creates a tapered front end 118 of housing 102 to help subcutaneous device 100 push through the tissue in the anterior mediastinum. Further, prong 106 is made of a stiff material to allow it to push through the tissue in the anterior mediastinum.

Subcutaneous device 100 can be anchored to xiphoid process X and sternum S with clip 104. When clip 104 is positioned on xiphoid process X, top portion 140 of clip 104 will be positioned superior to xiphoid process X and sternum S. Spring portion 144 of clip 104 will put tension on top portion 140 of clip 104 to push top portion 140 down onto xiphoid process X and sternum S. Clip 104 will hold subcutaneous device 100 in position on xiphoid process X and sternum S. Further, openings 148 in top portion 140 of clip 104 can be used to suture clip 104 to xiphoid process X and sternum S, or openings 148 can receive additional fixation mechanisms, such as tines, pins, or screws. This will further anchor subcutaneous device 100 to xiphoid process X and sternum S.

When subcutaneous device 100 is anchored to xiphoid process X and sternum S, prong 106 will extend from housing 102 and come into contact with heart H of the patient. Specifically, contact portion 170 and electrode 172 of prong 106 will come into contact with the pericardium. The pericardium is the fibrous sac that surrounds heart H. Electrode 172 will be positioned on the portion of the pericardium that surrounds right ventricle RV of heart H. An electrical stimulation can be applied to right ventricle RV of heart H, causing heart H to contract, by transmitting the electrical signal from electrode 172 on distal end 162 of prong 106 through the pericardium and epicardium and into the myocardium of heart H. Prong 106 can also sense electrical signals from heart H to determine a surface ECG of heart H.

As heart H beats, it will move in a vertical and a three-dimensional pattern. Spring portion 166 of prong 106 provides some flexibility to prong 106 to allow prong 106 to move with heart H as it beats. This will ensure that prong 106 does not puncture or damage heart H.

Anchoring subcutaneous device 100 to xiphoid process X and sternum S ensures that subcutaneous device 100 will not migrate in the patient's body. Maintaining the position of subcutaneous device 100 in the body ensures that prong 106 is properly positioned and will not lose contact with heart H. Further, subcutaneous device 100 is able to accurately and reliably determine a heart rate and other physiological parameters of the patient, as subcutaneous device 100 will not move in the patient's body. For instance, the ECG morphology will not change due to movement of subcutaneous device 100 within the patient's body.

Subcutaneous device 100 can be implanted with a simple procedure where subcutaneous device 100 is injected onto xiphoid process X using a surgical instrument. The surgical procedure for implanting subcutaneous device 100 is less invasive than the surgical procedure required for more traditional pacemaker devices, as subcutaneous device is placed subcutaneously in the body. No leads need to be positioned in the vasculature of the patient, lowering the risk of thrombosis to the patient. A surgical instrument and a method for implanting subcutaneous device 100 are described in greater details below.

Injectable Tool 200

Figure 10A:
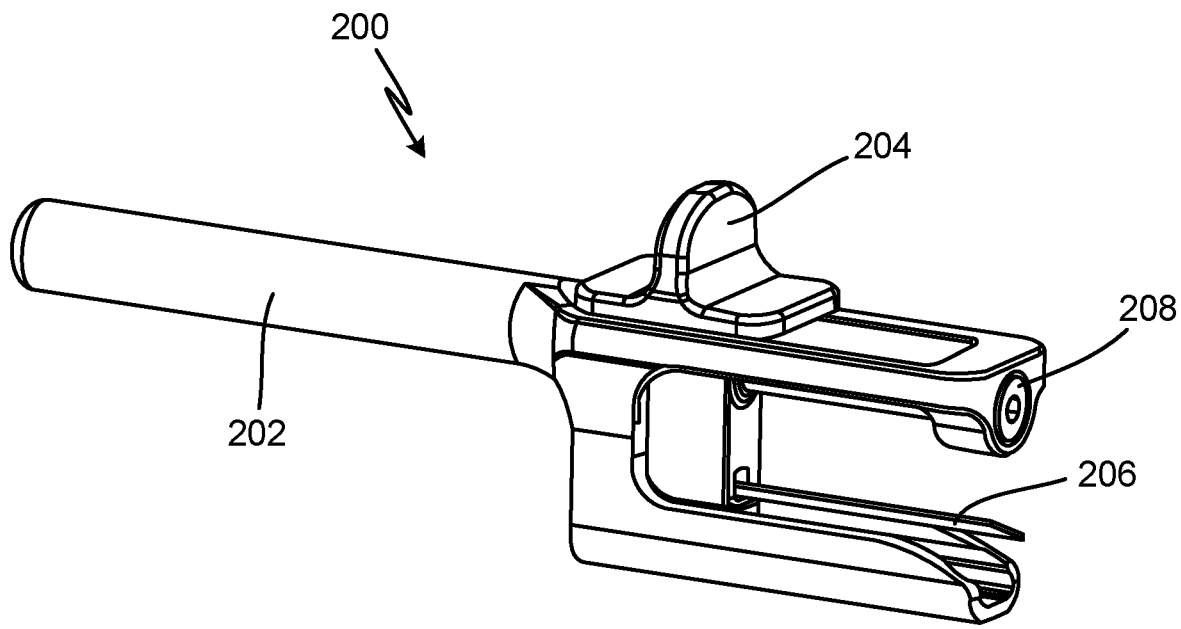
FIG. 10A is a perspective view of a surgical instrument in a first position.
Figure 10B:
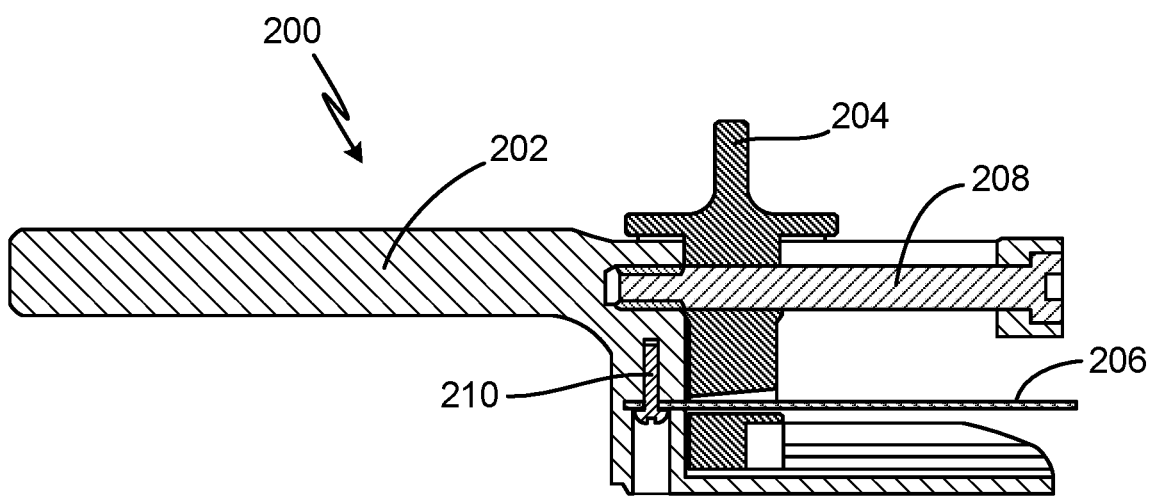
FIG. 10B is a cross-sectional view of the surgical instrument in the first position.

FIG. 10A is a perspective view of surgical instrument 200 in a first position. FIG. 10B is a cross-sectional perspective view of surgical instrument 200 in the first position. Surgical instrument 200 includes body 202, slider 204, blade 206, bolt 208, and screw 210.

Surgical instrument 200 can be used to implant a medical device in a patient. In the following discussion, subcutaneous device 100 (shown in FIGS. 1-9) will be used as an example of a device that can be implanted in a patient using surgical instrument 200. However, surgical instrument 200 can be used to implant any suitable medical device in a patient, including any of subcutaneous devices 400, 500, 600, 700, 800, 900, 1000, 1100, 1200, 1300, 1400, and 1500 shown in FIGS. 20-37.

Surgical instrument 200 includes body 202 that can be grasped by a user to hold and maneuver surgical instrument 200. Surgical instrument 200 further includes slider 204 and blade 206 that are attached to body 202. Bolt 208 extends through body 202 and slider 204 to hold slider 204 in position in surgical instrument 200. Slider 204 is configured to deploy a subcutaneous device into a body of a patient when a subcutaneous device is stowed in surgical instrument 200. Screw 210 extends through blade 206 and into body 202 to mount blade 206 to body 202. Blade 206 is configured to extend past a front end of surgical instrument 200 and can be used to cut through tissue prior to deploying a subcutaneous device that is stowed in surgical instrument 200 into a patient. In an alternate embodiment, blade 206 can be a separate blade that is not connected to surgical instrument 200.

Surgical instrument 200 in shown in a first position in FIGS. 10A-10B. In the first position, slider 204 is positioned to abut body 202 and subcutaneous device 100 (shown in FIGS. 1-9) can be loaded into surgical instrument 200. Surgical instrument 200 can be used to inject subcutaneous device 100 onto a bone, a muscle, or a tissue of a patient. In one example, surgical instrument 200 can be used to inject subcutaneous device 100 onto a xiphoid process and a sternum of a patient.

Figure 11A:
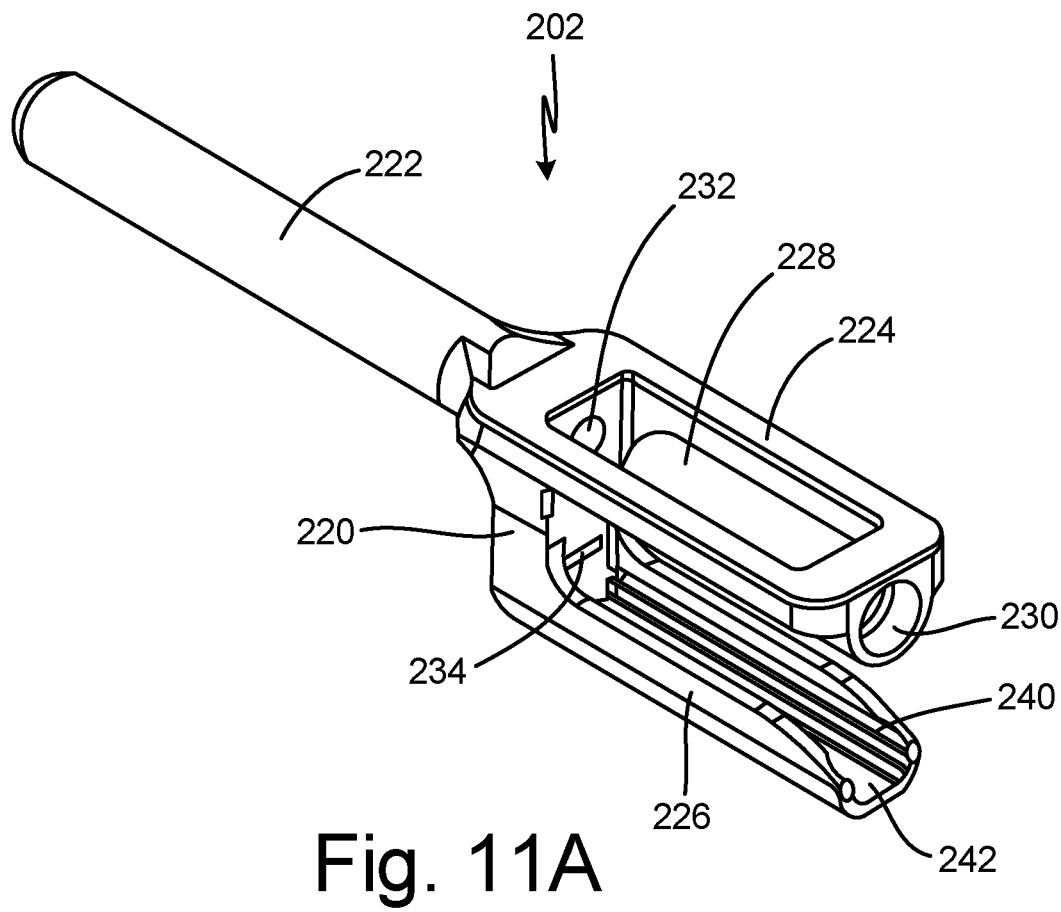
FIG. 11A is a perspective view of a body of the surgical instrument.
Figure 11B:
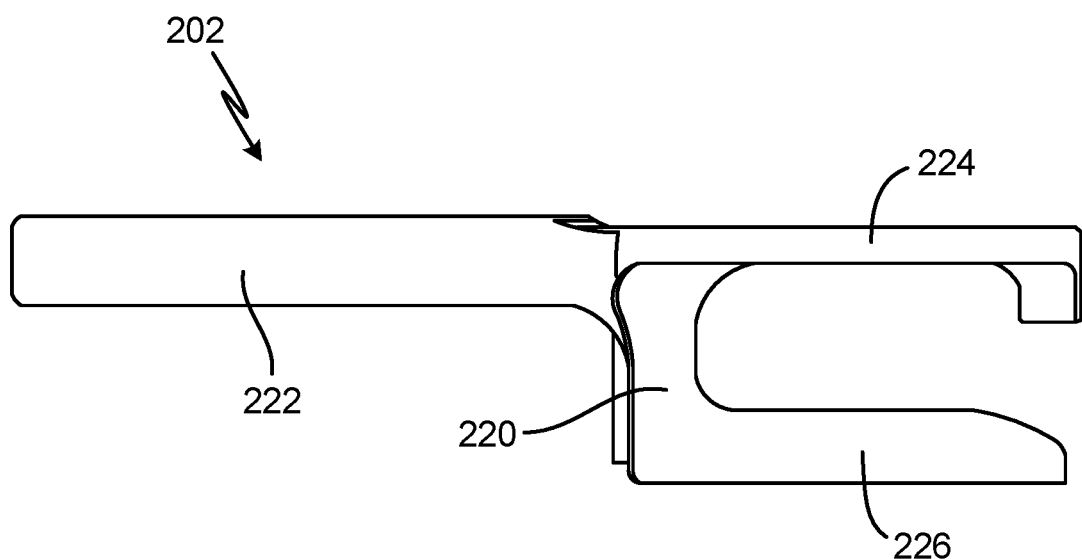
FIG. 11B is a side view of the body of the surgical instrument.
Figure 11C:
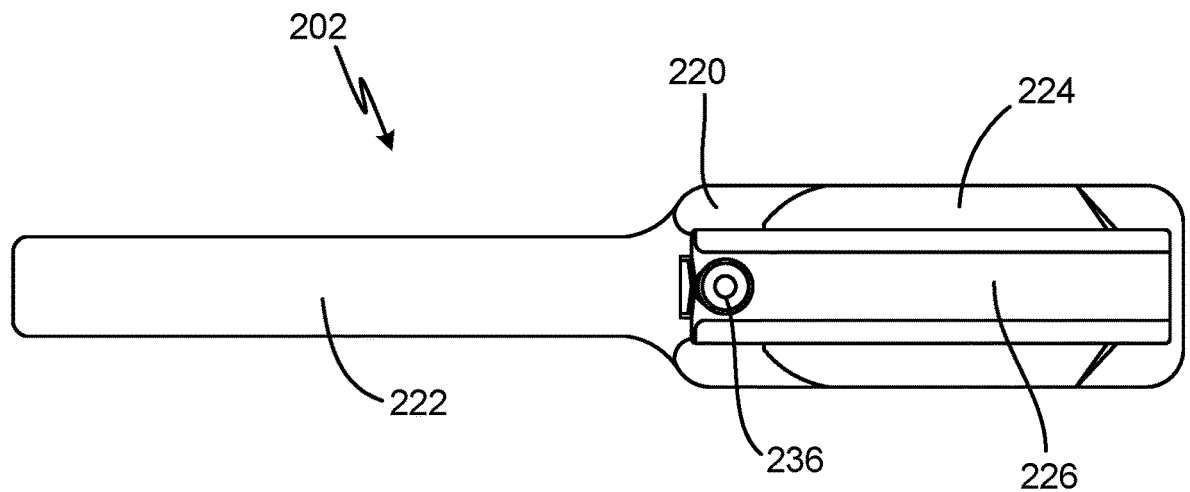
FIG. 11C is a bottom view of the body of the surgical instrument.
Figure 11D:
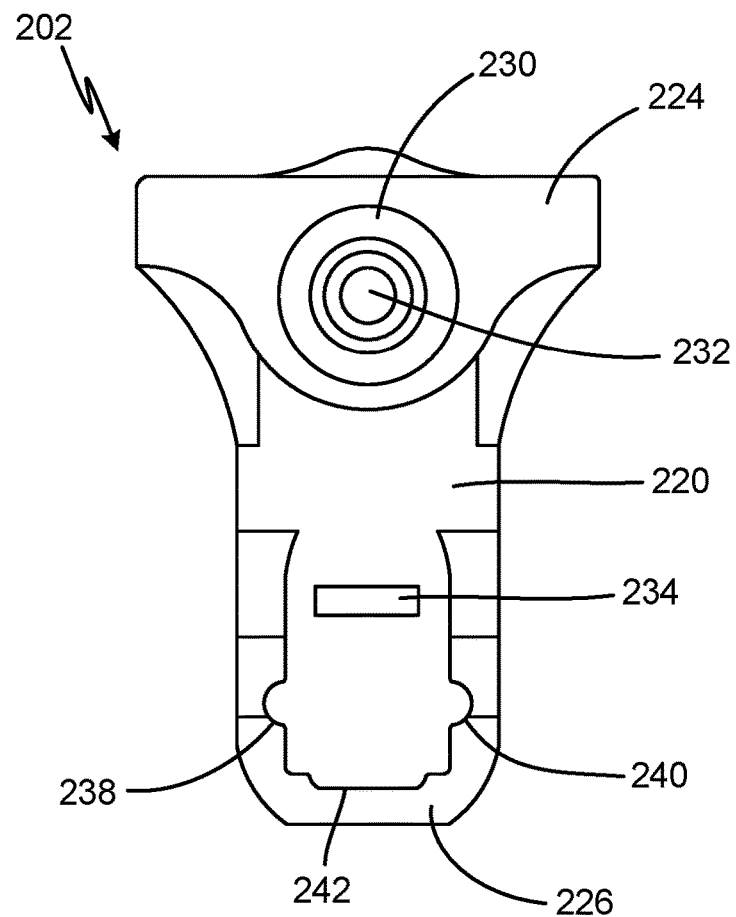
FIG. 11D is a front view of the body of the surgical instrument.

FIG. 11A is a perspective view of body 202 of surgical instrument 200. FIG. 11B is a side view of body 202 of surgical instrument 200. FIG. 11C is a bottom view of body 202 of surgical instrument 200. FIG. 11D is a front view of body 202 of surgical instrument 200. Body 202 includes base 220, handle 222, upper arm 224, lower arm 226, slider slot 228, bolt aperture 230, bolt aperture 232, blade slot 234, screw aperture 236, guide track 238, guide track 240, and prong track 242.

Body 202 includes base 220, handle 222, upper arm 224, and lower arm 226 that are integral with one another to form body 202. Base 220 forms a support portion in the middle of body 202. Handle 220 extends away from a back end of base 220. Handle 220 can be grasped by a user to grasp body 202 of surgical instrument 200. Upper arm 224 and lower arm 226 extend away from a front end of base 220. Upper arm 224 is positioned on an upper side of base 220, and lower arm 226 is positioned on a lower side of base 220. Body 202 can be made out of any suitable metallic or plastic material.

Upper arm 224 includes slider slot 228 that forms an opening in upper arm 224. Slider slot 228 is configured to allow slider 204 of surgical instrument 200 (shown in FIGS. 10A-10B) to slide through upper arm 224. Upper arm 224 further includes bolt aperture 230 that extends through a front end of upper arm 224. Bolt aperture 230 of upper arm 224 is configured to receive bolt 208 of surgical instrument 200 (shown in FIGS. 10A-10B). Bolt aperture 230 has a recessed portion that is configured to receive a head of bolt 208 so that bolt 208 is flush with a front end of body 202.

Base 210 includes bolt aperture 232 that extends into an upper end of base 210. Bolt aperture 232 of base 210 is configured to receive bolt 208 of surgical instrument 200 (shown in FIGS. 10A-10B). Bolt aperture 232 is threaded to receive threads on bolt 208. Base 210 further includes blade slot 234 that extends into a middle of base 210. Blade slot 234 of base 210 is configured to receive blade 206 of surgical instrument 200 (shown in FIGS. 10A-10B). Base 210 also includes screw aperture 236 extending up into base 210 from a bottom side of base 210. Screw aperture 236 is configured to receive screw 210 of surgical instrument 200 (shown in FIGS. 10A-10B). Blade slot 234 extends into screw aperture 236 so that screw 210 can extend through blade 206 to mount blade 206 to surgical instrument 200.

Lower arm 226 includes first guide track 238 and second guide track 240. First guide track 238 is a groove extending along an inner surface of a first side of lower arm 226, and second guide track 240 is a groove extending along an inner surface of a second side of lower arm 226. First guide track 238 and second guide track 240 are configured to receive first guide 130 and second guide 132 of housing 102 of subcutaneous device 100 (shown in FIGS. 3A-3D and 6A-6E), respectively. Lower arm 226 further includes prong track 242. Prong track 242 is a groove extending along a top surface of lower arm 226. Prong track 242 is configured to receive prong 106 of subcutaneous device 100.

Figure 12A:
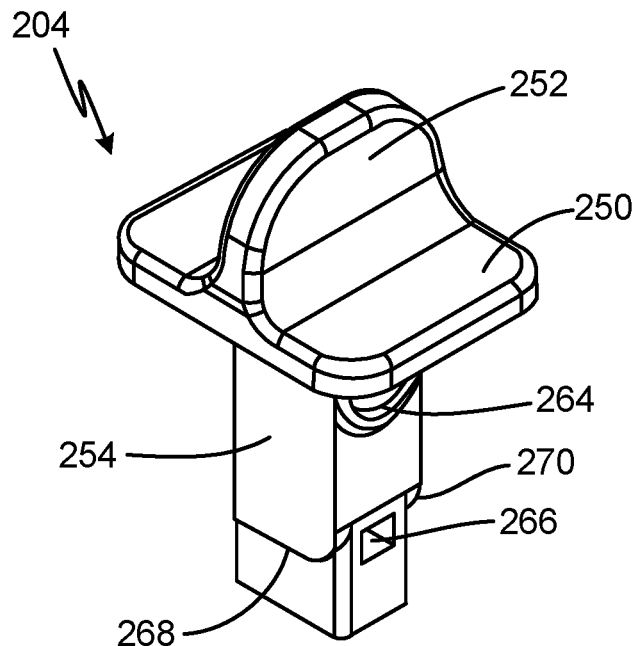
FIG. 12A is a perspective view of a slider of the surgical instrument.
Figure 12B:
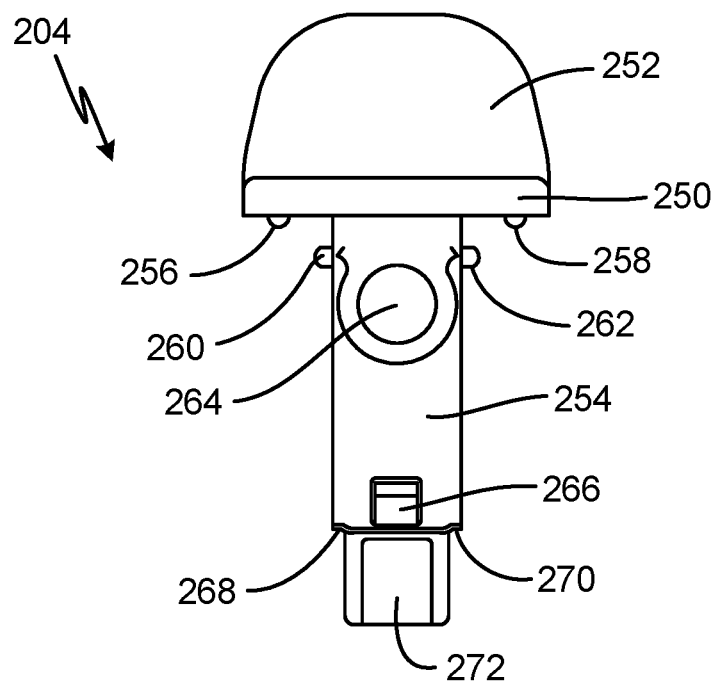
FIG. 12B is a front view of the slider of the surgical instrument.
Figure 12C:
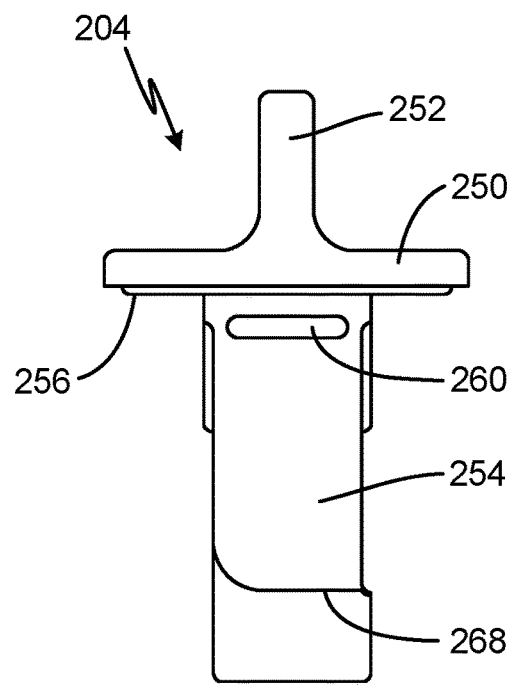
FIG. 12C is a side view of the slider of the surgical instrument.
Figure 12D:
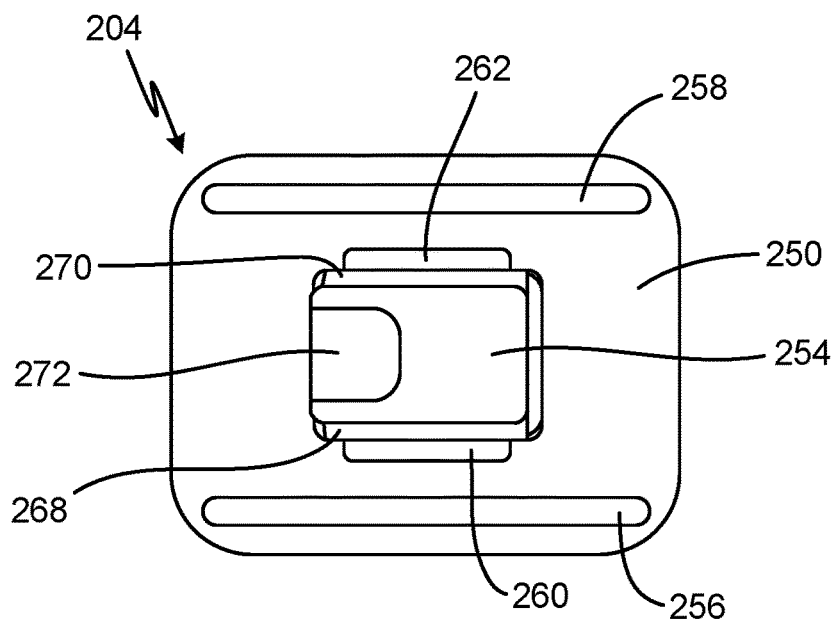
FIG. 12D is a bottom view of the slider of the surgical instrument.

FIG. 12A is a perspective view of slider 204 of surgical instrument 200. FIG. 12B is a front view of slider 204 of surgical instrument 200. FIG. 12C is a side view of slider 204 of surgical instrument 200. FIG. 12D is a bottom view of slider 204 of surgical instrument 200. Slider 204 includes base 250, knob 252, shaft 254, first guide 256, second guide 258, third guide 260, fourth guide 262, bolt aperture 264, blade slot 266, first shoulder 268, second shoulder 270, and device notch 272.

Slider 204 includes base 250, knob 252, and shaft 254 that are integral with one another to form slider 204. Base 250 form a support portion in the middle of slider 204. Knob 252 extends upwards from base 250. Knob 252 can be grasped by a user to slide slider 204 within surgical instrument 200. Shaft 254 extends downwards from base 250.

Base 250 includes first guide 256 and second guide 258 on a bottom surface of base 250. First guide 256 is positioned on a first side of base 250 and extends from a front end to a back end of base 250, and second guide 258 is positioned on a second side of base 250 and extends from a front end to a back end of base 250. Shaft 254 includes third guide 260 and fourth guide 262. Third guide 260 extends from a front end to a back end of shaft 254 on a first side of shaft 254, and fourth guide 262 extends from a front end to a back end of shaft 254 on a second side of shaft 254. First guide 256, second guide 258, third guide 260, and fourth guide 262 are configured to reduce friction as slider 204 slides through surgical instrument 200 (shown in FIGS. 10A-10B).

Shaft 254 also includes bolt aperture 264 that extends from a front end to a back end of slider 204. Bolt aperture 264 is configured to receive a portion of bolt 208 of surgical instrument 200 (shown in FIGS. 10A-10B). Shaft 254 further includes blade slot 266 that extends from a front end to a back end of slider 204. Blade slot 266 is configured to receive a portion of blade 206 of surgical instrument 200 (shown in FIGS. 10A-10B). Shaft 254 also includes first shoulder 268 and second shoulder 270. First shoulder 268 is a ridge on a first side of slider 204, and second shoulder 270 is a ridge on a second side of slider 204. First shoulder 268 and second shoulder 270 are configured to slide along lower arm 226 of body 202. Shaft 254 additionally includes device notch 272. Device notch 272 is a groove on a front end of shaft 254. Device notch 272 is configured to receive a portion of subcutaneous device 100 (shown in FIGS. 1-9).

Figure 13A:
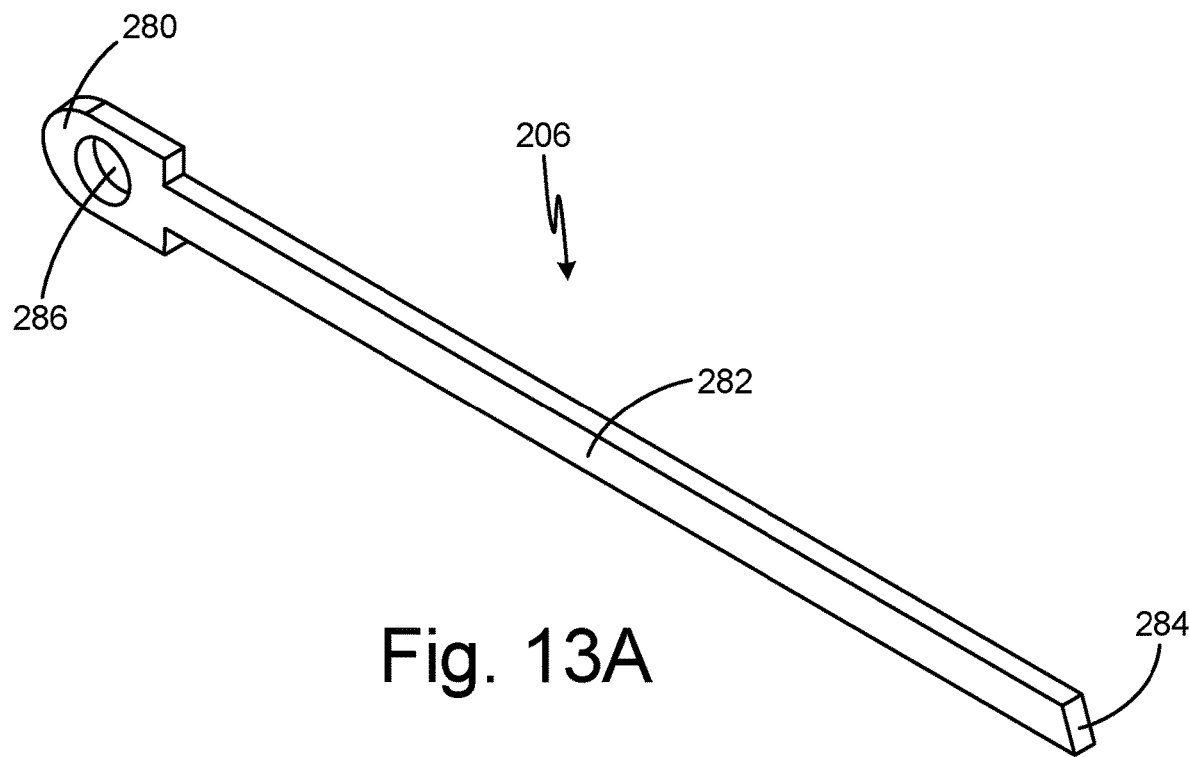
FIG. 13A is a perspective view of a blade of the surgical instrument.
Figure 13B:
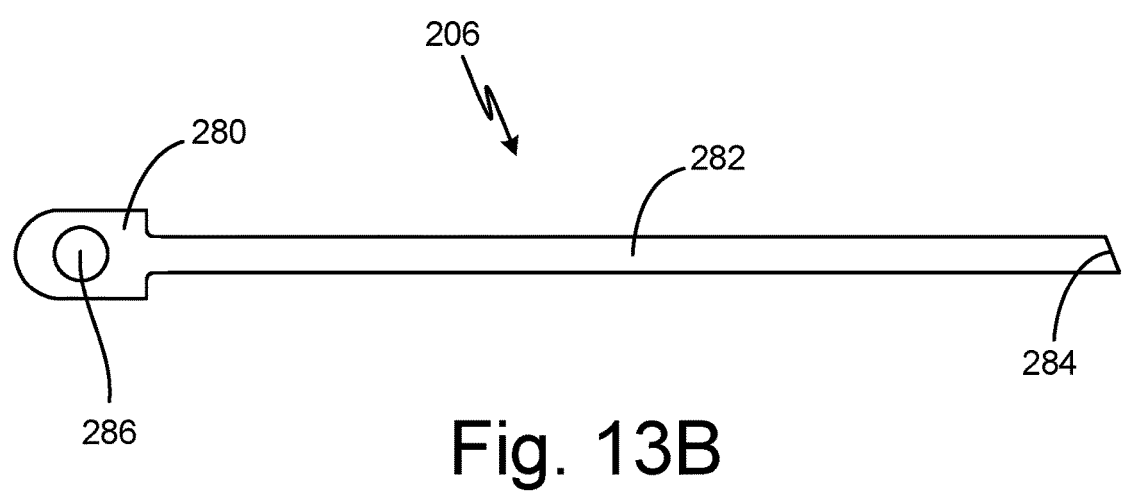
FIG. 13B is a side view of the blade of the surgical instrument.

FIG. 13A is a perspective view of blade 206 of surgical instrument 200. FIG. 13B is a side view of blade 206 of surgical instrument 200. Blade 206 includes base 280, shaft 282, tip 284, and opening 286.

Blade 206 includes base 280, shaft 282, and tip 284. Base 280 forms a back end of blade 206. A back end of shaft 282 is connected to base 280. Tip 284 is connected to a front end of shaft 282. Tip 284 is a blade tip. Blade 206 also includes opening 286 that extends through base 280 of blade 206. Opening 286 is configured to receive screw 210 of surgical instrument 200 (shown in FIGS. 10A-10B) to mount blade 206 in surgical instrument 200.

Figure 14A:
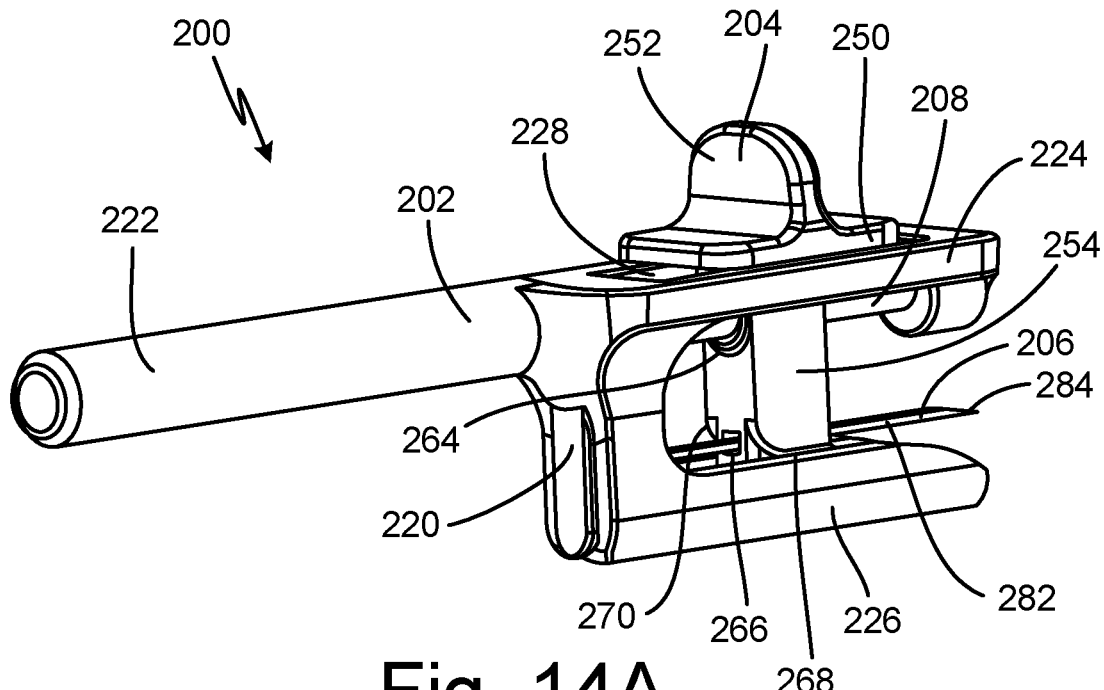
FIG. 14A is a perspective view of the surgical instrument in a second position.
Figure 14B:
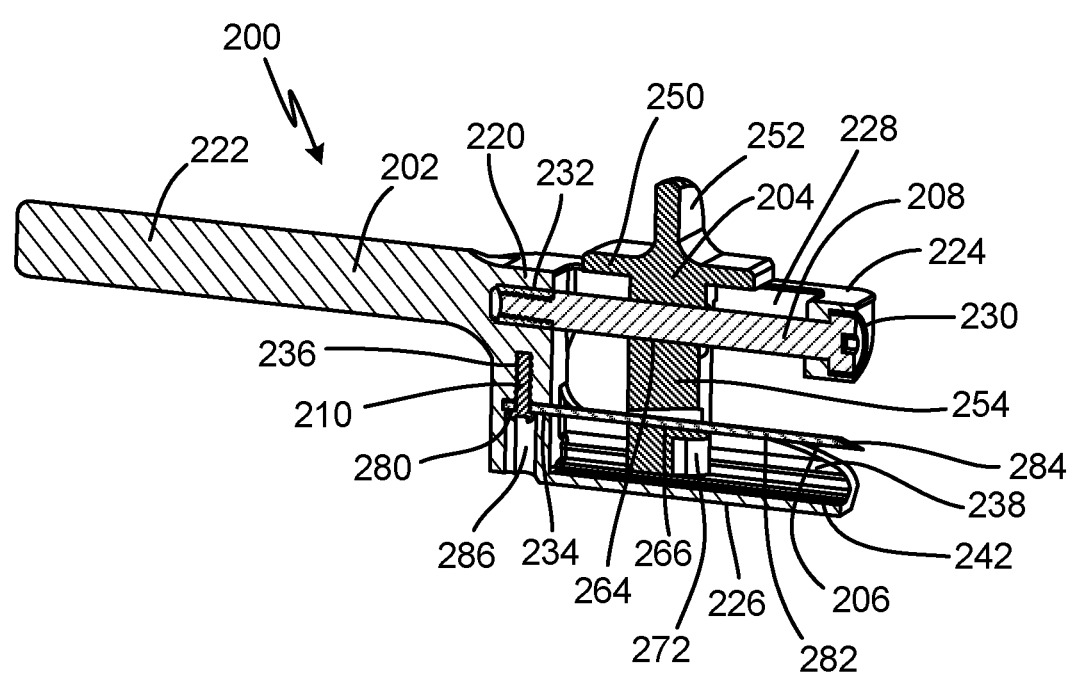
FIG. 14B is a cross-sectional view of the surgical instrument in a second position.
Method 300

FIG. 14A is a perspective view of surgical instrument 200. FIG. 14B is a cross-sectional view of surgical instrument 200. Surgical instrument 200 includes body 202, slider 204, blade 206, bolt 208, and screw 210. Body 202 includes base 220, handle 222, upper arm 224, lower arm 226, slider slot 228, bolt aperture 230, bolt aperture 232, blade slot 234, screw aperture 236, guide track 238, guide track 240, and prong track 242. Slider 204 includes base 250, knob 252, shaft 254, first guide 256, second guide 258, third guide 260, fourth guide 262, bolt aperture 264, blade slot 266, first shoulder 268, second shoulder 270, and device notch 272. Blade 206 includes base 280, shaft 282, tip 284, and opening 286.

Surgical instrument 200 includes body 202, slider 204, blade 206, bolt 208, and screw 210. Body 202 is described in reference to FIGS. 11A-11D above. Slider 204 is described in reference to FIGS. 12A-12D above. Blade 206 is described in reference to FIGS. 13A-13B above.

Slider 204 is positioned in and is capable of sliding in slider slot 228 of body 202 of surgical instrument 200. Base 250 of slider 204 slides along on upper arm 224 of body 202 as slider 204 slides through slider slot 228 of body 202. Bolt 208 extends through bolt aperture 230 in body 202, bolt aperture 264 in slider 204, and into bolt aperture 232 in body 202. Slider 204 can slide along bolt 208 as it slides through slider slot 228 of body 202. In an alternate embodiment, bolt 208 can be a shaft or any other suitable mechanism upon which slider 204 can slide. Further, blade 206 extends through blade slot 266 of slider 204. Slider 204 can slide along blade 206 as it slides through slider slot 228 of body 202. Slider 204 also includes first shoulder 268 and second shoulder 270 that abut and slide along upper sides of lower arm 226 as slider 204 slides through slider slot 228 of body 202.

Slider 204 is a mechanism that can be manually pushed by a surgeon to deploy a device pre-loaded in surgical instrument 200 out of surgical instrument 200. In an alternate embodiment, slider 204 can be automatic and the device pre-loaded in surgical instrument 200 can be automatically deployed out of surgical instrument 200.

Blade 206 is positioned in and mounted to body 202 of surgical instrument 200. Base 150 of blade 206 is positioned in blade slot 234 of body 202 so that opening 286 in base 150 of blade 206 is aligned with screw aperture 236 in body 202. Screw 210 can be inserted through opening 286 in base 280 of blade 206 and then screwed into screw aperture 236 of body 202 to mount blade 206 to body 202 of surgical instrument 200. When blade 206 is mounted in surgical instrument 202, tip 284 of blade 206 will extend past a front end of surgical instrument 200 so that a surgeon can use tip 284 of blade 206 to cut through tissue in a patient. In an alternate embodiment, blade 206 can include a blunt edge that a surgeon can use to ensure that a pocket that is created for subcutaneous device 100 is a correct width and depth.

Surgical instrument 200 can be used to implant subcutaneous device 100 in a patient. Slider 204 of surgical instrument 200 acts as an injection mechanism to inject subcutaneous device 100 onto a bone, a muscle, or a tissue of a patient. When surgical instrument 200 is positioned adjacent to the bone, the muscle, or the tissue, a surgeon pushes slider 204 of surgical instrument 200 forward to inject subcutaneous device 100 onto the bone, the muscle, or the tissue. A method for injecting the subcutaneous device 100 onto the bone, the muscle, or the tissue is described in greater detail below with reference to FIGS. 15-19.

Method 300

Figure 15:
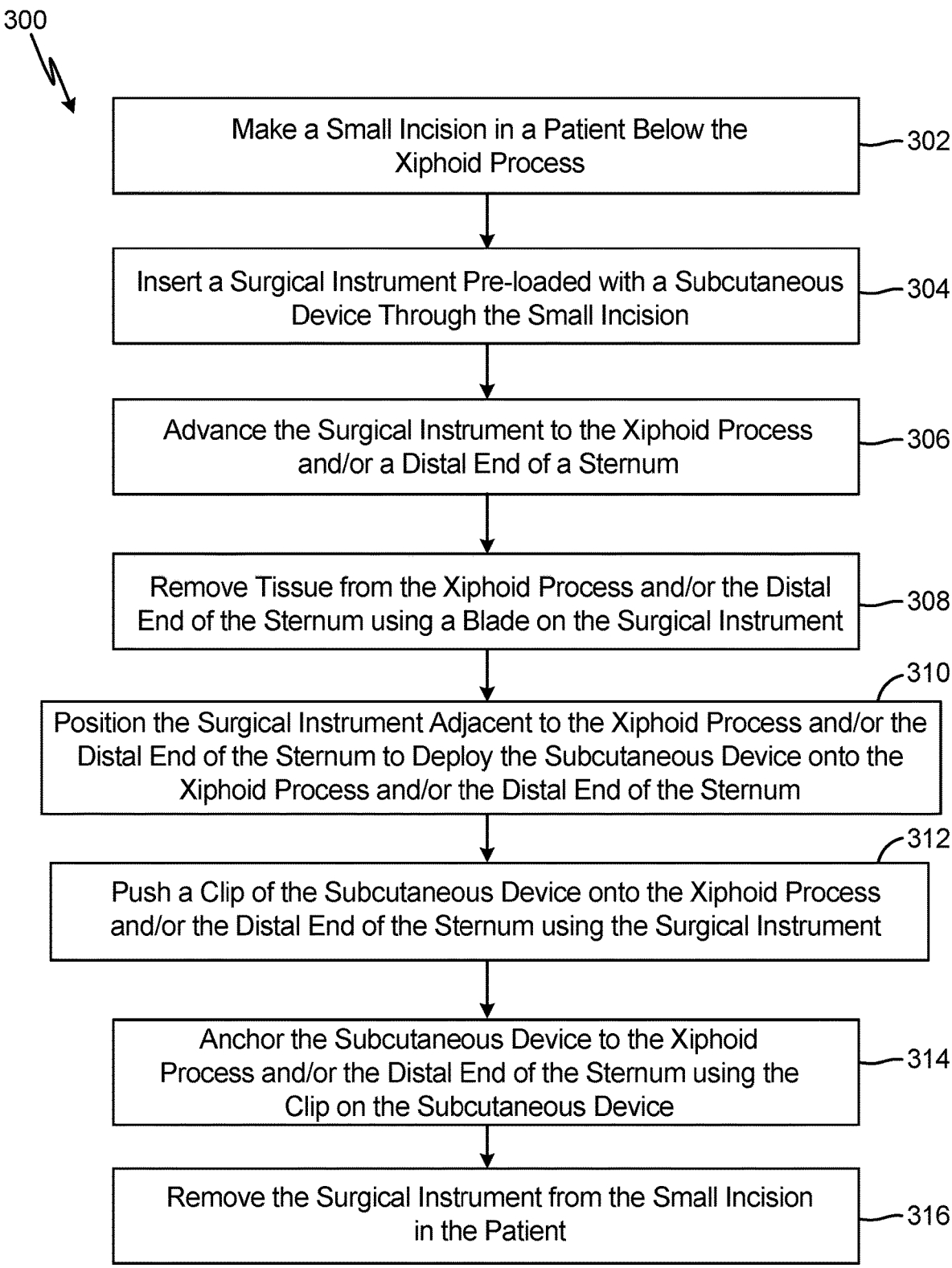
FIG. 15 is a flow chart showing the method for implanting the first embodiment of the subcutaneous device using the surgical instrument.
Figure 16A:
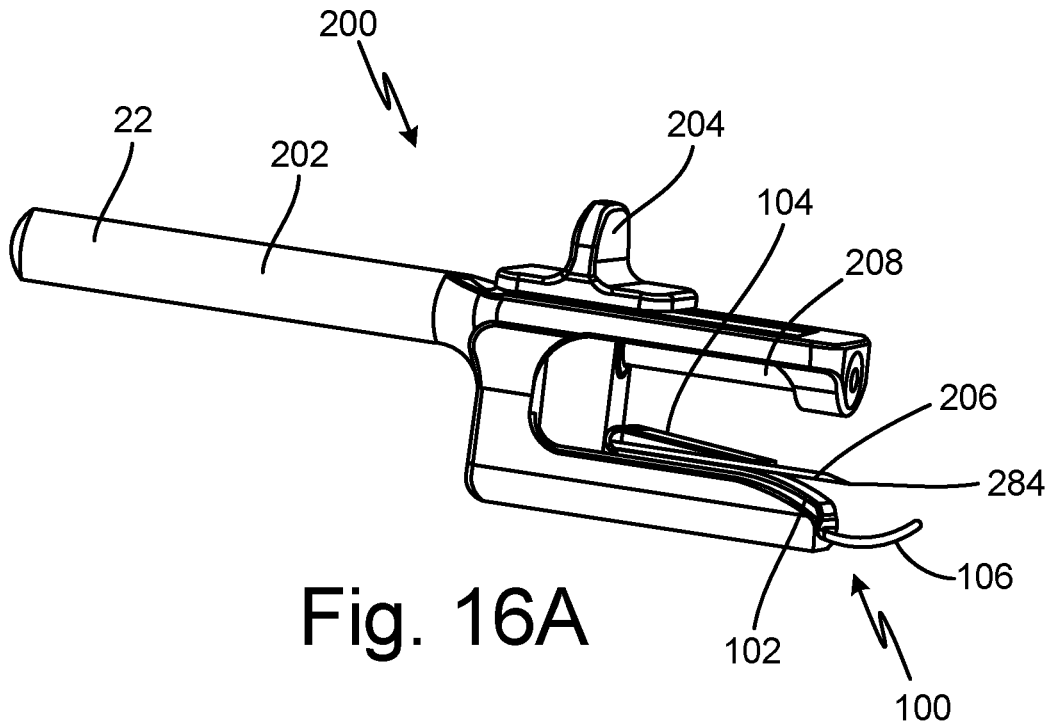
FIG. 16A is a perspective view of the first embodiment of the subcutaneous device in a first position in the surgical instrument.
Figure 16B:
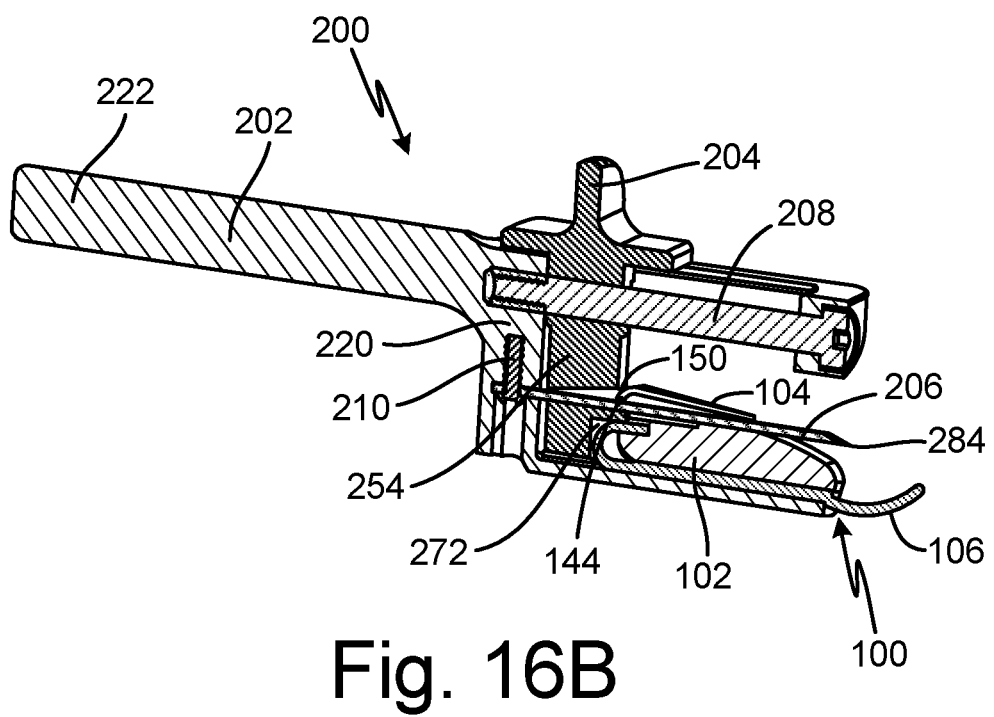
FIG. 16B is a cross-sectional view of the first embodiment of the subcutaneous device in the first position in the surgical instrument.
Figure 17A:
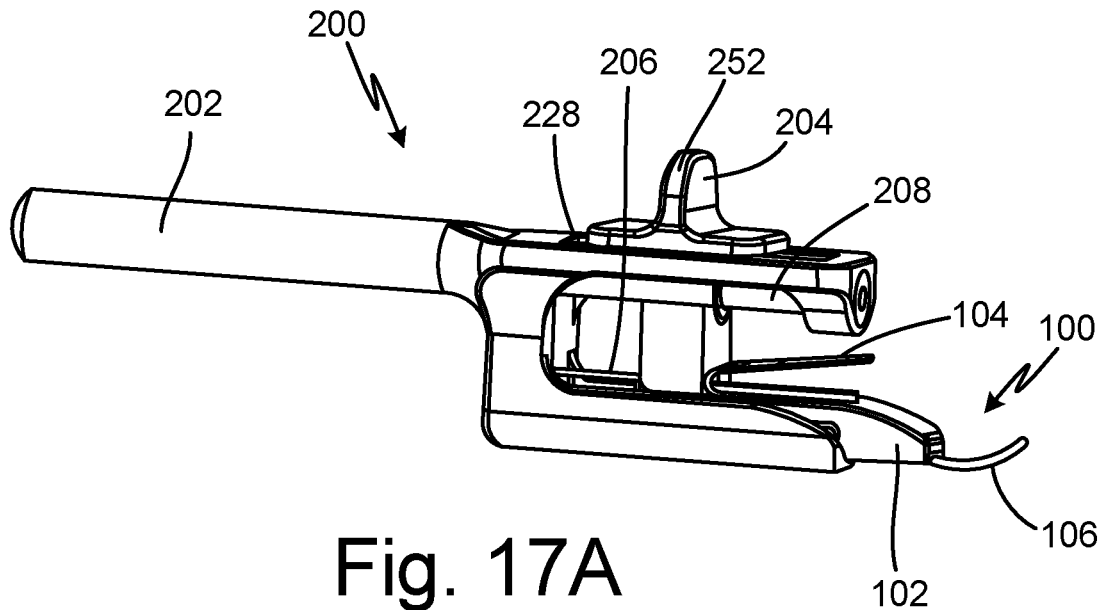
FIG. 17A is a perspective view of the first embodiment of the subcutaneous device in a second position in the surgical instrument as the subcutaneous device is being implanted.
Figure 17B:
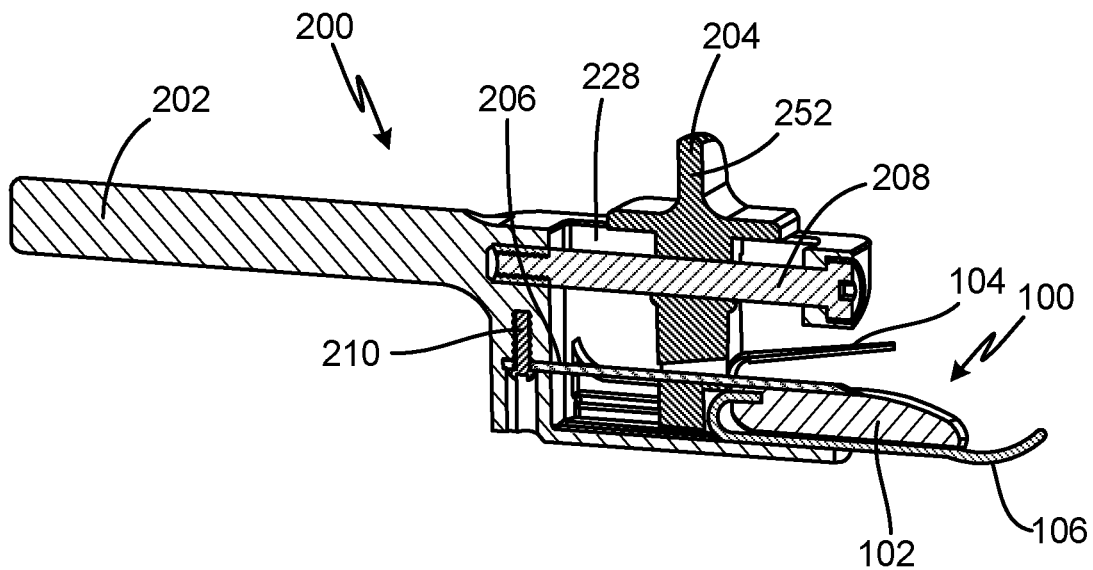
FIG. 17B is a cross-sectional view of the first embodiment of the subcutaneous device in the second position in the surgical instrument as the subcutaneous device is being implanted.
Figure 17C:
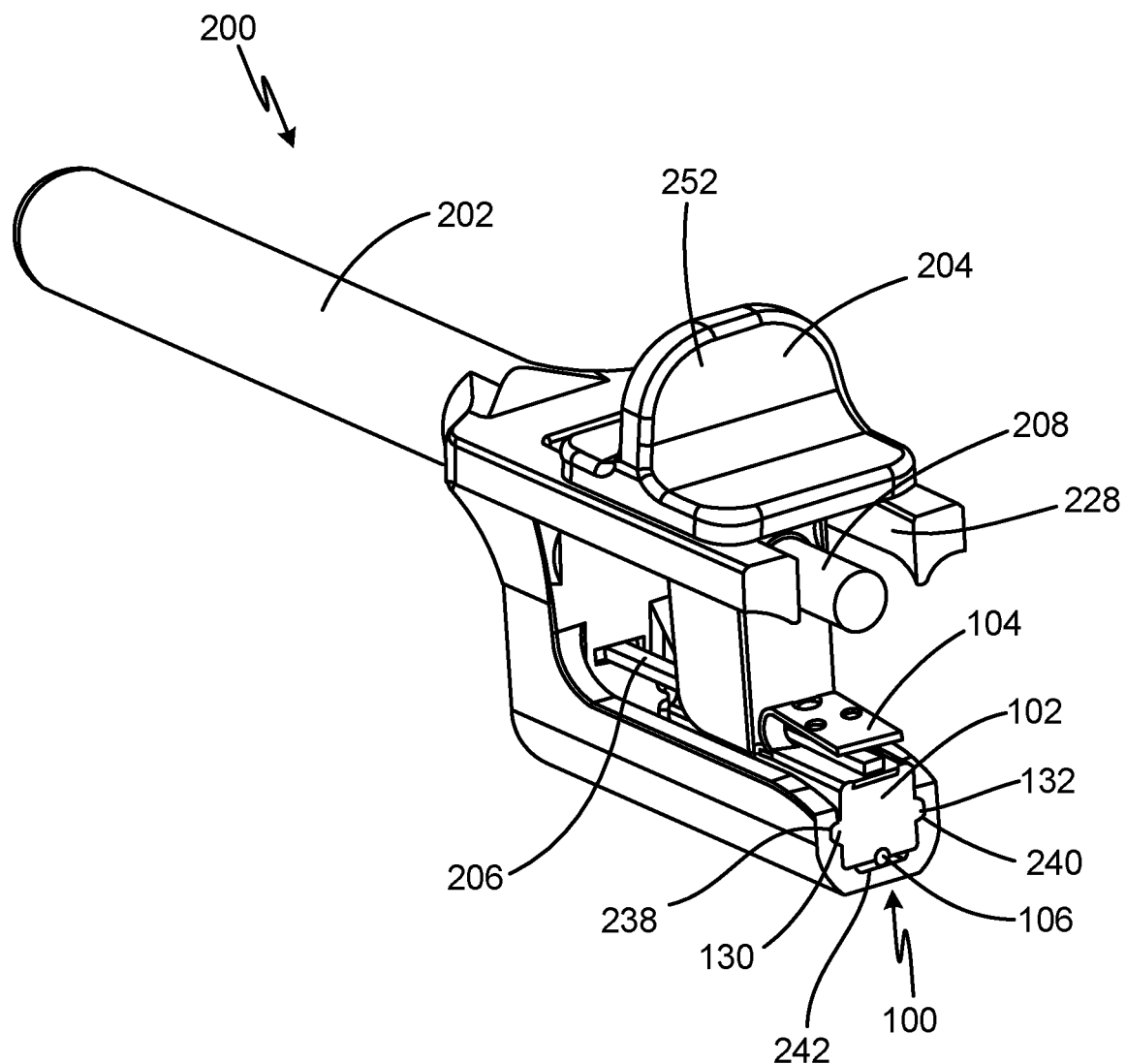
FIG. 17C is a cross-sectional view of the first embodiment of the subcutaneous device in the second position in the surgical instrument as the subcutaneous device is being implanted.
Figure 18A:
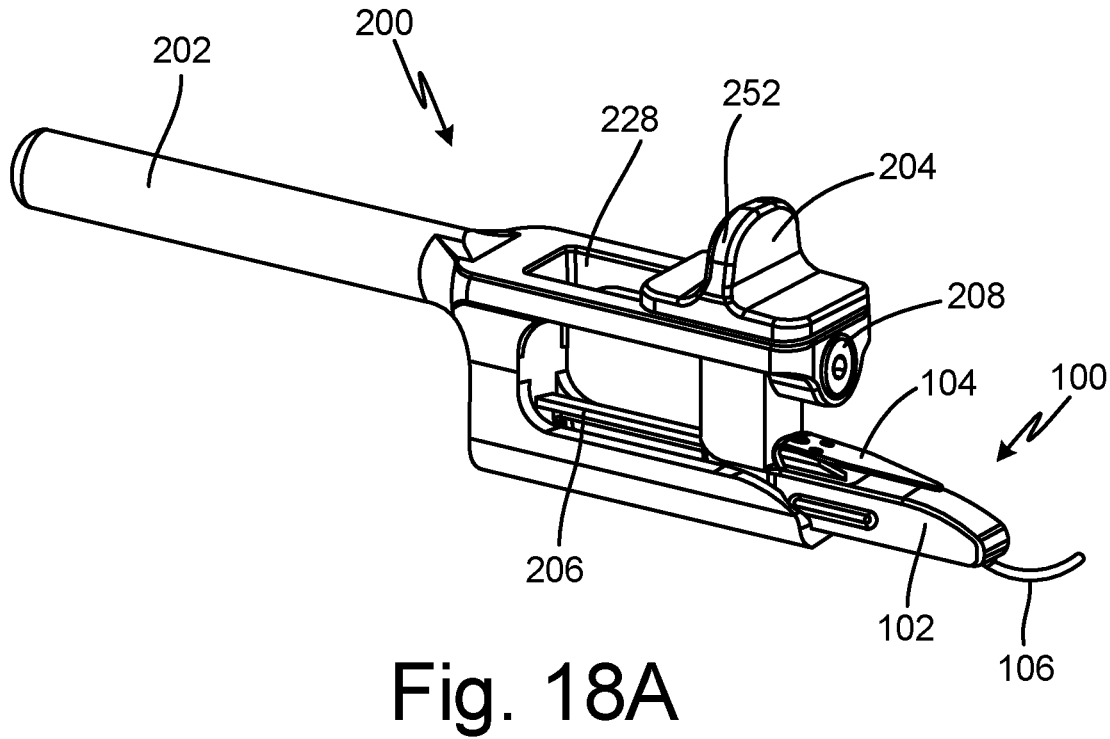
FIG. 18A is a perspective view of the first embodiment of the subcutaneous device in a third position in the surgical instrument as the subcutaneous device is being implanted.
Figure 18B:
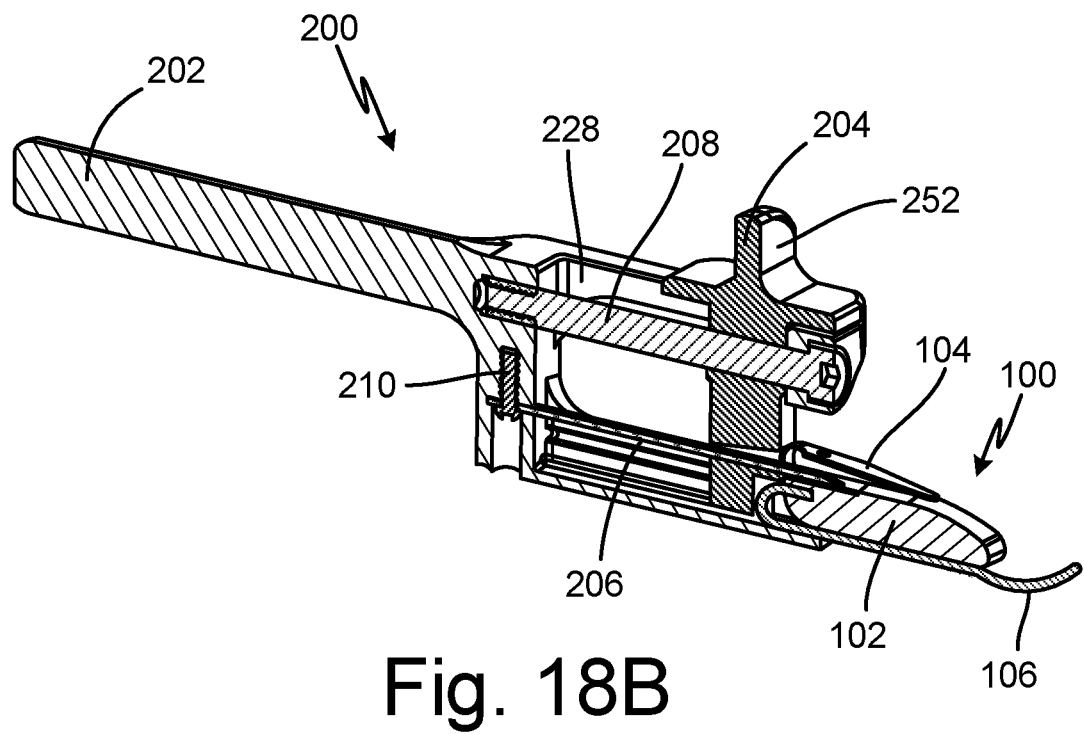
FIG. 18B is a cross-sectional view of the first embodiment of the subcutaneous device in the third position in the surgical instrument as the subcutaneous device is being implanted.
Figure 19:
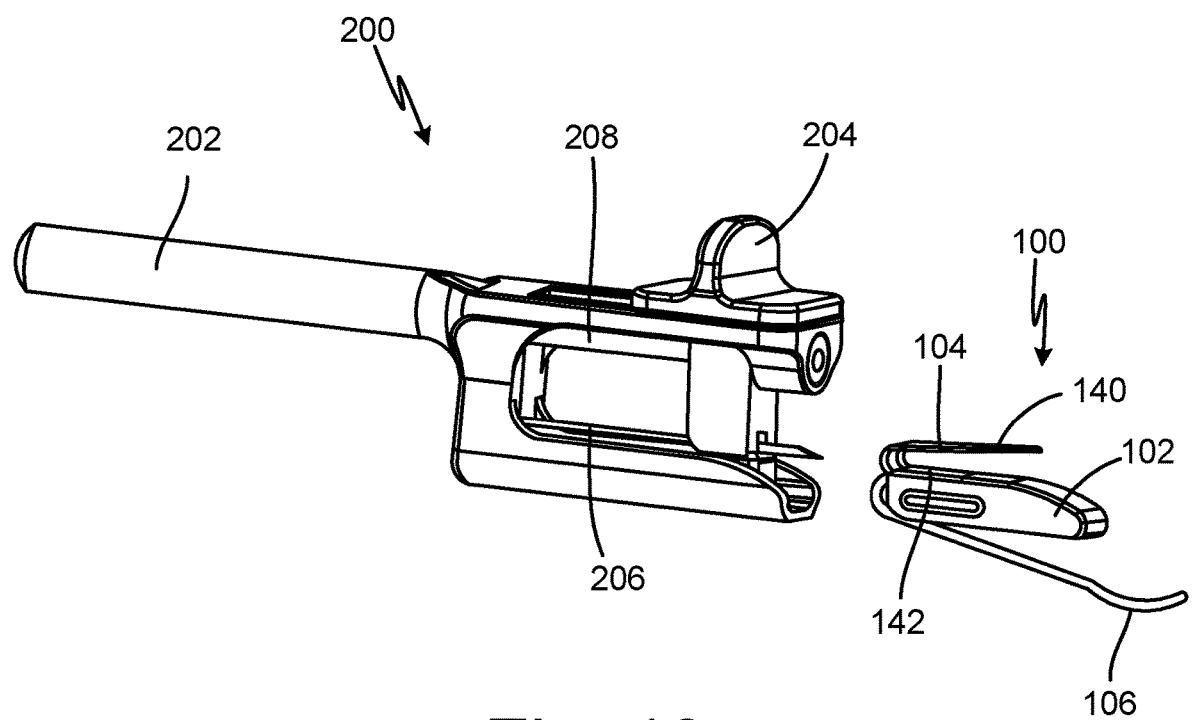
FIG. 19 is a perspective view of the first embodiment of the subcutaneous device after it has been deployed from the surgical instrument.
Subcutaneous Device 400

FIG. 15 is a flow chart showing method 300 for implanting subcutaneous device 100 using surgical instrument 200. FIGS. 16A-19 show subcutaneous device 100 at different positions in surgical instrument 200 as subcutaneous device 100 is being implanted with surgical instrument 200. FIG. 16A is a perspective view of subcutaneous device 100 in a first position in surgical instrument 200. FIG. 16B is a cross-sectional view of subcutaneous device 100 in the first position in surgical instrument 200. FIG. 17A is a perspective view of subcutaneous device 100 in a second position in surgical instrument 200 as the subcutaneous device is being implanted. FIG. 17B is a cross-sectional view of subcutaneous device 100 in the second position in surgical instrument 200 as subcutaneous device 100 is being implanted. FIG. 17C is a cross-sectional view of subcutaneous device 100 in the second position in surgical instrument 200 as subcutaneous device 100 is being implanted. FIG. 18A is a perspective view of subcutaneous device 100 in a third position in surgical instrument 200 as subcutaneous device 100 is being implanted. FIG. 18B is a cross-sectional view of subcutaneous device 100 in the third position in surgical instrument 200 as subcutaneous device 100 is being implanted. FIG. 19 is a perspective view of subcutaneous device 100 after it has been deployed from surgical instrument 200. Subcutaneous device 100 includes housing 102, clip 104, and prong 106. Clip 104 includes top portion 140, bottom portion 142, spring portion 144, and slot 150. Prong 106 includes spring portion 144. Surgical instrument 200 includes body 202, slider 204, blade 206, bolt 208, and screw 210. Body 202 includes base 220, handle 222, and slider slot 228. Slider 204 includes shaft 254 and knob 252. Blade 206 includes tip 284. Method 300 includes steps 302-314.

Method 300 is described here in relation to implanting subcutaneous device 100 (shown in FIGS. 1-9) on a xiphoid process and a sternum of a patient. However, method 300 can be used to implant any suitable medical device (including any of subcutaneous devices 400, 500, 600, 700, 800, 900, 1000, 1100, 1200, 1300, 1400, and 1500 shown in FIGS. 20-37) on any bone, muscle, or tissue in a patient. Further, method 300 is described here in relation to using surgical instrument 200 (shown in FIGS. 10A-14B) to implant subcutaneous device 100. However, any suitable surgical instrument 200 can be used to implant subcutaneous device 100.

Step 302 includes making a small incision in a patient below a xiphoid process. The patient may be under local or general anesthesia. A surgeon can make a small incision through the skin right below the xiphoid process using a scalpel.

Step 304 includes inserting surgical instrument 200 through the small incision. Surgical instrument 200 will be pre-loaded with subcutaneous device 100 when it is inserted through the small incision, as shown in FIGS. 16A-16B. When surgical instrument 200 is pre-loaded with subcutaneous device 100, surgical instrument 200 will be in a first position. In the first position, shaft 254 of slider 204 of surgical instrument 200 will abut base 220 of body 202 of surgical instrument 200. Subcutaneous device 100 is loaded into surgical instrument 200 so that a front end of subcutaneous device 100 is aligned with a front end of surgical instrument 200. A back end of subcutaneous device 100 will abut slider 204 of surgical instrument 200. Spring portion 144 of clip 104 of subcutaneous device 100 will be positioned in device notch 272 of slider 204 of surgical instrument 200. First guide 130 and second guide 132 of housing 102 of subcutaneous device 100 sit in guide track 238 and guide track 240 of body 202 of surgical instrument 200, respectively. Blade 206 of surgical instrument 200 will extend through slot 150 of clip 104 of subcutaneous device 100. Tip 284 of blade 206 will extend past a front end of subcutaneous device 100, allowing tip 284 of blade 206 to be used to cut tissue in the patient.

Step 306 includes advancing surgical instrument 200 to the xiphoid process and a distal end of the sternum. A surgeon who is holding handle 222 of body 202 of surgical instrument 200 can move surgical instrument 200 into and through the patient. The surgeon can manipulate surgical instrument 200 to use tip 284 of blade 206 of surgical instrument 200 to cut tissue in the patient to provide a pathway to the xiphoid process and the distal end of the sternum.

Step 308 includes removing tissue from the xiphoid process and a distal end of the sternum using blade 206 of surgical instrument 200. A surgeon can manipulate surgical instrument 200 to use tip 284 of blade 206 of surgical instrument 200 to scrape tissue on the xiphoid process and the distal end of the sternum off to expose the xiphoid process and the distal end of the sternum. In an alternate embodiment, a surgeon can use a scalpel or other surgical instrument to scrape tissue off of the xiphoid process and the distal end of the sternum.

Step 310 includes positioning surgical instrument 200 to deploy subcutaneous device 100 onto the xiphoid process and the distal end of the sternum. After the xiphoid process and the distal end of the sternum have been exposed, the surgeon can position surgical instrument 200 in the patient so that blade 206 of surgical instrument 200 is positioned to abut the top side of the xiphoid process and the distal end of the sternum. In this position, prong 206 of subcutaneous device 100 will be positioned beneath the xiphoid process and the distal end of the sternum. Further, the surgeon can adjust the position of subcutaneous device 100 with surgical instrument 200 to ensure that prong 106 has good contact with the pericardium, fat, muscle, or tissue.

Step 312 includes pushing subcutaneous device 100 onto the xiphoid process and the distal end of the sternum using surgical instrument 200. Subcutaneous device 100 is pushed out of surgical instrument 200 and onto the xiphoid process and the distal end of the sternum by pushing slider 204 of surgical instrument 200. FIGS. 17A-17C show surgical instrument 200 in a second position. In the second position, slider 204 of surgical instrument 200 has been pushed halfway through slider slot 228 of body 202 of surgical instrument 200. Further, in the second position, subcutaneous device 100 is pushed partially out of surgical instrument 200. FIGS. 18A-18B show surgical instrument 200 in a third position. In the third position, slider 204 of surgical instrument 200 has been pushed to the front end slider slot 228 of body 202 of surgical instrument 200. Further, in the third position, subcutaneous device 100 is pushed almost fully out of surgical instrument 100.

The surgeon will push knob 252 of slider 204 of surgical instrument 200 along slider slot 228 of body 202 of surgical instrument 200. As slider 204 is pushed through surgical instrument 200, subcutaneous device 100 is pushed out of surgical instrument 200. As subcutaneous device 100 is pushed out of surgical instrument 200, first guide 130 and second guide 132 of housing 102 of subcutaneous device 100 slide along guide track 238 and guide track 240 of body 202 of surgical instrument 200, respectively, as shown in FIG. 17C. As subcutaneous device 100 is pushed out of surgical instrument 200, subcutaneous device 100 will be pushed on the xiphoid process and the distal end of the sternum of the patient. In an alternate embodiment, surgical instrument 200 can be configured to automatically advance subcutaneous device 100 out of surgical instrument 200 and onto the xiphoid process and the distal end of the sternum.

Step 314 includes anchoring subcutaneous device 100 onto the xiphoid process and the distal end of the sternum. As subcutaneous device 100 is pushed out of surgical instrument 200, top portion 140 of clip 104 of subcutaneous device 100 will be pushed on top of the xiphoid process and the distal end of the sternum, and bottom portion 142 of clip 104, housing 102, and prong 106 of subcutaneous device 100 will be pushed underneath the xiphoid process and the distal end of the sternum. Subcutaneous device 100 will be pushed onto the xiphoid process and the distal end of the sternum until spring portion 144 of clip 104 of subcutaneous device 100 abuts the xiphoid process. The tension in spring portion 144 of clip 104 of subcutaneous device 100 will force top portion 140 of clip 104 of subcutaneous device 100 down onto the xiphoid process and the distal end of the sternum. This tension will anchor subcutaneous device 100 onto the xiphoid process and the distal end of the sternum.

When subcutaneous device 100 is stowed in surgical instrument 200, prong 106 of subcutaneous device 100 is positioned in channel 128 of housing 102 of subcutaneous device 100. When subcutaneous device 100 is deployed and anchored to the xiphoid process and the distal end of the sternum, spring portion 166 of prong 106 will push arm portion 168 and contact portion 170 downwards and away from housing 102. As subcutaneous device 100 is implanted onto the xiphoid process and the distal end of the sternum, prong 106 will push through tissue in the anterior mediastinum. When subcutaneous device 100 is implanted on the xiphoid process and the distal end of the sternum, contact portion 170 of prong 106 should be positioned on the right ventricle of the heart. A surgeon can check and adjust the placement of prong 106 as needed during implantation of subcutaneous device 100.

Step 316 includes removing surgical instrument 200 from the small incision in the patient. After subcutaneous device 100 has been anchored onto the xiphoid process and the distal end of the sternum, surgical instrument 200 can be removed from the small incision in the patient, as shown in FIG. 19. When surgical instrument 200 is removed, subcutaneous device 100 will remain anchored to the xiphoid process and the distal end of the sternum.

Subcutaneous device 100 remains anchored to the xiphoid process and the distal end of the sternum due to the tension being put on top portion 140 of clip 104 from spring portion 144 of clip 104. The tension of clip 104 will hold subcutaneous device 100 in position on the xiphoid process and the distal end of the sternum, with little risk that subcutaneous device 100 will move. Two to four weeks post-surgery, fibrosis will begin to develop around subcutaneous device 100. The fibrosis that develops around subcutaneous device 100 will further hold subcutaneous device 100 in position in the patient.

If subcutaneous device 100 needs to be removed from the patient within two to four weeks post-surgery and before fibrosis has formed around subcutaneous device 100, a surgeon can make a small incision below the xiphoid process and insert an instrument through the small incision to pull subcutaneous device 100 out of the patient. The instrument will lift top portion 140 of clip 104 of subcutaneous device 100 and pull clip 104 of subcutaneous device 100 off of the xiphoid process and the distal end of the sternum, thus removing subcutaneous device 100 from the patient. The instrument that is used to remove subcutaneous device 100 can be the same instrument used to insert subcutaneous device 100 or a separate instrument.

If subcutaneous device 100 needs to be removed from the patient after fibrosis has formed around subcutaneous device 100, a surgeon can use a scalpel and other surgical instruments to cut through the skin, tissue, and fibrosis to access subcutaneous device 100. The surgeon can then use any suitable instrument to remove subcutaneous device 100 from the patient.

Method 300 is a non-invasive surgery. Leads are not implanted in the vasculature of the patient using invasive techniques. Rather, subcutaneous device 100 is anchored to the xiphoid process and the distal end of the sternum using surgical instrument 200 and prong 106 extends through the anterior mediastinum and comes into contact with the heart. This lowers the risk of infection, complications during surgery, and potential failure of the device. Method 300 can be used to implant subcutaneous device 300 on any bone, muscle, or tissue in the body of a patient. In an alternate embodiment, any suitable method, including traditional surgical methods, and any suitable instrument can be used to implant subcutaneous device 100.

FIGS. 20-37 below show different embodiments of subcutaneous device 100. These embodiments are intended to be exemplary. Subcutaneous device 100 can have any suitable design and function. Each of the embodiments shown in FIGS. 20-37 below can be implanted into the patient using surgical instrument 200 shown in FIGS. 10A-14B and/or using method 300 shown in FIGS. 15-19. As shown in the different embodiments of subcutaneous device 100 shown in FIGS. 20-37 below, subcutaneous device 100 can include any suitable number of prongs 106. Prongs 106 can have any suitable length and shape to be positioned and/or come into contact with various organs, nerves, and tissues in the patient's body. Further, subcutaneous device 100 can function as a monitoring device, a diagnostic device, a pacemaker device, a defibrillator device, or any combinations thereof.

Subcutaneous Device 400

Figure 20:
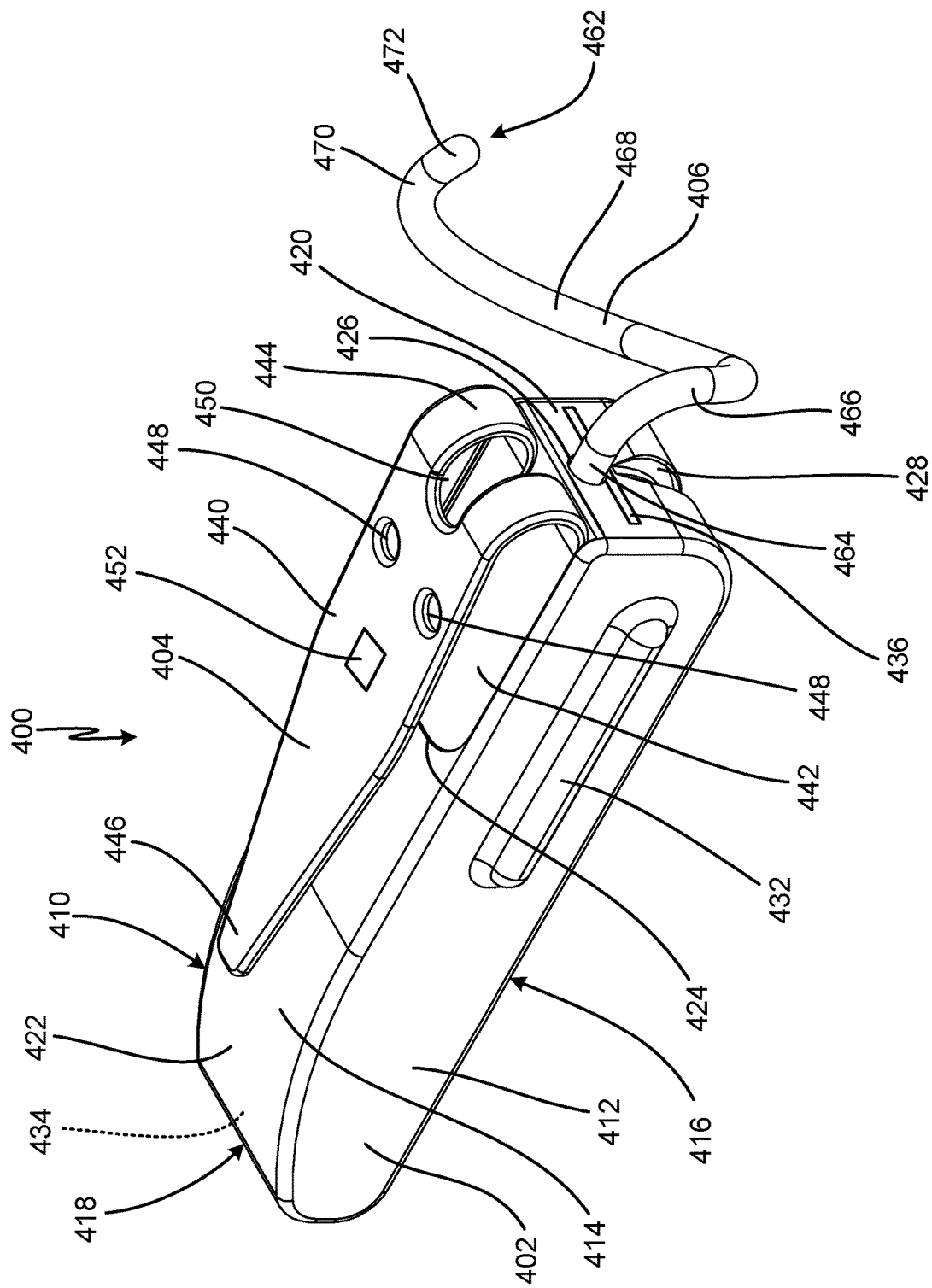
FIG. 20 is a perspective view of a second embodiment of a subcutaneous device.

FIG. 20 is a perspective view of subcutaneous device 400. Subcutaneous device 400 includes housing 402, clip 404, and prong 406. Housing 402 includes first side 410, second side 412, top side 414, bottom side 416, front end 418, back end 420, curved surface 422, recess 424, port 426, channel 428, first guide 430 (not shown in FIG. 20), second guide 432, electrode 434, and electrode 436. Clip 404 includes top portion 440, bottom portion 442, spring portion 444, tip 446, openings 448, slot 450, and electrode 452. Prong 406 includes proximal end 460 (not shown in FIG. 20), distal end 462, base portion 464, spring portion 466, arm portion 468, contact portion 470, and electrode 472.

Subcutaneous device 400 includes housing 402, clip 404, and prong 406. Housing 402 has the same general structure and design as housing 102 of subcutaneous device 100 shown in FIGS. 1-9C. Clip 404 has the same general structure and design as clip 104 of subcutaneous device 100 shown in FIGS. 1-9C. The reference numerals that refer to the parts of housing 402 and clip 404 are incremented by three-hundred compared to the reference numerals that refer to the parts of housing 102 and clip 104 of subcutaneous device 100 shown in FIGS. 1-9C.

Prong 406 includes the same parts as prong 106 of subcutaneous device 100 as shown in FIGS. 1-9C, and the reference numerals that refer to the parts of prong 406 are incremented by three-hundred compared to the reference numerals that refer to the parts of prong 106 of subcutaneous device 100 shown in FIGS. 1-9C. However, prong 406 has a different shape. Spring portion 466 and arm portion 468 extend away from first side 410 of housing 402. Contact portion 470 is a portion of prong 406 adjacent to distal end 462 of prong 406 that is configured to come into contact with a left ventricle of a patient's heart. Electrode 472 positioned on contact portion 470 will also come into contact with a left ventricle of a patient's heart.

In one example, subcutaneous device 400 can be anchored to a xiphoid process and a sternum of a patient. Clip 404 is configured to anchor subcutaneous device 400 to the xiphoid process and the sternum. Clip 404 will expand as it is slid around the xiphoid process and the sternum. Spring portion 444 acts as a spring for clip 404 and is under tension. Top portion 440 acts as a tension arm and the forces from spring portion 444 translate to and push down on top portion 440. When clip 404 is positioned on the xiphoid process and the sternum, the tension in spring portion 444 will force top portion 440 down onto the xiphoid process and the sternum to anchor clip 404 to the xiphoid process and the sternum. Further, sutures, tines, pins, or screws can be inserted through openings 448 on top portion 440 of clip 404 to further anchor subcutaneous device 400 to the xiphoid process and the sternum.

Subcutaneous device 400 can include a power source, a controller, a memory, a transceiver, sensors, sensing circuitry, therapeutic circuitry, electrodes, and/or any other component of a medical device. In the embodiment shown in FIG. 20, subcutaneous device 400 is configured to be a single chamber pacemaker. Any one or combination of electrode 434, electrode 436, electrode 452, and electrode 472 can sense the electrical activity of a heart. The sensed electrical activity can be transmitted to the sensing circuitry and the controller in housing 402 of subcutaneous device 400. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the left ventricle. In this manner, subcutaneous device 400 functions as a monitoring device, a diagnostic device, and a therapeutic device. In alternate embodiments, subcutaneous device 400 can function only as a monitoring device, a diagnostic device, a therapeutic device, or any combinations thereof.

Subcutaneous Device 500

Figure 21A:
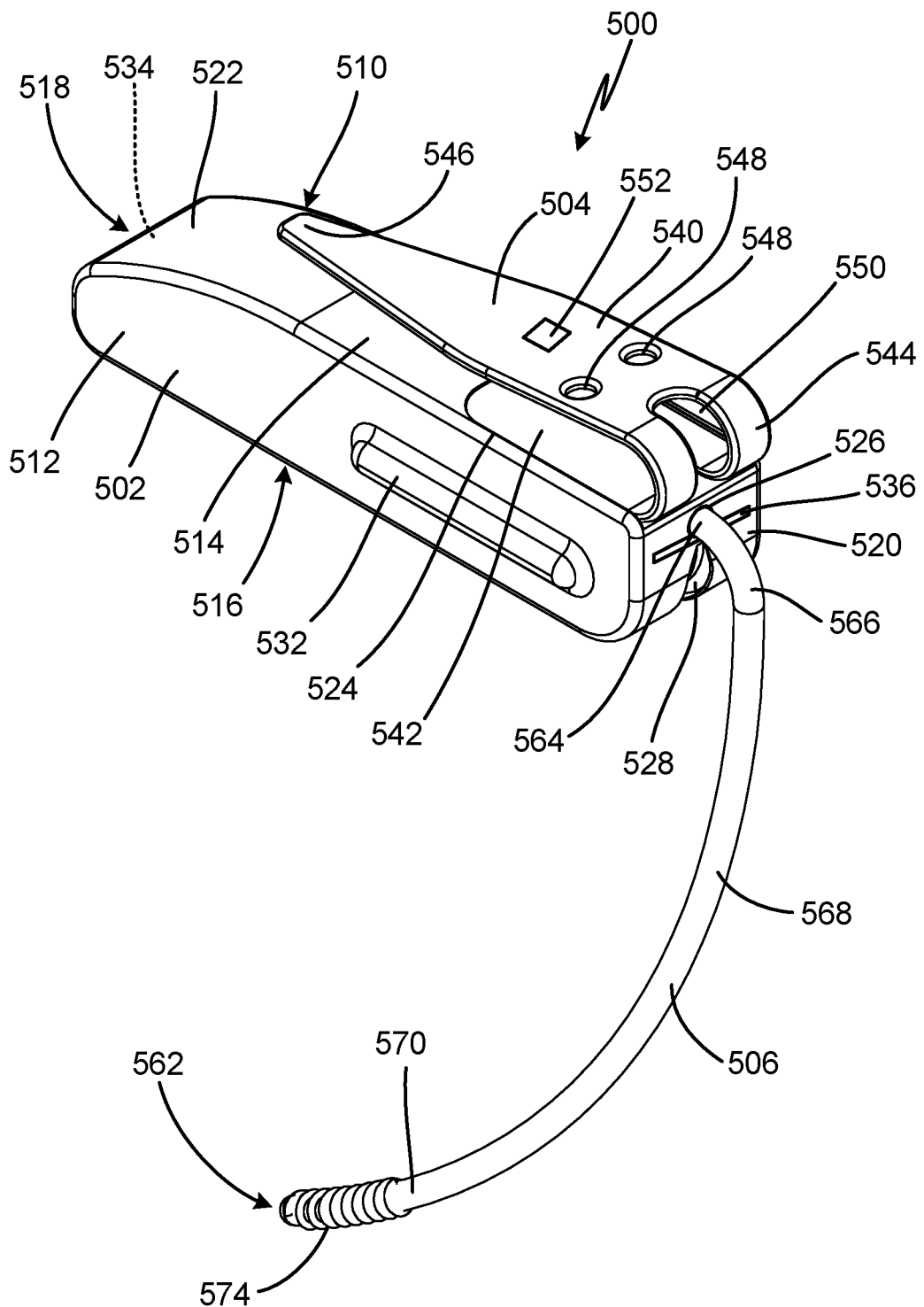
FIG. 21A is a perspective view of a third embodiment of a subcutaneous device.
Figure 21B:
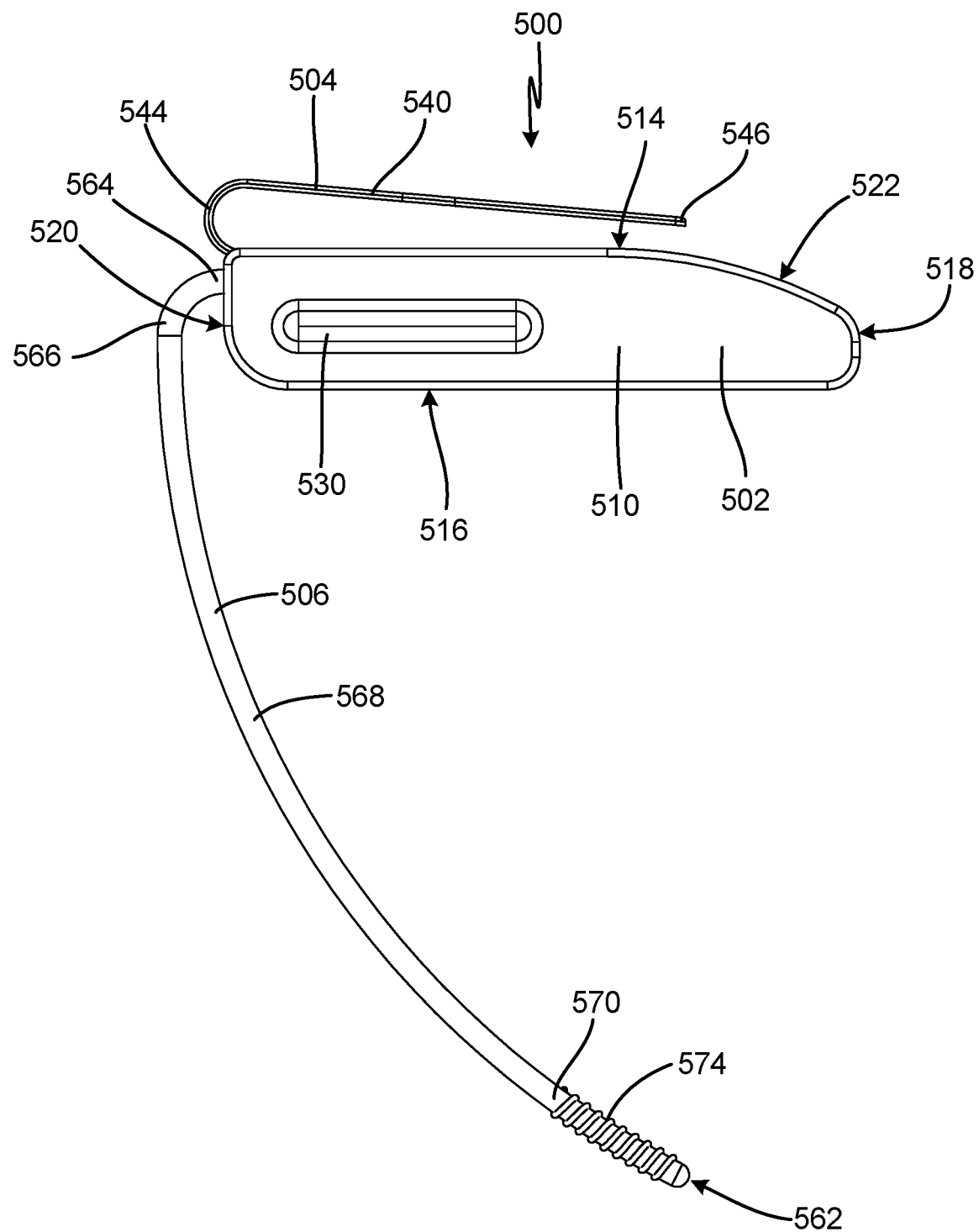
FIG. 21B is a side view of the third embodiment of the subcutaneous device.
Subcutaneous Device 600

FIG. 21A is a perspective view of subcutaneous device 500. FIG. 21B is a side view of subcutaneous device 500. Subcutaneous device 500 includes housing 502, clip 504, and prong 506. Housing 502 includes first side 510, second side 512, top side 514, bottom side 516, front end 518, back end 520, curved surface 522, recess 524, port 526, channel 528, first guide 530, second guide 532, electrode 534, and electrode 536. Clip 504 includes top portion 540, bottom portion 542, spring portion 544, tip 546, openings 548, slot 550, and electrode 552. Prong 506 includes proximal end 560 (not shown in FIGS. 21A-21B), distal end 562, base portion 564, spring portion 566, arm portion 568, contact portion 570, and defibrillator coil 574.

Subcutaneous device 500 includes housing 502, clip 504, and prong 506. Housing 502 has the same general structure and design as housing 102 of subcutaneous device 100 shown in FIGS. 1-9C. Clip 504 has the same general structure and design as clip 104 of subcutaneous device 100 shown in FIGS. 1-9C. The reference numerals that refer to the parts of housing 502 and clip 504 are incremented by four-hundred compared to the reference numerals that refer to the parts of housing 102 and clip 104 of subcutaneous device 100 shown in FIGS. 1-9C.

Prong 506 generally includes the same parts as prong 106 of subcutaneous device 100 as shown in FIGS. 1-9C, and the reference numerals that refer to the parts of prong 506 are incremented by four-hundred compared to the reference numerals that refer to the parts of prong 106 of subcutaneous device 100 shown in FIGS. 1-9C. However, prong 406 has a different shape and includes defibrillator coil 574 instead of an electrode at distal end 562. Spring portion 566 and arm portion 568 extend away from bottom side 520 of housing 502. Contact portion 570 is a portion of prong 506 adjacent to distal end 562 of prong 506 that is configured to come into contact with tissue inferior to a patient's heart. Defibrillator coil 574 is positioned on contact portion 570 adjacent to distal end 562 of prong 506. When an electrical signal is delivered to defibrillator coil 574, defibrillator coil 574 will create a vector with electrode 534 on front end 518 of housing 502. In the embodiment shown, defibrillator coil 574 serves as the negative electrode and electrode 534 serves as the positive electrode. However, in alternate embodiments this can be reversed. Prong 506 is positioned so that distal end 562, and thus contact portion 570 and defibrillator coil 574, are positioned inferior to the heart. Thus, the vector created between defibrillator coil 574 and electrode 534 will pass through a patient's heart to provide a high voltage electrical shock to the patient's heart.

In one example, subcutaneous device 500 can be anchored to a xiphoid process and a sternum of a patient. Clip 504 is configured to anchor subcutaneous device 500 to the xiphoid process and the sternum. Clip 504 will expand as it is slid around the xiphoid process and the sternum. Spring portion 544 acts as a spring for clip 504 and is under tension. Top portion 540 acts as a tension arm and the forces from spring portion 544 translate to and push down on top portion 540. When clip 504 is positioned on the xiphoid process and the sternum, the tension in spring portion 544 will force top portion 540 down onto the xiphoid process and the sternum to anchor clip 504 to the xiphoid process and the sternum. Further, sutures, tines, pins, or screws can be inserted through openings 548 on top portion 540 of clip 504 to further anchor subcutaneous device 500 to the xiphoid process and the sternum.

Subcutaneous device 500 can include a power source, a controller, a memory, a transceiver, sensors, sensing circuitry, therapeutic circuitry, electrodes, and/or any other component of a medical device. In the embodiment shown in FIGS. 21A-21B, subcutaneous device 500 is configured to be a defibrillator. Any one or combination of electrode 534, electrode 536, and electrode 552 can sense the electrical activity of a heart. Further, defibrillator coil 574 can act as an electrode that senses the electrical activity of the heart. The sensed electrical activity can be transmitted to the sensing circuitry and the controller in housing 502 of subcutaneous device 500. The controller can determine the heart rate of the patient and can detect whether an abnormality is present. If an abnormality is detected, the controller can send instructions to therapeutic circuitry to provide a high voltage electrical shock to the heart using defibrillator coil 574. In this manner, subcutaneous device 500 functions as a monitoring device, a diagnostic device, and a therapeutic device. In alternate embodiments, subcutaneous device 500 can function only as a monitoring device, a diagnostic device, or a therapeutic device, or any combinations thereof.

Subcutaneous Device 600

Figure 22A:
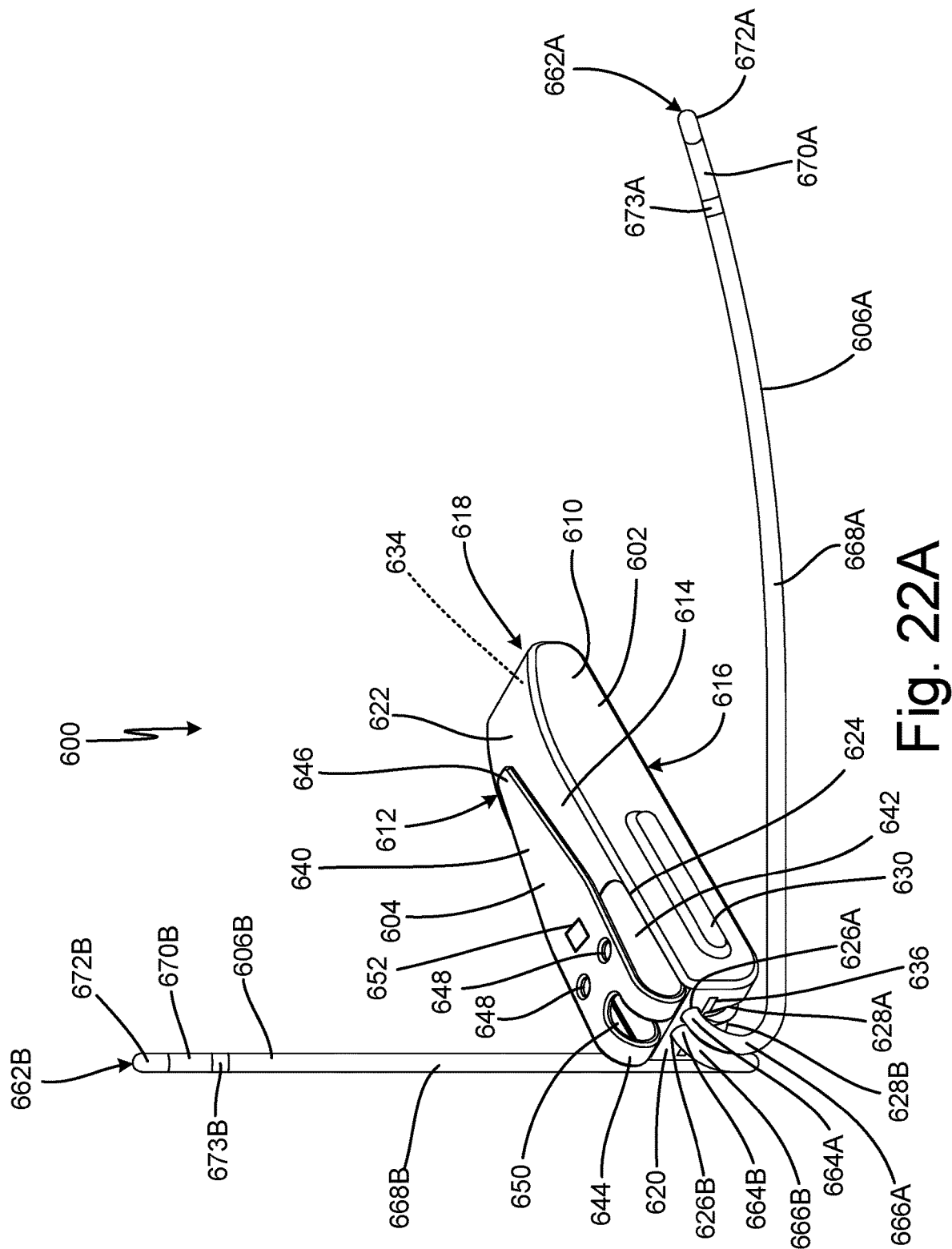
FIG. 22A is a perspective view of a fourth embodiment of a subcutaneous device.
Figure 22B:
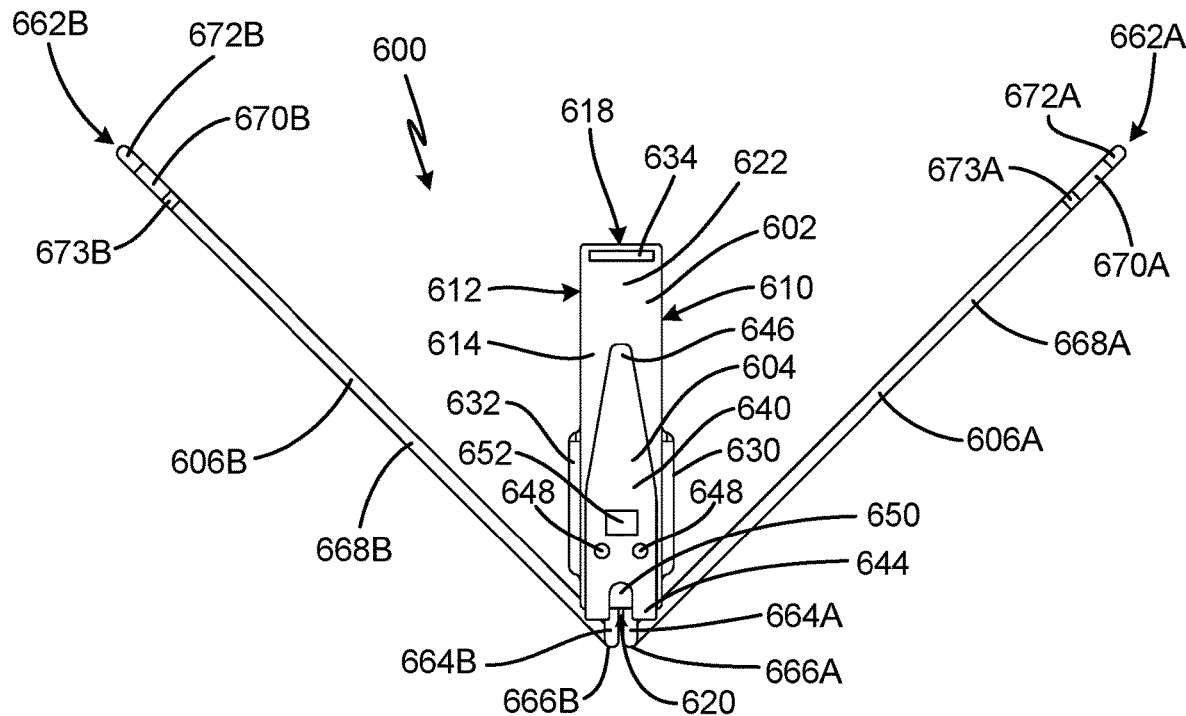
FIG. 22B is a top view of the fourth embodiment of the subcutaneous device.
Figure 22C:
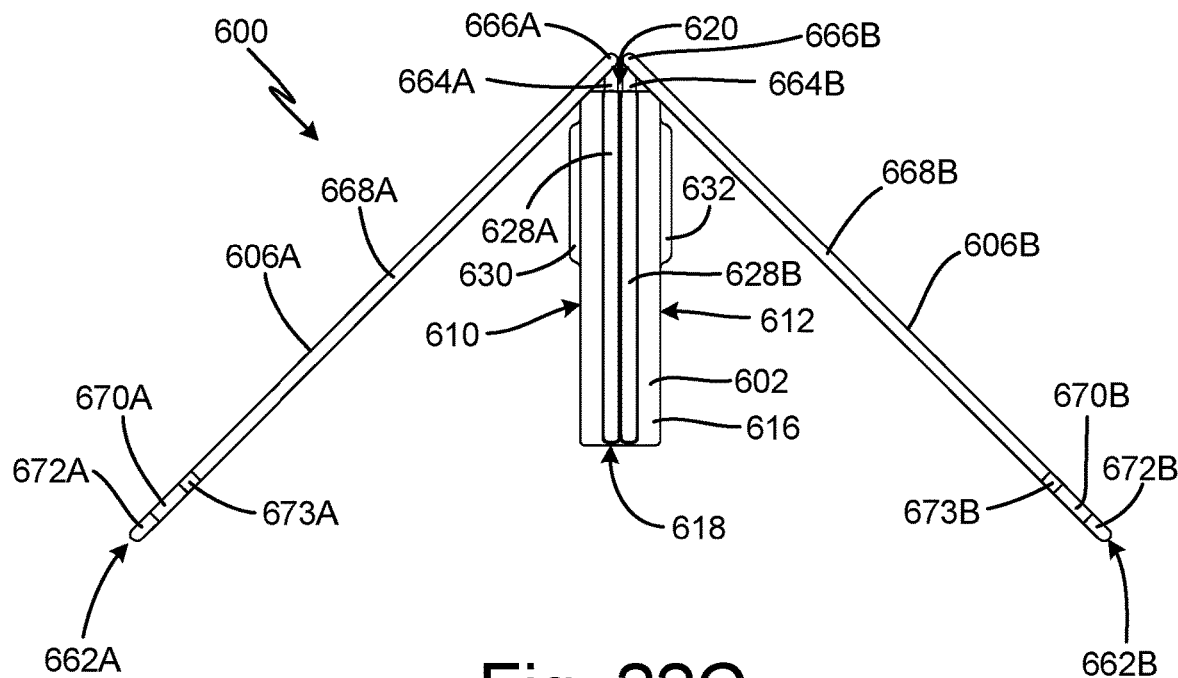
FIG. 22C is a bottom view of the fourth embodiment of the subcutaneous device.
Figure 22D:
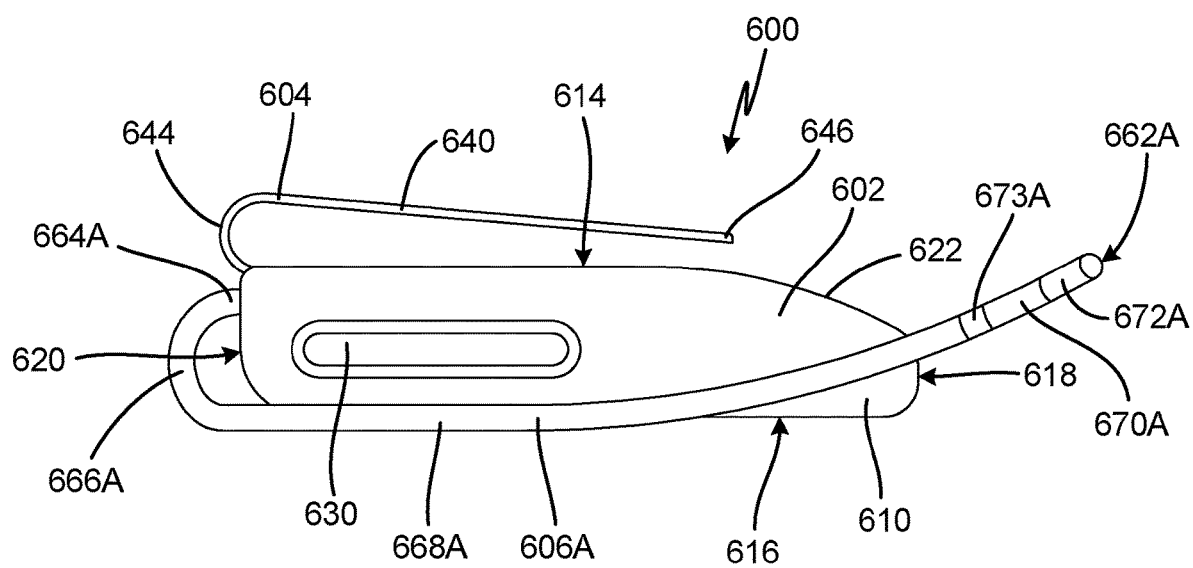
FIG. 22D is a side view of the fourth embodiment of the subcutaneous device.
Figure 22E:
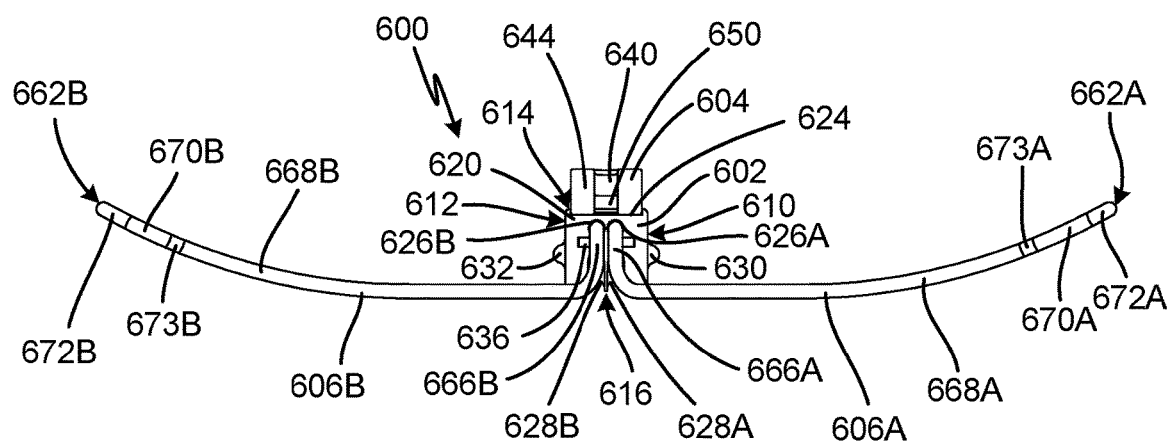
FIG. 22E is a back view of the fourth embodiment of the subcutaneous device.
Figure 23A:
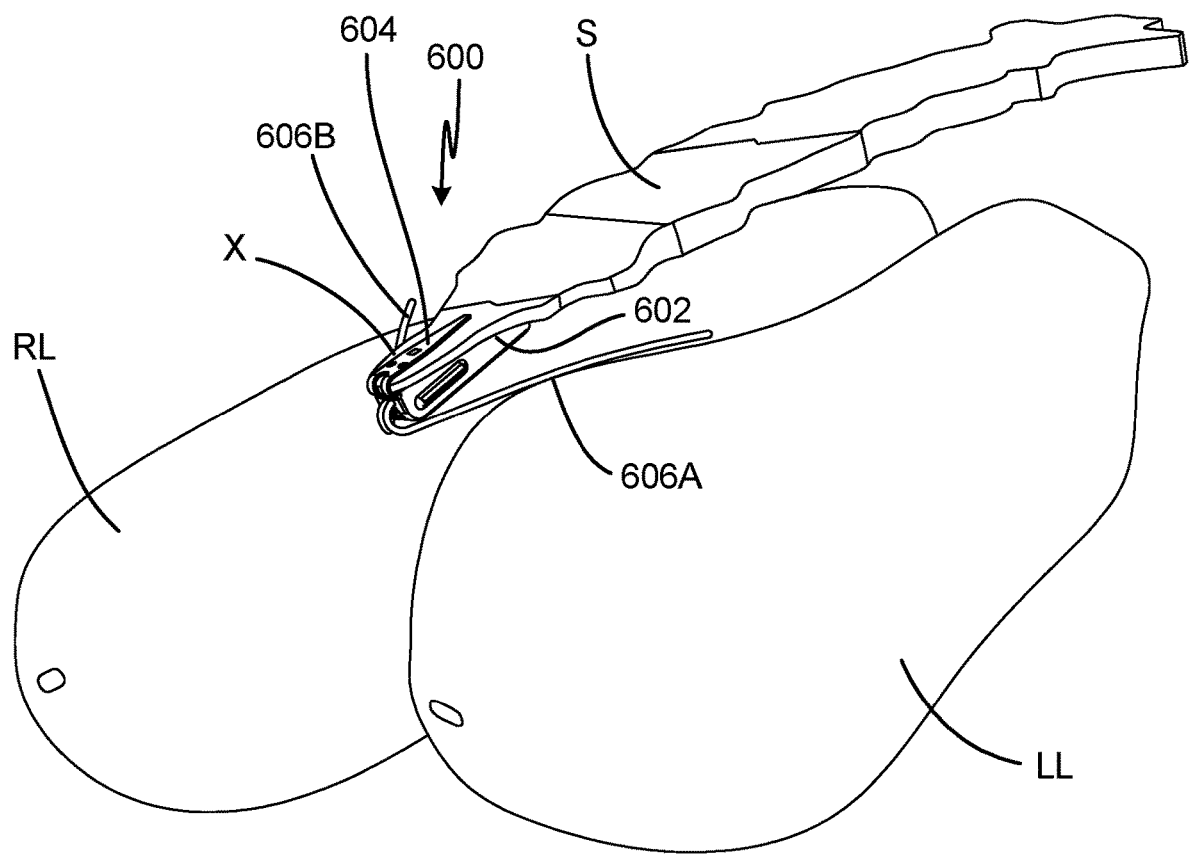
FIG. 23A is a perspective view of the fourth embodiment of the subcutaneous device positioned on a xiphoid process and a sternum and showing a positioning of prongs on lungs.
Figure 23B:
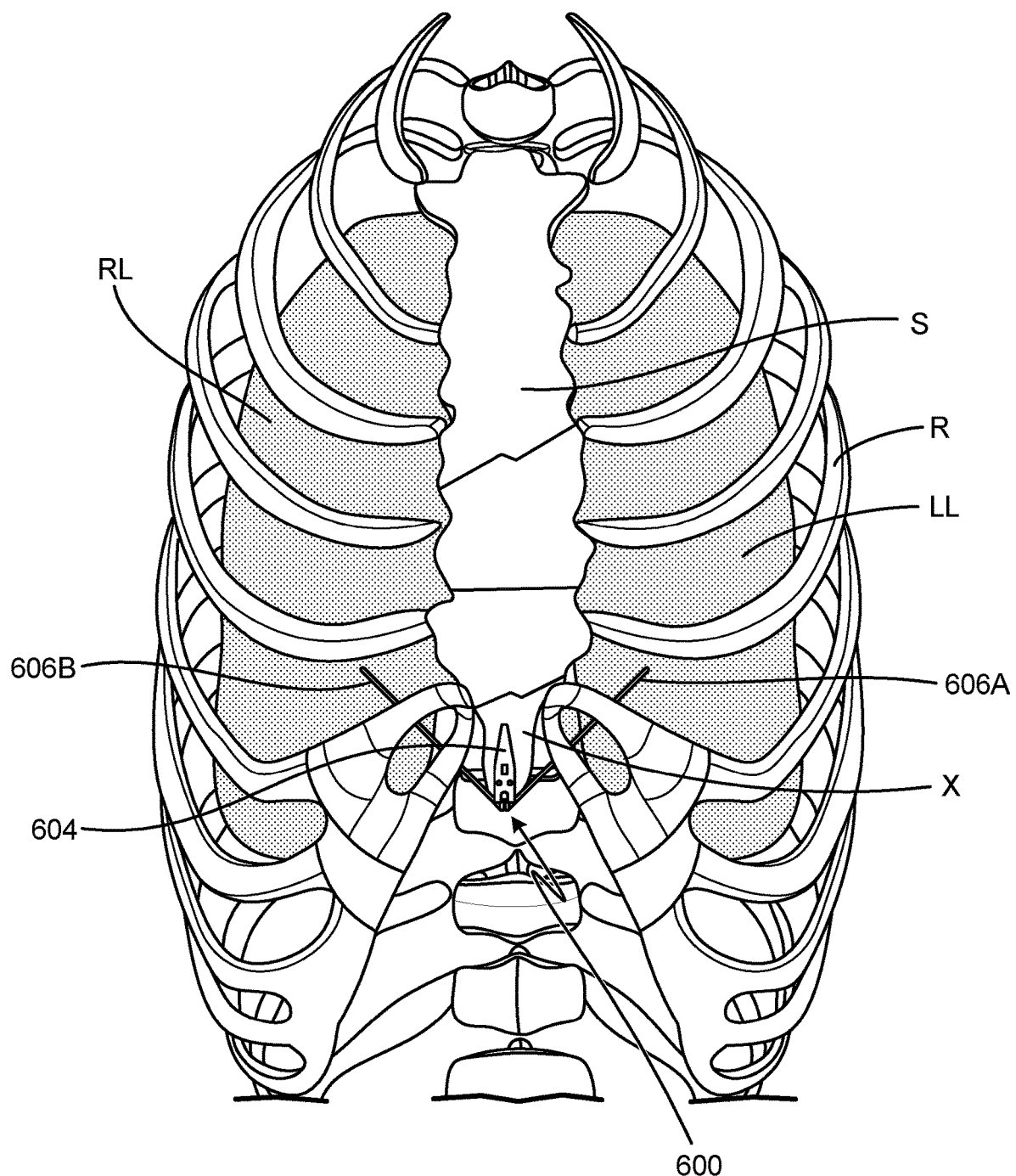
FIG. 23B is a front view of the fourth embodiment of the subcutaneous device positioned on the xiphoid process and the sternum and showing a positioning of the prongs on the lungs.
Figure 23C:
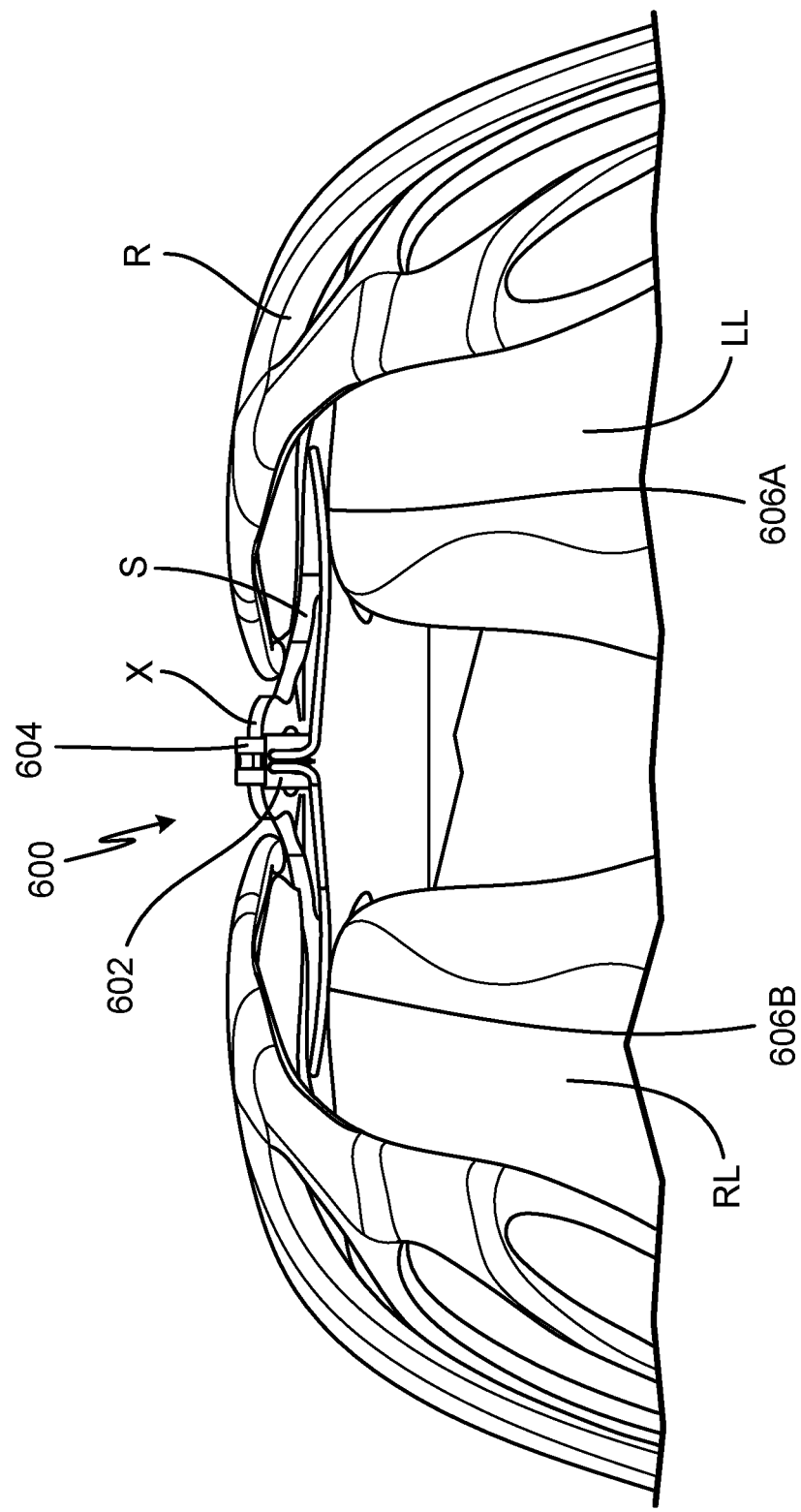
FIG. 23C is a side view of the fourth embodiment of the subcutaneous device positioned on the xiphoid process and the sternum and showing a positioning of the prongs on the lungs.
Subcutaneous Device 700

FIG. 22A is a perspective view of subcutaneous device 600. FIG. 22B is a top view of subcutaneous device 600. FIG. 22C is a bottom view of subcutaneous device 600. FIG. 22D is a side view of subcutaneous device 600. FIG. 22E is a back view of subcutaneous device 600. FIG. 23A is a perspective view of subcutaneous device 600 positioned on xiphoid process X and sternum S and showing a positioning of prongs 606A and 606B on left lung LL and right lung RL. FIG. 23B is a front view of subcutaneous device 600 positioned on xiphoid process X and sternum S and showing a positioning of prongs 606A and 606B on left lung LL and right lung RL. FIG. 23C is a side view of subcutaneous device 600 positioned on xiphoid process X and sternum S and showing a positioning of prongs 606A and 606B on left lung LL and right lung RL. Subcutaneous device 600 includes housing 602, clip 604, prong 606A, and prong 606B. Housing 602 includes first side 610, second side 612, top side 614, bottom side 616, front end 618, back end 620, curved surface 622, recess 624, port 626A, port 626B, channel 628A, channel 628B, first guide 630, second guide 632, electrode 634, and electrode 636. Clip 604 includes top portion 640, bottom portion 642, spring portion 644, tip 646, openings 648, slot 650, and electrode 652. Prong 606A includes proximal end 660A (not shown in FIGS. 22A-22B), distal end 662A, base portion 664A, spring portion 666A, arm portion 668A, contact portion 670A, and electrode 672A. Prong 606B includes proximal end 660B (not shown in FIGS. 22A-22B), distal end 662B, base portion 664B, spring portion 666B, arm portion 668B, contact portion 670B, and electrode 672B. FIGS. 23A-23C show xiphoid process X, sternum S, left lung LL, and right lung RL. FIG. 23B also shows ribs R.

Subcutaneous device 600 includes housing 602, clip 604, prong 606A, and prong 606B. Housing 602 has the same general structure and design as housing 102 of subcutaneous device 100 shown in FIGS. 1-9C. However, housing 602 includes two ports, including port 626A and port 626B, and two channels, including channel 628A and channel 628B. The reference numerals that refer to the parts of housing 602 are incremented by five-hundred compared to the reference numerals that refer to the parts of housing 102 of subcutaneous device 100 shown in FIGS. 1-9C. Port 626A and port 626B are positioned next to one another on housing 602, and channel 628A and channel 628B are positioned next to one another on housing 602. Prong 606A is configured to be connected to port 626A and can be positioned in channel 628A when subcutaneous device 600 is in a stowed position. Prong 606B is configured to be connected to port 626B and can be positioned in channel 628B when subcutaneous device 600 is in a stowed position.

Clip 604 has the same general structure and design as clip 104 of subcutaneous device 100 shown in FIGS. 1-9C. The reference numerals that refer to the parts of clip 604 are incremented by five-hundred compared to the reference numerals that refer to the parts of clip 104 of subcutaneous device 100 shown in FIGS. 1-9C.

Prong 606A and prong 606B each include the same parts as prong 106 of subcutaneous device 100 as shown in FIGS. 1-9C, and the reference numerals that refer to the parts of prong 606A and prong 606B are incremented by five-hundred compared to the reference numerals that refer to the parts of prong 106 of subcutaneous device 100 shown in FIGS. 1-9C. However, prong 606A and 606B have different shapes than prong 106 shown in FIGS. 1-9C. Spring portion 666A and arm portion 668A of prong 606A extend away from first side 610 of housing 602. Contact portion 670A is a portion of prong 606A adjacent to distal end 662A of prong 606A that is configured to come into contact with left lung LL of a patient. Electrode 672A positioned on contact portion 670A will also come into contact with left lung LL. Spring portion 666B and arm portion 668B of prong 606B extend away from second side 612 of housing 602. Contact portion 670B is a portion of prong 606B adjacent to distal end 662B of prong 606B that is configured to come into contact with right lung RL of a patient. Electrode 672B positioned on contact portion 670B will also come into contact with right lung RL.

In one example, subcutaneous device 600 can be anchored to xiphoid process X and sternum S of a patient. Clip 604 is configured to anchor subcutaneous device 600 to xiphoid process X and sternum S. Clip 604 will expand as it is slid around xiphoid process X and sternum S. Spring portion 644 acts as a spring for clip 604 and is under tension. Top portion 640 acts as a tension arm and the forces from spring portion 644 translate to and push down on top portion 640. When clip 604 is positioned on xiphoid process X and sternum S, the tension in spring portion 644 will force top portion 640 down onto xiphoid process X and sternum S to anchor clip 604 to xiphoid process X and sternum S. Further, sutures, tines, pins, or screws can be inserted through openings 648 on top portion 640 of clip 604 to further anchor subcutaneous device 600 to xiphoid process X and sternum S.

Subcutaneous device 600 can include a power source, a controller, a memory, a transceiver, sensors, sensing circuitry, electrodes, and/or any other component of a medical device. In the embodiment shown in FIGS. 22A-23C, subcutaneous device 600 is configured to be a pulmonary monitoring and diagnostic device. Any one or combination of electrode 634, electrode 636, electrode 652, electrode 672A, and electrode 672B can sense the electrical activity of left lung LL, right lung RL, and tissue surrounding left lung LL and right lung RL. The sensed electrical activity can be transmitted to the sensing circuitry and the controller in housing 602 of subcutaneous device 600. The controller can determine physiological parameters of the patient for monitoring and diagnostic purposes. In this manner, subcutaneous device 600 functions as a monitoring device and a diagnostic device. In alternate embodiments, subcutaneous device 600 can function only as a monitoring device or a diagnostic device.

Subcutaneous Device 700

Figure 24A:
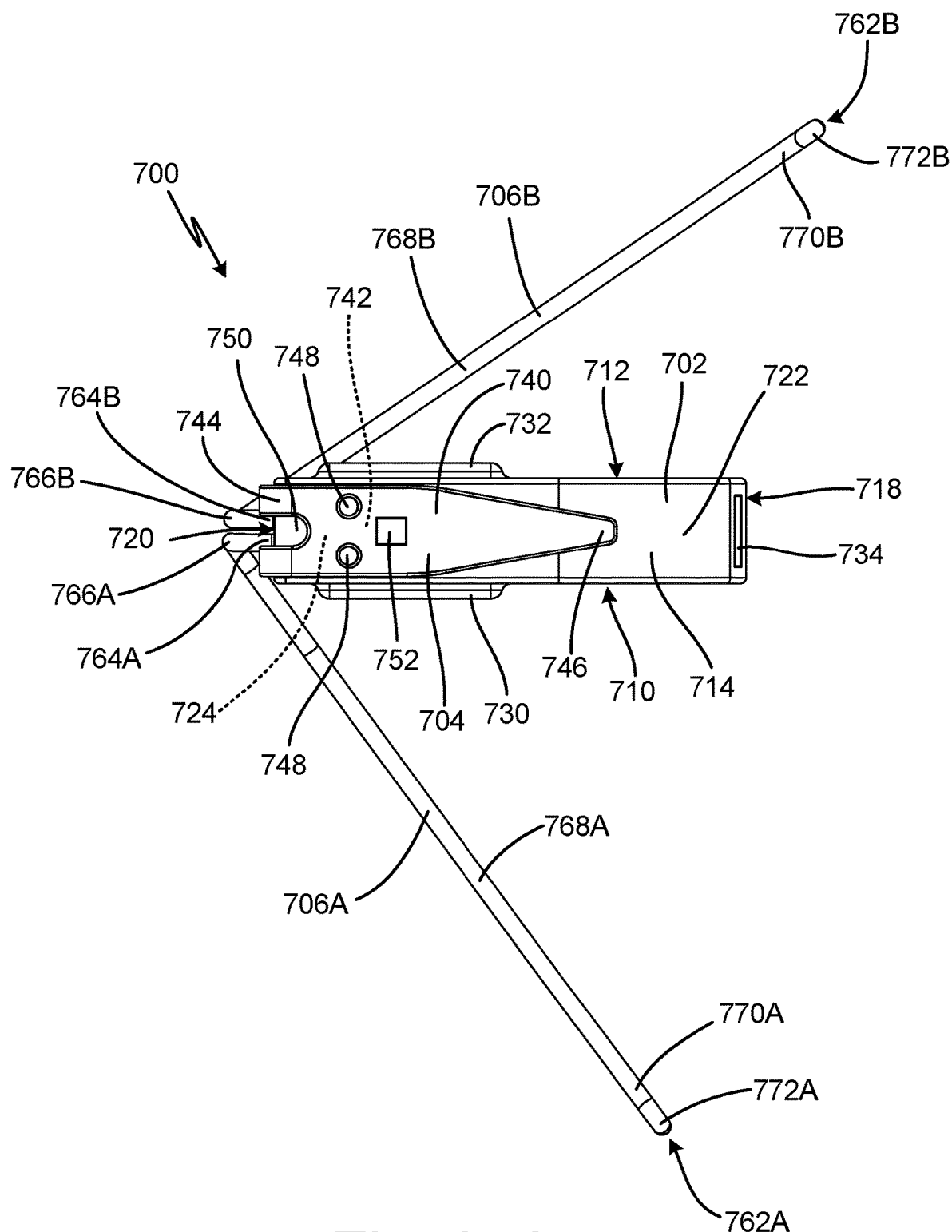
FIG. 24A is a top view of a fifth embodiment of a subcutaneous device.
Figure 24B:
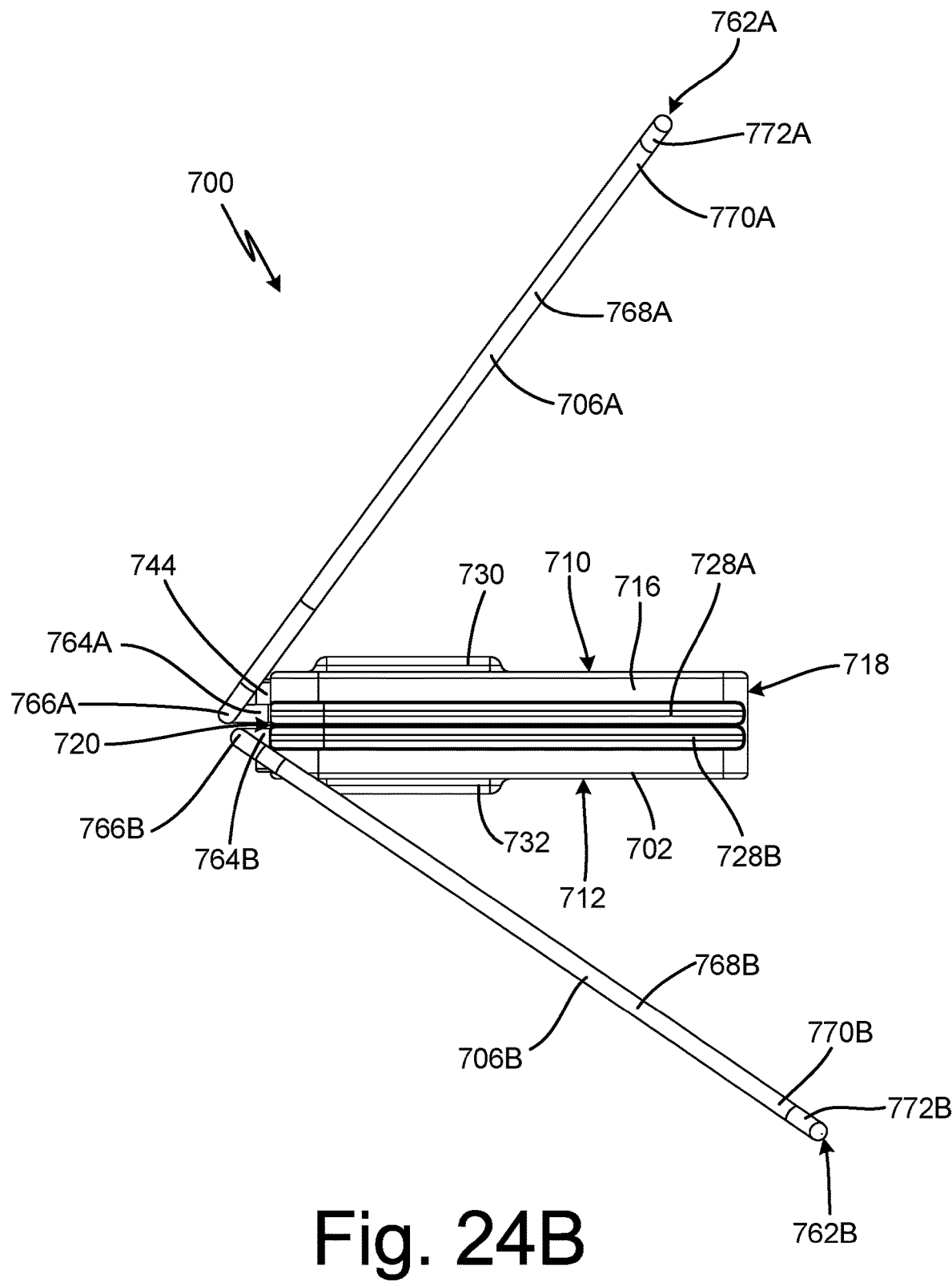
FIG. 24B is a bottom view of the fifth embodiment of the subcutaneous device.
Figure 24C:
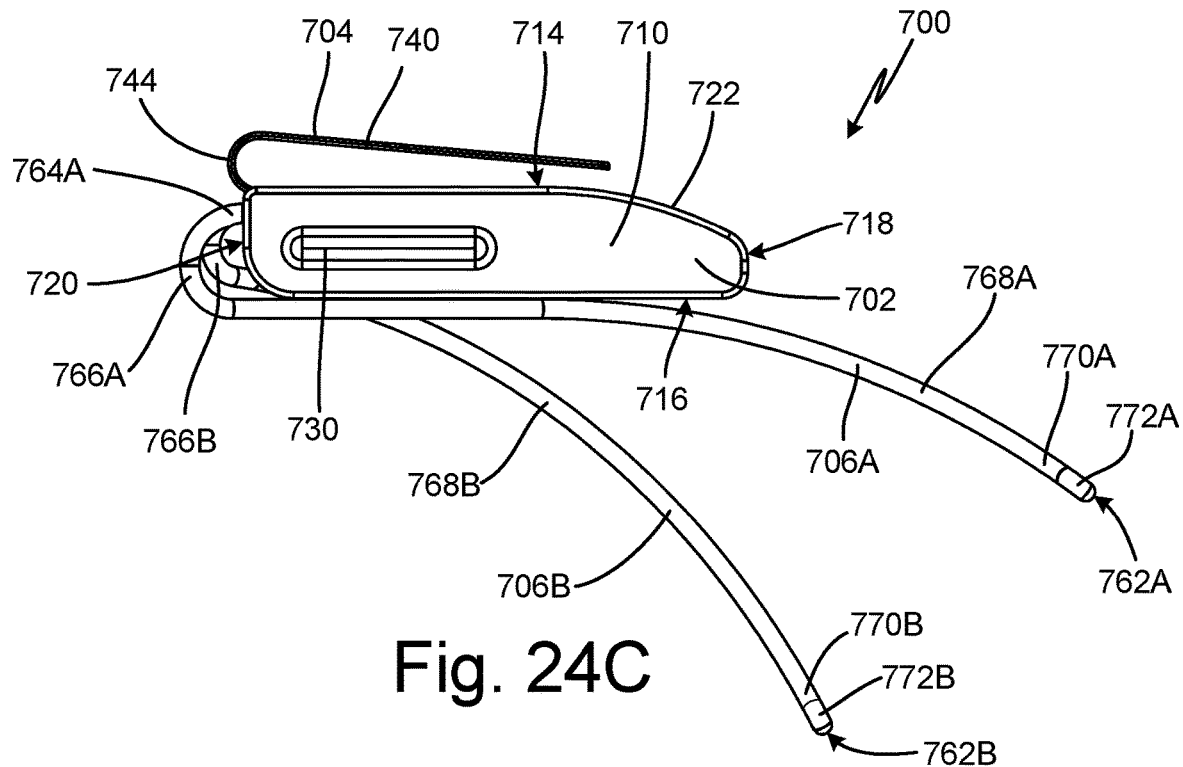
FIG. 24C is a side view of the fifth embodiment of the subcutaneous device.
Figure 24D:
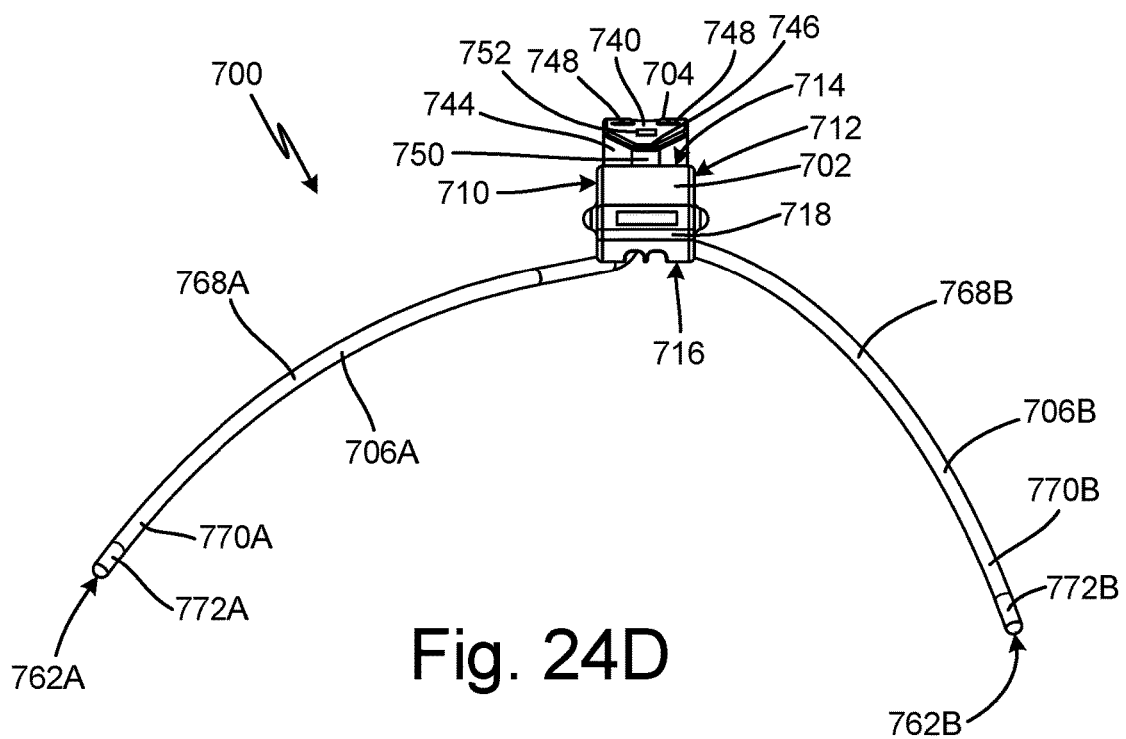
FIG. 24D is a front view of the fifth embodiment of the subcutaneous device.
Figure 25A:
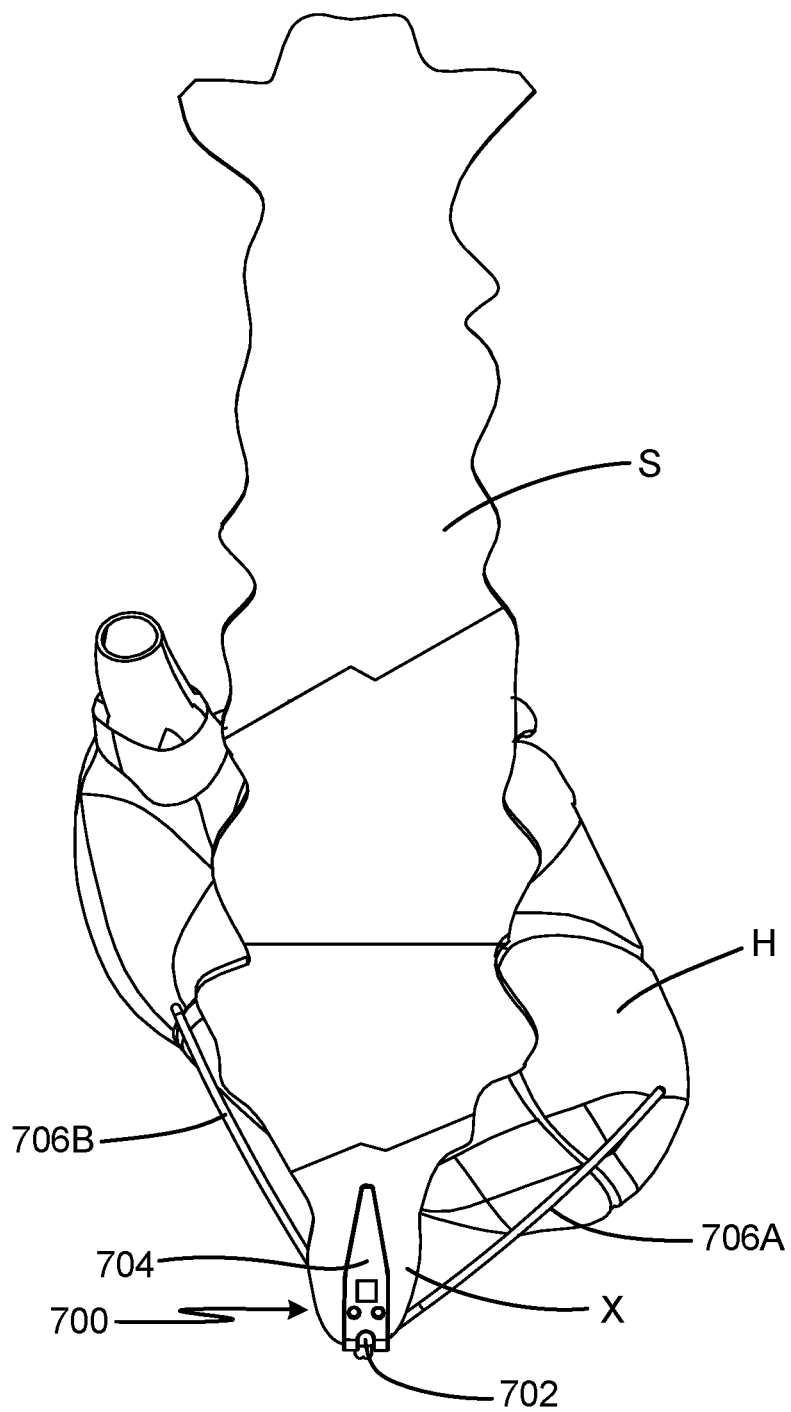
FIG. 25A is a front view of the fifth embodiment of the subcutaneous device positioned on a xiphoid process and a sternum and showing a positioning of prongs around a heart.
Figure 25B:
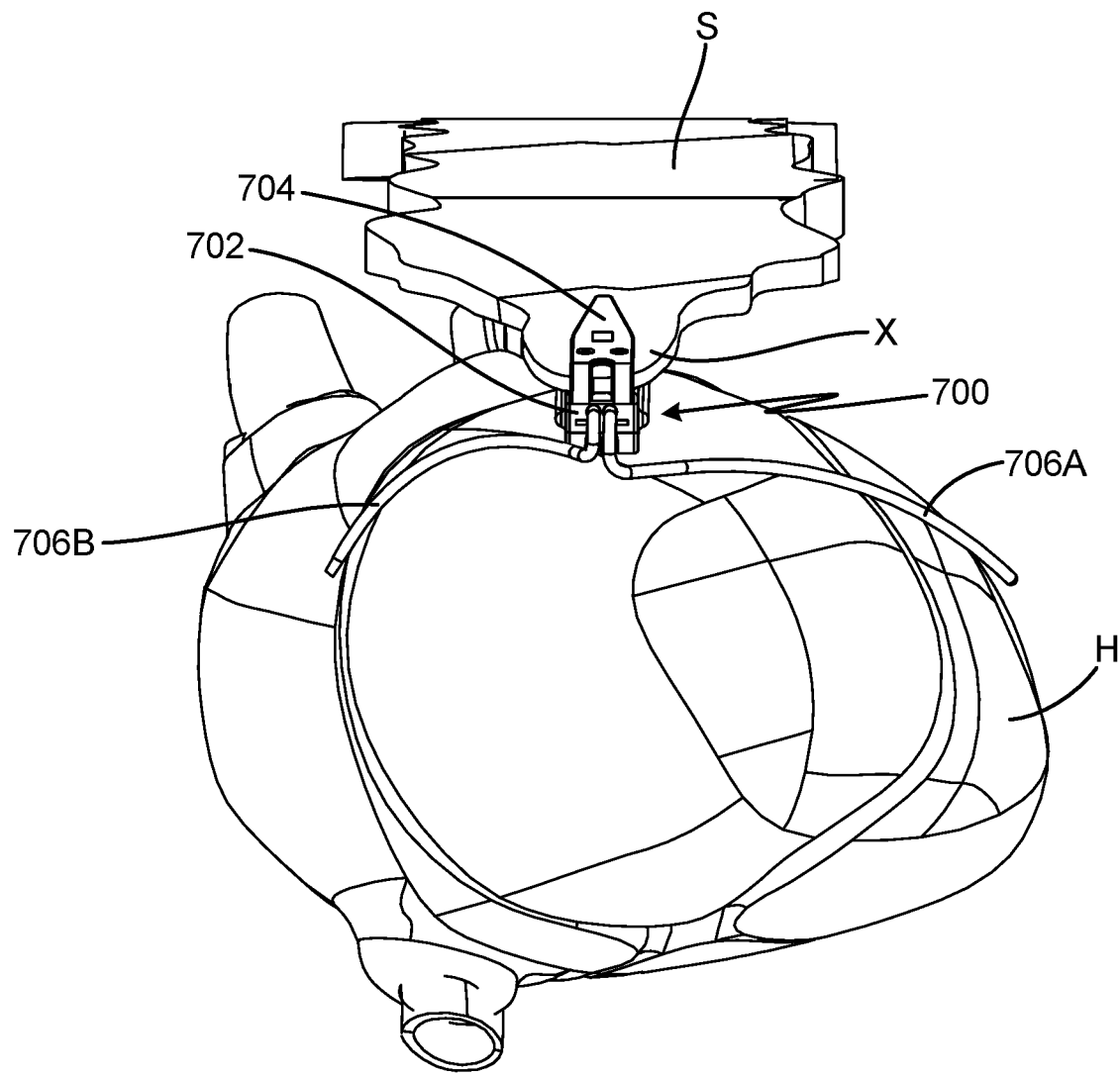
FIG. 25B is a perspective view of the fifth embodiment of the subcutaneous device positioned on the xiphoid process and the sternum and showing a positioning of the prongs around the heart.
Subcutaneous Device 800

FIG. 24A is a top view of subcutaneous device 700. FIG. 24B is a bottom view of subcutaneous device 700. FIG. 24C is a side view of subcutaneous device 700. FIG. 24D is a front view of subcutaneous device 700. FIG. 25A is a front view of subcutaneous device 700 positioned on xiphoid process X and sternum S and showing a positioning of prongs 706A and 706B around heart H. FIG. 25B is a perspective view of subcutaneous device 700 positioned on xiphoid process X and sternum S and showing a positioning of prongs 706A and 706B around heart H. Subcutaneous device 700 includes housing 702, clip 704, prong 706A, and prong 706B. Housing 702 includes first side 710, second side 712, top side 714, bottom side 716, front end 718, back end 720, curved surface 722, recess 724, port 726A, port 726B, channel 728A, channel 728B, first guide 730, second guide 732, electrode 734, and electrode 736. Clip 704 includes top portion 740, bottom portion 742, spring portion 744, tip 746, openings 748, slot 750, and electrode 752. Prong 706A includes proximal end 760A (not shown in FIGS. 24A-25B), distal end 762A, base portion 764A, spring portion 766A, arm portion 768A, contact portion 770A, and electrode 772A. Prong 706B includes proximal end 760B (not shown in FIGS. 24A-25B), distal end 762B, base portion 764B, spring portion 766B, arm portion 768B, contact portion 770B, and electrode 772B. FIGS. 25A-25B show xiphoid process X, sternum S, and heart H.

Subcutaneous device 700 includes housing 702, clip 704, prong 706A, and prong 706B. Housing 702 has the same general structure and design as housing 102 of subcutaneous device 100 shown in FIGS. 1-9C. However, housing 702 includes two ports, including port 726A and port 726B, and two channels, including channel 728A and channel 728B. The reference numerals that refer to the parts of housing 702 are incremented by six-hundred compared to the reference numerals that refer to the parts of housing 102 of subcutaneous device 100 shown in FIGS. 1-9C. Port 726A and port 726B are positioned next to one another on housing 702, and channel 728A and channel 728B are positioned next to one another on housing 702. Prong 706A is configured to be connected to port 726A and can be positioned in channel 728A when subcutaneous device 700 is in a stowed position. Prong 706B is configured to be connected to port 726B and can be positioned in channel 728B when subcutaneous device 700 is in a stowed position.

Clip 704 has the same general structure and design as clip 104 of subcutaneous device 100 shown in FIGS. 1-9C. The reference numerals that refer to the parts of clip 704 are incremented by six-hundred compared to the reference numerals that refer to the parts of clip 104 of subcutaneous device 100 shown in FIGS. 1-9C.

Prong 706A and prong 706B each include the same parts as prong 106 of subcutaneous device 100 as shown in FIGS. 1-9C, and the reference numerals that refer to the parts of prong 706A and prong 706B are incremented by six-hundred compared to the reference numerals that refer to the parts of prong 106 of subcutaneous device 100 shown in FIGS. 1-9C. However, prong 706A and 706B have a different shape than prong 106 shown in FIGS. 1-9C. Spring portion 766A and arm portion 768A of prong 706A extend away from first side 710 of housing 702. Contact portion 770A is a portion of prong 706A adjacent to distal end 762A of prong 706A that is configured to come into contact with tissue surrounding heart H of a patient. Electrode 772A positioned on contact portion 770A will also come into contact with tissue surrounding heart H of a patient. Spring portion 766B and arm portion 768B of prong 706B extend away from second side 712 of housing 702. Contact portion 770B is a portion of prong 706B adjacent to distal end 762B of prong 706B that is configured to come into contact with tissue surrounding heart H of a patient. Electrode 772B positioned on contact portion 770B will also come into contact with tissue surrounding heart H of a patient.

In one example, subcutaneous device 700 can be anchored to xiphoid process X and sternum S of a patient. Clip 704 is configured to anchor subcutaneous device 700 to xiphoid process X and sternum S. Clip 704 will expand as it is slid around xiphoid process X and sternum S. Spring portion 744 acts as a spring for clip 704 and is under tension. Top portion 740 acts as a tension arm and the forces from spring portion 744 translate to and push down on top portion 740. When clip 704 is positioned on xiphoid process X and sternum S, the tension in spring portion 744 will force top portion 740 down onto xiphoid process X and sternum S to anchor clip 704 to xiphoid process X and sternum S. Further, sutures, tines, pins, or screws can be inserted through openings 748 on top portion 740 of clip 704 to further anchor subcutaneous device 700 to xiphoid process X and sternum S.

Subcutaneous device 700 can include a power source, a controller, a memory, a transceiver, sensors, sensing circuitry, electrodes, and/or any other component of a medical device. In the embodiment shown in FIGS. 24A-25B, subcutaneous device 700 is configured to be a cardiac monitoring and diagnostic device. Any one or combination of electrode 734, electrode 736, electrode 752, electrode 772A, and electrode 772B can sense the electrical activity of tissue surrounding heart H. The sensed electrical activity can be transmitted to the sensing circuitry and the controller in housing 702 of subcutaneous device 700. The controller can determine physiological parameters of the patient for monitoring and diagnostic purposes. In this manner, subcutaneous device 700 functions as a monitoring device and a diagnostic device. In alternate embodiments, subcutaneous device 700 can function only as a monitoring device or a diagnostic device.

Specifically, in the embodiment shown in FIGS. 24A-25B, a surface ECG of heart H can be determined using electrode 734, electrode 736, electrode 772A, and electrode 772B. A first lead can be determined between electrode 734 and electrode 736 on housing 702 of subcutaneous device 700. A second lead can be determined between electrode 772A on first prong 706A and electrode 772B on second prong 706B. The information gathered from these two leads can then be extrapolated to give the surface ECG across six leads. Anchoring subcutaneous device 700 to xiphoid process X and sternum S allows for consistency and accuracy in the surface ECG readings, as subcutaneous device 700 is not moving within the body and causing the ECG morphology to change.

Subcutaneous Device 800

Figure 26:
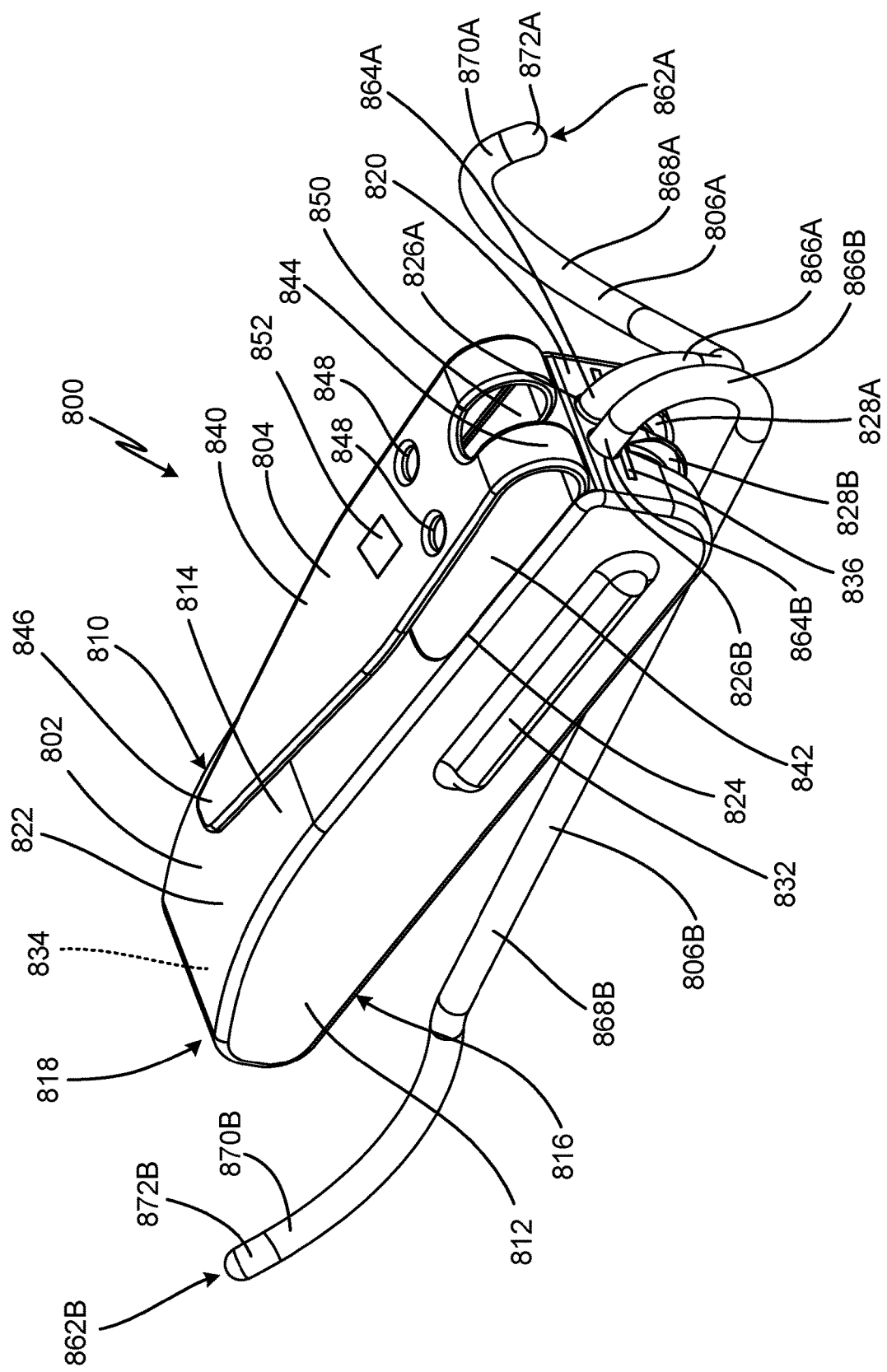
FIG. 26 is a perspective view of a sixth embodiment of a subcutaneous device.
Subcutaneous Device 900

FIG. 26 is a perspective view of subcutaneous device 800. Subcutaneous device 800 includes housing 802, clip 804, prong 806A, and prong 806B. Housing 802 includes first side 810, second side 812, top side 814, bottom side 816, front end 818, back end 820, curved surface 822, recess 824, port 826A, port 826B, channel 828A, channel 828B, first guide 830 (now shown in FIG. 26) second guide 832, electrode 834, and electrode 836. Clip 804 includes top portion 840, bottom portion 842, spring portion 844, tip 846, openings 848, slot 850, and electrode 852. Prong 806A includes proximal end 860A (not shown in FIG. 26), distal end 862A, base portion 864A, spring portion 866A, arm portion 868A, contact portion 870A, and electrode 872A. Prong 806B includes proximal end 860B (not shown in FIG. 26), distal end 862B, base portion 864B, spring portion 866B, arm portion 868B, contact portion 870B, and electrode 872B.

Subcutaneous device 800 includes housing 802, clip 804, prong 806A, and prong 806B. Housing 802 has the same general structure and design as housing 102 of subcutaneous device 100 shown in FIGS. 1-9C. However, housing 802 includes two ports, including port 826A and port 826B, and two channels, including channel 828A and channel 828B. The reference numerals that refer to the parts of housing 802 are incremented by seven-hundred compared to the reference numerals that refer to the parts of housing 102 of subcutaneous device 100 shown in FIGS. 1-9C. Port 826A and port 826B are positioned next to one another on housing 802, and channel 828A and channel 828B are positioned next to one another on housing 802. Prong 806A is configured to be connected to port 826A and can be positioned in channel 828A when subcutaneous device 800 is in a stowed position. Prong 806B is configured to be connected to port 826B and can be positioned in channel 828B when subcutaneous device 800 is in a stowed position.

Clip 804 has the same general structure and design as clip 104 of subcutaneous device 100 shown in FIGS. 1-9C. The reference numerals that refer to the parts of clip 804 are incremented by seven-hundred compared to the reference numerals that refer to the parts of clip 104 of subcutaneous device 100 shown in FIGS. 1-9C.

Prong 806A and prong 806B each include the same parts as prong 106 of subcutaneous device 100 as shown in FIGS. 1-9C, and the reference numerals that refer to the parts of prong 806A and prong 806B are incremented by seven-hundred compared to the reference numerals that refer to the parts of prong 106 of subcutaneous device 100 shown in FIGS. 1-9C. However, prong 806A has a different shape than prong 106 shown in FIGS. 1-9C. Spring portion 866A and arm portion 868A of prong 806A extend away from first side 810 of housing 802. Contact portion 870A is a portion of prong 806A adjacent to distal end 862A of prong 806A that is configured to come into contact with the left ventricle of the patient's heart. Electrode 872A positioned on contact portion 870A will also come into contact with the left ventricle of the patient's heart. Prong 806B has the same shape as prong 106 shown in FIGS. 1-9C. Spring portion 866B and arm portion 868B of prong 806B extend underneath bottom side 816 of housing 802. Contact portion 870B is a portion of prong 806B adjacent to distal end 862B of prong 806B that is configured to come into contact with the right ventricle of a patient's heart. Electrode 872B positioned on contact portion 870B will also come into contact with the right ventricle of patient's heart.

In one example, subcutaneous device 800 can be anchored to a xiphoid process and a sternum of a patient. Clip 804 is configured to anchor subcutaneous device 800 to the xiphoid process and the sternum. Clip 804 will expand as it is slid around the xiphoid process and the sternum. Spring portion 844 acts as a spring for clip 804 and is under tension. Top portion 840 acts as a tension arm and the forces from spring portion 844 translate to and push down on top portion 840. When clip 804 is positioned on the xiphoid process and the sternum, the tension in spring portion 844 will force top portion 840 down onto the xiphoid process and the sternum to anchor clip 804 to the xiphoid process and the sternum. Further, sutures, tines, pins, or screws can be inserted through openings 848 on top portion 840 of clip 804 to further anchor subcutaneous device 800 to the xiphoid process and the sternum.

Subcutaneous device 800 can include a power source, a controller, a memory, a transceiver, sensors, sensing circuitry, therapeutic circuitry, electrodes, and/or any other component of a medical device. In the embodiment shown in FIG. 26, subcutaneous device 800 is configured to be a dual chamber pacemaker. Any one or combination of electrode 834, electrode 836, electrode 852, electrode 872A, and electrode 872B can sense the electrical activity of a heart. The sensed electrical activity can be transmitted to the sensing circuitry and the controller in housing 802 of subcutaneous device 800. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the right ventricle and the left ventricle. In this manner, subcutaneous device 800 functions as a monitoring device, a diagnostic device, and a therapeutic device. In alternate embodiments, subcutaneous device 800 can function only as a monitoring device, a diagnostic device, or a therapeutic device, or any combinations thereof.

Subcutaneous Device 900

Figure 27:
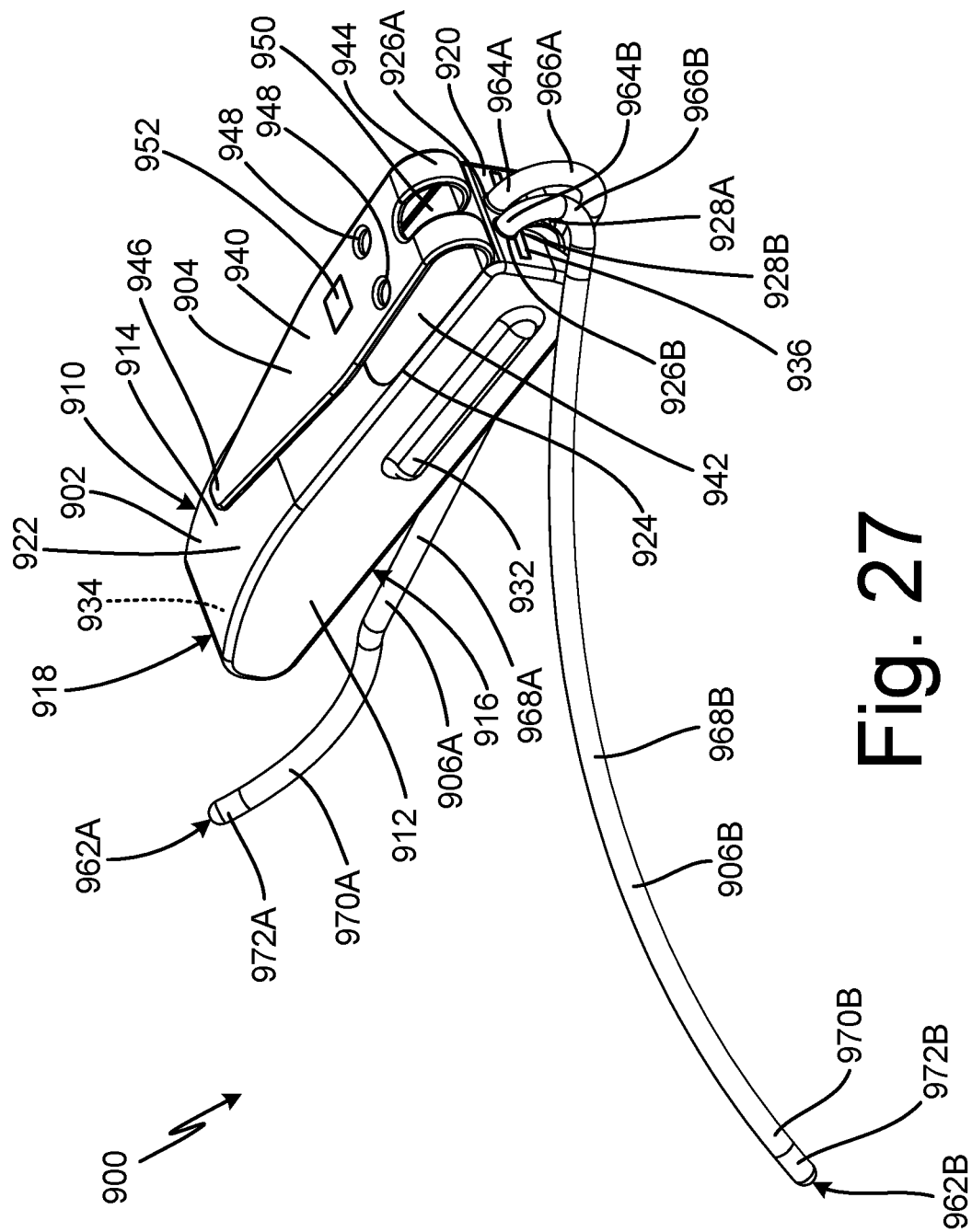
FIG. 27 is a perspective view of a seventh embodiment of a subcutaneous device.
Figure 28:
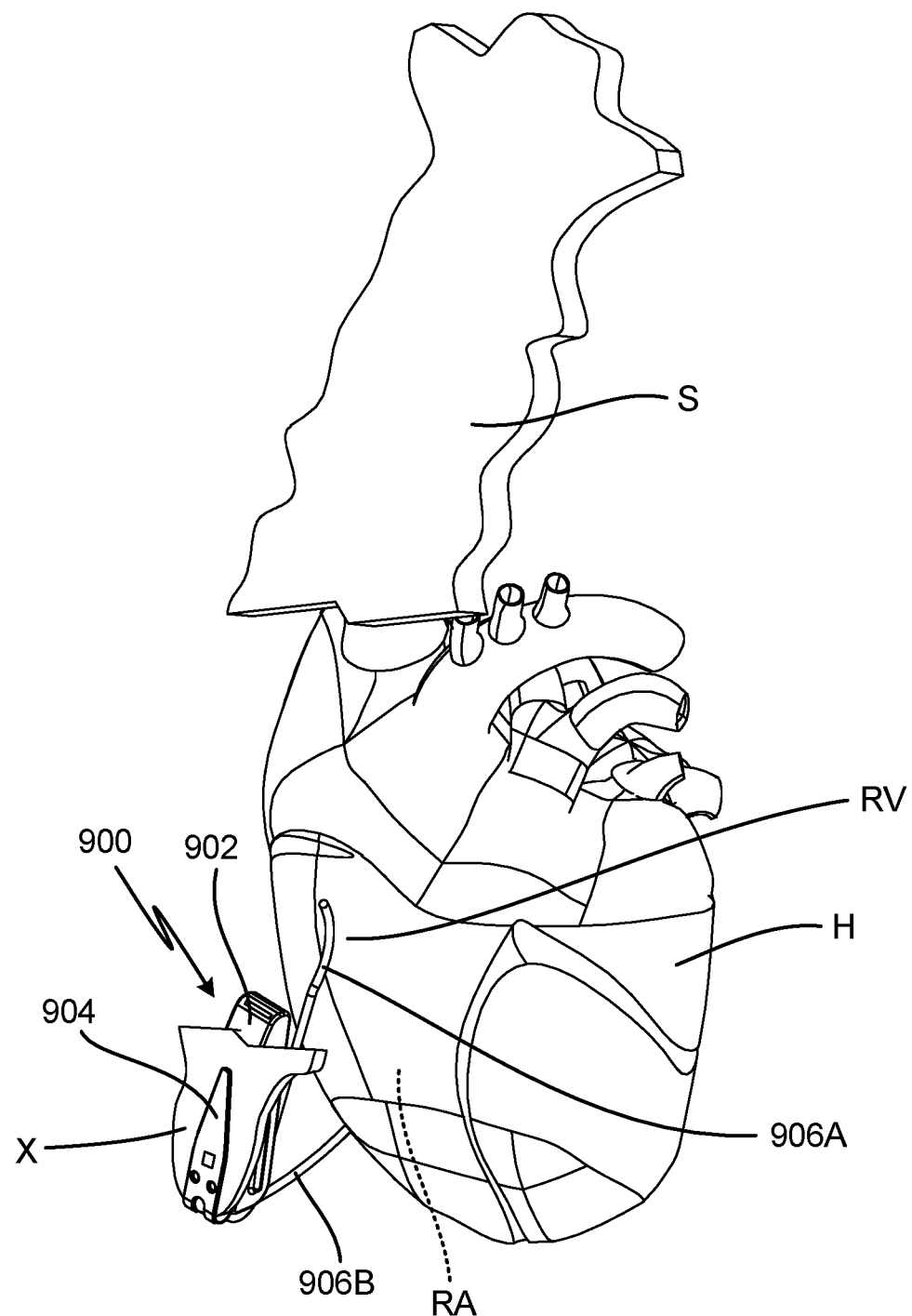
FIG. 28 is a cut-away perspective view of the seventh embodiment of the subcutaneous device positioned on a xiphoid process and a sternum and showing a positioning of prongs on a heart.
Subcutaneous Device 1000

FIG. 27 is a perspective view of subcutaneous device 900. FIG. 28 is a cut-away perspective view of subcutaneous device 900 positioned on xiphoid process X and sternum S and showing a positioning of prongs 906A and 906B on heart H. Subcutaneous device 900 includes housing 902, clip 904, prong 906A, and prong 906B. Housing 902 includes first side 910, second side 912, top side 914, bottom side 916, front end 918, back end 920, curved surface 922, recess 924, port 926A, port 926B, channel 928A, channel 928B, first guide 930 (not shown in FIG. 27), second guide 932, electrode 934, and electrode 936. Clip 904 includes top portion 940, bottom portion 942, spring portion 944, tip 946, openings 948, slot 950, and electrode 952. Prong 906A includes proximal end 960A (not shown in FIGS. 27-28), distal end 962A, base portion 964A, spring portion 966A, arm portion 968A, contact portion 970A, and electrode 972A. Prong 906B includes proximal end 960B (not shown in FIGS. 27-28), distal end 962B, base portion 964B, spring portion 966B, arm portion 968B, contact portion 970B, and electrode 972B. FIG. 28 shows xiphoid process X, sternum S, heart H, right ventricle RV, and right atrium RA.

Subcutaneous device 900 includes housing 902, clip 904, prong 906A, and prong 906B. Housing 902 has the same general structure and design as housing 102 of subcutaneous device 100 shown in FIGS. 1-9C. However, housing 902 includes two ports, including port 926A and port 926B, and two channels, including channel 928A and channel 928B. The reference numerals that refer to the parts of housing 902 are incremented by eight-hundred compared to the reference numerals that refer to the parts of housing 102 of subcutaneous device 100 shown in FIGS. 1-9C. Port 926A and port 926B are positioned next to one another, and channel 928A and channel 928B are positioned next to one another. Prong 906A is configured to be connected to port 926A and can be positioned in channel 928A when subcutaneous device 900 is in a stowed position. Prong 906B is configured to be connected to port 926B and can be positioned in channel 928B when subcutaneous device 900 is in a stowed position.

Clip 904 has the same general structure and design as clip 104 of subcutaneous device 100 shown in FIGS. 1-9C. The reference numerals that refer to the parts of clip 904 are incremented by eight-hundred compared to the reference numerals that refer to the parts of clip 104 of subcutaneous device 100 shown in FIGS. 1-9C.

Prong 906A and prong 906B each include the same parts as prong 106 of subcutaneous device 100 as shown in FIGS. 1-9C, and the reference numerals that refer to the parts of prong 906A and prong 906B are incremented by eight-hundred compared to the reference numerals that refer to the parts of prong 106 of subcutaneous device 100 shown in FIGS. 1-9C. Prong 906A has the same shape as prong 106 shown in FIGS. 1-9C. Spring portion 966A and arm portion 968A of prong 906A extend underneath bottom side 916 of housing 902. Contact portion 970A is a portion of prong 906A adjacent to distal end 962A of prong 906A that is configured to come into contact with right ventricle RV of heart H of the patient. Electrode 972A positioned on contact portion 970A will also come into contact with right ventricle RV of heart H of the patient. However, 906B has a different shape than prong 106 shown in FIGS. 1-9C. Spring portion 966B and arm portion 968B of prong 906B extend away from second side 912 of housing 902. Contact portion 970B is a portion of prong 906B adjacent to distal end 962B of prong 906B that is configured to come into contact with right atrium RA of heart H of the patient. Electrode 972B positioned on contact portion 970B will also come into contact with right atrium RA of heart H of the patient.

In one example, subcutaneous device 900 can be anchored to xiphoid process X and sternum S of a patient. Clip 904 is configured to anchor subcutaneous device 900 to xiphoid process X and sternum S. Clip 904 will expand as it is slid around xiphoid process X and sternum S. Spring portion 944 acts as a spring for clip 904 and is under tension. Top portion 940 acts as a tension arm and the forces from spring portion 944 translate to and push down on top portion 940. When clip 904 is positioned on xiphoid process X and sternum S, the tension in spring portion 944 will force top portion 940 down onto xiphoid process X and sternum S to anchor clip 904 to xiphoid process X and sternum S. Further, sutures, tines, pins, or screws can be inserted through openings 948 on top portion 940 of clip 904 to further anchor subcutaneous device 900 to xiphoid process X and sternum S.

Subcutaneous device 900 can include a power source, a controller, a memory, a transceiver, sensors, sensing circuitry, therapeutic circuitry, electrodes, and/or any other component of a medical device. In the embodiment shown in FIGS. 27-28, subcutaneous device 900 is configured to be a dual chamber pacemaker. Any one or combination of electrode 934, electrode 936, electrode 952, electrode 972A, and electrode 972B can sense the electrical activity of heart H. The sensed electrical activity can be transmitted to the sensing circuitry and the controller in housing 902 of subcutaneous device 900. The controller can determine the heart rate of the patient and can detect whether an arrhythmia is present. If an arrhythmia is detected, the controller can send instructions to therapeutic circuitry to provide a therapeutic electrical stimulation to heart H. Specifically, a therapeutic electrical stimulation can be provided to the right ventricle and the right atrium. In this manner, subcutaneous device 900 functions as a monitoring device, a diagnostic device, and a therapeutic device. In alternate embodiments, subcutaneous device 900 can function only as a monitoring device, a diagnostic device, or a therapeutic device, or any combinations thereof.

Subcutaneous Device 1000

Figure 29:
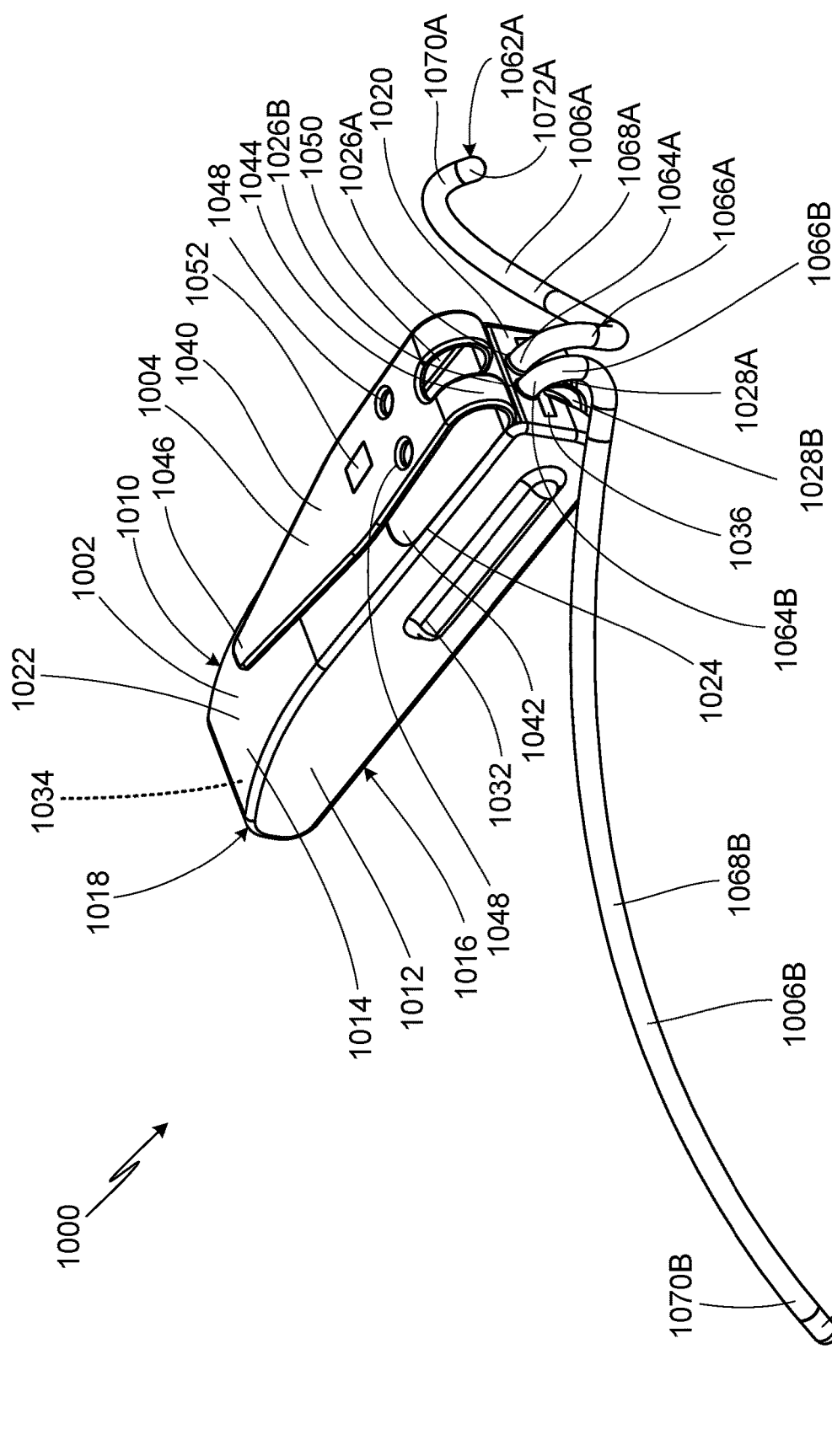
FIG. 29 is a perspective view of an eighth embodiment of a subcutaneous device.
Subcutaneous Device 1100

FIG. 29 is a perspective view of subcutaneous device 1000. Subcutaneous device 1000 includes housing 1002, clip 1004, prong 1006A, and prong 1006B. Housing 1002 includes first side 1010, second side 1012, top side 1014, bottom side 1016, front end 1018, back end 1020, curved surface 1022, recess 1024, port 1026A, port 1026B, channel 1028A, channel 1028B, first guide 1030 (not shown in FIG. 29), second guide 1032, electrode 1034, and electrode 1036. Clip 1004 includes top portion 1040, bottom portion 1042, spring portion 1044, tip 1046, openings 1048, slot 1050, and electrode 1052. Prong 1006A includes proximal end 1060A (not shown in FIG. 29), distal end 1062A, base portion 1064A, spring portion 1066A, arm portion 1068A, contact portion 1070A, and electrode 1072A. Prong 1006B includes proximal end 1060B (not shown in FIG. 29), distal end 1062B, base portion 1064B, spring portion 1066B, arm portion 1068B, contact portion 1070B, and electrode 1072B.

Subcutaneous device 1000 includes housing 1002, clip 1004, prong 1006A, and prong 1006B. Housing 1002 has the same general structure and design as housing 102 of subcutaneous device 100 shown in FIGS. 1-9C. However, housing 1002 includes two ports, including port 1026A and port 1026B, and two channels, including channel 1028A and channel 1028B. The reference numerals that refer to the parts of housing 1002 are incremented by nine-hundred compared to the reference numerals that refer to the parts of housing 102 of subcutaneous device 100 shown in FIGS. 1-9C. Port 1026A and port 1026B are positioned next to one another on housing 1002, and channel 1028A and channel 1028B are positioned next to one another on housing 1002. Prong 1006A is configured to be connected to port 1026A and can be positioned in channel 1028A when subcutaneous device 1000 is in a stowed position. Prong 1006B is configured to be connected to port 1026B and can be positioned in channel 1028B when subcutaneous device 1000 is in a stowed position.

Clip 1004 has the same general structure and design as clip 104 of subcutaneous device 100 shown in FIGS. 1-9C. The reference numerals that refer to the parts of clip 1004 are incremented by nine-hundred compared to the reference numerals that refer to the parts of clip 104 of subcutaneous device 100 shown in FIGS. 1-9C.

Prong 1006A and prong 1006B each include the same parts as prong 106 of subcutaneous device 100 as shown in FIGS. 1-9C, and the reference numerals that refer to the parts of prong 1006A and prong 1006B are incremented by nine-hundred compared to the reference numerals that refer to the parts of prong 106 of subcutaneous device 100 shown in FIGS. 1-9C. However, prong 1006A and 1006B have a different shape than prong 106 shown in FIGS. 1-9C. Spring portion 1066A and arm portion 1068A of prong 1006A extend away from first side 1010 of housing 1002. Contact portion 1070A is a portion of prong 1006A adjacent to distal end 1062A of prong 1006A that is configured to come into contact with the left ventricle of the patient's heart. Electrode 1072A positioned on contact portion 1070A will also come into contact with the left ventricle of the patient's heart. Spring portion 1066B and arm portion 1068B of prong 1006B extend away from second side 1012 of housing 1002. Contact portion 1070B is a portion of prong 1006B adjacent to distal end 1062B of prong 1006B that is configured to come into contact with the right atrium of a patient's heart. Electrode 1072B positioned on contact portion 1070B will also come into contact with the right atrium of patient's heart.

In one example, subcutaneous device 1000 can be anchored to a xiphoid process and a sternum of a patient. Clip 1004 is configured to anchor subcutaneous device 1000 to the xiphoid process and the sternum. Clip 1004 will expand as it is slid around the xiphoid process and the sternum. Spring portion 1044 acts as a spring for clip 1004 and is under tension. Top portion 1040 acts as a tension arm and the forces from spring portion 1044 translate to and push down on top portion 1040. When clip 1004 is positioned on the xiphoid process and the sternum, the tension in spring portion 1044 will force top portion 1040 down onto the xiphoid process and the sternum to anchor clip 1004 to the xiphoid process and the sternum. Further, sutures, tines, pins, or screws can be inserted through openings 1048 on top portion 1040 of clip 1004 to further anchor subcutaneous device 1000 to the xiphoid process and the sternum.

Subcutaneous device 1000 can include a power source, a controller, a memory, a transceiver, sensors, sensing circuitry, therapeutic circuitry, electrodes, and/or any other component of a medical device. In the embodiment shown in FIG. 29, subcutaneous device 1000 is configured to be a dual chamber pacemaker. Any one or combination of electrode 1034, electrode 1036, electrode 1052, electrode 1072A, and electrode 1072B can sense the electrical activity of a heart. The sensed electrical activity can be transmitted to the sensing circuitry and the controller in housing 1002 of subcutaneous device 1000. The controller can determine the heart rate of the patient and can detect whether an arrhythmia is present. If an arrhythmia is detected, the controller can send instructions to therapeutic circuitry to provide a therapeutic electrical stimulation to the heart. Specifically, a therapeutic electrical stimulation can be provided to the left ventricle and the right atrium. In this manner, subcutaneous device 1000 functions as a monitoring device, a diagnostic device, and a therapeutic device. In alternate embodiments, subcutaneous device 1000 can function only as a monitoring device, a diagnostic device, a therapeutic device, or any combinations thereof.

Subcutaneous Device 1100

Figure 30:
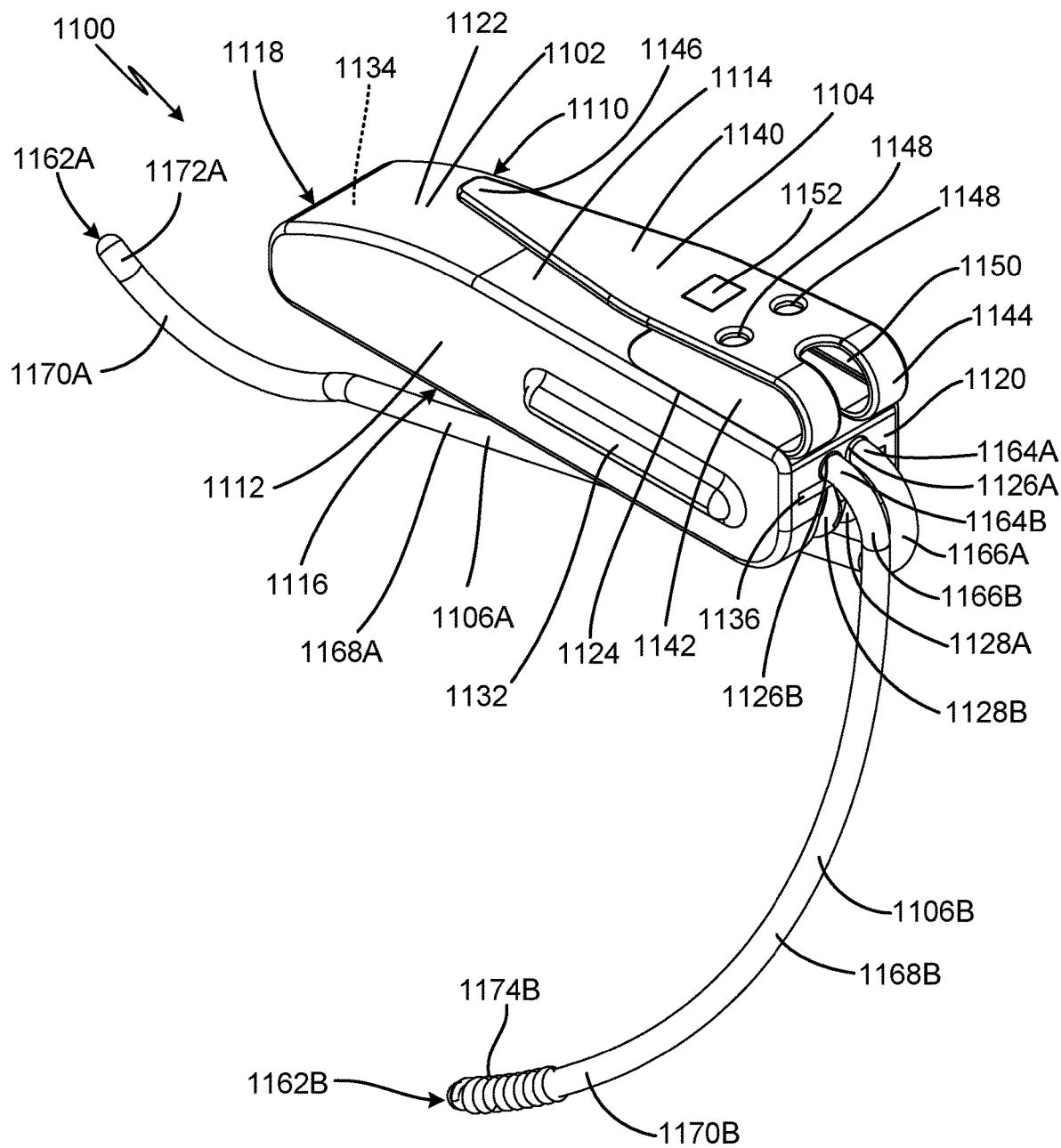
FIG. 30 is a perspective view of a ninth embodiment of a subcutaneous device.
Subcutaneous Device 1200

FIG. 30 is a perspective view of subcutaneous device 1100. Subcutaneous device 1100 includes housing 1102, clip 1104, prong 1106A, and prong 1106B. Housing 1102 includes first side 1110, second side 1112, top side 1114, bottom side 1116, front end 1118, back end 1120, curved surface 1122, recess 1124, port 1126A, port 1126B, channel 1128A, channel 1128B, first guide 1130 (not shown in FIG. 30), second guide 1132, electrode 1134, and electrode 1136. Clip 1104 includes top portion 1140, bottom portion 1142, spring portion 1144, tip 1146, openings 1148, slot 1150, and electrode 1152. Prong 1106A includes proximal end 1160A (not shown in FIG. 30), distal end 1162A, base portion 1164A, spring portion 1166A, arm portion 1168A, contact portion 1170A, and electrode 1172A. Prong 1106B includes proximal end 1160B (not shown in FIG. 30), distal end 1162B, base portion 1164B, spring portion 1166B, arm portion 1168B, contact portion 1170B, and defibrillator coil 1174B.

Subcutaneous device 1100 includes housing 1102, clip 1104, prong 1106A, and prong 1106B. Housing 1102 has the same general structure and design as housing 102 of subcutaneous device 100 shown in FIGS. 1-9C. However, housing 1102 includes two ports, including port 1126A and port 1126B, and two channels, including channel 1128A and channel 1128B. The reference numerals that refer to the parts of housing 1102 are incremented by ten-hundred compared to the reference numerals that refer to the parts of housing 102 of subcutaneous device 100 shown in FIGS. 1-9C. Port 1126A and port 1126B are positioned next to one another on housing 1102, and channel 1128A and channel 1128B are positioned next to one another on housing 1102. Prong 1106A is configured to be connected to port 1126A and can be positioned in channel 1128A when subcutaneous device 1100 is in a stowed position. Prong 1106B is configured to be connected to port 1126B and can be positioned in channel 1128B when subcutaneous device 1100 is in a stowed position.

Clip 1104 has the same general structure and design as clip 104 of subcutaneous device 100 shown in FIGS. 1-9C. The reference numerals that refer to the parts of clip 1104 are incremented by ten-hundred compared to the reference numerals that refer to the parts of clip 104 of subcutaneous device 100 shown in FIGS. 1-9C.

Prong 1106A and prong 1106B generally include the same parts as prong 106 of subcutaneous device 100 as shown in FIGS. 1-9C, and the reference numerals that refer to the parts of prong 1106A and 1106B are incremented by ten-hundred compared to the reference numerals that refer to the parts of prong 106 of subcutaneous device 100 shown in FIGS. 1-9C. Prong 1106A has the same shape as prong 106 shown in FIGS. 1-9C. Spring portion 1166A and arm portion 1168A extend away from bottom side 1120 of housing 1102. Contact portion 1170A is a portion of prong 1106A adjacent to distal end 1162A of prong 1106A that is configured to come into contact with the right ventricle of the patient's heart. Electrode 1172A positioned on contact portion 1170A will also come into contact with the right ventricle of the patient's heart. However, prong 1106B has a different shape than prong 106 shown in FIGS. 1-9C and includes defibrillator coil 1174B instead of an electrode. Spring portion 1166B and arm portion 1168B extend away from bottom side 1120 of housing 1102. Contact portion 1170B is a portion of prong 1106B adjacent to distal end 1162B of prong 1106B that is configured to come into contact with tissue inferior to a patient's heart. Defibrillator coil 1174B is positioned on contact portion 1170B adjacent to distal end 1162B of prong 1106B. When an electrical signal is delivered to defibrillator coil 1174B, defibrillator coil 1174B will create a vector with electrode 1134 on front end 1118 of housing 1102. In the embodiment shown, defibrillator coil 1174B serves as the negative electrode and electrode 1134 serves as the positive electrode. However, in alternate embodiments this can be reversed. Prong 1106B is positioned so that distal end 1162B, and thus contact portion 1170B and defibrillator coil 1174B, are positioned inferior to the heart. Thus, the vector created between defibrillator coil 1174B and electrode 1134 will pass through a patient's heart to provide a high voltage electrical shock to the patient's heart.

In one example, subcutaneous device 1100 can be anchored to a xiphoid process and a sternum of a patient. Clip 1104 is configured to anchor subcutaneous device 1100 to the xiphoid process and the sternum. Clip 1104 will expand as it is slid around the xiphoid process and the sternum. Spring portion 1144 acts as a spring for clip 1104 and is under tension. Top portion 1140 acts as a tension arm and the forces from spring portion 1144 translate to and push down on top portion 1140. When clip 1104 is positioned on the xiphoid process and the sternum, the tension in spring portion 1144 will force top portion 1140 down onto the xiphoid process and the sternum to anchor clip 1104 to the xiphoid process and the sternum. Further, sutures, tines, pins, or screws can be inserted through openings 1148 on top portion 1140 of clip 1104 to further anchor subcutaneous device 1100 to the xiphoid process and the sternum.

Subcutaneous device 1100 can include a power source, a controller, a memory, a transceiver, sensors, sensing circuitry, therapeutic circuitry, electrodes, and/or any other component of a medical device. In the embodiment shown in FIG. 30, subcutaneous device 1100 is configured to be a single chamber pacemaker and a defibrillator. Any one or combination of electrode 1134, electrode 1136, electrode 1152, and electrode 1172A can sense the electrical activity of a heart. Further, defibrillator coil 1174B can act as an electrode that senses the electrical activity of the heart. The sensed electrical activity can be transmitted to the sensing circuitry and the controller in housing 1102 of subcutaneous device 1100. The controller can determine the heart rate of the patient and can detect whether an arrhythmia or abnormality is present. If an arrhythmia is detected, the controller can send instructions to therapeutic circuitry to provide a therapeutic stimulation to the heart with electrode 1172A. If an abnormality is detected, the controller can send instructions to therapeutic circuitry to provide a high voltage electrical shock to the heart with defibrillator coil 1174B. In this manner, subcutaneous device 1100 functions as a monitoring device, a diagnostic device, and a therapeutic device. In alternate embodiments, subcutaneous device 1100 can function only as a monitoring device, a diagnostic device, or a therapeutic device, or any combinations thereof.

Subcutaneous Device 1200

Figure 31A:
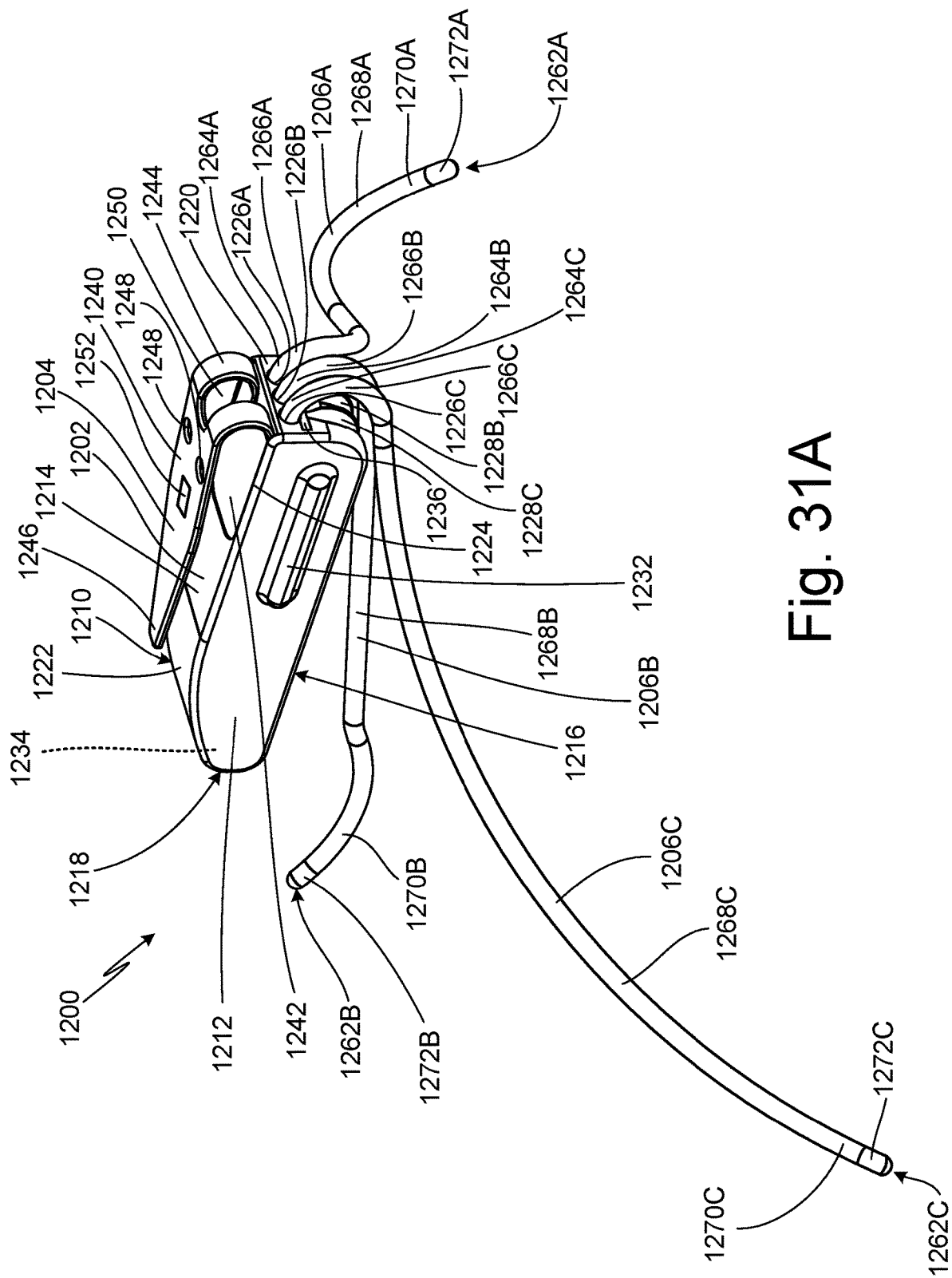
FIG. 31A is a perspective view of a tenth embodiment of a subcutaneous device.
Figure 31B:
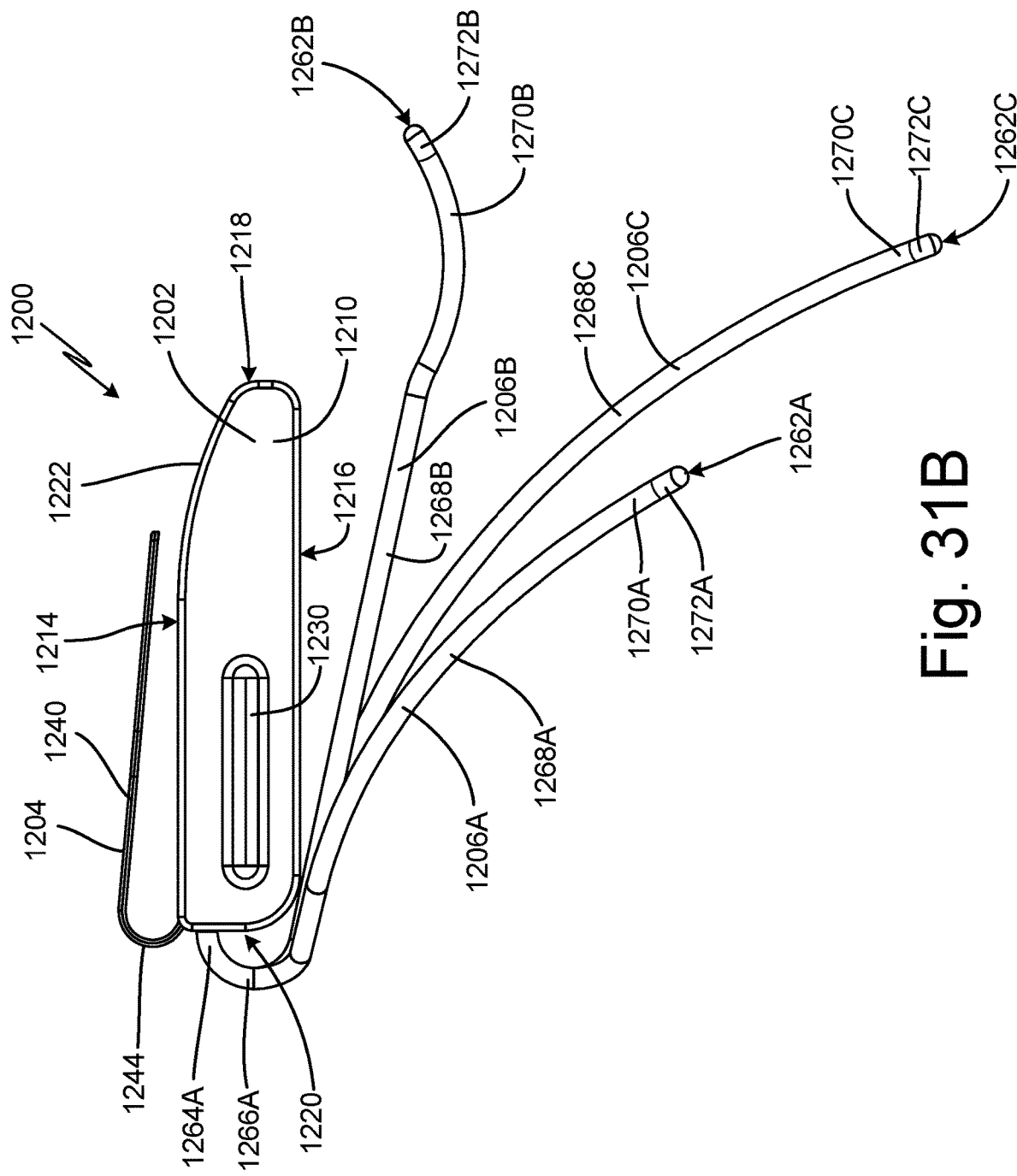
FIG. 31B is a side view of the tenth embodiment of the subcutaneous device.
Figure 31C:
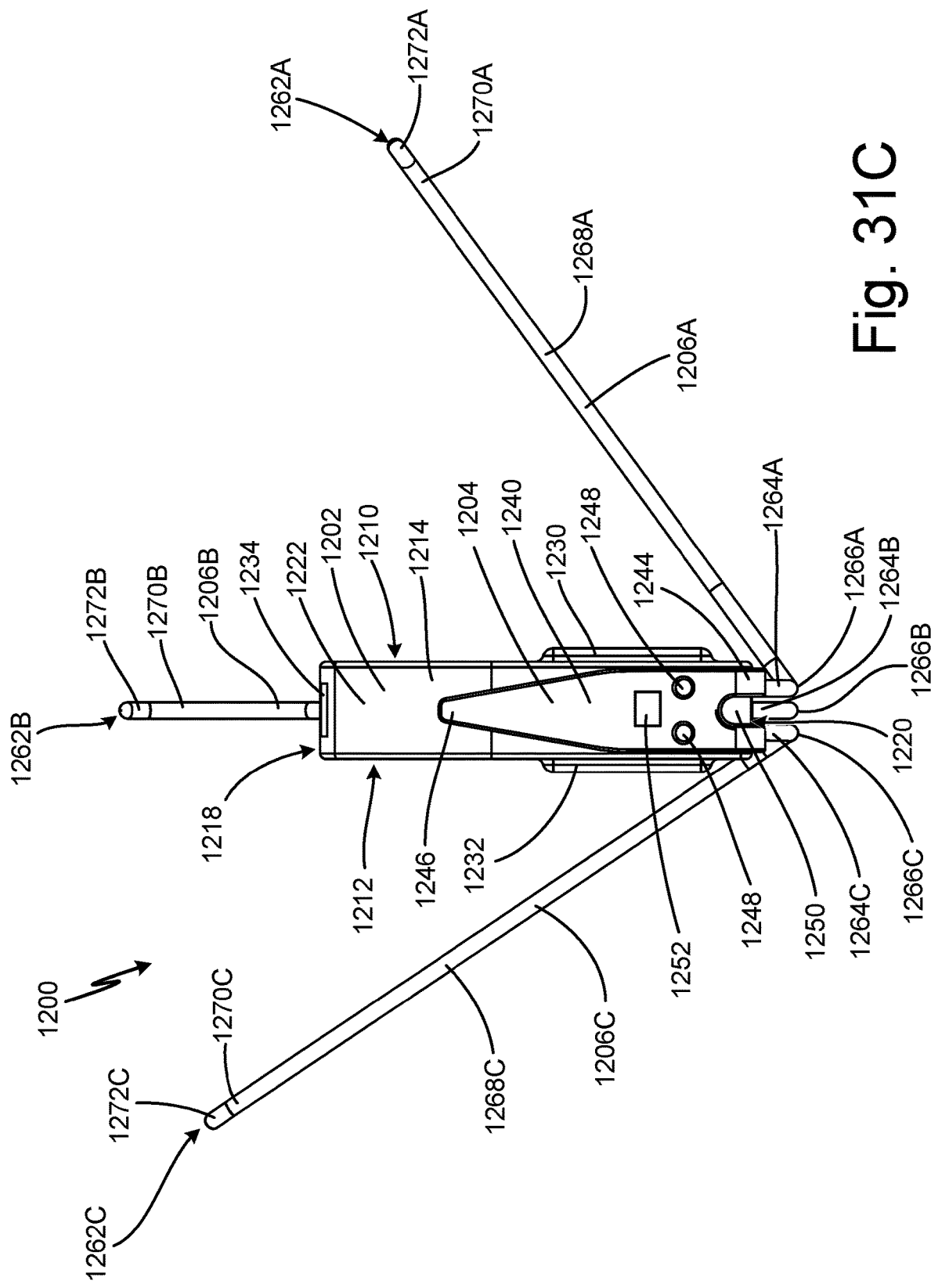
FIG. 31C is a top view of the tenth embodiment of the subcutaneous device.
Figure 31D:
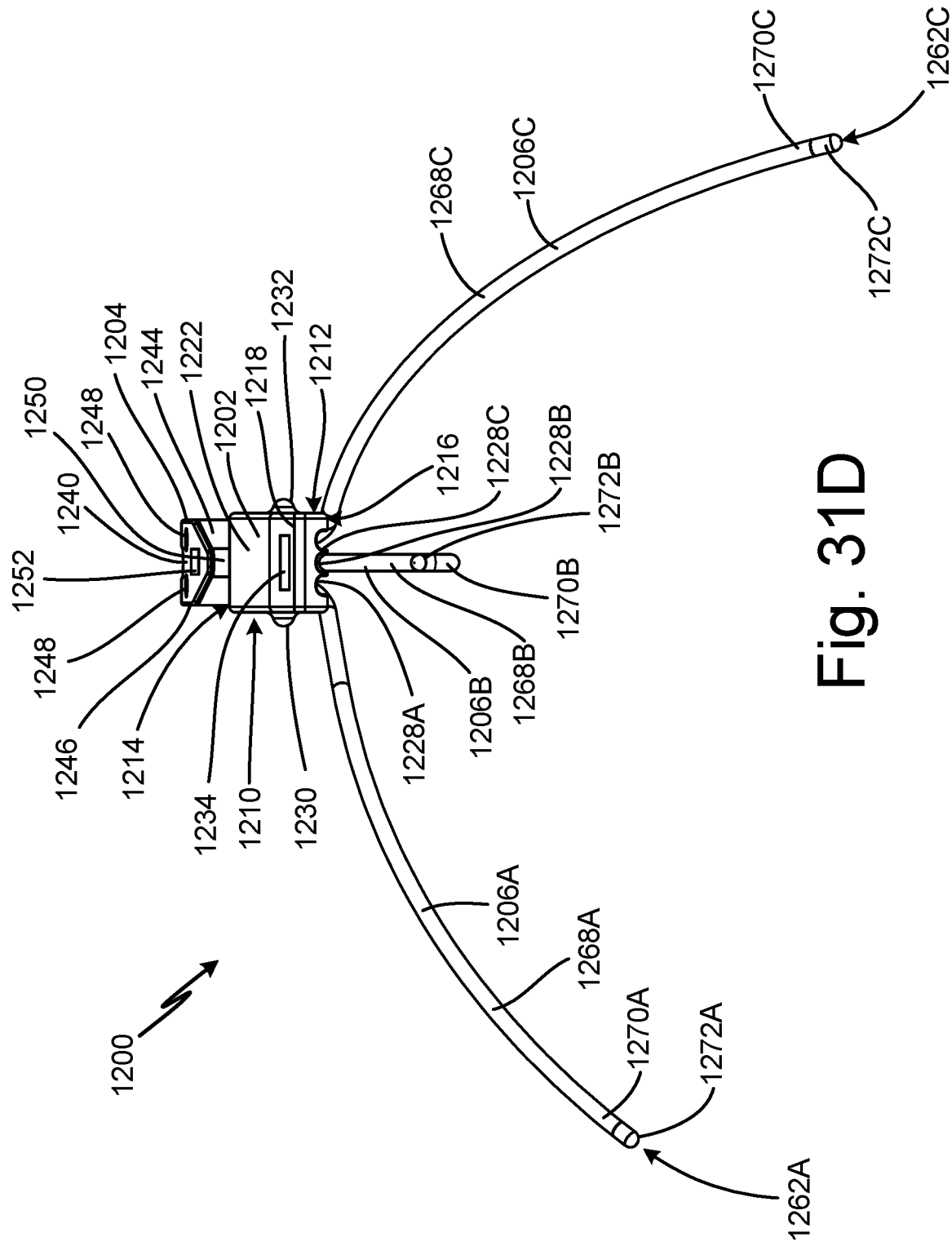
FIG. 31D is a front view of the tenth embodiment of the subcutaneous device.
Figure 31E:
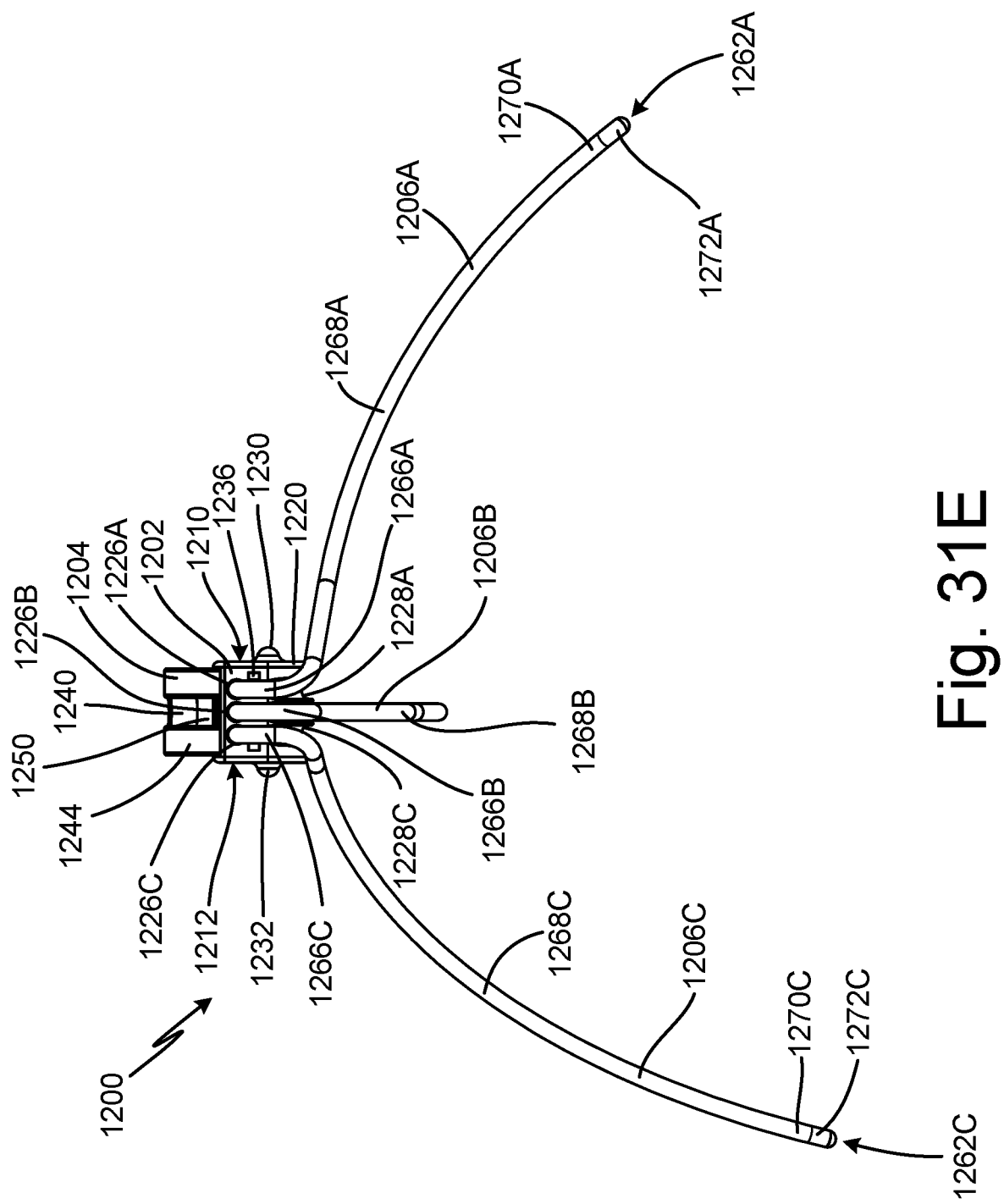
FIG. 31E is a back view of the tenth embodiment of the subcutaneous device.
Figure 32A:
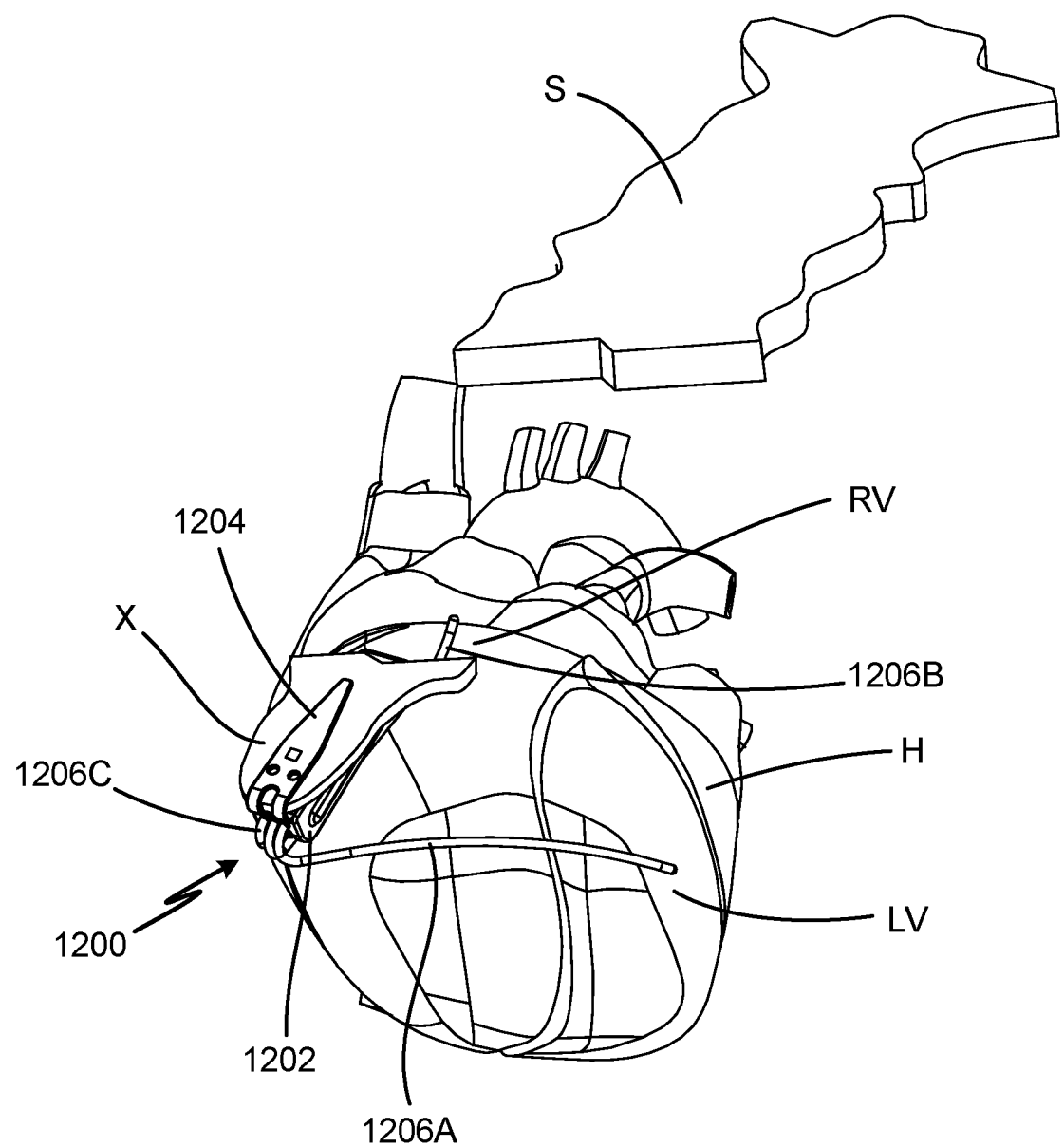
FIG. 32A is a cut-away perspective view of the tenth embodiment of the subcutaneous device positioned on a xiphoid process and a sternum and showing a positioning of prongs on a heart.
Figure 32B:
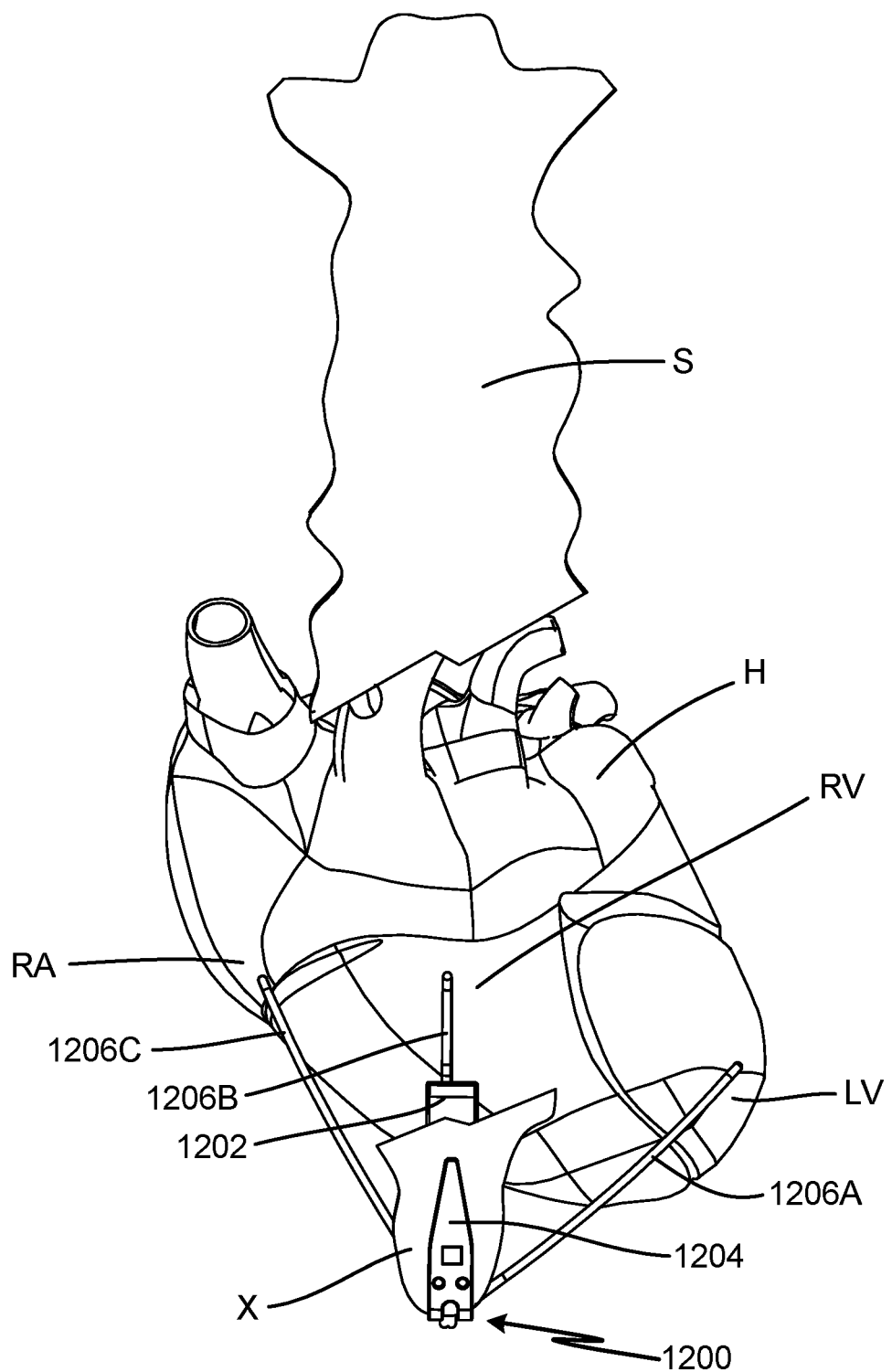
FIG. 32B is a cut-away front view of the tenth embodiment of the subcutaneous device positioned on the xiphoid process and the sternum and showing a positioning of the prongs on the heart.
Figure 32C:
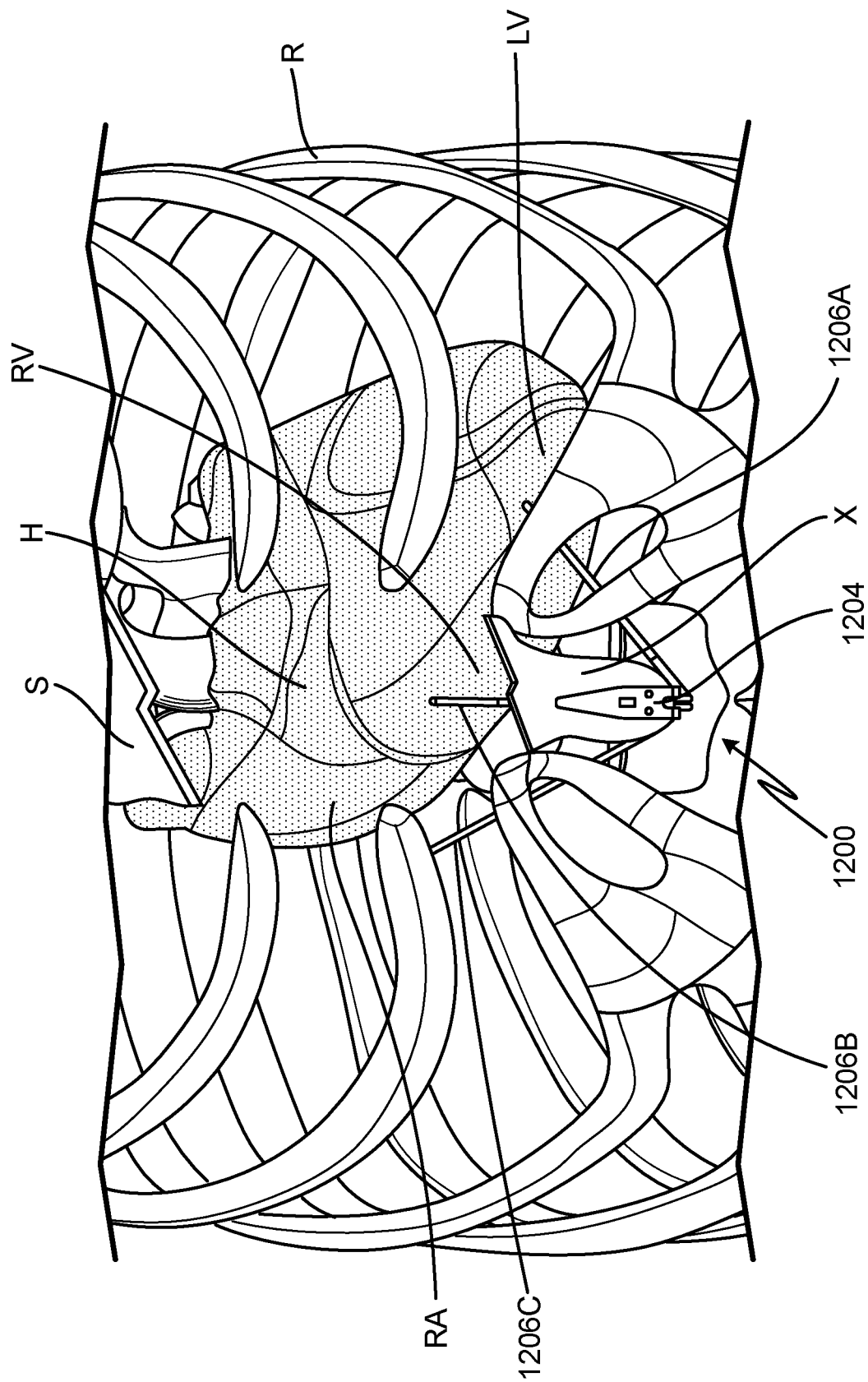
FIG. 32C is a cut-away front view of the tenth embodiment of the subcutaneous device positioned on the xiphoid process and the sternum and showing a positioning of the prongs on the heart.

FIG. 31A is a perspective view of subcutaneous device 1200. FIG. 31B is a side view of subcutaneous device 1200. FIG. 31C is a top view of subcutaneous device 1200. FIG. 31D is a front view of subcutaneous device 1200. FIG. 31E is a back view of subcutaneous device 1200. FIG. 32A is a cut-away perspective view of subcutaneous device 1200 positioned on xiphoid process X and sternum S and showing a positioning of prongs 1206A, 1206B, and 1206C on heart H. FIG. 32B is a cut-away front view of subcutaneous device 1200 positioned on xiphoid process X and sternum S and showing a positioning of 1206A, 1206B, and 1206C on heart H. FIG. 32C is a cut-away front view of subcutaneous device 1200 positioned on xiphoid process X and sternum S and showing a positioning of prongs 1206A, 1206B, and 1206C on heart H. Subcutaneous device 1200 includes housing 1202, clip 1204, prong 1206A, prong 1206B, and prong 1206C. Housing 1202 includes first side 1210, second side 1212, top side 1214, bottom side 1216, front end 1218, back end 1220, curved surface 1222, recess 1224, port 1226A, port 1226B, port 1226C, channel 1228A, channel 1228B, channel 1228C, first guide 1230, second guide 1232, electrode 1234, and electrode 1236. Clip 1204 includes top portion 1240, bottom portion 1242, spring portion 1244, tip 1246, openings 1248, slot 1250, and electrode 1252. Prong 1206A includes proximal end 1260A (not shown in FIGS. 31A-32C), distal end 1262A, base portion 1264A, spring portion 1266A, arm portion 1268A, contact portion 1270A, and electrode 1272A. Prong 1206B includes proximal end 1260B (not shown in FIGS. 31A-32C), distal end 1262B, base portion 1264B, spring portion 1266B, arm portion 1268B, contact portion 1270B, and electrode 1272B. Prong 1206C includes proximal end 1260C (not shown in FIGS. 31A-32C), distal end 1262C, base portion 1264C, spring portion 1266C, arm portion 1268C, contact portion 1270C, and electrode 1272C. FIGS. 32A-32C include xiphoid process X, sternum S, heart H, left ventricle LV, right ventricle RV, and right atrium RA. FIG. 32C also show ribs R.

Subcutaneous device 1200 includes housing 1202, clip 1204, prong 1206A, prong 1206B, and prong 1206C. Housing 1202 has the same general structure and design as housing 102 of subcutaneous device 100 shown in FIGS. 1-9C. However, housing 1202 includes three ports, including port 1226A, port 1226B, and port 1226C, and three channels, including channel 1228A, channel 1228B, and channel 1228C. The reference numerals that refer to the parts of housing 1202 are incremented by eleven-hundred compared to the reference numerals that refer to the parts of housing 102 of subcutaneous device 100 shown in FIGS. 1-9C. Port 1226A, port 1226B, and port 1228C are positioned next to one another on housing 1202, and channel 1228A, channel 1228B, and channel 1228C are positioned next to one another on housing 1202. Prong 1206A is configured to be connected to port 1226A and can be positioned in channel 1228A when subcutaneous device 1200 is in a stowed position. Prong 1206B is configured to be connected to port 1226B and can be positioned in channel 1228B when subcutaneous device 1200 is in a stowed position. Prong 1206C is configured to be connected to port 1226C and can be positioned in channel 1228C when subcutaneous device 1200 is in a stowed position.

Clip 1204 has the same general structure and design as clip 104 of subcutaneous device 100 shown in FIGS. 1-9C. The reference numerals that refer to the parts of clip 1204 are incremented by eleven-hundred compared to the reference numerals that refer to the parts of clip 104 of subcutaneous device 100 shown in FIGS. 1-9C.

Prong 1206A, prong 1206B, and prong 1206C each include the same parts as prong 106 of subcutaneous device 100 as shown in FIGS. 1-9C, and the reference numerals that refer to the parts of prong 1206A, prong 1206B, and prong 1206C are incremented by eleven-hundred compared to the reference numerals that refer to the parts of prong 106 of subcutaneous device 100 shown in FIGS. 1-9C. However, prong 1206A and prong 1206C have a different shape than prong 106 shown in FIGS. 1-9C. Spring portion 1266A and arm portion 1268A of prong 1206A extend away from first side 1210 of housing 1202. Contact portion 1270A is a portion of prong 1206A adjacent to distal end 1262A of prong 1206A that is configured to come into contact with left ventricle LV of heart H of the patient. Electrode 1272A positioned on contact portion 1270A will also come into contact with left ventricle LV of heart H of the patient. Spring portion 1266C and arm portion 1268C of prong 1206C extend away from second side 1212 of housing 1202. Contact portion 1270C is a portion of prong 1206C adjacent to distal end 1262C of prong 1206C that is configured to come into contact with right atrium RA of heart H of the patient. Electrode 1272C positioned on contact portion 1270C will also come into contact with right atrium RA of heart H of the patient. Prong 1206B has the same shape as prong 106 shown in FIGS. 1-9C. Spring portion 1266B and arm portion 1268B of prong 1206B extend underneath bottom side 1216 of housing 1202. Contact portion 1270B is a portion of prong 1206B adjacent to distal end 1262B of prong 1206B that is configured to come into contact with right ventricle RV of heart H of the patient. Electrode 1272B positioned on contact portion 1270B will also come into contact with right ventricle RV of heart H of the patient.

In one example, subcutaneous device 1200 can be anchored to xiphoid process X and sternum S of a patient. Clip 1204 is configured to anchor subcutaneous device 1200 to xiphoid process X and sternum S. Clip 1204 will expand as it is slid around xiphoid process X and sternum S. Spring portion 1244 acts as a spring for clip 1204 and is under tension. Top portion 1240 acts as a tension arm and the forces from spring portion 1244 translate to and push down on top portion 1240. When clip 1204 is positioned on xiphoid process X and sternum S, the tension in spring portion 1244 will force top portion 1240 down onto xiphoid process X and sternum S to anchor clip 1204 to xiphoid process X and sternum S. Further, sutures, tines, pins, or screws can be inserted through openings 1248 on top portion 1240 of clip 1204 to further anchor subcutaneous device 1200 to xiphoid process S and sternum S.

Subcutaneous device 1200 can include a power source, a controller, a memory, a transceiver, sensors, sensing circuitry, therapeutic circuitry, electrodes, and/or any other component of a medical device. In the embodiment shown in FIGS. 31A-32C, subcutaneous device 1200 is configured to be a triple chamber pacemaker. Any one or combination of electrode 1234, electrode 1236, electrode 1252, electrode 1272A, electrode 1274B, and electrode 1274C can sense the electrical activity of heart H. The sensed electrical activity can be transmitted to the sensing circuitry and the controller in housing 1202 of subcutaneous device 1200. The controller can determine the heart rate of the patient and can detect whether an arrhythmia is present. If an arrhythmia is detected, the controller can send instructions to therapeutic circuitry to provide a therapeutic electrical stimulation to heart H. Specifically, a therapeutic electrical stimulation can be provided to the right ventricle, the left ventricle, and the right atrium. In this manner, subcutaneous device 1200 functions as a monitoring device, a diagnostic device, and a therapeutic device. In alternate embodiments, subcutaneous device 1200 can function only as a monitoring device, a diagnostic device, or a therapeutic device, or any combinations thereof.

Subcutaneous Device 1300

FIG. 33 is a perspective view of subcutaneous device 1300. Subcutaneous device 1300 includes housing 1302, clip 1304, prong 1306A, prong 1306B, and prong 1306C. Housing 1302 includes first side 1310, second side 1312, top side 1314, bottom side 1316, front end 1318, back end 1320, curved surface 1322, recess 1324, port 1326A, port 1326B, port 1326C, channel 1328A (not shown in FIG. 33), channel 1328B, channel 1328C, first guide 1330 (not shown in FIG. 33), second guide 1332, electrode 1334, and electrode 1336. Clip 1304 includes top portion 1340, bottom portion 1342, spring portion 1344, tip 1346, openings 1348, slot 1350, and electrode 1352. Prong 1306A includes proximal end 1360A (not shown in FIG. 33), distal end 1362A, base portion 1364A, spring portion 1366A, arm portion 1368A, contact portion 1370A, and electrode 1372A. Prong 1306B includes proximal end 1360B (not shown in FIG. 33), distal end 1362B, base portion 1364B, spring portion 1366B, arm portion 1368B, contact portion 1370B, and electrode 1372B. Prong 1306C includes proximal end 1360C (not shown in FIG. 33), distal end 1362C, base portion 1364C, spring portion 1366C, arm portion 1368C, contact portion 1370C, and defibrillator coil 1374C.

Subcutaneous device 1300 includes housing 1302, clip 1304, prong 1306A, prong 1306B, and prong 1306C. Housing 1302 has the same general structure and design as housing 102 of subcutaneous device 100 shown in FIGS. 1-9C. However, housing 1302 includes three ports, including port 1326A, port 1326B, and port 1326C, and three channels, including channel 1328A, channel 1328B, and channel 1328C. The reference numerals that refer to the parts of housing 1302 are incremented by twelve-hundred compared to the reference numerals that refer to the parts of housing 102 of subcutaneous device 100 shown in FIGS. 1-9C. Port 1326A, port 1326B, and port 1326C are positioned next to one another on housing 1302, and channel 1328A, channel 1328B, and channel 1328C are positioned next to one another on housing 1302. Prong 1306A is configured to be connected to port 1326A and can be positioned in channel 1328A when subcutaneous device 1300 is in a stowed position. Prong 1306B is configured to be connected to port 1326B and can be positioned in channel 1328B when subcutaneous device 1300 is in a stowed position. Prong 1306C is configured to be connected to port 1326C and can be positioned in channel 1328C when subcutaneous device 1300 is in a stowed position.

Clip 1304 has the same general structure and design as clip 104 of subcutaneous device 100 shown in FIGS. 1-9C. The reference numerals that refer to the parts of clip 1304 are incremented by twelve-hundred compared to the reference numerals that refer to the parts of clip 104 of subcutaneous device 100 shown in FIGS. 1-9C.

Prong 1306A, prong 1306B, and prong 1306C generally include the same parts as prong 106 of subcutaneous device 100 as shown in FIGS. 1-9C, and the reference numerals that refer to the parts of prong 1306A, prong 1306B, and prong 1306C are incremented by twelve-hundred compared to the reference numerals that refer to the parts of prong 106 of subcutaneous device 100 shown in FIGS. 1-9C. However, prong 1306A and prong 1306C have a different shape than prong 106 shown in FIGS. 1-9C, and prong 1306C includes defibrillator coil 1374C instead of an electrode. Spring portion 1366A and arm portion 1368A extend away from first side 1310 of housing 1302. Contact portion 1370A is a portion of prong 1306A adjacent to distal end 1362A of prong 1306A that is configured to come into contact with the left ventricle of the patient's heart. Electrode 1372A positioned on contact portion 1370A will also come into contact with the left ventricle of the patient's heart. Spring portion 1366C and arm portion 1368C extend away from bottom side 1320 of housing 1302. Contact portion 1370C is a portion of prong 1306C adjacent to distal end 1362C of prong 1306C that is configured to come into contact with tissue inferior to a patient's heart. Defibrillator coil 1374C is positioned on contact portion 1370C adjacent to distal end 1362C of prong 1306C. When an electrical signal is delivered to defibrillator coil 1374C, defibrillator coil 1374C will create a vector with electrode 1334 on front end 1318 of housing 1302. In the embodiment shown, defibrillator coil 1374C serves as the negative electrode and electrode 1334 serves as the positive electrode. However, in alternate embodiments this can be reversed. Prong 1306C is positioned so that distal end 1362C, and thus contact portion 1370C and defibrillator coil 1374C, are positioned inferior to the heart. Thus, the vector created between defibrillator coil 1374C and electrode 1334 will pass through a patient's heart to provide a high voltage electrical shock to the patient's heart. Prong 1306B has the same shape as prong 106 shown in FIGS. 1-9C. Spring portion 1366B and arm portion 1368B extend away from bottom side 1320 of housing 1302. Contact portion 1370B is a portion of prong 1306B adjacent to distal end 1362B of prong 1306B that is configured to come into contact with the left ventricle of the patient's heart. Electrode 1372B positioned on contact portion 1370B will also come into contact with the left ventricle of the patient's heart.

In one example, subcutaneous device 1300 can be anchored to a xiphoid process and a sternum of a patient. Clip 1304 is configured to anchor subcutaneous device 1300 to the xiphoid process and the sternum. Clip 1304 will expand as it is slid around the xiphoid process and the sternum. Spring portion 1344 acts as a spring for clip 1304 and is under tension. Top portion 1340 acts as a tension arm and the forces from spring portion 1344 translate to and push down on top portion 1340. When clip 1304 is positioned on the xiphoid process and the sternum, the tension in spring portion 1344 will force top portion 1340 down onto the xiphoid process and the sternum to anchor clip 1304 to the xiphoid process and the sternum. Further, sutures, tines, pins, or screws can be inserted through openings 1348 on top portion 1340 of clip 1304 to further anchor subcutaneous device 1300 to the xiphoid process and the sternum.

Subcutaneous device 1300 can include a power source, a controller, a memory, a transceiver, sensors, sensing circuitry, therapeutic circuitry, electrodes, and/or any other component of a medical device. In the embodiment shown in FIG. 33, subcutaneous device 1300 is configured to be a two chamber pacemaker and a defibrillator. Any one or combination of electrode 1334, electrode 1336, electrode 1352, electrode 1372A, and electrode 1372B can sense the electrical activity of a heart. Further, defibrillator coil 1374C can act as an electrode that senses the electrical activity of the heart. The sensed electrical activity can be transmitted to the sensing circuitry and the controller in housing 1302 of subcutaneous device 1300. The controller can determine the heart rate of the patient and can detect whether an arrhythmia or an abnormality is present. If an arrhythmia is detected, the controller can send instructions to therapeutic circuitry to provide a therapeutic electrical stimulation to the heart with electrode 1372A and electrode 137B. Specifically, a therapeutic electrical stimulation can be provided to the right ventricle and the left ventricle. If an abnormality is detected, the controller can send instructions to therapeutic circuitry to provide a high voltage electrical shock to the heart with defibrillator coil 1374C. In this manner, subcutaneous device 1300 functions as a monitoring device, a diagnostic device, and a therapeutic device. In alternate embodiments, subcutaneous device 1300 can function only as a monitoring device, a diagnostic device, or a therapeutic device, or any combinations thereof.

Subcutaneous Device 1400

FIG. 34A is a perspective view of subcutaneous device 1400. FIG. 34B is a perspective view of subcutaneous device 1400. FIG. 34C is a side view of subcutaneous device 1400. Subcutaneous device 1400 includes housing 1402, clip 1404, prong 1406A, prong 1406B, prong 1406C, and prong 1406D. Housing 1402 includes first side 1410, second side 1412, top side 1414, bottom side 1416, front end 1418, back end 1420, curved surface 1422, recess 1424, port 1426A, port 1426B, port 1426C, port 1426D, channel 1428A (not shown in FIGS. 34A-34C), channel 1428B, channel 1428C, channel 1428D, first guide 1430, second guide 1432, electrode 1434, and electrode 1436. Clip 1404 includes top portion 1440, bottom portion 1442, spring portion 1444, tip 1446, openings 1448, slot 1450, and electrode 1452. Prong 1406A includes proximal end 1460A (not shown in FIGS. 34A-34C), distal end 1462A, base portion 1464A, spring portion 1466A, arm portion 1468A, contact portion 1470A, and defibrillator coil 1474A. Prong 1406B includes proximal end 1460B (not shown in FIGS. 34A-34C), distal end 1462B, base portion 1464B, spring portion 1466B, arm portion 1468B, contact portion 1470B, and defibrillator coil 1474B. Prong 1406C includes proximal end 1460C (not shown in FIGS. 34A-34C), distal end 1462C, base portion 1464C, spring portion 1466C, arm portion 1468C, contact portion 1470C, and electrode 1474C. Prong 1406D includes proximal end 1460D (not shown in FIGS. 34A-34C), distal end 1462D, base portion 1464D, spring portion 1466D, arm portion 1468D, contact portion 1470D, and defibrillator coil 1474D.

Subcutaneous device 1400 includes housing 1402, clip 1404, prong 1406A, prong 1406B, prong 1406C, and prong 1406D. Housing 1402 has the same general structure and design as housing 102 of subcutaneous device 100 shown in FIGS. 1-9C. However, housing 1402 includes four ports, including port 1426A, port 1426B, port 1426C, and port 1426D, and four channels, including channel 1428A, channel 1428B, channel 1428C, and channel 1428D. The reference numerals that refer to the parts of housing 1402 are incremented by thirteen-hundred compared to the reference numerals that refer to the parts of housing 102 of subcutaneous device 100 shown in FIGS. 1-9C. Port 1426A, port 1426B, port 1426C, and port 1426D are positioned next to one another on housing 1402, and channel 1428A, channel 1428B, channel 1428C, and channel 1428D are positioned next to one another on housing 1402. Prong 1406A is configured to be connected to port 1426A and can be positioned in channel 1428A when subcutaneous device 1400 is in a stowed position. Prong 1406B is configured to be connected to port 1426B and can be positioned in channel 1428B when subcutaneous device 1400 is in a stowed position. Prong 1406C is configured to be connected to port 1426C and can be positioned in channel 1428C when subcutaneous device 1400 is in a stowed position. Prong 1406D is configured to be connected to port 1426D and can be positioned in channel 1428D when subcutaneous device 1400 is in a stowed position.

Clip 1404 has the same general structure and design as clip 104 of subcutaneous device 100 shown in FIGS. 1-9C. The reference numerals that refer to the parts of clip 1404 are incremented by thirteen-hundred compared to the reference numerals that refer to the parts of clip 104 of subcutaneous device 100 shown in FIGS. 1-9C.

Prong 1406A, prong 1406B, prong 1406C, and prong 1406D generally include the same parts as prong 106 of subcutaneous device 100 as shown in FIGS. 1-9C, and the reference numerals that refer to the parts of prong 1406A, prong 1406B, prong 1406C, and prong 1406D are incremented by thirteen-hundred compared to the reference numerals that refer to the parts of prong 106 of subcutaneous device 100 shown in FIGS. 1-9C. However, prong 1406A, prong 1406B, and prong 1406D have a different shape than prong 106 shown in FIGS. 1-9C and include defibrillator coil 1474A, defibrillator coil 1474B, and defibrillator coil 1474D, respectively, instead of an electrode.

Spring portion 1466A and arm portion 1468A extend along first side 1410 of housing 1402. Contact portion 1470A is a portion of prong 1406A adjacent to distal end 1462A of prong 1406A that is configured to come into contact with tissue on first side 1410 of housing 1402. Defibrillator coil 1474A is positioned on contact portion 1470A adjacent to distal end 1462A of prong 1406A. Defibrillator coil 1474A is configured to create a vector with defibrillator coil 1474B. Spring portion 1466D and arm portion 1468D extend along second side 1412 of housing 1402. Contact portion 1470D is a portion of prong 1406D adjacent to distal end 1462D of prong 1406D that is configured to come into contact with tissue on second side 1412 of housing 1402. Defibrillator coil 1474D is positioned on contact portion 1470D adjacent to distal end 1462D of prong 1406D. Defibrillator coil 1474D is configured to create a vector with defibrillator coil 1474B.

Spring portion 1466B and arm portion 1468B extend away from bottom side 1420 of housing 1402. Contact portion 1470B is a portion of prong 1406B adjacent to distal end 1462B of prong 1406B that is configured to come into contact with tissue inferior to a patient's heart. Defibrillator coil 1474B is positioned on contact portion 1470B adjacent to distal end 1462B of prong 1406B. When an electrical signal is delivered to defibrillator coil 1474B, defibrillator coil 1474B will create a first vector with electrode 1434 on front end 1418 of housing 1402, a second vector with defibrillator coil 1474A on prong 1406A, and a third vector with defibrillator coil 1474D on prong 1406D. In the embodiment shown, defibrillator coil 1474B serves as the negative electrode and electrode 1434, defibrillator coil 1474A, and defibrillator coil 1474D serve as the positive electrodes. However, in alternate embodiments this can be reversed. Prong 1406B is positioned so that distal end 1462B, and thus contact portion 1470B and defibrillator coil 1474B, are positioned inferior to the heart. Thus, the vectors created between defibrillator coil 1474B and electrode 1434, defibrillator coil 1474A, and defibrillator coil 1474D will pass through a patient's heart to provide a high voltage electrical shock to the patient's heart.

Prong 1406C has the same shape as prong 106 shown in FIGS. 1-9C. Spring portion 1466C and arm portion 1468C extend away from bottom side 1420 of housing 1402. Contact portion 1470C is a portion of prong 1406C adjacent to distal end 1462C of prong 1406C that is configured to come into contact with the left ventricle of the patient's heart. Electrode 1472C positioned on contact portion 1470C will also come into contact with the left ventricle of the patient's heart.

In one example, subcutaneous device 1400 can be anchored to a xiphoid process and a sternum of a patient. Clip 1404 is configured to anchor subcutaneous device 1400 to the xiphoid process and the sternum. Clip 1404 will expand as it is slid around the xiphoid process and the sternum. Spring portion 1444 acts as a spring for clip 1404 and is under tension. Top portion 1440 acts as a tension arm and the forces from spring portion 1444 translate to and push down on top portion 1440. When clip 1404 is positioned on the xiphoid process and the sternum, the tension in spring portion 1444 will force top portion 1440 down onto the xiphoid process and the sternum to anchor clip 1404 to the xiphoid process and the sternum. Further, sutures, tines, pins, or screws can be inserted through openings 1448 on top portion 1440 of clip 1404 to further anchor subcutaneous device 1400 to the xiphoid process and the sternum.

Subcutaneous device 1400 can include a power source, a controller, a memory, a transceiver, sensors, sensing circuitry, therapeutic circuitry, electrodes, and/or any other component of a medical device. In the embodiment shown in FIGS. 34A-34C, subcutaneous device 1400 is configured to be a single chamber pacemaker and a multi-vector defibrillator. Any one or combination of electrode 1434, electrode 1436, electrode 1452, and electrode 1472C can sense the electrical activity of a heart. Further, defibrillator coil 1474A, defibrillator coil 1474B, and defibrillator coil 1474D can act as an electrode that senses the electrical activity of the heart. The sensed electrical activity can be transmitted to the sensing circuitry and the controller in housing 1402 of subcutaneous device 1400. The controller can determine the heart rate of the patient and can detect whether an arrhythmia or abnormality is present. If an arrhythmia is detected, the controller can send instructions to therapeutic circuitry to provide a therapeutic electrical shock to the heart with electrode 1472C. If an abnormality is detected, the controller can send instructions to therapeutic circuitry to provide a high voltage electrical shock to the heart with defibrillator coil 1474B. In this manner, subcutaneous device 1400 functions as a monitoring device, a diagnostic device, and a therapeutic device. In alternate embodiments, subcutaneous device 1400 can function only as a monitoring device, a diagnostic device, a therapeutic device, or any combinations thereof.

Subcutaneous Device 1500

FIG. 35A is a perspective view of subcutaneous device 1500. FIG. 35B is a perspective view of subcutaneous device 1500. FIG. 35C is a bottom view of subcutaneous device 1500. FIG. 35D is a side view of subcutaneous device 1500. FIG. 35E is a back view of subcutaneous device 1500. FIG. 35F is a front view of subcutaneous device 1500. FIG. 36A is a schematic diagram of subcutaneous device 1500. FIG. 36B is a sectional diagram illustrating portions of subcutaneous device 1500 from the side. FIG. 36C is a sectional diagram illustrating portions of subcutaneous device 1500 from the bottom. FIG. 37 is a perspective view of subcutaneous device 1500 positioned on xiphoid process X and sternum S. Subcutaneous device 1500 includes housing 1502, clip 1504, prong 1506A, and prong 1506B. Housing 1502 includes first side 1510, second side 1512, top side 1514, bottom side 1516, front end 1518, back end 1520, curved surface 1522, recess 1524, port 1526A, port 1526B, first guide 1530, second guide 1532, electrode 1534, and electrode 1536. Clip 1504 includes top portion 1540, bottom portion 1542, spring portion 1544, tip 1546, openings 1548, slot 1550, and electrode 1552. Prong 1506A includes proximal end 1560A, distal end 1562A, base portion 1564A, spring portion 1566A, arm portion 1568A, contact portion 1570A, opening 1576A, and lumen 1578A. Prong 1508B includes proximal end 1560B, distal end 1562B, base portion 1564B, spring portion 1566B, arm portion 1568B, opening 1576B, and lumen 1578B. Subcutaneous device 1500 further includes drug reservoir 1580, drug pump 1582, fluid connector 1584, fluid connector 1586, fluid connector 1588, electronic components 1590, and battery 1592. FIG. 37 shows xiphoid process X and sternum S.

Subcutaneous device 1500 includes housing 1502, clip 1504, prong 1506A, and prong 1506B. Housing 1502 has the same general structure and design as housing 102 of subcutaneous device 100 shown in FIGS. 1-9C. However, housing 1502 includes two ports, including port 1526A and port 1526B. The reference numerals that refer to the parts of housing 1502 are incremented by fourteen-hundred compared to the reference numerals that refer to the parts of housing 102 of subcutaneous device 100 shown in FIGS. 1-9C. Port 1526A and port 1526B are positioned next to one another on housing 1502. Prong 1506A is configured to be connected to port 1526A. Prong 1506B is configured to be connected to port 1526B.

Clip 1504 has the same general structure and design as clip 104 of subcutaneous device 100 shown in FIGS. 1-9C. The reference numerals that refer to the parts of clip 1504 are incremented by fourteen-hundred compared to the reference numerals that refer to the parts of clip 104 of subcutaneous device 100 shown in FIGS. 1-9C.

Prong 1506A and prong 1506B generally include the same parts as prong 106 of subcutaneous device 100 as shown in FIGS. 1-9C, and the reference numerals that refer to the parts of prong 1506A and prong 1506B are incremented by fourteen-hundred compared to the reference numerals that refer to the parts of prong 106 of subcutaneous device 100 shown in FIGS. 1-9C. However, prong 1506A and prong 1506B have a different shape than prong 106 shown in FIGS. 1-9C, and include opening 1576A and lumen 1578A, and opening 1576B and lumen 1578B, respectively. Spring portion 1566A and arm portion 1568A extend underneath bottom side 1516 of housing 1502. Contact portion 1570A is a portion of prong 1506A adjacent to distal end 1562A of prong 1506A that is configured to come into contact with an organ, a nerve, or a tissue. Prong 1506A has opening 1576A at distal end 1562A and includes lumen 1578A extending from proximal end 1560A to distal end 1562A. Spring portion 1566B and arm portion 1568B extend upwards along back side 1520 of housing 1502. Prong 1506B has opening 1576B at distal end 1562B and includes lumen 1578B extending from proximal end 1560B to distal end 1562B.

In one example, subcutaneous device 1500 can be anchored to xiphoid process X and sternum S of a patient. Clip 1504 is configured to anchor subcutaneous device 1500 to xiphoid process X and sternum S. Clip 1504 will expand as it is slid around xiphoid process X and sternum S. Spring portion 1544 acts as a spring for clip 1504 and is under tension. Top portion 1540 acts as a tension arm and the forces from spring portion 1544 translate to and push down on top portion 1540. When clip 1504 is positioned on xiphoid process X and sternum S, the tension in spring portion 1544 will force top portion 1540 down onto xiphoid process X and sternum S to anchor clip 1504 to xiphoid process X and sternum S. Further, sutures, tines, pins, or screws can be inserted through openings 1548 on top portion 1540 of clip 1504 to further anchor subcutaneous device 1500 to xiphoid process X and sternum S.

Subcutaneous device 1500 can include a power source, a controller, a memory, a transceiver, sensors, sensing circuitry, therapeutic circuitry, electrodes, and/or any other component of a medical device. In the embodiment shown in FIGS. 35A-37, subcutaneous device 1500 is configured to be a drug delivery device. As shown in FIGS. 36A-36C, subcutaneous device 1500 includes drug reservoir 1580 and drug pump 1582 positioned in housing 1502. Drug reservoir 1580 includes fluid connector 1584 that fluidly connects drug reservoir 1580 to prong 1506B and fluid connector 1586 that fluidly connects drug reservoir 1580 to drug pump 1582. Drug pump 1582 also includes fluid connector 1588 that fluidly connects drug pump 1582 to prong 1506A. A drug can be inserted into opening 1576B of prong 1506B and then travel through lumen 1578B of prong 1506B to drug reservoir 1580. In this way, drug reservoir 1580 can be replenished and refilled as needed. An injector can be positioned in opening 1578B to inject the drug into prong 1506B. The drug in drug reservoir 1580 can then be pumped out of drug reservoir 1580 with drug pump 1582. Drug pump 1582 will pump the drug in drug reservoir 1580 through fluid connector 1586, drug pump 1582, fluid connector 1588, and into prong 1506A. The drug in prong 1506A can travel through lumen 1578A of prong 1506A and exit prong 1506A at opening 1576A. Opening 1576A is positioned to contact an organ, a nerve, or a tissue, so the drug can be applied to the organ, the nerve, or the tissue. FIGS. 36A-36C also show electronic components 1590, which can include a controller, a memory, a transceiver, sensors, sensing circuitry, therapeutic circuitry, electrodes, and/or any other component of a medical device, and battery 1592. Battery 1592 powers subcutaneous device 1500, including electronic components 1590 and drug pump 1592. Electronic components 1590 can specifically include therapeutic circuitry that can send a signal to drug pump 1592 to administer a drug to the patient through prong 1506A. In this manner, subcutaneous device 1500 functions as a drug delivery device that is capable of providing a targeted or systemic therapeutic drug to an organ, a nerve, or a tissue. Providing a targeted or systemic therapeutic drug can be used to treat cancer, diabetes, and hypertension. Treating cancer with targeted or systemic therapeutic drug can reduce side effects. In alternate embodiments, subcutaneous device 1500 can include components to allow it to also function as a monitoring and diagnostic device, as a pacemaker device, or as a defibrillator device.

Subcutaneous devices 100, 400, 500, 600, 700, 800, 900, 1000, 1100, 1200, 1300, 1400, and 1500 disclose various embodiments of the subcutaneous devices, including: a single prong cardiac monitoring device, a multi-prong cardiac monitoring device, a pulmonary monitoring device, a single chamber pacemaker, a dual chamber pacemaker, a triple chamber pacemaker, an atrial defibrillator, a single-vector ventricular defibrillator, a multi-vector ventricular defibrillator, and an implantable drug pump and/or drug delivery device. Each of the pacemaker embodiments can also function as a monitoring and diagnostic device and/or a drug delivery device; each of the defibrillator embodiments can also function as a monitoring and diagnostic device, a pacemaker device, and/or a drug delivery device; and each of the drug delivery embodiments can also function as a monitoring and diagnostic device, a pacemaker device, and/or a defibrillator device. Further, the features of each embodiment may be combined and/or substituted with features of any other embodiment, unless explicitly disclosed otherwise.

Subcutaneous Device 1600

FIG. 38 is a side view of subcutaneous device 1600 anchored to structural body component A. Subcutaneous device 1600 includes clip 1604, prong 1606, wire 1608, and connector 1609. FIG. 38 also shows structural body component A, remote body component B, skin SK, and external device ED.

Subcutaneous device 1600 is a medical device that is configured to be anchored to structural body component A. Structural body component A may be a muscle, a bone, or a tissue of a patient. Subcutaneous device 1600 can be a monitoring device, a diagnostic device, a therapeutic device, or any combination thereof. Subcutaneous device 1600 is configured to be a temporary medical device that can be implanted in a patient for a short period of time and then easily removed from the patient. As shown in FIG. 38, clip 1604 and prong 1606 of subcutaneous device 1600 are positioned inside of a patient's body. Wire 1608 extends from prong 1606 inside of the patient's body, through the patient's skin SK, to outside of the patient's body. Connector 1609 is positioned outside of the patient's body. Subcutaneous device 1600 is conductively coupled to external device ED that is positioned outside of the patient's body.

Subcutaneous device 1600 includes clip 1604. Clip 1604 is configured to anchor subcutaneous device 1600 to structural body component A. Clip 1604 will expand as it is advanced around structural body component A. Clip 1604 can be a passive clip or an active clip. A passive clip only uses the stiffness of clamping components to attach to the bone, the muscle, or the tissue. This stiffness can be the result of design or active crimping during the implant procedure. An active clip may additionally use an active fixation method such as sutures, tines, pins, or screws to secure the clip to the bone, the muscle, or the tissue. In the embodiment shown in FIG. 38, clip 1604 has a spring bias that will put tension on the structural body component when it is expanded and fit onto structural body component A. The spring bias of clip 1604 will anchor subcutaneous device 1600 to structural body component A.

Prong 1606 is connected to and extends away from clip 1604 of subcutaneous device 1600. Prong 1606 is configured to contact remote body component B that is positioned away from structural body component A. Remote body component B may be an organ, a nerve, or tissue of the patient. For example, remote body component B can include a heart, a lung, or any other suitable organ in the body. Prong 1606 includes one or more electrodes that are capable of sensing an electrical activity or physiological parameter of remote body component B and/or providing therapeutic electrical stimulation to remote body component B.

Wire 1608 extends from the one or more electrodes on prong 1606, through one or more lumens in prong 1606, and out of a proximal end of prong 1606. Wire 1608 extends away from prong 1606 and through a transcutaneous port in skin SK of the patient. Connector 1609 is connected to a proximal end of wire 1608 that is positioned outside of the patient's body. Connector 1609 can be any electrical connector. Connector 1609 is configured to connect to external device ED that is positioned outside of a patient's body. External device ED can contain a controller, sensing circuitry, therapy circuitry, memory, a power source, a transceiver, a display screen, and/or any other component of a medical device. External device ED is configured to receive a signal from the one or more electrodes on prong 1606 and deliver an electrical signal to the one or more electrodes on prong 1606.

Subcutaneous device 1600 can be implanted into a patient while they are undergoing another surgery. For example, at the end of open-heart surgery, a surgeon can position clip 1604 around a muscle, a bone, and/or a first tissue to anchor subcutaneous device 1600 to the muscle, the bone, and/or the first tissue. As the incision in the patient is closed following surgery, wire 1609 can be positioned to extend through the incision in the patient's skin SK. Alternatively, subcutaneous device 1600 can be implanted in a patient by making a small incision in the patient's skin SK and then a surgical instrument can be used to insert subcutaneous device 1600 into the patient's body and anchor subcutaneous device 1600 to a muscle, a bone, and/or a first tissue. Wire 1609 can extend through the small incision made in the patient's skin SK.

In one example, subcutaneous device 1600 can be a temporary pacemaker and the one or more electrodes on prong 1606 of subcutaneous device 1600 can sense the electrical activity of a heart. The sensed electrical activity can be transmitted to sensing circuitry and a controller in external device ED. The controller can determine the heart rate of the patient and can detect whether an arrhythmia is present. If an arrhythmia is detected, the controller can send instructions to therapeutic circuitry to provide a therapeutic electrical stimulation to the heart through the one or more electrodes on prong 1606. In this manner, subcutaneous device 1600 functions as a monitoring device, a diagnostic device, and a therapeutic device. Subcutaneous device 1600 is controlled by external device ED. External device ED can be a sensing device, a pacemaker device, a defibrillator device, or any other device that can be electrically connected to subcutaneous device 1600 to receive signals from and send signals to subcutaneous device 1600.

Subcutaneous device 1600 will be discussed in greater detail in relation to FIGS. 39A-40 below. Subcutaneous device 1600 will be discussed as a temporary pacemaker that can be used for monitoring, diagnostics, and therapeutics in the discussion of FIGS. 39A-40 below. Subcutaneous device 1600 can also be used only for monitoring, diagnostics, or a combination of the two in alternate embodiments. Further, subcutaneous device 1600 can be a unipolar pacemaker or a bipolar pacemaker.

FIG. 39A is a perspective view of subcutaneous device 1600. FIG. 39B is a side view of subcutaneous device 1600. FIG. 39C is a back view of clip 1604 and prong 1606 of subcutaneous device 1600. Subcutaneous device 1600 includes clip 1604, prong 1606, wire 1608, and connector 1609. Clip 1604 includes top portion 1640, bottom portion 1642, spring portion 1644, tip 1646, openings 1648, slot 1650, and groove 1651. Prong 1606 includes proximal end 1660, distal end 1662, base portion 1664, arm portion 1668, contact portion 1670, opening 1671, electrode 1672, and electrode 1673.

Subcutaneous device 1600 includes clip 1604 and prong 1606 that are implanted in a patient. Wire 1608 extends through a proximal end of prong 1606 and terminates at connector 1609. Wire 1608 is configured to extend transcutaneously through a port in a patient's skin. Connector 1609 is configured to be connected to an external device positioned outside of a patient's body.

Clip 1604 includes top portion 1640, bottom portion 1642, and spring portion 1644. Top portion 1640 is a flat portion that forms a top of clip 1604, and bottom portion 1642 is a flat portion that forms a bottom of clip 1604. Spring portion 1644 is a curved portion positioned on a back end of clip 1604 that extends between and connects top portion 1640 to bottom portion 1642. Clip 1604 can be made out of stainless steel, titanium, nitinol, epoxy, silicone, polyurethane with metallic reinforcements, or any other material that is suitable for non-porous implants.

Top portion 1640 of clip 1604 includes tip 1646 adjacent to a front end of clip 1604. Top portion 1640 tapers from a middle of top portion 1640 to tip 1646. The taper of tip 1646 of top portion 1640 of clip 1604 helps clip 1604 push through tissue when clip 1604 is being anchored to a muscle, a bone, or a tissue of a patient. The taper of tip 1646 of top portion 1640 of clip 1604 will create a path through tissue when clip 1604 is anchored to a bone, a muscle, and/or a tissue.

Top portion 1640 can optionally include openings 1648. Openings 1648 extend through top portion 1640. There are two openings 1648 in top portion 1640 in the embodiment shown in FIGS. 39A-39C, but there could be any number of openings 1648 in alternate embodiments. Openings 1648 are configured to allow clip 1604 to be sutured to a muscle, a bone, or a tissue in a patient to secure subcutaneous device 1600 to the muscle, the bone, or the tissue. Further, openings 1648 can receive additional fixation mechanisms, such as tines, pins, or screws, to secure subcutaneous device 1600 to the muscle, the bone, or the tissue. These additional fixation mechanisms can be made from bioabsorbable materials. Clip 1604 also includes slot 1650. Slot 1650 is an opening that extends through spring portion 1644 of clip 1604. Slot 1650 is configured to receive a blade of a surgical instrument that can be used to implant subcutaneous device 1600 in a patient.

Bottom portion 1642 also includes groove 1651. Bottom portion 1642 is thicker than top portion 1640 and groove 1651 extends from a front end to a back end of a bottom side of bottom portion 1642. Groove 1651 is configured to receive prong 1606. Prong 1606 is attached to clip 1404 at groove 1651 and extends from the front end to the back end of groove 1651. Prong 1606 can be attached to groove 1651 using adhesive, mechanical latches, or any other suitable attachment means.

Spring portion 1644 acts as a spring for clip 1604 and is under tension. Top portion 1640 acts as a tension arm and the forces from spring portion 1644 translate to and push down on top portion 1640. In its natural state, a spring bias of spring portion 1644 forces tip 1646 of top portion 1640 towards bottom portion 1642 of clip 1604. Tip 1646 of top portion 1640 can be lifted up and clip 1604 can be positioned on a muscle, a bone, or tissue of a patient. When clip 1604 is positioned on a muscle, a bone, or tissue of a patient, the tension in spring portion 1644 will force top portion 1640 down onto the muscle, the bone, or the tissue. This tension will anchor clip 1604 to the muscle, the bone, or the tissue. Additional fixation mechanisms, such as tines, pins, or screws can also be used to anchor clip 1604 to the bone, the muscle, or the tissue.

Prong 1606 includes proximal end 1660 and distal end 1662 that is opposite of proximal end 1660. Proximal end 1660 of prong 1606 may have strain relief or additional material to support movement. Prong 1606 includes base portion 1664, arm portion 1668, and contact portion 1670. A first end of base portion 1664 is aligned with proximal end 1660 of prong 1606, and a second end of base portion 1664 is connected to a first end of arm portion 1668. Base portion 1664 is a straight portion that is positioned in and attached to groove 1651 of clip 1604. The first end of arm portion 1668 is connected to the second end of base portion 1664, and a second end of arm portion 1668 is connected to a first end of contact portion 1670. The first end of contact portion 1670 is connected to the second end of arm portion 1668, and a second end of contact portion 1670 is aligned with distal end 1662 of prong 1606. Contact portion 1670 can be positioned to contact a remote body component.

One or more lumens extend through prong 1606 through which wire 1608 extends. Opening 1671 extends through proximal end 1660 of prong 1606 and provides access to the one or more lumens in prong 1606. Prong 1606 further includes electrode 1672 and electrode 1673. Prong 1606 can include one lumen corresponding to each of electrode 1672 and electrode 1673. Electrode 1672 and electrode 1673 can be ring electrodes or disk electrodes. Electrode 1672 is shown as being on distal end 1662 in the embodiment shown in FIGS. 39A-39C. Electrode 1673 is shown as being positioned adjacent to electrode 1672 on distal end 1662 in the embodiment shown in FIGS. 39A-39C. In alternate embodiments, electrode 1672 and electrode 1673 can be positioned at any point on contact portion 1670 and can have any shape and configuration. Further, prong 1606 can have a single electrode or more than two electrodes in alternate embodiments. Electrode 1672 and electrode 1673 are positioned on contact portion 1670 of prong 1606 to sense an electrical activity or physiological status of the remote body component. Electrode 1672 and electrode 1673 can also provide therapeutic electrical stimulation to the remote body component.

Prong 1606 is made of a stiff material so that it is capable of pushing through tissue in the body when subcutaneous device 1600 in implanted into a patient. Prong 1606 can be made out of nickel titanium, also known as Nitinol. Nitinol is a shape memory alloy with superelasticity, allowing prong 1606 to go back to its original shape and position if prong 1606 is deformed as subcutaneous device 1600 is implanted into a patient. Prong 1606 can also be made out of silicone, polyurethane, stainless steel, titanium, epoxy, polyurethane with metallic reinforcements, or any other material that is suitable for non-porous implants. As an example, prong 1606 can be made out of a composite made of polyurethane and silicone and reinforced with metal to provide spring stiffness.

Wire 1608 extends through opening 1671 at proximal end 1660 of prong 1606 and through the one or more lumens in prong 1606. In the embodiment shown in FIGS. 39A-39C, prong 1606 includes two lumens and wire 1608 splits into two leads in prong 1606. A first lead extends through a first lumen to connect to electrode 1672, and a second lead extends through a second lumen to connect to electrode 1673. The two leads form wire 1608 and wire 1608 extends through opening 1671 at proximal end 1660 of prong 1606. Wire 1608 is hermetically sealed in opening 1671. In an alternate embodiment, wire 1608 or one or more leads of wire 1608 may contact conductive leads formed in prong 1606 that contact electrode 1672 and electrode 1673.

Clip 1604 can be anchored to a muscle, a bone, and/or a tissue in similar ways to those discussed with respect to clip 104 of subcutaneous device 100 shown in FIGS. 1-9C. Further, subcutaneous device 1600 is described here as having a single prong 1606. In alternate embodiments, subcutaneous device 1600 can include any number of prongs and those prongs can have any shape. For example, subcutaneous device 1600 can include any the prongs shown and discussed in reference to FIGS. 1-37.

FIG. 40 is a side view of subcutaneous device 1600 anchored to xiphoid process X and/or sternum S. Subcutaneous device 1600 includes clip 1604, prong 1606, wire 1608, and connector 1609. Clip 1604 includes top portion 1640, bottom portion 1642, spring portion 1644, tip 1646, openings 1648 (not shown in FIG. 40), slot 1650 (not shown in FIG. 40), and groove 1651 (not shown in FIG. 40). Prong 1606 includes proximal end 1660, distal end 1662, base portion 1664, arm portion 1668, contact portion 1670, opening 1671 (not shown in FIG. 40), electrode 1672, and electrode 1673. FIG. 40 also shows xiphoid process X, sternum S, heart H, skin SK, and external pacemaker EP.

Subcutaneous device 1600 includes clip 1604, prong 1606, wire 1608, and connector 1609, as describe above in reference to FIGS. 38-39C. In the embodiment shown in FIG. 40, subcutaneous device 1600 is a temporary pacemaker device that, in connection with external pacemaker EP, is capable of monitoring a patient's heart rate, diagnosing an arrhythmia of the patient's heart, and providing therapeutic electrical stimulation to the patient's heart. Temporary pacemaker devices can be implanted in a patient after surgery, in emergency situations, or any other time that cardiac monitoring and/or pacing is required for a short period of time, typically anywhere from one to thirty days. Traditionally, temporary pacemakers include leads that are connected to a patient's heart and that extend through a transcutaneous port in the patient's skin to be connected to an external pacing device.

As shown in FIG. 40, clip 1604 is anchored to xiphoid process X and sternum S. Subcutaneous device 1600 can be anchored to xiphoid process X and sternum S by a surgeon during another surgery, for example open-heart surgery. Subcutaneous device 1600 can also be anchored to xiphoid process X and sternum S using a surgical instrument similar to surgical instrument 200 shown in FIGS. 10A-14B and a method similar to method 300 discussed in reference to FIGS. 15-19. The surgical instrument can be designed to accommodate the shape of subcutaneous device 1600 and can be configured to push subcutaneous device 1600 out of the surgical instrument and onto xiphoid process X and sternum S.

When clip 1604 is anchored to xiphoid process X and sternum S, prong 1606 extends away from clip 1604 and comes into contact with heart H. Prong 1606 can be shaped so that contact portion 1670 of prong 1606 contacts the right ventricle, left ventricle, right atrium, or left atrium of heart H. Electrode 1672 and electrode 1673 on prong 1606 contact heart H to sense an electrical signal from heart H and/or deliver a therapeutic signal to heart H. Wire 1608 extends from electrode 1672 and electrode 1673, through a lumen in prong 1606, and out of a transcutaneous port in the patient's skin SK. Connector 1609 is connected to a proximal end of wire 1608 and is positioned outside of the patient's body. Connector 1609 is connected to external pacemaker EP and electrically connects subcutaneous device 1600 to external pacemaker EP. Connector 1609 and external pacemaker EP can be connected using a standard electrical connector, alligator clips, or other connection mechanisms.

In the embodiment shown in FIG. 40, subcutaneous device 1600 functions as a bipolar pacemaker, with one of electrode 1672 or electrode 1673 serving as a positive electrode and the other of electrode 1672 or electrode 1673 serving as a negative electrode. In alternate embodiments, subcutaneous device 1600 can function as a unipolar pacemaker, with a single electrode on prong 1606 serving as the first electrode and clip 1604 serving as the second electrode.

Clip 1604 and prong 1606 are designed to be narrow so that subcutaneous device 1600 can be pulled out of a small incision in the patient. Specifically, clip 1604 can be designed to be thinner than xiphoid process X. When subcutaneous device 1600 is to be removed from a patient, the transcutaneous port through which wire 1608 extends can be opened up slightly so that clip 1604 and prong 1606 can be pulled through the incision.

External pacemaker EP can be a small device that a patient can carry around in a pocket or that can be taped to a patient's chest. Alternatively, external pacemaker EP can be a larger device that is supported on a table or other support structure. External pacemaker EP can include a power source, a controller, a memory, a transceiver, sensing circuitry, therapeutic circuitry, and/or any other component of a medical device. External pacemaker EP is electrically connected to subcutaneous device 1600 through connector 1609. In the embodiment shown in FIG. 40, any one or a combination of electrode 1672 and electrode 1673 can sense the electrical activity of heart H. The sensed electrical activity can be transmitted to the sensing circuitry and the controller in external pacemaker EP. The controller can determine the heart rate of the patient and can detect whether an arrhythmia is present. If an arrhythmia is detected, the controller can send instructions to therapeutic circuitry to provide a therapeutic electrical stimulation to heart H through electrode 1672 and/or electrode 1673. In this manner, subcutaneous device 1600 functions as a monitoring device, a diagnostic device, and a therapeutic device. In alternate embodiments, subcutaneous device 1600 can function only as a monitoring device, a diagnostic device, a therapeutic device, or any combinations thereof. When the patient no longer requires pacing therapy, subcutaneous device 1600 can be easily removed from the patient.

Subcutaneous Device 1700

FIG. 41 is a side view of subcutaneous device 1700 anchored to xiphoid process X and/or sternum S. Subcutaneous device 1700 includes clip 1704, prong 1706, wire 1708, and connector 1709. Clip 1704 includes top portion 1740, bottom portion 1742, spring portion 1744, tip 1746, openings 1748 (not shown in FIG. 41), slot 1750 (not shown in FIG. 41), and groove 1751 (not shown in FIG. 41). Prong 1706 includes proximal end 1760, distal end 1762, base portion 1764, arm portion 1768, contact portion 1770, opening 1771 (not shown in FIG. 41), and electrode 1772. FIG. 41 also shows xiphoid process X, sternum S, heart H, skin SK, and external pacemaker EP.

Subcutaneous device 1700 includes clip 1704, prong 1706, wire 1708, and connector 1709. Connector 1709 is configured to electrically connect subcutaneous device 1700 to external pacemaker EP. As shown in FIG. 41, clip 1704 and prong 1706 of subcutaneous device 1700 are positioned inside of a patient's body. Wire 1708 extends from prong 1706 inside of the patient's body, through the patient's skin SK, to outside of the patient's body. Connector 1709 is positioned outside of the patient's body. Subcutaneous device 1700 is conductively coupled to external pacemaker EP that is positioned outside of the patient's body.

Clip 1704 has the same general structure and design as clip 1604 of subcutaneous device 1600 shown in FIGS. 38-40. The reference numerals that refer to the parts of clip 1704 are incremented by one-hundred compared to the reference numerals that refer to the parts of clip 1604 of subcutaneous device 1600 shown in FIGS. 38-40.

Prong 1706 includes the same parts as prong 1606 of subcutaneous device 1600 as shown in FIGS. 38-40, and the reference numerals that refer to the parts of prong 1706 are incremented by one-hundred compared to the reference numerals that refer to the parts of prong 1606 of subcutaneous device 1600 shown in FIGS. 38-40. However, prong 1706 has a different shape and only includes a single electrode. Arm portion 1768 gradually curves downwards in a convex shape as it extends away from clip 1706. Contact portion 1770 is a portion of prong 1706 adjacent to distal end 1762 of prong 1706 that is configured to come into contact with heart H. Electrode 1772 is positioned on contact portion 1770 and will come into contact with heart H.

In the embodiment shown in FIG. 41, subcutaneous device 1700 can be anchored to xiphoid process X and sternum S of a patient. Clip 1704 is configured to anchor subcutaneous device 1700 to xiphoid process X and sternum S. Clip 1704 will expand as it is positioned around xiphoid process X and sternum S. Spring portion 1744 acts as a spring for clip 1704 and is under tension. Top portion 1740 acts as a tension arm and the forces from spring portion 1744 translate to and push down on top portion 1740. When clip 1704 is positioned on xiphoid process X and sternum S, the tension in spring portion 1744 will force top portion 1740 down onto xiphoid process X and sternum S to anchor clip 1704 to xiphoid process X and sternum S. Further, sutures, tines, pins, or screws can be inserted through openings 1748 on top portion 1740 of clip 1704 to further anchor subcutaneous device 1700 to xiphoid process X and sternum S.

In the embodiment shown in FIG. 41, subcutaneous device 1700 functions as a unipolar pacemaker, with clip 1704 serving as the positive electrode and electrode 1772 on prong 1706 serving as the negative electrode. In alternate embodiments, subcutaneous device 1700 can have two electrodes on prong 1706 and can function as a bipolar pacemaker.

External pacemaker EP can be a small device that a patient can carry around in a pocket or that can be taped to a patient's chest. Alternatively, external pacemaker EP can be a larger device that is supported on a table or other support structure. External pacemaker EP can include a power source, a controller, a memory, a transceiver, sensing circuitry, therapeutic circuitry, and/or any other component of a medical device. External pacemaker EP is electrically connected to subcutaneous device 1700 through connector 1709. In the embodiment shown in FIG. 41, electrode 1772 can sense the electrical activity of heart H. The sensed electrical activity can be transmitted to the sensing circuitry and the controller in external pacemaker EP. The controller can determine the heart rate of the patient and can detect whether an arrhythmia is present. If an arrhythmia is detected, the controller can send instructions to therapeutic circuitry to provide a therapeutic electrical stimulation to heart H through electrode 1772. In this embodiment, electrode 1772 serves as a negative electrode and clip 1704 serves as the positive electrode. In this manner, subcutaneous device 1700 functions as a monitoring device, a diagnostic device, and a therapeutic device. In alternate embodiments, subcutaneous device 1700 can function only as a monitoring device, a diagnostic device, a therapeutic device, or any combinations thereof. When the patient no longer requires pacing therapy, subcutaneous device 1700 can be easily removed from the patient.

Subcutaneous Device 1800

FIG. 42A is a perspective view of subcutaneous device 1800. FIG. 42B is a back view of clip 1804, first prong 1806A, and second prong 1806B of subcutaneous device 1800. FIG. 43 is a side view of subcutaneous device 1800 anchored to xiphoid process X and/or sternum S. Subcutaneous device 1800 includes clip 1804, prong 1806A, prong 1806B, wire 1808, and connector 1809. Clip 1804 includes top portion 1840, bottom portion 1842, spring portion 1844, tip 1846, openings 1848, slot 1850, groove 1851A, and groove 1851B. Prong 1806A includes proximal end 1860A, distal end 1862A, base portion 1864A, arm portion 1868A, contact portion 1870A, opening 1871A, electrode 1872A, and electrode 1873A. Prong 1806B includes proximal end 1860B, distal end 1862B, base portion 1864B, arm portion 1868B, contact portion 1870B, opening 1871B, and defibrillator coil 1874B. FIG. 43 also shows xiphoid process X, sternum S, heart H, skin SK, and external defibrillator EF.

Subcutaneous device 1800 is a temporary defibrillator device. Patients who have experienced a myocardial infarction and/or who have undergone an angioplasty procedure are at risk of sudden cardiac arrest for a period of thirty to sixty days following. Subcutaneous device 1800 can be temporarily implanted in a patient to monitor a patient's heart following a myocardial infarction and/or angioplasty procedure. When therapy is no longer needed, subcutaneous device 1800 can be removed through a small incision in the patient.

Subcutaneous device 1800 includes clip 1804, prong 1806A, prong 1806B, wire 1808, and connector 1809. Connector 1809 is configured to electrically connect subcutaneous device 1800 to external defibrillator EF. As shown in FIG. 43, clip 1804, prong 1806A, and prong 1806B of subcutaneous device 1800 are positioned inside of a patient's body. Wire 1808 extends from prong 1806A and prong 1806B inside of the patient's body, through the patient's skin SK, to outside of the patient's body. Connector 1809 is positioned outside of the patient's body. Subcutaneous device 1800 is conductively coupled to external defibrillator EF that is positioned outside of the patient's body.

Clip 1804 has the same general structure and design as clip 1604 of subcutaneous device 1600 shown in FIGS. 38-40. However, clip 1804 includes two grooves, including groove 1851A and groove 1851B. The reference numerals that refer to the parts of clip 1804 are incremented by two-hundred compared to the reference numerals that refer to the parts of clip 1604 of subcutaneous device 1600 shown in FIGS. 38-40. Groove 1851A and groove 1851B are positioned next to one another on clip 1804. Prong 1806A is configured to be positioned in and attached to groove 1851A to attach prong 1806A to clip 1804. Prong 1806B is configured to be positioned in and attached to groove 1851B to attached prong 1806B to clip 1804.

Prong 1806A and prong 1806B generally include the same parts as prong 1606 of subcutaneous device 1600 as shown in FIGS. 38-40, and the reference numerals that refer to the parts of prong 1806A and 1806B are incremented by two-hundred compared to the reference numerals that refer to the parts of prong 1606 of subcutaneous device 1600 shown in FIGS. 38-40. Prong 1806A has the same shape as prong 1606 shown in FIGS. 38-40. Arm portion 1868A extends away from clip 1804. Contact portion 1870A is a portion of prong 1806A adjacent to distal end 1862A of prong 1806A that is configured to come into contact with heart H. Electrode 1872A and electrode 1873A positioned on contact portion 1870A will also come into contact with heart H. However, prong 1806B has a different shape than prong 1606 shown in FIGS. 38-40 and includes defibrillator coil 1874B instead of an electrode. Arm portion 1868B extends away from clip 1804. Contact portion 1870B is a portion of prong 1806B adjacent to distal end 1862B of prong 1806B that is configured to come into contact with tissue inferior to heart H. Defibrillator coil 1874B is positioned on contact portion 1870B adjacent to distal end 1862B of prong 1806B. When an electrical signal is delivered to defibrillator coil 1874B, defibrillator coil 1874B will create a vector with electrode 1872A on prong 1806A. In the embodiment shown, defibrillator coil 1874B serves as the negative electrode and electrode 1872A serves as the positive electrode. However, in alternate embodiments this can be reversed. Prong 1806B is positioned so that distal end 1862B, and thus contact portion 1870B and defibrillator coil 1874B, are positioned inferior to the heart. Thus, the vector created between defibrillator coil 1874B and electrode 1872A will pass through heart H to provide a high voltage electrical shock to heart H. Defibrillator coil 1874B and electrode 1872A can be positioned so that the vector passes through the ventricles of heart H. Further, due to the close proximity of defibrillator coil 1874B and electrode 1872A to heart H, relatively low energy is required to shock heart H.

In the embodiment shown in FIG. 43, subcutaneous device 1800 can be anchored to xiphoid process X and sternum S of a patient. Clip 1804 is configured to anchor subcutaneous device 1800 to xiphoid process X and sternum S. Clip 1804 will expand as it is positioned around xiphoid process X and sternum S. Spring portion 1844 acts as a spring for clip 1804 and is under tension. Top portion 1840 acts as a tension arm and the forces from spring portion 1844 translate to and push down on top portion 1840. When clip 1804 is positioned on xiphoid process X and sternum S, the tension in spring portion 1844 will force top portion 1840 down onto xiphoid process X and sternum S to anchor clip 1804 to xiphoid process X and sternum S. Further, sutures, tines, pins, or screws can be inserted through openings 1848 on top portion 1840 of clip 1804 to further anchor subcutaneous device 1800 to xiphoid process X and sternum S.

External defibrillator EF can include a power source, a controller, a memory, a transceiver, sensing circuitry, therapeutic circuitry, and/or any other component of a medical device. In the embodiment shown in FIG. 43, subcutaneous device 1800 is configured to be a single chamber pacemaker and a defibrillator. Any one or combination of electrode 1872A and electrode 1873A can sense the electrical activity of a heart. Further, defibrillator coil 1874B can act as an electrode that senses the electrical activity of the heart. The sensed electrical activity can be transmitted to the sensing circuitry and the controller in external defibrillator EF. The controller can determine the heart rate of the patient and can detect whether an arrhythmia or abnormality is present. If an arrhythmia is detected, the controller can send instructions to therapeutic circuitry to provide a therapeutic stimulation to the heart with electrode 1872A and/or electrode 1873A. If an abnormality is detected, the controller can send instructions to therapeutic circuitry to provide a high voltage electrical shock to the heart with defibrillator coil 1874B. In this manner, subcutaneous device 1800 functions as a monitoring device, a diagnostic device, and a therapeutic device. In alternate embodiments, subcutaneous device 1800 can function only as a monitoring device, a diagnostic device, or a therapeutic device, or any combinations thereof. When the patient no longer requires monitoring and defibrillator therapy, subcutaneous device 1800 can be easily removed from the patient.

DISCUSSION OF POSSIBLE EMBODIMENTS

The following are non-exclusive descriptions of possible embodiments of the present invention.

A subcutaneously implantable device includes a housing, a clip attached to a top side of the housing, and an electrode. The clip is configured to anchor the device to a muscle, a bone, and/or a first tissue. The electrode is configured to contact an organ, a nerve, the first tissue, and/or a second tissue. Circuitry in the housing is in electrical communication with the electrode that is configured to sense an electrical signal from the organ, the nerve, the first tissue, and/or the second tissue through the electrode; deliver electrical stimulation to the organ, the nerve, the first tissue, and/or the second tissue through the electrode; and/or deliver a signal to a drug pump to provide a targeted or systemic therapeutic drug to the organ, the nerve, the first tissue, and/or the second tissue.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip is configured with respect to the housing such that when the clip is attached to the xiphoid process and/or the sternum, the housing of the device is positioned below the xiphoid process and/or the sternum of the patient.

Wherein the electrode is positioned on the housing.

Wherein the housing further includes a recess on a top side of the housing, wherein the clip is positioned in the recess.

Wherein the clip is welded to the top side of the housing.

Wherein the clip includes a top portion, a bottom portion, and a spring portion extending between and connecting the top portion to the bottom portion.

Wherein the electrode is positioned on the top portion of the clip.

Wherein the spring portion is curved and is configured to act as a spring for the clip to push the top portion of the clip onto the bone, the muscle, and/or the first tissue to which it is anchored.

Wherein the clip further includes a first opening and a second opening extending through the top portion of the clip, wherein the first opening and the second opening are configured to receive sutures, tines, pins, or screws to secure the device to the bone, the muscle, and/or the first tissue on which the clip is anchored.

The device further includes a prong with a proximal end attached to the housing and a distal end extending away from the housing that is configured to contact the organ, the nerve, and/or the second tissue, wherein the electrode is positioned on the distal end of the prong.

Wherein the housing further includes a channel on the bottom side of the housing extending from a back end to a front end of the housing, wherein when the device is in a stowed position, the prong is positioned in the channel.

Wherein the prong further includes a base portion on the proximal end of the prong; a spring portion extending from the base portion; an arm portion extending from the spring portion; and a contact portion extending from the arm portion and terminating at the distal end of the prong.

Wherein the housing further includes a port on a back side of the housing, wherein the base portion of the prong is positioned in the port.

Wherein the spring portion is curved and is configured to act as a spring for the prong.

Wherein the electrode is positioned on the contact portion of the prong.

Wherein a lumen extending from the proximal end to the distal end of the prong is configured to provide the targeted or systemic therapeutic drug to the organ, the nerve, and/or the second tissue with which the distal end of the prong is in contact with.

A subcutaneously implantable device includes a housing, a clip attached to a top side of the housing, a prong with a proximal end attached to the housing and a distal end extending away from the housing that, and an electrode. The clip is configured to anchor the device to a muscle, a bone, and/or a first tissue. The prong is configured to contact an organ, a nerve, and/or a second tissue. The electrode is configured to contact the organ, the nerve, the first tissue, and/or the second tissue. Circuitry in the housing is in electrical communication with the electrode that is configured to sense an electrical signal from the organ, the nerve, the first tissue, and/or the second tissue through the electrode; deliver electrical stimulation to the organ, the nerve, the first tissue, and/or the second tissue through the electrode; and/or deliver a signal to a drug pump to provide a targeted or systemic therapeutic drug to the organ, the nerve, the first tissue, and/or the second tissue.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip is configured with respect to the housing such that when the clip is attached to the xiphoid process and/or the sternum, the housing of the device is positioned below the xiphoid process and/or the sternum of the patient.

Wherein the clip further includes a top portion, a bottom portion, and a spring portion extending between and connecting the top portion to the bottom portion.

Wherein the spring portion is curved and is configured to act as a spring for the clip to push the top portion of the clip onto the bone, the muscle, and/or the first tissue to which it is anchored.

Wherein the clip further includes a first opening and a second opening extending through the top portion of the clip, wherein the first opening and the second opening are configured to receive sutures, tines, pins, or screws to secure the device to the bone, the muscle, and/or the first tissue on which the clip is anchored.

Wherein the prong further includes a base portion on a proximal end of the prong; a spring portion extending from the base portion; an arm portion extending from the spring portion; and a contact portion extending form the arm portion and terminating at a distal end of the prong.

Wherein the housing further includes a port on a back side of the housing, wherein the base portion of the prong is positioned in the port.

Wherein the spring portion is curved and is configured to act as a spring for the prong.

Wherein the electrode is positioned on the contact portion of the prong.

Wherein the electrode is configured to come into contact with a heart.

Wherein the electrode is configured to provide therapeutic stimulation to the heart.

Wherein a lumen extending from the proximal end to the distal end of the prong is configured to provide the targeted or systemic therapeutic drug to the organ, the nerve, and/or the second tissue with which the distal end of the prong is in contact with.

A method of subcutaneously injecting and anchoring a device to a bone, a muscle, and/or a tissue in a patient, the device having a clip configured to anchor the device to the bone, the muscle, or the tissue, includes making an incision in the patient. An instrument pre-loaded with the device is inserted through the incision. The instrument is advanced to the bone, the muscle, and/or the tissue upon which the device is to be anchored. A clip of the device is pushed onto the bone, the muscle, and/or the tissue using the instrument. The device is anchored to the bone, the muscle, and/or the tissue using the clip on the device.

The method of the preceding paragraph can optionally include, additionally and/or alternatively, any one or more of the following features, configurations and/or additional components:

Wherein making the incision in the patient comprises making the incision below a xiphoid process and/or a sternum of the patient.

Wherein advancing the instrument to the bone, the muscle, and/or the tissue upon which the device is to be anchored comprises advancing the instrument to the xiphoid process and/or the sternum.

The method further includes removing tissue from the xiphoid process and/or the sternum using a blade on the instrument and/or a blade separate from the instrument.

The method further includes positioning the instrument to deploy the device onto the xiphoid process and/or the sternum.

Wherein pushing the clip of the device onto the bone, the muscle, and/or the tissue includes pushing the clip of the device onto the xiphoid process and/or the sternum.

Wherein pushing the clip of the device onto the bone, the muscle, and/or the tissue includes pushing a top portion of the clip of the device on top of the xiphoid process and/or the sternum and a housing of the device below the xiphoid process and/or the sternum.

Wherein anchoring the device to the bone, the muscle, and/or the tissue using the clip on the device includes anchoring the device to the xiphoid process and/or the sternum using the clip on the device.

The method further includes removing the instrument from the incision in the patient.

Wherein the clip on the device has a spring portion extending between a top portion and a bottom portion.

Wherein the spring portion has a spring bias that puts tension on the top portion of the clip to anchor the device to the xiphoid process and/or the sternum.

Wherein pushing the clip of the device onto the bone, the muscle, and/or the tissue using the instrument includes pushing a slider of the instrument forward to deploy the device from the instrument.

Wherein the device has a guide that moves through a guide track of the instrument when the device is pushed through the instrument.

The method further includes pushing a prong of the device through tissue below the xiphoid process and the sternum of the patient.

The method further includes securing the device to the bone, the muscle, and/or the tissue using sutures, tines, pins, and/or screws that extend through openings in the clip.

A subcutaneously implantable device capable of being injected and anchored to a muscle, a bone, and/or a first tissue using a surgical instrument includes a housing, a guide on the housing, a clip attached to a top side of the housing, and an electrode. The guide is configured to guide the device through the surgical instrument. The clip is configured to anchor the device to the muscle, the bone, and/or the first tissue. The electrode is configured to contact an organ, a nerve, the first tissue, and/or a second tissue. Circuitry in the housing is in electrical communication with the electrode that is configured to sense an electrical signal from the organ, the nerve, the first tissue, and/or the second tissue through the electrode; deliver electrical stimulation to the organ, the nerve, the first tissue, and/or the second tissue through the electrode; and/or deliver a signal to a drug pump to provide a targeted or systemic therapeutic drug to the organ, the nerve, the first tissue, and/or the second tissue.

The device of the preceding paragraph can optionally include, additionally and/or alternatively, any one or more of the following features, configurations and/or additional components:

Wherein the clip is configured to attach the device to a xiphoid process and/or a sternum of a patient so that the housing of the device is positioned below the xiphoid process and/or the sternum of the patient.

Wherein the housing has a curved surface on a top side of the housing adjacent a front end of the housing to form a tapered front end of the housing.

Wherein the guide on the housing includes a first guide on a first side of the housing, and a second guide on a second side of the housing, wherein the first guide and the second guide are configured to mount the device in and guide the device through a guide track in the surgical instrument.

Wherein the clip further includes a top portion, a bottom portion, and a spring portion extending between and connecting the top portion to the bottom portion.

Wherein the top portion of the clip tapers to a tip at a front end.

Wherein the clip further includes a slot extending through the spring portion, wherein the slot is configured to receive a blade of the surgical instrument.

The device further includes a first prong with a proximal end attached to the housing and a distal end extending away from the housing that is configured to contact the organ, the nerve, and/or the second tissue.

Wherein the housing further includes a channel on the bottom side of the housing extending from a back end to a front end of the housing, wherein when the device is positioned in a stowed position in the surgical instrument, the first prong is positioned in the channel.

A system for injecting and anchoring a subcutaneously implanted device to a muscle, a bone, and/or a first tissue using a surgical instrument includes a device and a surgical instrument. The device includes a housing, a clip attached to a top side of the housing, and an electrode. The clip is configured to anchor the device to the muscle, the bone, and/or the first tissue. The electrode is configured to contact an organ, a nerve, the first tissue, and/or a second tissue. Circuitry in the housing is in electrical communication with the electrode that is configured to sense an electrical signal from the organ, the nerve, the first tissue, and/or the second tissue through the electrode; deliver electrical stimulation to the organ, the nerve, the first tissue, and/or the second tissue through the electrode; and/or deliver a signal to a drug pump to provide a targeted or systemic therapeutic drug to the organ, the nerve, the first tissue, and/or the second tissue. The surgical instrument includes a body in which the device is positionable, and a slider positioned in and capable of sliding in the body. The slider is configured to push the device out of the surgical instrument.

The system of the preceding paragraph can optionally include, additionally and/or alternatively, any one or more of the following features, configurations and/or additional components:

Wherein a guide on the housing of the device is positionable in and movable along a guide track in the body of the surgical instrument.

Wherein the device includes a prong with a proximal end attached to the housing and a distal end extending away from the housing that is positionable in and movable along a prong track in the body of the surgical instrument.

Wherein the surgical instrument includes a blade attached to the body of the surgical instrument that extends through a slot in the clip of the device when the device is stowed in the surgical instrument.

Wherein the slider is positioned in and slides through a slider slot in an upper arm of the body.

Wherein the device is positionable in and slides along a lower arm of the body.

A subcutaneously implantable device includes a housing, a clip attached to a top side of the housing, a first prong with a proximal end attached to the housing and a distal end extending away from the housing, and a first electrode on the first prong. The clip is configured to anchor the device to a muscle, a bone, and/or a tissue. The first prong is configured to contact a heart. The first electrode is configured to contact the heart. Sensing circuitry in the housing that is configured to sense an electrical signal from the heart, and therapeutic circuitry in the housing is in electrical communication with the first electrode and is configured to deliver electrical stimulation to the heart through the first electrode.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the tissue to which it is anchored.

Wherein the sensing circuitry is in electrical communication with the first electrode and can sense the electrical signal from the heart through the first electrode.

Wherein the sensing circuitry is in electrical communication with a second electrode on the first prong, the housing, and/or the clip and can sense the electrical signal from the heart through the second electrode.

Wherein the first prong is configured to contact a right ventricle of the heart, a left ventricle of the heart, a right atrium of the heart, or a left atrium of the heart.

Wherein the therapeutic circuitry is configured to deliver a signal to a drug pump to provide a targeted or systemic therapeutic drug to the organ, the nerve, the first tissue, and/or the second tissue.

The device further includes a second prong with a proximal end attached to the housing and a distal end extending away from the housing that is configured to contact the heart, and a second electrode on the second prong that is in electrical communication with the therapeutic circuitry and is configured to deliver the electrical stimulation to the heart.

Wherein the first prong is configured to contact a right ventricle of the heart and the second prong is configured to contact a left ventricle of the heart; the first prong is configured to contact a left ventricle of the heart and the second prong is configured to contact a right atrium of the heart; and/or the first prong is configured to contact a right ventricle of the heart and the second prong is configured to contact a right atrium of the heart.

The device further includes a third prong with a proximal end attached to the housing and a distal end extending away from the housing that is configured to contact a heart, and a third electrode on the third prong that is in electrical communication with the therapeutic circuitry and is configured to deliver the electrical stimulation to the heart.

Wherein the first prong is configured to contact the right ventricle of the heart, the second prong is configured to contact the left ventricle of the heart, and the third prong is configured to contact the right atrium of the heart.

A subcutaneously implantable device includes a housing, a clip attached to a top side of the housing, a first prong with a proximal end attached to the housing and a distal end extending away from the housing, a first defibrillator coil on the distal end of the first prong, and a first electrode on a front end of the housing. The clip is configured to anchor the device to a muscle, a bone, and/or a tissue. The first prong is configured to be positioned inferior to a heart. Sensing circuitry in the housing is in electrical communication with the first electrode and is configured to sense an electrical signal from the heart through the first electrode. Therapeutic circuitry in the housing is in electrical communication with the first defibrillator coil and the first electrode and is configured to deliver a shock to the heart through the first defibrillator coil.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the tissue to which it is anchored.

Wherein the first defibrillator coil creates a first vector with the first electrode, and wherein the first vector passes through the heart.

The device further includes a second prong with a proximal end attached to the housing and a distal end extending away from the housing that is configured to be positioned on a first side of the housing, a third prong with a proximal end attached to the housing and a distal end extending away from the housing that is configured to be positioned on a second side of the housing, a second defibrillator coil on the distal end of the second prong, and a third defibrillator coil on the distal end of the third prong.

Wherein the first defibrillator coil creates a first vector with the first electrode, a second vector with the second defibrillator coil, and a third vector with a third defibrillator coil, and wherein the first vector, the second vector, and the third vector pass through the heart.

The device further includes a second prong with a proximal end attached to the housing and a distal end extending away from the housing that is configured to contact a heart, and a second electrode on the second prong that is in electrical communication with the therapeutic circuitry and is configured to deliver electrical stimulation to the heart.

Wherein the second prong is configured to contact a right ventricle of the heart, a left ventricle of the heart, a right atrium of the heart, or a left atrium of the heart.

A subcutaneously implantable device includes a housing, a clip attached to a top side of the housing, a first prong with a proximal end attached to the housing and a distal end extending away from the housing, a second prong with a proximal end attached to the housing and a distal end extending away from the housing, a first electrode on the first prong, and a second electrode on the second prong. The clip is configured to anchor the device to a muscle, a bone, and/or a first tissue. The first prong is configured to contact a first organ and/or a second tissue. The second prong is configured to contact the first organ, a second organ, the second tissue, and/or the third tissue. The first electrode is configured to contact the first organ and/or the second tissue. The second electrode is configured to contact the first organ, the second organ, the second tissue, and/or the third tissue. Sensing circuitry in the housing is in electrical communication with the first electrode and the second electrode and is configured to sense an electrical signal from the first organ, the second organ, the second tissue, and/or the third tissue.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the first tissue to which it is anchored.

Wherein the first prong is configured to contact the right lung and the second prong is configured to contact the left lung; the first prong and the second prong are configured to contact the heart; and/or the first prong and the second prong are configured to contact tissue surrounding the heart.

The device further includes a sensor in electrical communication with the sensing circuitry and selected from the group consisting of a temperature sensor, an accelerometer, a pressure sensor, a proximity sensor, an infrared sensor, an optical sensor, an ultrasonic sensor, a data storage device, and combinations thereof.

Wherein the sensor is positioned on the housing, the first prong, or the second prong.

A subcutaneously implantable device includes a housing, a clip attached to a top side of the housing, a drug pump having a drug reservoir in the housing, a prong with a lumen extending through the prong and having a proximal end attached to the housing and the drug pump, and a distal end extending away from the housing. The clip is configured to anchor the device to a muscle, a bone, and/or a first tissue. The prong is configured to contact an organ, a nerve, and/or a second tissue. Circuitry in the housing in electrical communication with the drug pump is configured to deliver a signal to the drug pump to provide a targeted or systemic therapeutic drug to the organ, the nerve, the first tissue, and/or the second tissue through the lumen running through the prong.

The device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the first tissue to which it is anchored.

Wherein a port in the housing fluidly connects to the drug reservoir and is configured to allow the drug reservoir to be replenished.

Wherein an electrode positioned on the housing, the clip, and/or the prong is in electrical communication with the circuitry and is configured to sense an electrical signal from the organ, the nerve, the first tissue and/or the second tissue and/or is configured to deliver electrical stimulation to the organ, the nerve, the first tissue and/or the second tissue.

A subcutaneously implantable device includes a clip that is configured to anchor the subcutaneously implantable device to a muscle, a bone, and/or a first tissue, and a first prong with a proximal end attached to the clip and a distal end extending away from the clip that is configured to contact an organ, a nerve, and/or a second tissue. A first electrode on the first prong is configured to contact the organ, the nerve, and/or the second tissue. A wire conductively connected to the first electrode is configured to be connected to an external device that is positioned outside of a patient's body to electrically connect the subcutaneously implantable device to the external device.

The subcutaneously implantable device of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the first tissue to which it is anchored.

Wherein the proximal end of the first prong is positioned in and attached to a groove in the clip.

Wherein the first prong includes a base portion on the proximal end of the first prong, an arm portion extending away from the base portion, and a contact portion extending from the arm portion and terminating at the distal end of the first prong.

Wherein the base portion of the first prong is attached to the clip.

Wherein a lumen extends through the first prong and the wire extends from the first electrode, through the lumen, and out of an opening in the proximal end of the first prong.

Wherein the first electrode is positioned on the contact portion of the first prong.

Wherein the first prong is configured to contact a right ventricle of the heart, a left ventricle of the heart, a right atrium of the heart, or a left atrium of the heart.

Wherein the wire electrically connects the first electrode to the external device.

The device further includes a second electrode on the first prong that is configured to contact the organ, the nerve, and/or the second tissue.

Wherein the wire is conductively connected to the second electrode to electrically connect the second electrode to the external device.

Wherein the distal end of the first prong is configured to contact a heart, and the device further includes a second prong with a proximal end attached to the clip and a distal end extending away from the clip that is configured to be positioned inferior to the heart, and a defibrillator coil on the distal end of the second prong.

Wherein the defibrillator coil creates a first vector with the first electrode, and wherein the first vector passes through the heart.

A system includes a subcutaneously implantable device and an external device positioned outside of a patient's body. The subcutaneously implantable device includes a clip that is configured to anchor the subcutaneously implantable device to a muscle, a bone, and/or a first tissue, and a first prong with a proximal end attached to the clip and a distal end extending away from the clip that is configured to contact a heart. A first electrode on the first prong is configured to contact the heart, and a wire is conductively connected to the first electrode. The wire is electrically connected to the external device to electrically connect the subcutaneously implantable device to the external device.

The system of the preceding paragraph can optionally include, additionally and/or alternatively, any one or more of the following features, configurations and/or additional components:

Wherein the clip is configured to attach the device to a xiphoid process and/or a sternum of a patient.

Wherein the clip further includes a top portion, a bottom portion, and a spring portion extending between and connecting the top portion to the bottom portion, wherein the spring portion is curved and is configured to act as a spring for the clip to push the top portion of the clip onto the bone, the muscle, and/or the first tissue to which it is anchored.

Wherein the external device further includes sensing circuitry in electrical communication with the first electrode that is configured to sense an electrical signal from the heart through the first electrode, and therapeutic circuitry in the housing in electrical communication with the first electrode that is configured to deliver electrical stimulation to the heart through the first electrode.

The device further includes a second electrode on the first prong that is configured to contact the heart.

Wherein the external device further includes sensing circuitry in electrical communication with the first electrode and the second electrode that is configured to sense an electrical signal from the heart through the first electrode and/or the second electrode, and therapeutic circuitry in the housing in electrical communication with the first electrode and the second electrode that is configured to deliver electrical stimulation to the heart through the first electrode and/or the second electrode.

The device further includes a second prong with a proximal end attached to the clip and a distal end extending away from the clip that is configured to be positioned inferior to the heart, and a defibrillator coil on the distal end of the second prong.

Wherein the external device further includes sensing circuitry in electrical communication with the first electrode that is configured to sense an electrical signal from the heart through the first electrode, and therapeutic circuitry in the housing in electrical communication with the first defibrillator coil and the first electrode that is configured to deliver shock to the heart through the first defibrillator coil, wherein the defibrillator coil creates a first vector with the first electrode, and wherein the first vector passes through the heart.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A subcutaneously implantable device comprising:
   a clip that is configured to anchor the subcutaneously implantable device to a muscle, a bone, and/or a first tissue;
   a first prong with a proximal end attached to the clip and a distal end extending away from the clip that is configured to contact an organ, a nerve, and/or a second tissue;
   a first electrode on the first prong that is configured to contact the organ, the nerve, and/or the second tissue; and
   a wire conductively connected to the first electrode, wherein the wire is configured to be connected to an external device that is positioned outside of a patient's body to electrically connect the subcutaneously implantable device to the external device.

2. The subcutaneously implantable device of claim 1, wherein the clip is configured to attach the device to a xiphoid process and/or a sternum of a patient.

3. The subcutaneously implantable device of claim 1, wherein the clip further comprises:
   a top portion;
   a bottom portion; and
   a spring portion extending between and connecting the top portion to the bottom portion, wherein the spring portion is curved and is configured to act as a spring for the clip to push the top portion of the clip onto the bone, the muscle, and/or the first tissue to which it is anchored.

4. The subcutaneously implantable device of claim 1, wherein the proximal end of the first prong is positioned in and attached to a groove in the clip.

5. The subcutaneously implantable device of claim 1, wherein the first prong comprises:
   a base portion on the proximal end of the first prong;
   an arm portion extending away from the base portion; and
   a contact portion extending from the arm portion and terminating at the distal end of the first prong.

6. The subcutaneously implantable device of claim 5, wherein the base portion of the first prong is attached to the clip.

7. The subcutaneously implantable device of claim 5, wherein a lumen extends through the first prong and the wire extends from the first electrode, through the lumen, and out of an opening in the proximal end of the first prong.

8. The subcutaneously implantable device of claim 5, wherein the first electrode is positioned on the contact portion of the first prong.

9. The subcutaneously implantable device of claim 1, wherein the first prong is configured to contact a right ventricle of the heart, a left ventricle of the heart, a right atrium of the heart, or a left atrium of the heart.

10. The subcutaneously implantable device of claim 1, wherein the wire electrically connects the first electrode to the external device.

11. The subcutaneously implantable device of claim 1, and further comprising:
    a second electrode on the first prong that is configured to contact the organ, the nerve, and/or the second tissue.

12. The subcutaneously implantable device of claim 11, wherein the wire is conductively connected to the second electrode to electrically connect the second electrode to the external device.

13. The subcutaneously implantable device of claim 1, wherein the distal end of the first prong is configured to contact a heart, and further comprising:
    a second prong with a proximal end attached to the clip and a distal end extending away from the clip that is configured to be positioned inferior to the heart; and
    a defibrillator coil on the distal end of the second prong.

14. The subcutaneously implantable device of claim 13, wherein the defibrillator coil creates a first vector with the first electrode, and wherein the first vector passes through the heart.

15. A system comprising:
    a subcutaneously implantable device that comprises:
       a clip that is configured to anchor the subcutaneously implantable device to a muscle, a bone, and/or a first tissue;
       a first prong with a proximal end attached to the clip and a distal end extending away from the clip that is configured to contact a heart;
       a first electrode on the first prong that is configured to contact the heart; and
       a wire conductively connected to the first electrode; and
    an external device positioned outside of a patient's body;
    wherein the wire is electrically connected to the external device to electrically connect the subcutaneously implantable device to the external device.

16. The system of claim 15, wherein the clip is configured to attach the device to a xiphoid process and/or a sternum of a patient.

17. The system of claim 15, wherein the clip further comprises:
    a top portion;
    a bottom portion; and
    a spring portion extending between and connecting the top portion to the bottom portion, wherein the spring portion is curved and is configured to act as a spring for the clip to push the top portion of the clip onto the bone, the muscle, and/or the first tissue to which it is anchored.

18. The system of claim 15, wherein the external device further comprises:
    sensing circuitry in electrical communication with the first electrode that is configured to sense an electrical signal from the heart through the first electrode; and
    therapeutic circuitry in the housing in electrical communication with the first electrode that is configured to deliver electrical stimulation to the heart through the first electrode.

19. The system of claim 15, wherein the subcutaneously implantable device further comprises:
    a second electrode on the first prong that is configured to contact the heart.

20. The system of claim 19, wherein the external device further comprises:
    sensing circuitry in electrical communication with the first electrode and the second electrode that is configured to sense an electrical signal from the heart through the first electrode and/or the second electrode; and
    therapeutic circuitry in the housing in electrical communication with the first electrode and the second electrode that is configured to deliver electrical stimulation to the heart through the first electrode and/or the second electrode.

21. The system of claim 15, wherein the subcutaneously implantable device further comprises:
    a second prong with a proximal end attached to the clip and a distal end extending away from the clip that is configured to be positioned inferior to the heart; and
    a defibrillator coil on the distal end of the second prong.

22. The system of claim 21, wherein the external device further comprises:
- sensing circuitry in electrical communication with the first electrode that is configured to sense an electrical signal from the heart through the first electrode; and
- therapeutic circuitry in the housing in electrical communication with the first defibrillator coil and the first electrode that is configured to deliver shock to the heart through the first defibrillator coil, wherein the defibrillator coil creates a first vector with the first electrode, and wherein the first vector passes through the heart.

\* \* \* \* \*